(12) United States Patent
Mankin et al.

(10) Patent No.: US 11,096,346 B2
(45) Date of Patent: *Aug. 24, 2021

(54) METHOD FOR TREATING POST-EMERGENT RICE

(71) Applicant: BASF SE, Ludwigshafen (DE)

(72) Inventors: S. Luke Mankin, Raleigh, NC (US); Leon Neuteboom, Morrisville, NC (US); Sherry R. Whitt, Raleigh, NC (US); Ulrich Schofl, Apex, NC (US); Haiping Hong, Cary, NC (US); Allan Wenck, Durham, NC (US); Dale R. Carlson, Apex, NC (US); John A. McElver, Durham, NC (US); Jill M. Stevenson-Paulik, Cary, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,714

(22) Filed: Feb. 27, 2017

(65) Prior Publication Data
US 2017/0265469 A1 Sep. 21, 2017

Related U.S. Application Data

(63) Continuation of application No. 15/395,832, filed on Dec. 30, 2016, which is a continuation-in-part of application No. 14/357,691, filed as application No. PCT/US2012/064831 on Nov. 13, 2012, now Pat. No. 9,540,627, said application No. 15/395,832 is a continuation-in-part of application No. 15/156,671, filed on May 17, 2016, which is a continuation of application No. 13/393,780, filed as application No. PCT/US2010/047571 on Sep. 1, 2010, now abandoned.

(60) Provisional application No. 61/559,618, filed on Nov. 14, 2011, provisional application No. 61/365,298, filed on Jul. 16, 2010, provisional application No. 61/238,906, filed on Sep. 1, 2009.

(51) Int. Cl.
| | |
|---|---|
| *A01H 5/10* | (2018.01) |
| *C12N 15/82* | (2006.01) |
| *A01H 1/04* | (2006.01) |
| *A01H 1/02* | (2006.01) |
| *A01N 43/40* | (2006.01) |
| *A01N 39/02* | (2006.01) |
| *A01N 43/60* | (2006.01) |

(52) U.S. Cl.
CPC ............... *A01H 5/10* (2013.01); *A01N 39/02* (2013.01); *A01N 43/40* (2013.01); *C12N 15/8274* (2013.01); *A01H 1/02* (2013.01); *A01H 1/04* (2013.01); *A01N 43/60* (2013.01)

(58) Field of Classification Search
CPC ........ A01H 5/10; A01H 1/04; C12N 15/8274; A01N 43/40; A01N 43/60; C12Y 604/01002

See application file for complete search history.

(56) References Cited

U.S. PATENT DOCUMENTS

| | | |
|---|---|---|
| 5,162,602 A | 11/1992 | Somers et al. |
| 5,290,696 A | 3/1994 | Somers et al. |
| 5,801,233 A | 9/1998 | Haselkorn |
| 5,910,626 A | 6/1999 | Haselkorn |
| 5,925,805 A | 7/1999 | Ohlrogge et al. |
| 6,027,945 A | 2/2000 | Smith |
| 6,069,298 A | 5/2000 | Gengenbach |
| 6,281,168 B1 | 8/2001 | Shaner et al. |
| 6,306,636 B1 | 10/2001 | Haselkorn et al. |
| 6,368,800 B1 | 4/2002 | Smith et al. |
| 2003/0236208 A1 | 12/2003 | Kmiec et al. |
| 2004/0123343 A1 | 6/2004 | La Rosa et al. |
| 2006/0039943 A1 | 2/2006 | Applebaum et al. |
| 2007/0074303 A1 | 3/2007 | McCutchen et al. |
| 2008/0234130 A1 | 9/2008 | McCutchen et al. |
| 2008/0256668 A1* | 10/2008 | Beetham ............... A01H 1/06 800/300.1 |
| 2009/0093366 A1* | 4/2009 | Wright ............... C12N 9/0069 504/142 |

(Continued)

FOREIGN PATENT DOCUMENTS

| | | |
|---|---|---|
| CN | 102083303 A | 6/2011 |
| CN | 102905516 A | 1/2013 |

(Continued)

OTHER PUBLICATIONS

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).*

Maneechote, Chanya, et al. "Resistance to ACCase-inhibiting herbicides in sprangletop (*Leptochloa chinensis*)." Weed science 53.3 (2005): 290-295. (Year: 2005).*

Till, Bradley J., et al. "Discovery of chemically induced mutations in rice by Tilling." BMC plant biology 7.1 (2007): 19. (Year: 2007).*

Anyszka, Zbigniew, and A. Dobrzanski. "The response of snap bean and barnyard grass [*Echinochloa crus-galli*] on quizalofop-P-tefuryl." Vegetable Crops Research Bulletin 51 (1999): 95-102. (Year: 1999).*

(Continued)

Primary Examiner — Weihua Fan
(74) Attorney, Agent, or Firm — Lowenstein Sandler LLP

(57) ABSTRACT

The present disclosure provides a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, postemergence; thereby creating a treated rice plant; and growing the resulting treated rice plant.

17 Claims, 46 Drawing Sheets

Figures 1, 1A, 1B, 1C:
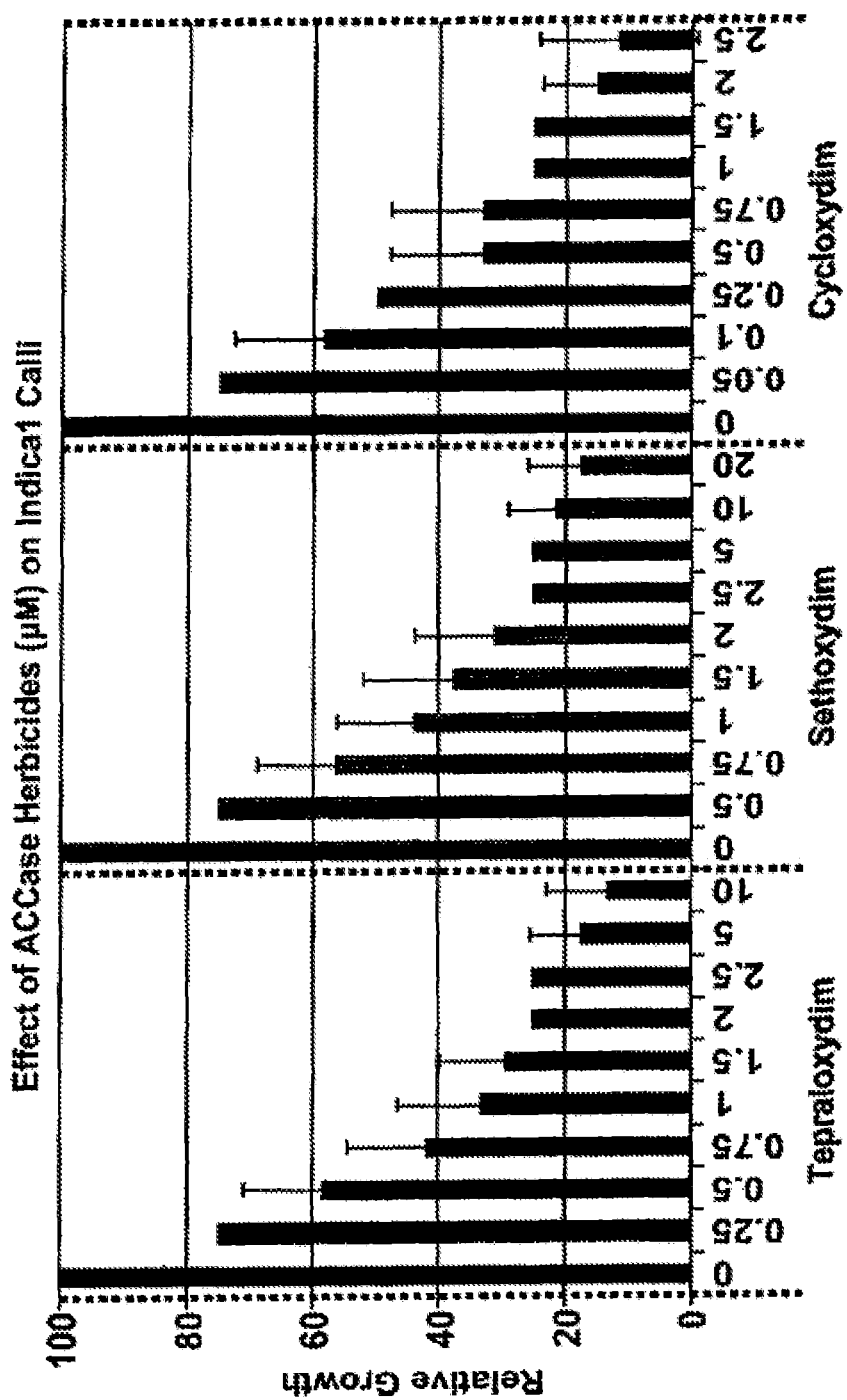

Specification includes a Sequence Listing.

(56) References Cited

U.S. PATENT DOCUMENTS

| | | |
|---|---|---|
| 2010/0048405 A1 | 2/2010 | Raymer et al. |
| 2011/0214196 A1 | 9/2011 | Raymer et al. |
| 2013/0023416 A1 | 1/2013 | Hinga et al. |
| 2013/0111618 A1 | 5/2013 | Mankin et al. |
| 2014/0045686 A1 | 2/2014 | Mankin et al. |
| 2016/0108423 A1 | 4/2016 | Mankin et al. |
| 2016/0244780 A1 | 8/2016 | Mankin et al. |
| 2016/0251677 A1 | 9/2016 | Mankin et al. |
| 2017/0275645 A1 | 9/2017 | Mankin et al. |

FOREIGN PATENT DOCUMENTS

| | | | | |
|---|---|---|---|---|
| EP | 0374753 A2 | 6/1990 | | |
| EP | 0374853 A1 | 6/1990 | | |
| EP | 0427529 A1 | 5/1991 | | |
| EP | 0451878 A1 | 10/1991 | | |
| EP | 2473024 A2 | 7/2012 | | |
| GB | WO-1998054330 A1 * | 5/1998 | ............ | C12N 15/82 |
| JP | 2013-526833 | 7/2012 | | |
| JP | 2013526833 A | 6/2013 | | |
| WO | 1993/007278 | 4/1993 | | |
| WO | 93007278 A1 | 4/1993 | | |
| WO | 9534656 A1 | 12/1995 | | |
| WO | WO-1998054330 A1 * | 5/1998 | ............ | C12N 15/54 |
| WO | 9854330 A1 | 12/1998 | | |
| WO | 0192512 A2 | 12/2001 | | |
| WO | 02015701 A2 | 2/2002 | | |
| WO | 03018810 A2 | 3/2003 | | |
| WO | 03052073 A2 | 6/2003 | | |
| WO | 2005123946 A1 | 12/2005 | | |
| WO | 2008089061 A2 | 7/2008 | | |
| WO | 2009056333 A2 | 5/2009 | | |
| WO | 2011028832 A2 | 3/2011 | | |
| WO | 2011028836 A2 | 3/2011 | | |

OTHER PUBLICATIONS

Okuzaki, A., and K. Toriyama. "Chimeric RNA/DNA oligonucleotide-directed gene targeting in rice." Plant cell reports 22.7 (2004): 509-512 (Year: 2004).*

Heong, Kong Luen, and M. M. Escalada, eds. Pest management of rice farmers in Asia. Int. Rice Res. Inst., 1997. (Year: 1997).*

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).*

Maneechote, Chanya, et al. "Resistance to ACCase-inhibiting herbicides in sprangletop (*Leptochloa chinensis*)." Weed science 53.3 (2005): 290-295. (Year: 2005).*

Délye, et al. "Cross-resistance patterns to ACCase-inhibiting herbicides conferred by mutant ACCase isoforms in *Alopecurus myosuroides* Huds.(black-grass), re-examined at the recommended herbicide field rate." Pest management science 64.11 (2008): 1179-1186. (Year: 2008).*

Tong et al., Systematic Genetic Analysis with Ordered Arrays of Yeast Deletion Mutants, Science, vol. 294, No. 5550, pp. 2364-2368, 2001.

Tong, A.H.Y. and Boone, C., "Synthetic Genetic Array Analysis in *Saccharomyces cerevisiae*," Methods Mol Biol, vol. 313, pp. 171-192, 2006.

"Extended European Search Report issued in European Application No. 10814446.0", dated Jun. 6, 2013, 14 pages.

"Extended European Search Report issued in European Application No. 16202167.9", dated Mar. 16, 2017, 9 pages.

"Genotyping Sethoxydim Resistant Maize: A method for the detection of the ACC1-11781 (Am)L allele in *Zea mays*", BASF internal manual.

"International Search Report issued in International Application No. PCT/US2010/047571", dated May 18, 2011, 4 pages.

Ashley, Jr., James Elton, "Evaluation of Weed Control and Crop Tolerance With Postemergence Herbicides in Sethoxydim-Tolerant Corn", Thesis submitted to Virginia Polytechnic Institute, Apr. 27, 1998, 4 pages.

Balgheim, et al., "Resistance to ACCase inhibiting herbicides is due to target-site modification in a biotype of Alopecurus myosuroides Huds", The BCPC International Congress-Crop Science & Technology, 2005, pp. 155-162.

Buell, C. Robin, "Poaceae Genomes: Going from Unattainable to Becoming a Model Glade for Comparative Plant Genomics", Plant Physiology, vol. 149, Issue 1, Jan. 2009, pp. HI-116.

Callan, "In Vitro Selection for and Biochemical Analysis of Sethoxydim-Tolerant winter Wheat (*Triticum aestivum*L.)", In partial fulfillment of the requirements for the Degree of Doctor of Philosophy, Colorado State University, Fort Collins, Colorado, Fall, 1996, 30 pages.

Carlson, et al., "Tissue Culture Selection System in Poa Pratensis", NCWSS Proceedings, vol. 45, 1990, Abstract, 1 page.

Christoffers, et al., "An Isoleucine to Leucine Mutation in Acetyl-CoA Carboxylas Confers Herbicide Resistance in Wild Oat", Genome, National Research Council Canada, vol. 45, Issue 6, Jan. 1, 2002, pp. 1049-1056.

Delye, et al., "An isoleucine-leucine substitution in chloroplastic acetyl-CoA carboxylase from green foxtail (*Setaria viridis*L. Beauv.) is responsible for resistance to the cyclohexanedione herbicide sethoxydim", Planta. vol. 214, Issue 3, Jan. 2002, pp. 421-427.

Delye, et al., "Molecular Bases for Sensitivity to Acetyl-Coenzyme A Carboxylase Inhibitors in Black-Grass", Plant Physiology, vol. 137, Mar. 2005, pp. 794-806.

Delye, et al., "PCR-based detection of resistance to acetyl-CoA Carboxylase-inhibitor herbicides in black-grass (*Alopecurus myosuroides* Huds) and ryegrass (*Lolium rigidum* Gaud)", Pest Management Science, vol. 58, Issue 5, May 2002, pp. 474-478.

Delye, et al., "SNP markers for black-grass (*Alopecurus myosuroides* Huds) genotypes resistant to acetyl CoA-carboxylase inhibiting herbicides", Theoretical and Applied Genetics, vol. 104, Issue 6-7, May 2002, pp. 1114-1120.

Delye, et al., "Universal' primers for PCR-sequencing of grass chloroplastic acetyl-CoA carboxylase domains involved in resistance to herbicides", Weed Research, vol. 45, 2005, pp. 323-330.

Delye, "Weed resistance to acetyl coenzyme A carboxylase inhibitors: an update", Weed Science, vol. 53, No. 5, Sep. 2005, pp. 728-746.

Heckart, et al., "Obtaining Sethoxydim Resistance in Seashore Paspalum", Crop Science, vol. 50, Nov.-Dec. 2010, pp. 2632-2640.

Heckart, Douglas Lee, "Obtaining Sethoxydim Resistance in Seashore Paspalum (*Paspalum vaginatum*)", A Thesis Submitted to the Graduate Faculty of the University of Georgia in Partial Fulfillment of the Requirements for the Degree, Athens, GA, 2009, 51 pages.

Herbert, et al., "Susceptibilities of Different Test Systems from Maize (*Zea mays*), Pea annua, and Festuca rubrato Herbicides that Inhibit the Enzyme Acetyl-Coenzyme a Carboxylase", Pesticide Biochemistry and Physiology, vol. 55, Issue 2, Jun. 1996, pp. 129-139.

Hiei, et al., "Agrobacterium-mediated Transformation of Rice Using Immature Embryos or Call Induced from Mature Seed", Nature Protocols, vol. 3, No. 5, Apr. 17, 2008, pp. 824-834.

Jain, S.M., "Tissue culture-derived variation in crop improvement", Euphytica, vol. 118, Issue 2, Mar. 2001, pp. 153-166.

Joachimiak, et al., "Wheat cytosolic acetyl-CoA carboxylase complements an ACC1 null mutation in yeast", Proceeding of the National Academy Science, Plant Biology, vol. 94, Sep. 1997, pp. 9990-9995.

Maneechote et al., "Controlling invasive wild rice with ACCase-inhibiting herbicides." Proceedings of the 4th International Crop Science Congress, Brisbane, Australia. 2004. (Year: 2004).

JP Ruiz-Santaella, et al., "Basis of selectivity of cyhalofop-butyl in *Oryza sativa* L.", Planta, vol. 223, Issue 2, Jan. 2006, pp. 191-199.

JP Ruiz-Santaella, et al., "Detection of a new mutation of glycine to serine in the ACCase of a Resistant Biotype of Phalaris Paradoxa", Weed Science Sec. Am. Abstr. 46:93, 2006 (New York: WSSA 2006 Annual Meeting, Abstract, 1 page.

(56) References Cited

OTHER PUBLICATIONS

JP Ruiz-Santaella, et al., "Is it possible to detect *Echinochloa* spp. tolerance to ACCaseinhibiting herbicides using a simple quick tolerance test?", Commun. Agric. Appl. Biol. ScL, vol. 68, (4 Pt A), 2003, pp. 331-334.
Kellogg, Elizabeth A., "The Evolutionary History of Ehrhartoideae, Oryzeae, and Oryza", Rice, vol. 2, Issue 1, Mar. 2009, pp. 1-14.
Liu, et al., "Single-site mutations in the carboxyltransferase domain of plastid acetyl-CoA carboxylase confer resistance to grass-specific herbicides", PNAS, vol. 104, Issue 9, Feb. 2007, pp. 3627-3632.
Madoka, et al., "Chloroplast Transformation with Modified accD Operon Increases Acetyl-CoA Carboxylase and Causes Extension of Leaf Longevity and Increase in Seed Yield in Tobacco", Plant and Cell Physiology, vol. 43, Issue 12, Dec. 15, 2002, pp. 1518-1525.
Marshall, et al., "Allelic mutations in acetyl-coenzyme A carboxylase confer herbicide tolerance in maize", Theoretical and Applied Genetics, vol. 83, Issue 4, Feb. 1992, pp. 435-442.
Mathews, et al., "Phylogenetic Structure in the Grass Family (Poaceae): Evidence From the Nuclear Gene Phytochrome B", American Journal of Botany 87(1), 2000, pp. 96-107.
Menchari, et al., "Fitness costs associated with three mutant acetyl-coenzyme A carboxylase alleles endowing herbicide resistance in black-grass Alopecurus myosuroides", Journal of Applied Ecology, vol. 45, Issue 3, Jun. 2008, pp. 939-947.
Neve, et al., "High survival frequencies at low herbicide use rates in populations of Lolium rigidum result in rapid evolution of herbicide resistance", Heredity, vol. 95, Jul. 2005, pp. 485-492.
Nikolau, et al., "Plant biotin-containing carboxylases", Archives of Biochemistry and Biophysics, vol. 414, Issue 2, Jun. 15, 2003, pp. 211-222.
Nikolskaya, et al., "Herbicide sensitivity determinant of wheat plastid acetyl-CoA carboxylase is located in a 400-amino acid fragment of the carboxyltransferase domain", PNAS, vol. 96 No. 25, Dec. 7, 1999, pp. 14647-14651.
Parker, et al., "Dominant mutations causing alterations in acetyl-coenzyme A carboxylase confer tolerance to cyclohexanedione and aryloxyphenoxypropionate herbicides in maize", Proceedings of the National Academy of Science, vol. 87, Sep. 1990, pp. 7175-7179.
Parker, et al., "Selection and Characterization of Sethoxydim-Tolerant Maize Tissue Cultures", Plant Physiology, vol. 92, 1990, pp. 1220-1225.
Podkowinski, et al., "Expression of Cytosolic and Plastid Acetyl-Coenzyme A Carboxylase Genes in Young Wheat Plants", Plant Physiology, vol. 131, Feb. 2003, pp. 763-772.
Rafael De Prado, et al., "Resistance to ACCase inhibitor herbicides in a green foxtail (*Setaria viridis*) biotype in Europe", Weed Science, vol. 52, No. 4, Jul.-Aug. 2004, pp. 506-512.
Roesler, et al., "Targeting of the Arabidopsis Homomeric Acetyl-Coenzyme A Carboxylase to Plastids of Rapeseeds", Plant Physiology, vol. 113, Issue 1, Jan. 1997, pp. 75-81.
Ruiter, et al., "Spontaneous Mutation Frequency in Plant Obscures the Effect of Chimeraplasty", Plant Molecular Thology, vol. 53, Nov. 2003, pp. 715-729.
Anyszka, Zbigniew, and A. Dobrzanski. "The response of snap bean and barnyardgrass (*Echinochloa crus-galli*) on quizalorop-P-tefuryl." Vegetable Crops Research Bulletin 51 (1999):95-102. (Year 1999).
Maneechote, Chanya, et al. "Resistance to ACCase-inhibiting herbicides in sprangletop (*Leptochloa chinensis*)." Weed science 53 (2005): 290-295. (Year: 2005).
Shivrain, et al., "Gene flow between Clearfield™ rice and red rice", Crop Protection, vol. 26, Issue 3, Mar. 2007, pp. 349-356.
Somers, David A., "Chapter 11: Aryloxyphenoxypropionate- and Cyclohexanedione-Resistant Crops", Herbicide-Resistant Crops: Agricultural, Environmental, Economic, Regulatory and Technical Aspects, CRC Press, Inc., 1996, pp. 175-188.
Xiang, et al., "A different mechanism for the inhibition of the carboxyltransferase domain of acetyl-coenzyme A carboxylase by tepraloxydim", PNAS, vol. 106, No. 49, Dec. 8. 2009, pp. 20723-0727.

Tal, et al., "Molecular characterization and inheritance of resistance to ACCase-inhibiting herbicides in Lolium rigidum", Pest Management Science, vol. 60, Issue 10, Oct. 2004, pp. 1013-1018.
Tate, Trent Matthew, "Characterization of acetyl coenzyme A inhibitor resistance in turfgrass and grassy weeds", A Thesis Submitted to the Graduate Faculty of the University of Georgia in Partial Fulfillment of the Requirements for the Degree, Dec. 2012, 64 pages.
White, et al., "Differences in the molecular basis of resistance to the cyclohexanedione herbicide sethoxydim in Lolium multiflorum", Weed Research, vol. 45, Issue 6, Dec. 2005, pp. 440-448.
Yu, et al., "Diversity of Acetyl-Coenzyme A Carboxylase Mutations in Resistant Lolium Populations: Evaluation Using Clethodim", Plant Physiology, vol. 145, Issue 2, Oct. 2007, pp. 547-558.
Baldwin, John L, et al. "Effect of growth stage and application site on tolerance of rice (*Oryza sativa*) to haloxyfop." Weed technology 10.2 (1996): 268-272. (Year: 1996).
Noldin, JosE A., et al. "Red rice (*Oryza sativa*) biology. II. Ecotype sensitivity to herbicides." Weed Technology (1999): 19-24. (Year: 1999).
Griffin, James L., and John B. Baker. "Tolerance of rice (*Oryza sativa*) cultivars to fenoxaprop, sethoxydim, and haloxyfop." Weed Science 38.6 (1990): 528-531. (Year: 1990).
O'Sullivan, P. A., WH Vanden Born, and H. A. Friesen. "Influence of herbicides for broad-leaved weeds and adjuvants with dichlorfop methyl on wild oat control." Canadian Journal of Plant Science 57.1 (1977): 117-125. (Year: 1977).
Khush, G.S., Plant Mol. Biol. (1997) 35:25-34.
Buell, C. Robin, "Poaceae Genomes: Going from Unattainable to Becoming a Model Glade for Comparative Plant Genomics", Plant Physiology, vol. 149, Issue 1, Jan. 2009, pp. 111-116.
Christoffers, et al., "An Isoleucine to Leucine Mutation in Acetyl-CoA Carboxylase Confers Herbicide Resistance in Wild Oat", Genome, National Research Council Canada, vol. 45, Issue 6, Jan. 1, 2002, pp. 1049-1056.
Delye, et al., "An isoleucine-leucine substitution in chloroplastic acetyl-CoA carboxylase from green foxtail (*Setaria Addis* L. Beauv.) is responsible for resistance to the cyclohexanedione herbicide sethoxydim", Planta. vol. 214, Issue 3, Jan. 2002, pp. 421-427.
Herbert, et al., "Susceptibilities of Different Test Systems from Maize (*Zea mays*), Poa annua, and Festuca rubrato Herbicides that Inhibit the Enzyme Acetyl-Coenzyme A Carboxylase", Pesticide Biochemistry and Physiology, vol. 55, Issue 2, Jun. 1996, pp. 129-139.
Hiei, et al., "Agrobacterium-mediated Transformation of Rice Using Immature Embryos or Calli Induced from Mature Seed", Nature Protocols, vol. 3, No. 5, Apr. 17, 2008, pp. 824-834.
Joachimiak et al., "Wheat cytosolic acetyl-CoA carboxylase complements an ACC1 null mutation in yeast," Proc. Natl. Acad. Sci. USA, vol. 94, pp. 9990-9995, Sep. 1997.
Liu et al., "Single-site mutations in the carboxyltransferase domain of plastid acetyl-CoA carboxylase confer resistance to grass-specific herbicides," PNAS, Feb. 27, 2007, vol. 104 No. 9, pp. 3627-3632.
Marshall et at, "Allelic mutations in acetyl-coenzyme A carboxylase confer herbicide tolerance in maize," Theor. Appl. Genet, 1992, vol. 83, pp. 435-442.
Neve et at, "High survival frequencies at low herbicide use rates in populations of Lolium rigidum result in rapid evolution of herbicide resistance," Heredity, 2005, vol. 95, pp. 485-492.
Nikolau et at, "Plant biotin-containing carboxylases," Archives of Biochemistry and Biophysics, vol. 414, 2003, pp. 211-222.
Nikolskaya et al., "Herbicide sensitivity determinant of wheat plastid acetyl-CoA carboxylase is located in a 400-amino acid fragment of the carboxyltransferase domain," PNAS, Dec. 7, 1999, vol. 96 No. 25, pp. 14647-14651.
Parker et al., "Selection and Characterization of Sethoxydim-Tolerant Maize Tissue Cultures," Plant Physiol., 1990, vol. 92, pp. 1220-1225.
Podkowlnski et al., "Expression of Cytosolic and Plastid Acetyl-Coenzyme A Carboxylase Genes in Young Wheat Plants," Plant Physiology, Feb. 2003, vol. 131, pp. 763-772.
Shivrain et al., "Gene flow between Cleartield(TM) rice and red rice," Crop Protection, vol. 26, 2007, pp. 349-356.

(56) References Cited

OTHER PUBLICATIONS

Tal et al., "Molecular characterization and inheritance of resistance to ACCase-inhibiting herbicides in Lolium rigidum," Pest Manag. Sci., Mar. 15, 2004, vol. 60, pp. 1013-1018.
Yu et al., "Diversity of Acetyl-Coenzyme A Carboxylase Mutations in Resistant Lolium Populations: Evaluation Using Clethodim," Plant Physiology, Oct. 2007, vol. 145, pp. 547-558.
Zagnitko et al., "An isoleucine/leucine residue in the carboxyltransferase domain of acetyl-CoA carboxylase is critical for interaction with aryloxyphenoxypropionate and cyclohexanedione inhibitors," PNAS, Jun. 5 2001, vol. 98 No. 12, pp. 6617-6622.
Roesler et al., "Targeting of the Arabidopsis Homomeric Acetyl-Coenzyme A Carboxylase to Plastids of Rapeseeds," Plant Physiol., 1997, vol. 113, pp. 75-81.
Zhu et al., "Computational Simulations of the Interactions between Acetyl-Coenzye-A Carboxylase and Clodinafop: Resistance Mechanism Due to Active and Nonactive Site Mutations," J. Chem. Inf. Model., 2009, vol. 29, pp. 1936-1943.
International Preliminary Report on Patentability, International Application No. PCT/US2010/047571, dated Mar. 6, 2012.
Liu et al, Proc. Natl. Acad. Sol. (2007) 104:3627-3632.
Liu et al., "Single-Site Mutations in the Carboxyltransferase Domain of Plastid Acetyl-CoA Carboxylase Confer Resistance to Grass-Specific Herbicides," Proc Natl Acad Sci USA, vol. 104, No. 9, pp. 3627-3632, 2007.
Mumberg et al., "Yeast Vectors for the Controlled Expression of Heterologous Proteins in Different Genetic Backgrounds," Gene, vol. 156, pp. 119-122, 1995.
Nikolau et al., "Plant Biotin-Containing Carboxylases," Arch Biochem Biophys, vol. 414, pp. 211-222, 2003.
Nikolskaya et al., "Herbicide Sensitivity Determinant of Wheat Plastid Acetyl-CoA Carboxylase is Located in a 400-Amino Acid Fragment of the Carboxyltransferase Domain," Proc Natl Acad Sci USA, vol. 96, No. 25, pp. 14647-14651, 1999.
Podkowinski et al., Expression of Cytosolic and Plastid Acetyl-Coenzyme A Carboxylase Genes in Young Wheat Plants, Plant Physiol, vol. 131, No. 2, pp. 763-772, 2003.
Schneiter et al., A Yeast Acetyl Coenzyme A Carboxylase Mutant Links Very-Long-Chain Fatty Acid Synthesis to the Structure and Function of the Nuclear Membrane-Pore Complex, Mol Cell Biol, vol. 16, pp. 7161-7172, 1996.
Shivrain et al., Gene Flow Between Clearfield® Rice and Red Rice, Crop Protection, vol. 26, pp. 349-356, 2007.
Somers, D.A., "Aryloxyphenoxypropionate and Cyclohexanedione-Resistant Crops," In: Duke SO (Editor), Herbicide-Resistant Crops Agricultural, Environmental, Economic, Regulatory and Technical Aspects, CRC Press, New York, pp. 175-187, 1996.
Varanasi, A.V., "Assessment of Acetyl-CoA Carboxylase Mutations Using Partial Gene Replacement in Yeast," Proquest Dissertations and Theses: the Science and Engineering Collection, 2008.
International Search Report and Written Opinion for application No. PCT/US2012/064831, filed Nov. 13, 2012.
International Preliminary Report on Patentability for application No. PCT/US2012/064831, filed Nov. 13, 2012.
Rafael De Prado et al., "Resistance to ACCase inhibitor herbicides in a green foxtail (Setaria vindis) biotype in Europe", Weed Science, vol. 52: 506-512 (2004).
Song Xiang etal., "A different mechanism for the inhibition of the carboxyltransferase domain of acetyl-coenzyme A carboxylase by tepraloxydim", PNAS, vol. 106, No. 49, pp. 20723-20727, Dec. 8, 2009.
Rutger et al, Crop Science (2005) 45:1170-1171.
Delye et al, Weed Res. (2005) 45:323-330.
Delye, Weed Science (2005) 53:728-746.
Suzuki et al, Mol. Genet. Genomics (2008) 279:213-223.
Okuzaki et al, Plant Cell Rep. (2004) 22:509-512.
UniProt Accession No. A2Y2U1, integrated into the database on Mar. 20, 2007.

JP Ruiz-Santaella et al., "Is it possible to detect Echinochioa spp. tolerance to ACCaseinhibiting herbicides using a simple quick tolerance test?," Commun. Agric. Appl. Biol. Sci. 68(4, pt A):331-34 (2003).
JP Ruiz-Santaella et al., "Basis of selectivity of cyhalofop-butyl in Oryza saliva L.," Planta 223(2):191-99 (Jan. 2006) (ePub Sep. 14, 2005).
A. Okuzaki et al., "Chimeric RNA/DNA Oligonucleotide-Directed Gene Targeting in Rice", Plant Cell Rep Laboratory of Plant Breeding and Genetics, Tohoku University, Sendai, Japan, (2004) 22:509-512.
Delye et al., "PCR-based detection of resistance to acetyl-CoA carboxylase-inhibiting herbicides in black-grass (Alopercurus myosuroides Huds) and ryegrass (Lolium rigidum Gaud)," Pest Management Science, vol. 58, No. 5, May 2002, pp. 474-478.
Delye et al., "An isoleucine-leucine substitution in chloroplastic acetyl-CoA carboxylase from green foxtail (Setaria viridis L. Beauv.) is responsible for resistance to the cyclohexanedione herbicide sethoxydium," Planta, vol. 214, No. 3, Jan. 1, 2002, pp. 421-427.
Delye et al., "SNP markers for black-grass (Alopecurus myosuroides Huds.) genotypes resistant to acetyl CoA-carboxylase inhibiting herbiddes," Theoretical and Applied Genetics, vol. 104, No. 6-7, May 1, 2002, pp. 1114-1120.
Christoffers et al., "An Isoleucine to 1-23 Leucine Mutation in Acetyl-CoA Carboxylase Confers Herbicide Resistance in Wild Oat," Genome, National Research Council Canada, vol. 45, No. 6, Jan. 1, 2002.
Menchari et al., "Fitness costs associated with three mutant acetyl-coenzyme A carboxylase alleles endowing herbicide resistance in black-grass Alopecurus myosuroides," Journal of Applied Ecology, vol. 45, No. 3, Jun. 2008, pp. 939-947.
Tate, "Characterization of Acetyl Coenzyme A Inhibitor Resistance in Turfgrass and Grassy Weeds," A Thesis Submitted to the Graduate Faculty of the University of Georgia in Partial Fulfillment of the Requirements for the Degree, 2012.
Somers, "Chapter 11: Aryloxyphenoxypropionate- and Cyclohexanedione-Resistant Crops," Herbicide-Resistant Crops: Agricultural, Environmental, Economic, Regulatory and Technical Aspects, CRC Press, Inc., 1996, pp. 175-188.
Callan, In Vitro Selection for and Biochemical Analysis of Sethoxydim-Tolerant Winter Wheat (Triticum Aestivum L), In partial fulfillment of the requirements for the Degree of Doctor of Philosophy, Colorado State University, Fort Collins, Colorado, Fall 1996.
Carlson et al., "Tissue Culture Selection System in Poa Pratensis," NCWSS Proceedings, vol. 45, p. 11, 1990.
White et al., "Differences in the molecular basis of resistance to the cyclohexanedione herbicide sethoxydim in Lolium multiflorum," Weed Research 45(6), pp. 440-448, Dec. 2005.
Zhang et al., "The molecular bases for resistance to acetyl co-enzyme A carboxylase (ACCase) inhibiting herbicides in two target-based resistant biotypes of annual ryegrass (Lolium rigidum)," Planta 223(3), pp. 550-557, Feb. 2006.
Collavo, "Resistance to graminicides in monocotyledons weeds: Case studies of Lolium spp. and Phalaris paradoxa in Italy," 2008 (Ph.D. Thesis, U. Padua/Padova).
Ruiz-Santaella et al., "Detection of a new mutation of glycine to serine in the ACCase of a resistant biotype of Phalaris paradoxa," Weed Sci. Soc. Am. Abstr. 46:93 (2006) (New York: WSSA 2006 Annual Meeting, Abstracts).
Makoda, Yuka, et al., "Chloroplast Transformation with Modified accD Operon Increases Acetyl-CoA Carboxylase and Causes Extension of Leaf Longevity and Increase in Seed Yield in Tobacco", 43(12): 1518-1525 (2002), Genesis Research Inst, Inc., Japan.
Heckart, Obtaining Sethoxydim Resistance in Seashore Paspalum (Paspalum vaginatum), A Thesis Submitted to the Graduate Faculty of the University of Georgia in Partial Fulfillment of the Requirements for the Degree, Athens, GA, 2009.
Herbert et al., "Susceptibilities of Different Test Systems from Maine (Zea mays), Poa annua, and Festuca rubra to Herbicides that Inhibit the Enzyme Acetyl-Coenzyme A Carboxylase," Pesticide Biochemistry and Physiology, No. 55, pp. 129-139, 1996.

(56) References Cited

OTHER PUBLICATIONS

Buell, Poaceae Genomes: Going from Unattainable to Becoming a Model Clade for Comparative Plant Genomics, Plant Physiology, Jan. 2009, vol. 149, pp. 111-116.

Kellogg, "The Evolutionary History of Ehrhartoideae, Oryzeae, and Oryza," Rice, Jan. 8 2009, vol. 2, pp. 1-14.

Mathews et al., "Phylogenetic Structure in the Grass Family (Poaceae): Evidence From the Nuclear Gene Phytochrome B," American Journal of Botany 87(1), pp. 96-107, 2000.

Ashley, JR., "Evaluation of Weed Control and Crop Tolerance With Postemergence Herbicides in Sethoxydim-Tolerant Corn," Thesis submitted to Virginia Polytechnic Institute, Apr. 27, 1998.

Delye et al., "An Isoleucine Residue within the Carboxyl-Transferase Domain of Multidomain Acetyl-Coenzyme A Carboxylase Is a Major Determinant of Sensitivity to Aryloxyphenoxypropionate But Not to Cydohexanedione Inhibitors," Plant Physiology, Jul. 2003, vol. 132, pp. 1716-1723.

Delye et al., "Molecular Bases for Sensitivity to Acetyl-Coenzyme A Carboxylase Inhibitors in Black-Grass," Plant Physiology, Mar. 2005, vol. 137, pp. 794-806.

Delye et al., "Cross-resistance patterns to ACCase-inhibiting herbicides conferred by mutant ACCase isoforms in *Alopecurus myosuroides* Huds. (black-grass), re-examined at the recommended herbicide field rate," Pest Manag. Sci,, 2008.

Hiei et al., "Agrobacterium-mediated transformation of rice using immature embryos or Galli induced from mature seed," Nature Protocols, 2008, vol. 3 No. 5, pp. 824-834.

Ruiter, et al., "Spontaneous Mutation Frequency in Plant Obscures the Effect of Chimeraplasty", Plant Molecular Biology, vol. 53, Nov. 2003, pp. 715-729.

Yu, et al., "The Genomes of *Oryza sativa*: A History of Duplications", PLoS Biology, vol. 3,Issue 2, e38, Feb. 2005, pp. 0266-0281.

Zagnitko, et al., "An isoleucine/leucine residue in the carboxyltransferase domain of acetyl-CoA carboxylase is critical for interaction with aryloxyphenoxypropionate and cyclohexanedione inhibitors", PNAS, vol. 98, No. 12, Jun. 5, 2001, pp. 6617-6622.

Zhang, et al., "The molecular bases for resistance to acetyl coenzyme A carboxylase (ACCase) inhibiting herbicides in two target-based resistant biotypes of annual ryegrass (*Lolium rigidum*)", Planta., vol. 223, Issue 3, Feb. 2006, pp. 550-557.

Zhu, et al., "Computational Simulations of the Interactions between Acetyl-Coenzyme-A Carboxylase and Clodinafop: Resistance Mechanism Due to Active and Non active Site Mutations", Journal of Chemical Information and Modeling, vol. 49, No. 8, Jul. 13, 2009, pp. 1936-1943.

Georges, F. and Ray H., GM Crops and Food 2017, 8:1-12, pp. 2-6.

Custers, R., Emerging Topics in Life Sciences (2017), Portland Press, "The regulatory status of gene-edited agricultural products in the EU and beyond" pp. 1-9.

Sprink, T. et al., "Regulatory hurdles for genome editing: process- vs. product-based approaches in different regulatory contexts." Plant Cell Rep 2016, 35: 1493-1506.

EU Directive 2001/18/EC, Official Journal of the European Communities (Apr. 17, 2001):L106/1-38.

M. Lusser & E. Rodriguez-Cerezo "Comparative Regulatory Approaches for New Plant Breeding Techniques," presented Jun. 26, 2012 at the 16th ICABR Conference, Ravello, Italy.

M. Lusser et al., "Deployment of new biotechnologies in plant breeding," Nature Biotechnology 30(3):231-239 (2012); Abstract.

BIO Product Launch Stewardship Policy of May 21, 2007.

CropLife International (CLI) Product Launch Stewardship Guidance of 2008.

Excellence Through Stewardship (ETS) Guide for Product Launch of Biotechnology-Derived Plant Products of 2009; 13 pages.

Diclofop Methyl herbicide directions for use, Cheminova Australia PTY LTD, pp. 1-4.

Aramo, Tepraloxydim herbicide directions for use, BASF (2015), pp. 1-8.

BASF, "Segment Herbicide" pp. 1-2, 2008. APN 08-14-002-0051.

Gressel, et al., "A strategy to provide long-term control of weedy rice while mitigating herbicide resistance transgene flow, and its potential use for other crops with related weeds," Wiley Interscience, Apr. 14, 2009. DOI 10.1002/ps. 1754 pp. 723-731.

Johnson, et al., "Managing the potential for developing herbicide-resistant weeds in herbicide-tolerant rice" Weed Science, pp. 551-557.

Valverde, et al., "Status and Management of Grass-Weed Herbicide Resistance in Latin America," Weed Technology 2007 21:310-323.

EMBL Accession No. EAY97401, Submitted on Sep. 12, 2003.

Zhu et al., "Engineering herbicide-resistant maize using chimeric RNA/DNA oligonucleotides." Nature Biotechnology Vol. May 18, 2000, pp. 555-558.

U.S. Department of Agriculture, Agricultural Resource Management Survey: U.S. Rice Industry. Jan. 2015, No. 2015-02, pp. 1-4.

K. Johnson et al., "Managing the potential for developing herbicide-resistant weeds in herbicide-tolerant rice," at p. 556 in J.E. Hill & B. Hardy (eds), Proceedings of the Second Temperate Rice Conference (Int. Rice Res Inst.) (2002).

Page 37 in "Implementing Integrated Weed Management for Herbicide Tolerant Crops" (CropLife International, Feb. 2012; https://croplife.org/wp-content/uploads/2014/04/Implementing-Integrated-Weed-Management-for-Herbicide-Folerant-Crops.pdf.

J.W. Heiser (U. Missouri—Weed Science), Rice News (Sep. 5, 2014), in AgFax (http://agfax.com/2014/09/05/ice-herbicide-tolerant-pro visia-highlighted-missouri-delta-center-field-day/).

Delye et al, Pest Manag. Sol (2008) 64:1179-1186.

Delye et al, Plant Physiol. (2003) 132:1716-1723.

Collavo, A., PhD Dissertation, University of Padova, Jan. 2008.

UniProt Accession No. A2Y2U1, integrated into database Mar. 20, 2007.

Powles et al., Resistance and World Grains, CRC Press (2001), Boca Raton Florida, pp. 31-33.

Beetham et al., "A Tool for Functional Plant Genomics: Chimeric RNA/DNA Oligonucleotides Cause in Vivo Gene-Specific Mutations," Proc Natl Acad Sci USA, vol. 96, pp. 8774-8778, 1999.

Chugh, A. and Eudes, F., "Study of Uptake of Cell Penetrating Peptides and Their Cargoes in Permeabilized Wheat Immature Embryos," FEBS J. vol. 275, pp. 2403-2414, 2008.

Delye et al., "An Isoleucine Residue Within the Carboxyltransferase Domain of Multidomain Acetyl-Coenzyme A Carboxylase is a Major Determinant of Sensitivity to Aryloxyphenoxypropionate but not to Cyclohexanedione Inhibitors," Plant Physiol, vol. 132, pp. 1716-1723, 2003.

Delye et al., "Molecular Bases for Sensitivity to Acetyl-Coenzyme A Carboxylase Inhibitors in Black-Grass," Plant Physiol, vol. 137, pp. 794-806, 2005.

Gietz et al., "Improved Method for High Efficiency Transformation of Intact Yeast Cells," Nucl Acids Res, vol. 20, p. 1425, 1992.

Hasslacher et al., "Acetyl-CoA Carboxylase from Yeast is an Essential Enzyme and is Regulated by Factors that Control Phospholipid Metabolism," J Biol Chem, vol. 268, No. 15, pp. 10946-10952, 1993.

Joachimiak et al., "Wheat Cytosolic Acetyl-CoA Carboxylase Complements an ACC1 Null Mutation in Yeast," Pro Natl Acad Sci USA, vol. 94, No. 18, pp. 9990-9995, 1997.

K. Johnson et al., "Managing the potential for developing herbicide-resistant weeds in herbicide-tolerant rice," at p. 556 in J.E. Hill & B. Hardy (ed ), Proceedings of the Second Temperate Rice Conference (Int. Rice Res Inst.) (2002).

Page 37 in "Implementing Integrated Weed Management for Herbicide Tolerant Crops" (CropLife International, Feb. 2012; https://croplife.org/wp-content/uploads/2014/04/Implementing-Integrated-Weed-Management-for-Herbicide-Tolerant-Crops.pdf.

J.W. Heiser (U. Missouri—Weed Science), Rice News (Sep. 5, 2014), in AgFax (http://agfax.com/2014/09/05/rice-herbicide-tolerant-provisia-highlighted-missouri-delta-center-field-day/).

Delye et al, Pest Management Science, 2008 64:1179-1186.

Okuzaki et al, "Chimeric RNA/DNA oligonucleotide-directed gene targeting in rice," Plant Cell Reports, 22:7, 2004, 509-512.

(56) References Cited

OTHER PUBLICATIONS

Schneiter et al., A Yeast Acetyl Coenzyme A Caboxylase Mutant Links Very-Long-Chain Fatty Acid Synthesis to the Structure and Function of the Nuclear Membrane-Pore Complex, Mol Cell Biol, vol. 16, pp. 7161-7172, 1996.
Till, et al, "Discovery of chemically induced mutations in rice by TILLLING." BMC Plant Biology 7.1, 2007, 19.
Hongle, et al, "Mutations of codon position 1991 of acetyl-CoA carboxylase confer resistance to ACCase-inhibiting herbicides in Japanese foxtail (*Alopecurus japonicas*)." Pest Management Science 70.12, 2014, 1894-1901.
Delye, Weed Science (2005) 56:728-746.
Liu et al, Proc. Natl. Acad. Sci. (2007) 104:3627-3632.
Beetham et al., "A Toold for Functional Plant Genomics: Chimeric RNA/DNA Oligonucleotides Cause in Vivo Gene-Specific Mutations," Proc Natl Acad Sci USA, vol. 96, pp. 8774-8778, 1999.
Chugh, K and Eudes, F., "Study of Uptake of Cell Penetrating Peptides and Their Cargoes in Permeabilized Wheat Immature Embryos," FEBS J. vol. 275, pp. 2403-2414, 2008.
Getz et al., "Improved Method for High Efficiency Transformation of Intact Yeast Cells," Nuci Acids Res, vol. 20, p. 1425, 1992.
Hasslacher et al, "Acetyl-CoA Carboxylase from Yeast is an Essential Enzyme and is Regulated by Factors that ontrol Phospholipid Metabolism," J Biol Chem, vol. 268, No. 15, pp. 10946-10952, 1993.

\* cited by examiner

FIGURE 5

```
   1  MGSTHLPIVG  FNASTTPSLS  TLRQINSRAA  AFQSSSPSRS  SKKKSRRVKS  IRDOGOQSVP
  61  DPAGHGQSIR  QGLAGIIDLP  KEGASAPDVD  ISHGSEDHKA  SYQMNGILNE  SHNGSHASLS
 121  KVYEPCTELG  GKTPIHSVLV  ANNGMAAAKF  MRSVRIWAND  TFGSEKAIQL  IAMATPEDMR
 181  IRAERIRIAD  QFVEVPGGTN  NNNYANVQLI  VEIAERTGVS  AVWPGWGHAS  SNPELPDALT
 241  AKGIVFLCPP  ASSMNALGDK  VGSALIAQAA  GVPTLAWSGS  SVEIPLELCL  DSIPEENYRK
 301  ACVTTADEAV  ASCQMIGYPA  MIKASWGGGG  KGIRKVNNDD  SVKALPKQVQ  GEVPGSPIFI
 361  MRLASQSRHL  EVQLLCDEYG  NVAALRSRDC  SVQRRHQKII  SEGPVTVAPR  ETVKELEQAA
 421  RRLAKAVGYV  GAATVEYLYS  MSTGEYYPLE  LNPRLQVEHP  VIESIAEVNL  PAAQVAVGMG
 481  IPIWQIPEIR  RFYGMDNGGG  YDIWRRTAAL  ATPFNEDEVD  SQWPKGHCVA  VRITSENPDD
 541  GFKPTGGKVK  KISFKSKPNV  WGYPSVKSGG  GIHEFADSQF  GHVFAYGETR  SAAITSMSLA
 601  LKEIQIRGEI  NTNVDYTVDL  LNAPDFRENT  IHTGWLDTRI  AMSVQAERFP  WYISVVGGAL
 661  YKTITTNAET  VSRYVSYLIK  GQIPPKHISL  VHSTISLNIS  ESKYIISIVR  SGQGSYRLRI
 721  NGSLIEANVQ  TLCDGGLLMQ  LDQNSHVIYA  EEEAGGTRLL  IDGKTCLLQN  DHDPSRLLAE
 781  TPCKLLRFLI  ADGAHVDADV  PYAEVEVMKM  CMPLLSPAAG  VINVLLSEGQ  AMQAGDLIAR
 841  LDLDDPSAVK  RAEPPEGSPP  EMSLPIAASG  QVHKRCAASL  NAARMVLAGY  DHAANKVVQD
 901  LVWCLDTPAL  PPLQWEELMS  VLAIRLPRRL  KSELEGKYNE  YKLNVDHVKI  KDFPTEMLRE
 961  TIEENLACVS  EKEMVTIERL  VDPLMSLLKS  YEGGRESHAM  FIVKSLPEEY  LSVEELFSDG
1021  IQSDVIERLR  LQYSKDLQKV  VDIVLSRQGV  RNKTKLILAL  MEKLVYPNPA  AYRDQLIRFS
1081  SLNHKRYYKL  ALKASELLSQ  FKLSELRTSI  ARNLSALDMF  TEEKADFSLQ  DRKYAINESM
1141  GDLVIAPLPV  EIDALVSLFDC  TDQTLQQRVI  QFYISRLYQP  QLVKDSIQLK  YQDSGVIALW
1201  EFTEGNHEKR  LGAMVILKSL  ESVSTAIGAA  LKDASHYASS  AGNTVHIALL  DADTQINTVE
1261  DSGENDQAQD  KMDKLSFVLK  QDVVMADLRA  ADVKVVSCIV  QRDGAIMPRR  RTFLLSEEKL
1321  CYEESPILRH  VEPPLSALLE  LDKLKVEGYN  EMKYTPSRDR  QWHIYILRET  ENPKMLNRVF
1381  FRTLVRQPSA  GNRPTSDHIT  DVEVGHAEEP  LSFTSGSILK  SLKIAKEELE  LHAIRTGHSN
1441  MYLCILKEQK  LLDLVPVSGN  TVVDVGQDRA  TACSLLKEMA  LKIHELVGAR  MHHLSVCQNE
1501  VKLKLVSDGP  ASGSWRVVTT  NVTGNTCTVD  IYREVEDTRS  QKLVYHSTAL  SSGPLHGVAL
1561  NTSYQFLSVI  DLKRCSAPNN  KTTYCYDPPL  TFEAAVCRSW  SNISSENSQC  YVKATELVFA
1621  EKNGSWGTPI  IPMQRAAGLN  DISMVAWILD  MSTPRFPSGR  QIIVIANDIT  FRAGSFGPRE
1681  DAFFEAVTNL  ACEKKLPLIY  LAANSGASIG  IADEVKSCFR  VGWTDDSSFE  RGFRYIYMTD
1741  EDHDRIGESSV  IAHKMQLDSG  KIRWVIDSVV  GKEDGLGVEN  IRGSAAIASA  YSRAYERTFT
1801  LIFVYGRTVG  IGAYLARLGI  RCIQRIDQPI  ILTGFSALNK  LLGREVYSSH  MQLGGPRIMA
1861  TNGVVRLTVP  DDLEGVSNIL  RWLSYVPANI  GGPLPITKSL  DPIDSPVAYI  PENTCDPRAA
1921  ISSGIDDSQGK  WIGGMPDKDS  PVETFEGWAK  TVVTGRAHLG  GIPVSVIAVE  TQTMMQLVPR
1981  DPGQFDSHER  SVPRAGQVWF  PDSATKTAQA  MLDFNREGLP  LFILANWBGP  SGGQRDLPEC
2041  ILQAGSTIVE  NLRTYNQPAF  VYIPKAAELR  GGAWVIDSK  INPDRIECYA  ERTAKGNVLS
2101  PQGLIEIKFR  SEELKECMGR  LDPELIDLKA  RLQGANGSLG  DGESLQKSIE  ARKKQLLPLY
2161  TQIAVRFAEL  HDTSLRMAAK  GVIRKVVDWE  DSRSFFYKRL  RARLSEQVLA  KEIRGVIGRN
2221  FPHKSAIELI  KKWYLASRAA  AAGSTDWDDD  DAFVAWRENP  SNYKEYIKEL  RAQRVERLLS
2281  DVAGSSSDLQ  ALPQGLSMLL  DKMDPSKRAQ  FIEEVMKVLK
```

FIGURE 6

```
   1 ATGGATCCA CACATCTGCC CATTGTCGGG TTTAATGCAT CCACAACACC ATGCTATCC
  61 ACTCTTCGCC AGATAAACTC AGCTGCTGCT GCATTCCAAT CTTCGTCCCC TTCAAGGTCA
 121 TCCAAGAAGA AAAGCCGACG TGTTAAGTCA ATAAGGGATG ATGGGGATGG AAGCGTGCCA
 181 GACCCTGCAG GCCATGGCCA GTCTATTCGC CAAGGTCTCG CTGGCATCAT CGACCTCCCA
 241 AAGGAGGGCG CATCAGCTCC AGATGTGGAC ATTTCACATG GGTCTGAAGA CCACAAGGCC
 301 TCCTACCAAA TGAATGGCAT ACTGAATGAA TCACATAACG GGAGCCACGC CTCTCTGTCT
 361 AAAGTTTATG AATTTGCAC GGAATTGGGT GGAAAAACAC CAATTCACAG TGTATTAGTC
 421 GCCAACAATG GAATGCCAGC AACTAAGTTC ATGCGCACTG TCCGGACATG GGCTAATGAT
 481 ACATTTGGGT GAGAAGGC GATTCAGTTG ATAGCTATGG CAACTCCGGA AGACATGAGA
 541 ATAAATGCAG AGCACATTAG AATTGCTGAT CAGTTTGTTG AAGTACCTGG TGGAACAAAC
 601 AATAACAACT ATGCAAATGT CCAACTCATA GTGGAGATAG CAGAGAGAAC TGGTGTCTCC
 661 GCCGTTTGGC CTGGTTGGG CCATGCATCT GAGAATCCTG AACTTCCAGA TGCACTAACT
 721 GCAAAAGGAA TTGTTTTCT TGGGCCACCA GCATCATCAA TGAACGCACT AGGCGACAAG
 781 GTTGTTCAG CTGTCATTGC TCAAGCAGCA GGGGTTCCCA CTCTTGCTTG GAGTGGATCA
 841 CATGTGGAAA TTCCATTAGA ACTTTGTTTG GACTCGATAC CTGAGGAGAT GTATAGGAAA
 901 GCCTGTGTTA CAACCCCTGA TGAAGCAGTT GCAAGTTGTC AGATGATTGG TTACCCTGCC
 961 ATGATCAAGG CATCCTGGGG TGGTGGTGGT AAACGGATTA GAAAGGTTAA TAATGATGAC
1021 GACTGAAAG CACTGTTAA GCAAGTACAG GGTGAAGTTC CTGGCTCCCC GATATTTATC
1081 ATGAGACTTG CATCTCAGAG TCGTCATCTT GAAGTCCAGC TGCTTTGTGA TGAATATGGC
1141 AATGTAGCAG CACTTCACAG TCTGATTGC AGTGTGCAAC GAGGACACCA AAAGATTATC
1201 GAGGAAGGAC CAGTTACTGT TGCTCCTCGT GAAACAGTGA AAGAGCTAGA GCAAGCAGCA
1261 AGGAGGCTTG CTAAGGCCGT GGGTTACGTC GGTGCTGCTA CTGTTGAATA TCTCTACAGC
1321 ATGTAGACTG GTGAATACTA TTTTCTGGAG CTTAATCCAC GGTTGCAGGT TGAGCACCCA
1381 GTCACCGAGT CGATAGCTGA AGTAAATTTG CCTGCAGCCC AAGTTGCAGT TGGGATGGGT
1441 ATACCTCTTT GGCAGATTCC AGAGATCAGA CGTTTCTACG GAATGGACAA TGGAGGAGGC
1501 TATGATATTT GGAGGAAAAC AGCAGCTCTC GCTACTCCAT TCAACTTGGA TGAAGTAGAT
1561 TCTCAATGGC CGAAGCGTCA TTGTGTGGCA GTTAGCATAA CCAGTGAGAA TCCAGATGAT
1621 GGATTCAAGC CTACTGTGG AAAAGTAAAG GAGATAAGTT TTAAAAGTAA GCCAAATGTC
1681 TGCCGATATT TCTCAGTTAA GTCTGGTGGA GGCATTCATG AATTGCGGA TTCTCAGTTT
1741 GGACACGTTT TTGCCTATGG AGAGACTAGA TCAGCAGCAA TAACGACGCAT GTCTCTTGCA
1801 CTAAAAGAGA TTCAAATTCG TGGAGAAATT CATACAAACG TTGATTACAC GGTTGATCTC
1861 TTGAATGCCC CAGACTTCAG AGAAACACG ATCCATACCG TTGGCTGGA TACCAGAATA
1921 GCTATGCGTG TTCAAGCTGA GAGGCCTCCG TGGTATATTT CAGTGGTTGG AGGAGCTCTA
1981 TATAAAACAA TAACCACCAA TGCGGAGACC GTTTCTGAAT ATGTTAGCTA TCTCATCAAG
2041 GGTCAGATTC CACCAAAGCA CATATCCCTT GTCCATTCAA CTATTTCTTT GAATATAGAG
2101 GAAAGCAAAT ATACAATTCA CATTGTGAGG AGTGGACAGG GTAGCTACAG ATTGAGACTG
2161 AATGGATCAC TTATTGAAGC CAATGTACAA ACATTATGTG ATGGAGGCCT TTTAATGCAG
2221 CTGGATGGAA ATAGCCATGT TATTTATGCT GAAGAAGAAG CGGGTGGTAC ACGGCTTCTT
2281 ATTGATGGAA AAACATGCTT GCTACAGAAT GACCATGATC CGTCAAGGTT ATTAGCTGAG
2341 ACGCCTGCA AACTTCTCG TTCTTCATT GCCATGGTC CTCAGTTGA TGCTGATGA
2401 CCATACGCGG AAGTTGAGGT TATGAAGATG TGCATGCCCC TCTTGTCGCC TGCTGCTGGT
2461 GTCATTAATC TTTGTTGTC TGGGGCCAG GCGATGCAGG CTGGTGATCT TATAGCGAGA
2521 CTTGATCTCG ATGACCCTTC TGCTGTGAAG AGAGCCGAGC CATTGAAGG ATCTTTCCA
2581 GAATGAGCC TTCCTATTGC TGCTTCTGGC CAAGTCACA AAAGATGTGC TGCAAGTTG
2641 AACGCTGCTC GAATGTCCT TGCAGGATAT GACCATGCGG CCAACAAAGT TGTGCAAGAT
2701 TTGCTATGGT GCCTTGATAC AGTTGCTCTT CCTTCCTAC AATGGAAGA GCTTATGTCT
2761 GTTTAGCAA CTAGCTTCC AAGACGTCTT AAGACGAGT GGAGGGCAA ATACAATGAA
2821 TACAAGTTAA ATGTTACCA TGTGAAGATC AAGGATTCC CTACCCAGAT GCTTAGAGAG
2881 ACAATCGAGG AAAATCTTGC ATGTGTTTCC GAGAAGGAAA TGGTGACAAT TGAGAGGCTT
2941 GTTCACCCTC TGATGAGCCT GCTGAAGTCA TACGAGGGTG GGAGAGAAAG CCATGCCCAC
```

FIGURE 6 (continued)

```
3001 TTTATTGTCA AGTCCCTTTT TGAGGAGTAT CTCTCGGTTG AGGAACTATT CAGTGATGGC
3061 ATTCAGTCTG ACGTGATTGA ACGCCTGCGC CTACAATATA GTAAAGACCT CCAGAAGGTT
3121 GTAGACATTG TTTTGTCTCA CCAGGGTGTG AGAAACAAAA CAAAGCTCAT ACTCGCGCTC
3181 ATGGAGAAAC TGGTCTATCC AAACCCTGCT GCCTACAGAG ATCAGTTGAT TGGCTTTCT
3241 TCCCTCAACC ATAAAGATA TTATAAGTTG GCTCTTAAAG CTAGTGAACT TCTTGAACAA
3301 ACCAAGCTCA GCGAACTCCG CACAAGCATT GCAAGGACC TTTCAGCGCT GGATATGTTC
3361 ACGGAGGAAA AGGCAGATTT CTCCTTGCAA GACAGAAAAT TGGCCATTAA TGAGAGCATG
3421 GGAGATTTAG TCACTGGCCC ACTGCCAGTT GAAGATGCAC TTGTTTCTTT GTTTGATTGT
3481 ACTGATCAAA CTCTTCAGCA GAGAGTGATT CAGACATACA TATCTCGATT ATACCAGCCT
3541 CAACTTGTGA AGGATAGCAT CCAGCTGAAA TATCAGGATT CTGGTGTTAT TGCTTTATCG
3601 GAATTCACTG AAGGAAATCA TGAAGAGAGA TTGGTGCTA TGGTTATCCT GAAGTCACTA
3661 GAATCTGTGT CAACAGCCAT TGGAGCTGCT CTAAAGGATG CATCACATTA TGCAAGCTCT
3721 GCGGCAACA CCGTGCATAT TGCTTTGTTG GATGCTGATA CCCAACTGAA TACAACTGAA
3781 GATAGTGGTG ATAATGACCA AGTCAAGAC AAGATGGATA AACTTTCTTT TCTACTCAAA
3841 CAAGATGTTG TCATGGCTGA TCTACGTGCT GCTGATGTCA AGGTTGTTAG TTGCATTGTT
3901 CAAACAGATG GAGCAATCAT CCCTATGCGC CGTACCTTCC TCTTGTCAGA GGAAAAACTT
3961 TGTTACGAGG AAGAGCCGAT TCTTCGGCAT GTGGAGCCTC CACTTCTGC ACTTCTTCAG
4021 TTGGATAAAT TGAAAGTGAA AGGATACAAT GAGATGAAGT ATACACCGTC ACGTGATCGT
4081 CAGTGGCATA TATACACACT TAGAAATACT GAAAATCCAA AAATGCTGCA CAGGGTATTT
4141 TTCCAACAC ATGTCAGACA ACCCAGTGCA GGCAACAGGT TTACATCAGA CCATATCACT
4201 GATGTTGAAG TAGGACACGC AGAGGAACCT CTTTCATTA CTTCAAGCAG CATATTAAAA
4261 TGGTTGAACA TTGCTAAAGA AGAATTGGAG CTTCACGCGA TCAGGACTGG CCATTCTCAT
4321 ATGTACTTGT GCATATTGAA AGAGCAAAAG CTTCTTGACC TTGTTCCTGT TTCAGGGAAC
4381 ACTGTTGTGG ATGTTGGTCA AGATGAAGCT ACTGCATGCT CTCTTTGAA AGAAATGGCT
4441 TTAAAGATAC ATGAACTTGT TGGTGCAAGA ATGCATCATC TTTCTCTATC CCAGTGGAA
4501 GTGAAACTTA AGTTGGTGAC CGATGCCCT GCCAGTGGTA GCTGGAGAGT TGTAACAACC
4561 AATGTTACTG GTCACACCTG CACTGTGGAT ATCTACGGG AGGTGGAAGA TACAGAATCA
4621 CAGAAACTAG TATACCACTC CACGCCATTG TCATCTCCTC CTTCCATGG TGTTGCACTG
4681 AATACTTCGT ATCAGCCTTT GAGTGTTATT GATTAAAAC GTTGCTCTGC CAGGAACAAC
4741 AAAACTACAT ACTGCTATGA TTTCCATTG ACATTTGAAG CTGCAGTGCA GAAGTCGTGG
4801 TCTAACATTT CCAGTGAAAA CAACCAATGT TATGTTAAAG CGACAGAGCT TGTGTTTGCT
4861 GAAAAGAATG CGTCGTGGGG CACTCCTATA ATTCCTATGC AGCGGCTGC TGGGCTGAAT
4921 GACATGGTA TGGTAGCCTG GATCTTGGAC AGGTCCACTC CTGAATTTCC CAGCACAGA
4981 CAGATCATTG TTATCGCAAA TGATATTACA TTTAGAGCTC GATCATTTGG CCCAACGGAA
5041 GATGCATTTT TCGAAGCTGT AACCAACCTG GCTTGTGAGA AGAAGCTTCC ACTTATCTAC
5101 TTGGCTGCAA ACTCTGGTGC TCGGATTGGC ATTGCTGATG AAGTAAAATC TTGCTTCCGT
5161 GTTGGATGGA CTGATGATAG CAGCCCTGAA CGTGGATTA GGTACATTTA TATGACTGAC
5221 GAAGACCATG ATCGTATTGG CTCTTCAGTT ATAGCACACA AGATGCAGCT AGATACTGGC
5281 GAGATCAGGT GGTTATTGA TTCTGTTGTG GGAAAGAGG ATGGACTAGG TGTGGAGAAC
5341 ATACATGGAA GTGCTGGTAT TGCCAGTGCC TATTCTAGGG CGTACGAGGA GACATTTACA
5401 CTTACATTCG TTACTGGACG AACTGTTGGA ATGGAGCCT ATCTTGCTCG ACTGGCATA
5461 CGGTGCATAC AGGTATTGA CCAGCCCATT ATTTTGACCG GGTTTCTGC CCTGAACAAG
5521 CTTCTTGGGC GGGAGGTGTA CAGCTCCCAC ATGCAGTTGG TGGTCCAA AATCATGCG
5581 ACGAATGTG TTGTCCATCT GACTGTTCCA GATGACCTTG AAGGTGTTTC TAATATATTG
5641 AGCTGCTCA GCTATGTTCC TCCAAACATT GCTGGACCTC TCCTATTAC AAAATCTTTG
5701 GACCCAATAG ACAGACCCGT TGCATACATC CCTGAGAATA CATGTGATCC TCGTGCAGCC
5761 ATCAGTGGCA TTGATGACAG CCAAGGGAAA TGGTTGGGTG GCATGTTTGA CAAAGACAGT
5821 TTTGTGGAGA CATTTGAAGG ATGGGCGAAG ACAGTAGTTA CTGCAGAGC AAAACTTGGA
5881 GCGATTCCTG TTGGTGTAT AGCTGTGGAG ACACAGACCA TGATGCAGCT CGTCCCGCT
5941 GATCCAGGCC AGCCTGATTC CCACGAGCGG TCTGTTCCTC CGCTGGGCA AGTTGTTT
6001 CCAGATTCTG CTACCAAGAC AGGCAGGCG ATGTTGGACT TCAACCGTGA AGGATTACCT
6061 CTTTTCATAC TTGCTAACTG GAGAGGCTTC TCTGGAGGC AAAGAGATCT TTTTGAAGGA
6121 ATTCTGCAGG CTGGGTCAAC AAATTGTTGAG AACCTTGGCA CATACAATCA GCCTGCCTTT
6181 GTATATATCC CCAAGGCTGC AGAGCTACGT GGAGGAGCCT GGGTCGTGAT TGATAGCAAG
```

FIGURE 6 (continued)

```
6241 ATAAACCAG ATGGATGGA GTGCTATGCT GAGAGGACTG CAAAGGGTAA TGTTCTCGAA
6301 GCTCAAGGT TCATTCACAT CAAGTTCACC TCACCGAAC TCAAAGAATC CATGGGTACC
6361 CTTGATCCAG AATTGATAGA TCTGAAAGCA AGACTCCAGG GAGCAAATGG AAGCCTATCT
6421 GATGGAGAAT CCCTTCAGAA GAGCATAGAA GCTCGGAAGA AACAGTTGCT GCCTCTGTAC
6481 ACCCAAATCG CGGTACTTT TGCGGAATTG CACGACACTT CCCTTAGAAT GGCTGCTAAA
6541 GGTGTGATCA GGAAAGTTGT AGACTGGGAA GACTCTCGGT CTTTCTTCTA CAAGAGATTA
6601 CGGAGGAGGC TATCCGAGGA CGTTCTGGCA AAGGAGATTA GAGGGGTAAT TGTGAGAAG
6661 TTTCCTCACA AATCACCGAT CGAGCTGATC AAGAAATGGT ACTTGGCTTC TGAGGCAGCT
6721 GCAGCAGGAA GCACCACTG GGATGACGAC GATGCTTTTG TCGCCTGGAG GGAGAACCCT
6781 CAAAACTATA AGGAGTATAT CAAGAGCTT AGGGCTCAAA GCGTATCTCG GTTGCTCTCA
6841 GATGTTGCAG GCTCCAGTTC GGATTTACAA GCCTTGCCGC AGGGTCTTTC CATGCTACTA
6901 GATAAGATGG ATCCCTCTAA GAGAGCACAG TTTATCGAGG AGGTCATGAA GGTCCTGAAA
6961 TGA
```

FIGURE 7A

>Oryza sativa Plastidic ACCase genomic sequence

```
ATGACATCCACACATGTGGCACATTGGGAGTTGGTCCCCAGGCACCTCCTCGTCACCAGAAAAGTCAGCTGG
CACTGCATTTGTATCATCTGGGTCATCAAGACCCTCATACGGAAAGAATTCTTCAGCGTACTCGGTCACTTAGGG
AAGAAAGCAATGGAGGAGTGTCTGATTCCAAAAAGCTTAACCACTCTATTCGCCAAGGTCACCACTAGCTACTT
TACATATGCTATAATTTGTGCCAAACATAAACATGCAATGGCTGCTATTATTTAAACGTTAATGTTGAAATAGC
TGCTATAGGATACGCAAAAATATATAATTGACTGGGCAAGATGCAACAATTGTTTTTCACTAAAGTTAGTTAT
CTTTTGCTCTAAAAGACAACTGTTTTTTACATAAAATGGTATTAATAACCTTGAAATATTCAATGCAACATGTT
CTCAAGTAAAAAAAACATTGCCTGGTTGTATAAGCAAACGTGTCGTTGTAGACATCTTATTAAACCTTTTTCT
GATATCTATTACCGTAGGGAACAGGGGACTGTTTAAATCTGTTATCATAGAGTAAATATGAGAAAGTGGATTG
TCCGACTTTGGCAGCTATACCTCCTCAATTTCAAATATACCTCTATGTCCAGCTCTTGCTGGCATCATTGACCT
CCCAAATGACGCAGCTCAGAAGTTGATATTTCACAGTAAGGACTTTATATTTATAATAATTATTATATATAATT
TTCTGACATGTTTTGACAACCTCAAAACATGTGATTGCACCTTCCTTTTTTATGTCTGGTTCAGAAACTGATAA
GTTTTGACAGTGTTTAGGATGGATCTTGATGCGCACAGTGCTTCTAATCTTTTCATTTTTGAAAGTAATGTT
TTAGGAAAAAATATCTGATTAAATTTATACTTTATCTTTACAAAAGTCAAATGGTTCTGTATCAATTGCGGTT
TGTAATATGCCAAGAACATGCTTTCAGAATTTGTTCATACAAGCTTTCTTTCTATTATTATGTAGAACAAATA
CCTAATACTTTGTTCACGTTTTATAGTGGACACGTCTCACAGCTTTTTCAGTAAGTGATGCAATTTTGTACATT
TGTAAGATGTGTTCAGAAACCTTTTCTCCTGCAATTCTAATGTACCCACTCAAACTGGTATCACCAAAGATCT
GCATCTGATTGAAAAAAAGCTGCCTGAAGTATGCTTATTTATGCTAACCATACATGATTTATACTGTTTTATAC
TACAATGCTTATTTATGCTAACCATACATAATTTTATTCTGTTTCTAGTACATTATTTGTGCCCCTGACCATA
AATGATCCTTCTTTTACAGTGGTTCCGAAGATCCCAGGGGGCCTACGGCCCAGGTTCCTACCAAAAGAATGG
GATTATCAAAGAAACACATAATGGGAGGCATGCTTCAGTCTCCAAGGTTGTTGAGTTTTGTACGGCACTTGGTG
GCAAAACACCAATTCACAGTGTATTAGTGGCCAACAATGGAATGGCAGCAGCTAAGTTCATGCGGAGTGTCCGA
ACATGGCTAACGATACTTTTGGATACAGAGAAGGCAATTCAGCTGATAGCTATGGCAACTCCGGAGGATCTGAG
GATAAATGCAGCAGCCACATCACAATTGCCCGATCAATTTGTAGAGGTACCTGGTGGAACAAACAACAACAACTATG
CAAATGTCCAACTCATAGTGGAGGTTAGTTCAGCTCATCCCTCAACACAACATTTCGTTTCTATTTAAGTTAG
GGAAAAATCTCTACGACCTCCAATTTCTGAACATCCAATTTTCACCATCAACTGCAATCACAGATAGCAGAGA
GAACAGGCGTTTCTGCTGTTGGCCTGGTTGGGGTCATGCATCTGAGAATCCTGAACTTCCAGATCCGCTGACT
GCAAAAGGAATTGTTTTTCTTGGGCCACTAGCATCATCAAGCATGCATTAGGAGACAAGGTTGGCTCAGGCTCT
CATTGCTCAAGCAGCTGGAGTTCCAACACTTGCTTGGAGTGGATCACATGTGAGCCTTGTCTTCTCTTTTTTAG
CTTATCAGCTTATCTTTTCGGTCATGCATTATGCCAATGACAACTAAACCATAGGTGGAAGTTCCTCTGGAGTGT
TGCTTGGACTCAATACTGATGAGATGTATAGAAAAGCTTGTGTTACTACCACAGAGGAAGCAGTTGCAAGTTC
TTACGTGCTTGGTTATCCTCCCATGATTAAGGGCATCTTGGGGTTGGTGGTAAAGGGATAAGGAAGGTTTGTT
CTTCTTGTAGTTATCAAGAGATTGTTTGGATTGCAAGTCTTTAGTGCCCATAGTTAACTCTGGTCTTTCTAACA
TGAGTAACTCAACTTGCTTGCAGGTTCATAATGATGATGAGGTTAGGACATTATTTAAGCAAGTTCAAGGCGAA
GTACCTGGTTGCCCAATATTTATCATGAGGCTAGCTGCTCAGGTGGGGCCTTTATGGAAGTTACAGCGTTTCC
CTTAATGTTGAGTTATTCCGGAGTTATTATGGTCATGTTCTGTATGTTTGATCTGTAAATTATTGAAATTCACC
TCCATTGGTTCTCCAGATTAGCAGAGCCTACAATTCTACATATGCTTTATACTTTATAAATACTAGGATTTAGGG
ATCTTCATATAGTTTATACATGGTATTTACATTTCATTTGTAACCCTATTGAAGACATCCTGATTGTTGTCTTA
TGTAGAGTGCACATTTTGAAGTTCAGTTGCTTTGTGATCAATATGCAACGTAGCAGCACTTCACAGTCAGAT
TGCAGTGTGACAACGGCACACAAAGGTTCTGCTGTCTCAGTTAAATCACCCCTCTGAATGATCTACTTCTTGC
CTGCTGGTGACACTGTGAAAGAGCTTGAGCAGGCAGCACGGAGCCTTGCTAAAGCTGTCGGTTATGTTGGTGCTG
CTACTGTTGAATACCTTTACAGGCATGGAAACTGGTGAATATTATTTCTGGAACTTAATCCACGGCTACAGGTC
GGCTCCTTTGACATTCTTCAGGAATTAATTTCTGTTGACCACATGATTTACATTGTCAAATGGTCTCACAGGTT
GAGCATCCTGTCACTGAGTGGATAGCTGAAGTAAATTGCCTGCGGCTCAAGTTGCTGTTGGAATGGGTATACC
CCTTTGGCAGATTCCAGGTAAGCTTCTTCATTAAGTTCCCGCTCTTGTTAATTGAATGAGCTCTTATACAGA
CCATGAGACACATTCTACTGTTAATTCATAGTATGCCCTGACTTGTTAGTGTTAGAGATACAGAGATGTATCAC
```

ACTGGAAGAATCACGATCTTTCTTCTATAAGAGATTACGGAGGACGATCTCTGAGGATGTTCTTGCAAAAGAA
ATTAGAGCTGTAGCAGGTGAGCAGTTTTCCCACCAACCAGCAATCGAGCTGATCAAGAAATGGTATTCAGCTTC
ACATGCAGCTGAATGGGATGATACGATCCTTTGTTTCTTGGATGGATAACCCTGAAAACTACAAGCATTATA
TTCAATATCTTAAGGCTCAAAGAGTATCCCAATCCCTCTCAAGTCTTTCAGATTCCAGCTCAGATTTGCAAGCC
CTCCCACAGGGTCTTTCATGTTACTAGATAAGGTAATTAGCTTACTGATGCTTATATAAATTCTTTTTCATTA
CATATGGCTGGAGAACTATCTAATCAAATAATGATTATAATTCCAATCGTTCTTTTTATGCCATTATGATCTTC
TGAAATTTCCTTCTTTGGACACTTATTCAGATGGATCCCTCTAGAACAGCTCAACTTGTTGAAGAAATCACGAA
GGTCCTTGGTTGA

FIGURE 7B

>Oryza sativa Plastidic ACCase protein coding sequence

ATGACATCCACACATGTGGCGACATTGGGAGTTGGTGCCCAGGCACCTCCTCGTCACCAGAAAAAGTCAGCTGG
CACTGCATTTGTATCATCTGGGTCATCAAGACCCTCATACCGAAAGAATGGTCAGGTACTCGGTCACTTAGGG
AAGAAAGCAATGGAGGCAGTGTCTGATTCCAAAAAGCTTAACCACTCTATTCGCCAAGGTCTTGCTGGCATCATT
GACCTCCCAAATGACGCAGCTTCAGAAGTTGATATTTCACATGGTTCCGAAGATCCGAGGGGCCTACGGTCCC
AGGTTCCTACCAAATGAATGGATATCAATGAAACACATAATGGAAGGCATGCTTCAGTCTCCAAGGTTGTTG
AGTTTTGTACGGCACTTGGTGGCAAAACACCAATTCACAGTGTATTAGTGGCCAACAATGAATGGCAGCAGCT
AAGTTCATCGGAGTGTCCGAACATGGTTAATGATACTTTTGGATCAGAGAAGGCAATTCAGCTGATAGCTAT
GGCAACTCCGGAGGATCTGAGGATAAATGCAGAGCACATCAGAATTGCCCATCAATTTGTAGAGGTACCTGGTG
GAACAAACAACAACAACTATGCAAATGTCCAACTCATAGTGGAGATAGCAGAGAGAACAGGTCTTTCTCCTCTT
TGGCCTGGTTGGGGTCATGCATCTGAGAATCCTGAACTTCCAGATGCGCTGACTGCAAAGGAATTGCTTTTCT
TGGGCCACCAGCATCATCAATTCATTCATTAGGAGACAAAGGTTGGCTCAGCTCTCATTGCTCAAGCAGCTGGAG
TTCAACACTTGCTTGGAGTGGATCACATGTGGAAGTTCCTCTGGAGTGTTGCTTGGACTCAATACCTGATGAG
ATGTATAGAAAAGCTTGTGTTACTACCACAGAGGAAGCAGTTGCAAGTTGTCAGCTGGTTGGTTATCCTGCCAT
GATTAAGCCATCTTCCCGTGCTGGTGGTAAAGGAATAAGGAAGGTTCATAATGATGATGAGGTTAGGACATTAT
TTAAGCAAGTTCAAGGCGAAGTACCTGGTTCCCCAATATTTATCATGAGGCTAGCTGCTCAGAGTCGACATCTT
GAAGTTCAGTTTGCTTGTGATCAATATGGCAACGTAGCAGCACTTCACAGTCGAGATTGCAGTGTACAACGGCG
ACACCAAAGATAATCGAGGAAGGACCAGTTACTGTTGCTCCTCGTGAGACTGTGAAAGAGCTTCGGCAGGCAG
CACCGGAGCTTTGCTAAAGCTGTGGGTTATGTTGGTGCTTCTACTGTTGAATACCTTTACAGCATGGAAACTGGT
GAATATTATTGTCTGGAACTTAATCCACGGCTACAAGTTGAGCATCCTGTCACTGAGTGGATAGCTGAAGTAAA
TTTGCCTGCGGCTCAAGTTGCTGTTGGAATGGGTATACCCCTTTGGCAGATTCCAGAGATCAGCGCTTCTACG
GAATGAACCATGGAGGAGGCTATGACCTTTGGAGGAAAACAGCAGCTCTAGCGACTCCATTTAACTTTGATGAA
GTAGATTCTAAATGGCCAAAAGCCCACTGCGTAGCTGTTAGAATAACTAGCGAGGATCCAGATGATCGGTTTAA
GCCTACTGCTGGAAAAGTAAAGGAGATAAGTTTCAAGAGTAAACCAAATGTTTGGCCTATTTCTCAGTAAAGT
CTGGTGGAGGCATCCATGAATCGCTGATTCTCAGTTCGGACATGTTTTGCTATGCAACTACTAGATCCGCA
GCAATACTACCATGGCTCCTTGCACTAAAAGAGGTTCAAATTCGTGGAGAATTCATTCAAACGTACGACTACAC
AGTTGACCTATTAAATGCCTCAGATTTTAGAGAAAATAAGATTCATACTCGTTGGCTGGATACCAGCATAGCCA
TGCGTGTTCAAGCTGAGAGGCCTCCATGGTATATTTCAGTCGTTGGAGCGGCTTTATATAAAACAGTAACTGCC
AACACGGCCACTGTTTCTGATTATGTTGGTTATCTTACCAAGGGCCAGATTCCACCAAAGCAATATCCCTTGT
CTATGCGACTGTTGCTTTGAATATAGATGGAAAAAATATACAATCGATACTGTGAGGAGTGGACATGGTAGCT
ACAGATGCGAATGAATGGATCAACGGTTGACGCAATGTACAAATATTATGTGATGCTGGGCTTTTAATGCAG
CTGGATGCAAACAGCCATGTAATTTATGCTGAAGAAGAGGCCAGTGGTACACGACTTCTTATTGATGGAAAGAC
ATGCATGTTACAGAATGACCTGACCCATCAAAGTTATTAGCTGAGACACCATGCAAACTTCTTCGTTTCTTGG
TTGCTGATGGTGCTCATGTTGATGCTGATGTACCATATGCGGAAGTTGAGGTTATGAAGATGTGCATGCCCCTC
TTATCACCCGCTTCTGGTGTCATACATGTTGTAATGTCTGAGGGCAAGCAATGCAGGCTGGTGATCTTATAGC
TAGGCTGGATCTTGATGACCCTTCTGCTGTTAAGAGAGTTGAGCCGTTCGAAGATACTTTCCACAAATGGGTC
TCCCTATTGCTGCTTCTGGCCAAGTTCACAAATATCTTCTGCAAGTCTGAATGCTTGTCGATGATCCTTGCG
GGGTATGGCATGATATTGACTGCTGGTTGTGCCAGAGTTGTATCATCGCCTAGACACTCCGGAGCTTCCTTTCCT
GCAGTGGAGGAGCTTATGCTGTGTTTAGCAACTAGACTTCCAAGAAATCTTAAAAGTGAGTTGAGGGCAAAT
ATGAGGAATACAAAGTAAAATTTGACTCTGGATAATCAATGATTTCCCTGCCAATATGCTACGAGTGATAATT
GAGGAAAATCTTGCATGTCGTTCTGAGAAGGAGAAGGCTACAAATGAGAGGCTTGTTGAGCCTCTTATGAGCCT
ACTGAAGTCATATGAGGGTGGGAGAGAAAGTCATGCTCACTTCGTTGTCAAGTCCCTTTTGAGGAGTATCTCT
ATGTTGAAGAATTGTTCAGTGATGGAATTCAGTCGATGTGATTGAGCCTCTGCGCTTCAACATAGTAAAGAC
CTACAGAAGGTCGTAGACATTGTGTTGTCCCACCAGAGTGTAGAAATAAACTAAGCTGATACTAAAACTCAT
GGAGAGTCTGGTCTATCCAAATCCTCCTGCCTACAGGGATCAATTGATTCGCTTTTCTTCCCTAATCACAAAG
CGTATTACAAGTTGCCACTTAAAGCTAGTGAACTTCTTGAACAAACAAAACTTAGTGAGCTCCGTGCAAGAATA
GCAGGGGCCTTTCAGAGCTGGAGATGTTTACTGAGGAAAGCAAGGGTCTCTCCATGCATAAGCGAGAAATTGC

FIGURE 7B (continued)

FIGURE 7C

```
>Oryza sativa Plastidic ACCase protein
MTSTHVATLGVGAQAPPPEQKKSAGTAFVSSGSSRPSYRKNGQRTRSLRRKSNGGVSDSKKINHSIRQSLAGII
DLPNDAASEVDISPGSEDPPGPTVPGSYQMNGIIRETENGRNASVSKVVEPCTALGGKTPIRSVLVANNGMAAA
KFMRSVETWANDTFCSEKAIQLIAMATPEDLRINAEHIRIADQFVEVPGGTNNNEIYANVQLIVEIAERTGVSAV
WPGWGHASENPELPDALTAKGIVPLGPPASSMRALGDKVGSALIAQAAGVPTLAWSGSHVEVPLSCCLDSIFDE
MYRKACVTTTEEAVASCQVVCYPNMIKASWSGGKGIRKVENDDEVRTLFRQVQSEVPGSPIFIMRLAAQSPHL
EVQLLCDQYGNVAALHSRDCSVQERHQEIIERGPVTVAPRETVKELSQAARRLAKAVGYVGAATVEYLYSMETG
SYYFLEINPRLQVEHPVTEWIAEVNLPAACVAVGMGIPLWQIPEIRRFYGMNHGGGYDLWRKTAALATPFNFDS
VDSKWPKGHCVAVRITSEDPDDGFKPTGGKVKEISESKSKPNVWAYPSVKSGGIHEFADSQFGRVFAYGTTRSA
AITTMALALKEVQIEGEIHSNVDYTVDLLNASCPRKNKIRTGNLDTRIAMFVQAERPPWYISVVSGALYKTVFA
NTATVSDYVSYLPKSQIPPKRISLVYTTVALNIDGKKYTIDTVRSGHGSYRLRMNGSTVDANVQILCDGGLLMQ
LDCNSRVIYAEEASGTRLLIDGKTCMLQNDHDPSKLLAETPCKLLRFLVADGAHVDADVPYAEVEVMNMCMPL
LSPASGVIHVVKSEGQAMQAGDLIARLDLDDPSAVKRASPFSDTFPQMGLPIAASGQVSKLCAASLNACRMILA
GYEHDIDKVVPELVYCLSTPELPFLQWEELMSVLATRLPRNLKSELRGKYEEYKVKFDSGIINDFPANMLRVII
EENLACGSEKEKATNERLVEPLMSLLKSYRGGRESHAKFVVRSLFEEYLVVEELFSDSIQSDVISRLRLQHSKD
LCKVVDIVLSHQSVENKTKLILKIMESLVYPNPAAYRDQLIPFSSLNHKAYYKLALKASELLSQFKLSELSARI
ARSLSELEMPTEESKGLSMHRREIAIKESMEDLVTAPLPVEDALISLFDCSDTFVQQRVIRTYIARLYQPHLVK
DSIKMKWIESGVIALWEFFRGRFDARNGGAVLGDKRWGAMVIVKSLESLSMAIRFALKETSHYTSGEONMMHIA
LLGADNEMRIIQESGDDADRIAKLFLILKENVTDLRASGVRTISPIVQRDEARMTMRRTFLWSDEKLSYSEEPI
LRHVEPPLSALLRLDRLKVKGYNEMKYTPSRDRQWHIYTLPNPENPKMLRRVFFRTLVRQFSVSNRKPSSGQIGD
MEVGSASEPLSPTSTSILRSIMTAIEELELEAIRTGESRMYLRVLFEQRLLDLVPVSGNTVLDVGQDSATRVSL
LKEMANKIRSLVGARMHELSVGQWEVKLKLDCDGPASGTWRIVPTNVTSRTCTVDIYREMEDKESRKLVYHPAT
PAAGPLHGVALMNFYQPLSVIDLRFCSARNNRTTYCYDFPLAPFTAVRKSWSSSTSGASKGVENAQCYVRATEL
VFADKRSSWGTPLVQMDRPAGINDIGMVAWTIKMSTPEFPSGRSIIVVANDITFRAGSFGPREDAFFSAVTNLA
CEKKLPLIYLAANSGARISIADEVKSCERVGWSDDGSPESGFQYIYLSEEDYARIGTSVIAHRMQLDSGEIRWV
IDSVVGKEIDGLGVENIRGSAAIASAYSRAYKETFTLTFVTGRTPVGIGAYLARLGIRCIQRLDQPIILTGYSAIN
KILGREVYSSRNQLGGEKIMATNGVVRLTVSDELEGVSNILRWLSYVPAYIGGPLPVTTPLDPPDRPVAYIPRN
SCDPRAAIRGVDDSQGRWLGGMPDKDSFVETFEGWAKIVVTGPAKLGGIPVGVIAVETQTMRQTIPADPGQLDS
REQSVPRACQVWFPDSATKTAQALLDFNREGLPLFILAWRGFSGGQRDLFEGILQAGSTIVENLRFYNQPAFV
YIPMAAELRGGANVYVDSKINPDRIECYAERTAKGNVLEPQGLIEIKFKSEELQDCMSRLDPTLIDLKAKLEVA
NRNGSADTRSLQENIEARTKQIMPLYTQIAIRFAELHDTSLRMAASKGVIKRVVDWEESRSFFYKRLRRRISEDV
LRKEIRAVAGSQFSHQPAIELTKHWYSASHAAEWDDDDAFVAWMDNPENYKDYIQYLKAQRVSQSLSSLSDSS
DLQALPQGLSMLLDKMEPSRRAQLVEEIRKVLG*
```

FIGURE 8A

FIGURE 8A (continued)

```
TTCCTCTGGTTGGATGACAAGAGTTGTTATGAAGAAGAGCAGATTCTCCGGCATGTGGAGCCTCCCTCTCTACACT
TCTTGAATGGATAAGTTGAAGCTGAAGGATAGAATGAATGGAAGTATACTCCTTCGCGTGACCGCCAATGCCATA
TCTACACACTAAGAAATACTGAAAACCCCAAAATGTTGCATAGGGTGTTTTTCCGAACTATTGTCAGGCAACCCAAT
GCAGGCAACAAGTTTACATCGGCTCAGATCAGCGACGCTGAAGTAGGATGTCCCGAAGAATCTCTTTCATTTACATC
AAATAGCATCTTAAGATCATTGATGACTGCTATTGAAGAATTAGAGCTTCATGCAATTAGGACAGGTCATTCTCACA
TGTATTTGTGCATACTGAAAGAGCAAAAGCTTCTTGACCTCATTCCATTTTCAGGGAGTACAATTGTTGATGTTGGC
CAAGATGAAGCTACCGCTTGTTCACTTTTAAAATCAATGGCTTTGAAGATACATGAGCTTGTTGGTGCAAGGATGCA
TCATCTGTCTGTATGGCAGTGGAGGTGAAACTGAAGTTGGACTGTGATGGCCCTGCAAGTGGTACCTGGAGAGTTG
TAGCTACAAATGTTACTGGTCACAGCTGCACCATTGATATATACCAGAAGTGGAGCAAATAGAATCGCAGAAGTTA
GTGTACCATTCGCCACTTCGTCAGCTGGACCATTGCATGGTGTTGCACTGAACAATCCATATCAACCTTTGAGTGT
GATTGATCTAAAGCGCTGCTCTGCTAGGAACAACAGAACAACATATTGCTATGATTTTCCGCTGGCCTTGAAACTG
CACTGCAGAAGTCATGGCAGTCCAATGGCTCTACTGTTTCTGAGGCAATGAAATAGTAAATCCTACGTGAAGGCA
ACTGAGCTAGTGTTTGCTGAAAAACATGGTCTTGGGCACTGTTATAATTCGATGGAACTCCTGCTGGCTCAA
CGACATTGGTATGGTCGTTTGGATCATGGAGATGTCAACACCTGAATTCCCAATGGCAGGCAGATTATTGTTGTAG
CAAATGATATCACTTTCAGAGCTGGATCATTGGCCCAAGGGAAGATGCATTTTTTGAAACTGTCACTAACCTGGCT
TGCGAAAGGAAACTTCCTCTTATATACTTGGCAGCAAACTCTGGTGCTAGGATTGGCATAGCTGATGAAGTAAAATC
TTGCTTCCGCGTGATGGTCTGACGAAGGCAGTCTTGAACGAGGGTTTCAGTACATTATCTGACTGAAGAAGACT
ATGCTGGCATTAGCTCTTCTGTTATGCCACATAAGCTCCAGCTAGATACTGGTCAAATTACCTGGATTATTGACTCT
GTTGTGGGCAGGAGGATGGCTTGGTGTCGAGAACATACATGGAAGTCCTGCTATTGCCAGTGCTTATTCTAGGGC
ATATGAGGAGACATTTACACTTACATTTGTGACTGGGCTGACTGTAGGAATAGGAGCTTATCTTGCTCGACTTGGTA
TACGGTGCATACAGCCTCTTGACCAGCCTATTATTTTAACAGGGCTTTCTGCCCTGAACAAGCTCCTTGGCGGCAA
GTGTACAGCTCCGCAGCATGCAGCTTGCTGGTCTTAAGATCATGGCGACTAATGGTGTTGTCCACCTCTGTCCAGA
TGACCTTGAAGGTGTTTCCAATATATTGAGGTGGCTCAGCTATGTTCCTGCAAACATTGGTGGACCTCTTCCTATTA
CCAAACCTCTGGACCCTCCAGACAGACCTGTTGCTTACATCCTGAGAACACATGCGATCCACGTGCAGCTATCTGT
GGTGTAGATGACAGCCAAGGGAAATGGTTGGGTGGTATGTTTCACAAAGACAGCTTTGTGCAGACATTTGAAGGATG
GGCAAAACAGTGGTTACTCCCAGCCAAAGCTTGAGCAATTCCTCTCGGCGTCATACCTCTGCAGACACAGACCA
TGATGCAGATCATCCCTGCTGATCCAGGTCAGCTTGATTCCCATGAGCGATCTGTCCCTCGTGCTGGACAAGTGTGG
TTCCCGCATTCTGCAACCAAGACCCGCTCAGGCATTATTAGACTTCAACCGTGAAGGATTGCCTCTGTTCATCCTGGC
TAATTGGAGAGGCTTCTCTGGTGAACAAGAGATCTCTTTGAAGGAATTCTTCAGGCTGGTCAACAATGTCGAGA
ACCTTAGGACATCTAATCAGCCTGCTTTGTTGTACATTCCTATGGCTGGACAGCTTCGTGCGAGCGCTTGCTTCTC
GTCGATAGCAAAATAAATCCAGACCGCATTGAGTGTTATGCTGAAAGGACTGCCAAAGGTAATGTTCTCGAACCTCA
AGGGTTAATTGAAATCAAGGTTCGGGTCAGAGGAACTCCAAGACTGTATGGGTAGGCTTGACCCGAGTTTATAAATC
TGAAAGCAAAACTCCAAGATGTAAATCATGGAAATGGAAGTCTACCTAGAGATAGAAGGGATCGCAAGATATAGAA
GCACGTAGGAAACAGTTGCTGCCTTTATATACCCAGAGTGCAATACGGTTTGCTGAATTGCATGATACTCCCTAAG
AATGGCAGCTAAGGTGTGATTAAGAAAGTTGTAGACGGGAAGAACACGCTCGTTCTTCTATAAAAGGCTACGGA
GGAGGATCGCAGAAGATGTTCTTGCAAAACAAATAACGCAGATAGTCGCTCATAAATTTACCCACCAATACCAATG
GAGCTCATCAAGGAGTGGTACCTTGCTTCTCAGGTCACAACAGGAAGCACTGGATGGATGACGATGATGCTTTGT
TGCCTGGAAGGACAGTCCTGAAAACTACAAGGGGCATATCCAAAAGCTTAGGGCTCAAAAGTGTCTCATCGCTCT
CTGATCTTGGCTGACTCCAGTTCAGATCTGCAAGCATTCTCGCAGGGTCTTCTACGCTATTAGATAAGATGGATCCC
TCTCAGAGAGCGAAGTTTGTTCAGGAAGTCAAGAAGGTCCTTGATTGA
```

FIGURE 8B

```
>AAP78897_Zea Mays
MSQLGLAAAASKALPLLPNRQBSSAGTTFSSSSLSRPLNRRKSRTRSLRDGCDGVSDAKKHSQEVRQGLAGIID
LPSEAPSEVDISHGSEDPRGFTDSYQNNGIINRTHNGRHASVSKVVEFCAALGGKTFIHSILVASNGMAAAKFM
RSVRTWANPTFGGEKAIQLIAMATPEDMRINAFHIRIADQFVEVPGGTNSKNYANVQLIVEMAQKLGVSAVWPG
WGHASENFELPDALTAKGIVFLGPPASSMNALGDKVGSALTAQAAGVFTLAPSGSRVEVPLSCCLDAIPESMYR
KACVTTTREAVASCQVVGYPAKIKASWGSGGKGIRKVHNDDEVRALFKQVQGEVPGSPIFVMRLASQSRRLEVQ
LLCDQYGNVAALESRDCSVQRRHQKIIEEGPVTVAPRETVKALEQAARRLAKAVGYVGAATVEYLYSNETSDYY
FLENPRLQVEHPVTEWIAFVNLPAAQVAVGMGIPLWQIPEIRRFYGMDYGGYDIWRKTAALATPFNFDEVDS
QWFKGHCVAVRITSEDFDDGFKPTGGKVKEISFKSKFNVWAYFSVKSGGGIHEFADSQFGKVFAYGLSRSAAIT
NMTLALKRIQIRGEIESNVDYTVDDLLSASDFRENKIHFGWLDTRIANRVQAERFPWYISVVGGALYKTVTTNAA
TVSRYVSYLTKQQIPFKHISLVNSTVFLNIEGSKYTIFTVRTGHGSYRLRMNDSTVEANVQSLCDKGLIMQLDG
NSHVIYAEEEAGGTRLQIDGRTCLLQNDHDPSKLLARTPCKILRFLVADGAHVDADVPYAEVEVMKMCNPLLSP
ASGVIHCMMSEGQALQRGDLIARLDLDDPSAVKRAKPFDGIFPQMELPVAVSSQVHKRYAASLNAARMVLAGYE
HNINEVVQDLVCCLDNFELPPLQWDELMSVLATRLPRNLKSELEDKYKEYKLNFYHGKNEDFPSKLLRDIIEEN
LSYGSEKEKATNERLVEPLMNLIKSYEGGRESHAHFVVKSLFEEYLTVEELFSDGIQSDVIETLRHQRSKDLQK
VVDIVLSSQGVRNRAKLVTAIMEKLVYPNPGGYRDLLVRFSSLNHKRYYKLALKASELLRQTKLSELRASVARS
LSDLGMHHPGENSIKDNMEDLVSAFLFVEDALISLFDYSDRTVQQKVIETYISRLYQPHLVKDSIQMKFKESGAI
TFWEFYESHVDTRNGHRAIIGGKRWGAMVVLKSLESASTAIVAALKDSAQFNSSKGNKMHIALLSAENESNISG
ISSDDQAGHRNEKLSKILKDTSVASDLQAAGLKVISGTVQRDEARMPNRHTFLWLDDKSCYEEEQIILRNVEPPL
STLLELDKLKVKGYNEMKYTPSRDKQNHIYTLRNTENFKMLHAVFFRTIVRQFNAGNMKFTSAQISDAEVGCPEE
SLSFTSNSILRSLMTAIEELELHAIRTGHSHMYLCILKEQKLLDLIPFSGSTIVDVQDEAYACSLLKSMALKI
HELVGARMHHLSVCQWEVKLKLDCDQFASGTWRVVTTNVTGHTCTIDIYREVEEIESQKLVYRSATSSAGFLSG
VAIENNPYQFLSVISLKRCSARMNRTTYCYDFPLAFETALQKSWQSNGSTVSEGNENSKSYVKATSLVFARKSGS
WGTPIIFMERPAGLMDIGNVAWIMEMSTPEFPNGRQIIVVAHDITFRAGSFGPREDAFFETVTNLACERKLELI
YLAANSGARIGIADEVKSCFRVGNSDEGSPERGFQKIYLTEEDYARISSSVIAHKLELDSGEIRWIIDSVVGKR
DGLGVENIHGSAAIASAYSRAYERTFTLTEVTGRTVGIGAYLABLGIRCIQRLDQPIILTGPSAINKLLGBEVY
SSHMQLGGFFKIMATNGVVRLTVPDDLEGVSNILPWLSYVFANIGGPLFITKPLDPPIRPVAYIPENTCDPRAAI
CGVDDSQSKWLGGMFDKDSFVETFRGWAKTVVTGRAKLGGIFVGVIAVETQTMRQIIPADPGQLOSKERSVPRA
GQVNFPDSATKTAQALLDFNRSGLPLFTLANWRGFSGGQRDLFEGILQAGSTIVENLRTSHQPAFVYIPMAGEL
RGGAWVVVDSKINPDRIECYAERTAKGNVLEPQGLIEIKFRSEELQDKMGRLDPELINLKAKLQDVNHGNGSLP
DIEGIRKSIEARTKQLLPLYTQIAIRFAELHDTSLRWAARGVIKRVVDNSESRSFFYKRLRRSIARSVLAKEIR
QIVGDKFTHQLAMELIKEWYLASQATTGSTGWDDDDAFVAWKDSPENYKSHIQKLRAQRVSHSLSDLADSSSDK
QAFSQGLSTLLDKMDPSQRAKFVQEVKKVLD
```

FIGURE 9A

```
>AY312171_Zea_mays
ATGTCACAGCTTGGATTAGCCGCAGCTGCCTCAAAGGCCTTGCCACTACTCCCTAATGCCAGAGAAGTTCAGCTGG
GACTACATTCTCATCATCTTCATTATCGAGGCCCTTAAACAAGAAGGAAAGCCGTATTCTTCACTCCTGATGCCG
GAGATGGGTATCAGATGCCAAAAGCCACAGCCAGTCTGTTGGTCAAGGTCTTGCTGGCATTATCGACCTCCAAGT
GAGCCACCTTCCGAAGTGGATATTTCACATGGATCTGAGGATCCTAGGGGGCCAACAGATTCTTATCAAATGAATGG
GATTATCAATGAAACACATAATGGAGCACATGCCTCAGTTCCAAGTTGTTGCATTTGTTGCGCCACTAGGTGGCA
AAACACCAATTCACAGTATATTATTGCCCAACAATGGAATGCAGAGGCAAAATTTATGAGGAGTGTCCGGACATGG
GCTAATGATACTTTTGGATCTGAGAAGGCAATTCAACTCATGCTATGGCACCTCCGGAAGACATGAGGATAAATGC
AGAACACATTAGAATTGCTGACCAATTCGTAGAGGTGCCTGGTGGAACAAACAATAATAACTACGCCAATGTTCAAC
TCATAGTGGAGATGGCACAAAAGCTAGGTGTTTCTGCTGTTGGCCTGGTTGGGGTCATGCTTCTGAGAATCCTGAA
CTGCCAGATGCATTGACCGCAAAAGCCATGCTTTTTGCTTGGCCCACCTGCATCATCAATAATCTTTGGGGGATAA
GGTCGGCTCAGCTCTCATGGCTCAAGCAGCCGGGTCCCAACTCTTGCTTGGAGTCGATCCATGTCAAGTTTCCAT
TAGAGTGCTGCTTAGACGCGATACCTCAGGAGATGTATAGAAAGCTTGCGTTACTACCACAGAGGAAGCAGTTGCA
AGTTGTCAAGTTGTTGGTTATCCTGCCATGATTAACGGCATCCTGGGGAGGTTGCTGGTAAAGGAATAAGAAAGGTTCA
TAATCATCATGAGGTTACAGCCGCTCTTTAAGCAAGTACAAGGTGAAGTCCCTGGCTCCCAATATTTGTCATGAGGC
TTGCATCCCAGAGTCCGCATCTTCAACTTCAGTTGCTTTGTCATCAATATGCTAATCTACCAGCACTTCACAGTCGT
GATTGCAGTGTGCAACGCGACGCAGAAGATTATTGAAGAAGGTCCAGTTACTGTTGCTCCTCGTGAGACAGTTAA
AGCACTTGAGCAGCAGCAAGGAGCGTTGCTAGGGCGTGGTTATGTTGGTGCTGCTACTGTTGAGTATCTTTACA
GCAGGGAAACTGGAGACTACTATTTTCTGGAACTTAATCCCGACTACAGGTTGAGCACCAGTCACCGAGTGGATA
GCTGAAGTAAATCTGCCTGCAGCTCAAGTTGCTGTTGGAATGGGCATACCTCTTGGCAGATTCAGAAATCAGACG
TTTCTATGGAATGGACTACGGAGGAGGCTATGACATTTGCAGGAAAACGGCAGCTCTTGCTACACCATTTAATTTG
ATGAAGTAGATTCTCAATGGCCAAAGGGCCATTGTGTAGCAGTTAGAATTACTAGTGAGGCCAGATGATGGTTTC
AACCTACTCGTGGCAAAGTGAAGGAGATAAGTTTTAAAAGCAAGCCTAATGTTTGGGCCTACTTCTCAGTAAAGTC
TGGTGGAGGCATTTATGAATTTGCTGATTCTCAGTTCGGACATGTTTTTGCATATGGGCTCTCTAGATCAGCAGCAA
TAGCAAACATGACTCTTGCATTAAAAGAGATTCAAATTCGTTGCGGAGATTCATTCAAATGTTGATTACACAGTTGAC
CTCTTAAATGCTTCAGGACTTTGAAGAAAACAAGATTCGTCTGGTTGCTCAAGACGAAATAGCTATCGGTGTTCA
AGCTGAGAGGCCCCATCGTATATTTCACTGTTGGGGGTCCTTTATATAAAACAGTAACCACCAATGCAGCCACTG
TTTCTGAATATGTTAGTTATCTCACCAGGGCCAGATTCCACCAAAGCATATATCCCTTGTCAATTCTACAGTTAAT
TTGAATATAGAAGGCAGCAAATACACAATTGAAACTGTAAGGACTGGACATGGTAGCTACAGGTTGAGAATAATGA
TTCAACAGTTGAAGCGAATGTACAATCTTTATGTGATGGTGGCTCTTAATCCAGTTGGATGGAAACAGCCATGTAA
TTTATGCAGAAGAAGAAGCTGGTGGTACACGGCTTCAGATTGATGGAAAGACATGTTTATTGCAGAATTACCATGCT
CCATCAAAGTTATTAGCTGAGACACCCTGGAACTTCTTCCTTTCTTGGTTGCTGATGCTGCTCAGTGTGATGCGGA
TGTACCATACGCGGAAGTGGAGGTTATCAAGATGTGCATGCCTCTCTTGTCGCCTGCTTCTGGTGTCATTCATTGTA
TGATTCTGAGCCACAGCAATGCATGCGTGGTGATCGTATAGCAAGGTTGGATCTTGAGACCCTTCCTGCTGTGAAA
AGAGCTGAGCCATTTGATGGAATATTTCCACAAATGCGAGCTCCCTGTTGCTGTCCTAGTCAGTTACACCAAAAGATA
TGCTGCAAAGTTTGAATGCTGCTGGAATGGTCCTTGCAGGATATGAGCACAATATTAATGAAGTCGTTCAAGATTTGG
TATCCTGCCTGGACAACCCTGAGCTTCCTTTCCTACAGTGGGATGAACTTATGTCTGTTCTAGCAACGAGGCTTCA
AGAAATCTCAAGAGTCAGTTAGAGGATAAATACAAGGAATACAATTGAATTTTTACCATGGAAAAACGAGGACTT
TCCATCCAAGTTGCTAGCAGACATCATTGAGGCAAATCTTTCTTATCGTTCAGAGAAGGAAAAGGCTACAAATGAGA
GGCTTGTTGAGCCTCTTATGAACCTACTGAAGTCATATAGGGGTGGGAGAGAGAGCCATGCACATTTGTTGTCAAG
TCTCTTTTCGAGGAGTATCTTACAGTGGAAGAACTTTTAGTGATGCATTCAGTCTGACGTGATTGAAACATTGCG
GCATCAGCACAGTAAAGACCTGCAGAAGGTGCTAGACATTGTGTTGTTCACTAGGTTGTGAGCAACAAAGCTAAGC
TTGTAACGGCACTTATGGAAAAGGCTGCTTTATCCAAATTCTGGTCGTTACACGGATCTGTTAGTTCGGTTTCTTCC
CTCAATCATAAAAGATATTATAAGTTGGCCCTTAAACGCAGTGAACTTCTTGAACAAACCAAACTAAGTGAACTCCC
TGCAAGCGTTGCAAGAAGCCTTTGGGATCTGGGGATGCATAAGGGAGAAATGAGTATTAAGGATAACATGGAAGCT
TAGTCTGCCCCCGTTACCTGTTGAAGATGTTGGTTCTTTGTTGATTACAGTGATCGACTGTTCAGCAGAAA
GTGATTGACAGACACATATCACGATTCTACCAGCCTCATCTTGTAAAGCATAGCATCAAATGAAATTCAAGGAATC
TGGTGCTATTACTTTTGGGAATTTTATGAAGGGCATGTTGATACTAGAAATGGACATGGGGCTATTATTGGTGGCA
AGCGATGGGGTGCCATGGTCGTTCTCAAATCACTTGAATCTGCGTCAACAGCCATTGTGGCTGCATTAAAGGATTCG
GCACAGTTCAACAGCTCTGAGGGCAACATCATGCACATTGCATTATTGATGCTGAAAATGAAAGTAATATAAGTGG
AATAACTGATGATCAAGCTCAACATAACATGGAAAAGCTTAGCAAGATACGAAGGATACTACCCTTGCAAGTGATC
TCCAAGCTGCTGGTTTGAAGGTTATAACTTGCATTGTTCAAAGAGATGAAGCTCGCATGCCAATGCGCCACACATTC
CTCTGGTTGGATGACAAGTTGTTATGAAGAAGACAGATTCCTGCATGTGGAGCCTCCCTTCTCTATACTTCT
TGAATGGATAAGTTCAAGGTGAAAGGCAAAAATGTTGCATAGCGTTCGCTTGCGGTGACCTGCCAATGGCATATCT
ACACACTAAGAAATACTGAAAACCCCAAAATGTTGCATAGGGTGTTTTTCCGAACTATTGTCAGGCAACCCAATGCA
```

FIGURE 9A (continued)

FIGURE 9B

```
>AAP78896_Zea mays
MSQLGLAAAASKALPLLFNRQRSSAGTTFSSSSLSRPLNRRKSRTRSLRDGKDGVSDAKKHSQSVRQGLAGIID
LPSRAPSSVDISHGSEDPRGPTDSYQMNGIINETHNGRSASVSKVVEFCAALGGRTPTRSILVANNGMAAAKFM
RSVRTWANDTFYGSERAIQLIAMATPEDMRINAEHIRIADQFVSVPGGTNNNNYARVQLIVEMAQKLGVSAVWPG
WGRASENPELFDALTARGIVFLGPPASSMNALGDKVGSALIAQAAGVPTLAWSGSRVEVPLSCCLDAIPEEMYR
KACVTTTSEAVASCQVVGYLAMLKASWQGGGRGIRKVHNDDEVRALFKQVQGEVPGSPIFVMRLASQSRHLEVQ
LLCDQYGNVAALHSRDCSVQRRHQKIIEEGPVTVAPRETVKALEQAARRLAKAVGYVGAATVEYLYSMETGDYY
FLELNPRLQVEHPVTEWIAEVWLPAAQVAVGMGIPLNQIPEIRRFYGMDYGKGYDIWRKIAALATPFNFDEVSS
QWPKGRCVAVRITSEDPDDGFKPTGGKVKEISFKSKPNVWAYFSVKSGGIHEFADSQFGHVFAYGLSRSAAIT
NMTLALKEIQIRGEIHSNVDYFVDLLMASDPRRNKIHTGWLDTRIAMRVQAERPPWYISVVGGALYKTVTTNAA
TVSRYVSYLTKGQIPPKHISLVNSTVNLNIEGSKYPIETVRTGHGSYRLPMNDSTVEANVQSLCDGGLLMQLDG
NSHVIYAEEEAGGTRLQIDGKTCILQNDHDPSKLLAETPCRLLRFLVADGAHVDADVPYAEVEVMRNCMPLLSF
ASGVIHCMMSEGQALQAGDLIARLDLDDPSAVKRALPFDGIFPQMELPVAVSSQVHKRYAASLNAARMVLAGYE
HNINEVVQDLVCCLDNPELPFLQSEELMSVLATRLPRNLKSELEDKYKEYKLNFYHGKNEDFPSKILRDIIEEN
LSYGSEKEKATNERLVEPLMNLLKSYEGGRESRAHFVVKSLFEEYLTVEELFSDGIQSDVISTLRHQRSKDLQK
VVDIVLSHQGVRNKAKLVTAIMEKLVYPNPGGYRDLIVRFGSINHKRYYNLALKASELLEQTKLSELRASVARS
LSDLGMHKGEMSIKDNMEDLVSAPLFVEDALISLFDYSDRTVQQKVIETYISRLYQPHLVKDSIQMKFKESGAI
TFWRFYEGRVDTRNGRGAIIGGKRWGAMVVLKSLESASTAIVAALKDSAQFNSSEGHMMHIALLSAENESNISG
ISDDQAQHKMEKLSKIIKDTSVASDLQAAGLFVISCIVQRDEARMPNRHTFLNLDDKSCYSERQILRAVEPPLS
TLLRLDKLKVKGYNEMKYTPSRDRQWHIYTLRNTENSKMLRVEFRTIVRQPEAGNKFTSAQISDAEVGCPIES
LSFTSNSILRSLMTAIEELELHAIRTGHSHMYLCILKEQKLLDLIPFSGSTIVDVGQDEATACSLLKSKALKIE
ELVGARMEHLSVCQWEVKLKLDCDGPASGTWRVVTTNVTGRTCTIDIYREVEEIESQKLVYESATSSAGPLRGV
ALNKPTQPLSVIDLRRCSARNMRTTYCYDFELAFETALQKSWQTNGSTVSEGNENSKSYVKATELVFAEKHGSW
GTFIIFMERPAGLSNDIQMVAWIMRMSFPEFFNGRQIIVVANDITFRAGSFGPREDAFPETVTNLACESKLPLIY
LAANSGARIGIADEVKSCFRVGWSDEGSPERGFQYIYLTEEDYARISSSVIAEKLELDSGEIRSIIDSVVGSED
GLGVENIHGSAAIASAYSRAYEETFTLIFVTGRTVGIGAYLARLGIRCIQRLSQPIILTGFSALNKLGREVYS
SRMQLGGPKIMATNGVVRLTVPDDLEGVSNILRWLSYVFANIGGPLPITKPLDEPDREPVAYIPENTCDPRAAIC
GVDDSQGXWLGGMFDKDSFVETFEGWAKTVVTGRAKLGGIPVGVIAVETQTMMQIIPADFGQLDSHERSVPRAG
QVWFPDSATKTAQALLDFNREGLFLSILANWRGFSGGQRDLFEGILQAGSTIVENLRTYNQPAFVYIPMAGELR
GGAWVVDSKINPDRIECYAERTAKGNVLSPQGLIEIRFRSEELQDDMQRLDPELINLKAKLQDVNSGNGSLFD
IRGIRKSIEARTMQLLPLYTQIAIRFAELHDTSLRMAAKGVIKSVVDWEESRSFFYRRLRRRIAEDVLAREIRQ
IVGDKFTHQLAMELIKEWYIASQATTGSTGWDDDAFVAWKDSPENYKGHIQKLRAQKVSRSLSDIADSSSDLQ
AFSQGLSTLLDKMDPSQRAKFVQEVKKVLD
```

FIGURE 10A

```
>AF029895_Triticum aestivum
ATGGATCCACACATTTGCCCATTCTCGGCCTTAATTGCCTGGACAACACCATGGCTATCCACTATTCGCCCGGTAAA
TTCAGCCGGTGCTGCATTCCAACCATCTGCCCCTTCTAGAACCTCCAAGAAGAAAAGTGGTCGTGTTCAGTCATTAA
GGGATGGAGGCGATGGACGTCTCAGACCCTAAGCAGTCTATTCGGCAAGGTCTTGCCGGCATCATTGACCTGCCA
AAGGAGGGCACATCAGCTCCCGAACTGGACATTTCAGATGGGTCCGGAGAACCCCAGGGGCTGCTGCTACCAAATGAATGG
GATGCTGAATGAAGCACATAATGGGAGGCATGCTTCGCTGTCTAAGGTTGTCCAATTTTGTATGGCATTGGGCGGCA
AAACGCCAATTCACAGTGTATTAGTTGCGAACAATGGAATGGCAGCAGCTAAGTTCATGCCGAGTGTCCAACATGG
GCTAATGAAACATTTGGGTCAGAGAAGGCAATTCAGTTGATAGCTATGGCTACTCCAGAAGGCATGAGGATAAATGC
AGAGCACATTACAATTGCTGATCAATTTGTTGAAGTACCCGTGGAAGCAAACAATAAGAACTATGTAAATTTCGAC
TCATAGTGCACATACCAGTGACAACCCGTGTTCTGCTCTTTGCCCTCGTTGGGGCCATGCATCTGAGAATCCTGAA
CTTCCAGATGCACTAAATGCAAACGGAATTGTTTTCTTGGGCCACCATCATCATCAATGAACGCACTAGGTGACAA
GGTTGGTTCAGCTCTCATTGCTGAAGCAGCAGGGGTTCCGACTCTTCCTTGAGTGGATCACAGGTGGAAATTCCAT
TAGAAGTTGTTTGCACTCGATACCCGCGGAGATGTATAGCAAAGCTTCTGTTAGTACTACCGGAGCGAAGCACTTGCG
AGTTGTCAGATCGATTGGGTATCCCCGCAGGATTAAAGCATCAGTGGCCTCCTGTTCCTAAGCCGATCCCAAAAGGTTAA
TAATGACGATGATGTCAGAGCACTGTTTAAGCAAGTGCAAGGTGAAGTTCCTGGCTCCCAATATTTATCATGAGAC
TTGCATCTCAGACTCGACATCTTGAAGTTCAGTTGTTTTGTGATGAATATGGCAATGTAGCTGCGCTTCACAGTCGT
GACTGCAGTGTGCAACGGCGACACCAAAAGATTAGTTGAGGAACGACTAGTTCCTCTTGCTCCTGGCACAGTCAA
AGAGCTAGAACAACCAGCAAGCGCCCTTGCTAAGGCTGTGGGTTATGTTGGTGCTGCTACTGTGAATATCTCTACA
GCATGGAGACTGCTGAATACTATTTTCTGGAACTTAATCCACGGTTGCAGGTTGAGCATCTAGTCACCGAGTGGATA
GCTGAAGTAAACTTGCCTGCAGCTCAAGTTGCAGTTGGAATGGGTATACCCCTTTGGCAGGTTCCAGAGATCAGACG
TTTCTATGTAATGGACAATGTAGCCAGGCTATGACATTTGGAGGAAAACAGCAGCTCTTGCTACTCCATTTAACTTCG
ATGAAGTGGATTCTCAAGGCGGAAAAGTCATTGTGTAGCAGTTAGGATAACCAGTGAGGGTCCAAATGACGGATTC
AAGCCTGACCCGTGGAAAAGTAAAGAGATTCAGTTTTAAAAGCAAGCCAAATGTTTGGGCCTATTTCTCGTTAACTC
CGGTGGAGGCATTCATTGAATTTGCTGATTCTCAGTTTGGACATGTTTTTGCATATGGAGTGTCTAGAGCAGCAGCAA
TAAGCAACATGTCTCTTGCGCTAAAGAGATTCAAATTCGTGGAGAAATTCATTCAAATGTTGATTACACAGTTGAT
CTCTTGAAATGCCTCACACTTCAAAGAAAACAGGATTCATACTGGCTGGCTGATAACAGAATAGCAATGCAGTCCA
AGCTGCACAGACCTCCGTGGTATATTCACTGGTTGGACCAGCTCTATATAAACAATAACCAGCAACACCAGCACTG
TTTCTGAATATGTTAGCTATCTCGTCAAGGGTCAGATTCCACCGAAGCATATACCCTTGTCCATTCAACTGTTCT
TTCAATATGACAAAAGGCAAATATACATTGAAGCTATAAGCAGCGCACAGCTACCTACAGATTCGAATGAATGG
ATCAGTTATTGAAGCAAATGTCCAAACATTATGTGATGGTGACTTTTAATGCAGTTGCATGGAAATACCCATGTAA
TTTATGCTAAGAACGACCCCTGCTAGACCCTTCTAATTGATGCAAACACATGCTTCTTACAGAATGATCACCGAG
CCTTGCAAGGTTATTAGCTGAGACACCCTGCAAACTTCTTCGTTTCTTGGTTGCCGATGGTGCTCATGTTGAAGCTGA
TGTACCATATGCGGAAGTTGAGGTTATGAAGAGTGCATGCCCCTCTTGTCACCTGCTGCTGGTGTCATTAATGTTT
TGTTGTCTGAGGGCCAGGCTATGCAGGCTGGTGATGCTATAGCAAGACTGGATCTTGATGACCCTGTCGTGTGAAG
AGAGCTGAGCCATTAACCGATCTTTCCCAGAAATGAGCCTTCCTATGCTGCTTCTGGCCAAGTTCACAAAGATG
TGCCACAAGCTTGAATGCTGCTGGATGGTCCTTGCAGGATATGATCACCCGGTCAACAAAGTTGTACAAGATCTGG
TATCCTGTCTAGAGCTCCTGAGCTTCCTTTCCTACAATGGAAGAGCTTATGTCTGTTTAGCAACTAGACTTCCA
AGGCTTCTTAAGACCGAGTTGGAGGGTAAATACAGTGAATATAAGTTAAATGTTGCCATGGGAGAGCAAGGATTT
CCCTTCCAAGGTCTAAGACACAGAATCGACGGAAAATCTTGCACATGGTTCTCAGAAGCAAATTGCTACAAATGAGA
GGCTTGTTGAGCCTCTTATGAGCCTACTGAAGTCATATCAGGGTGGCAGAGAAAAGCCATGCACACTTTATGTGAAG
TCCCTTTTGGAGGACTATCTCTCGGTTGAGGAACTATTCAGTGATGGCATTCAGTCTGATGTGATTGACAGCGCTGCG
CCAACAACATAGTAAAGATCTGCAGAAGGTTGTAGACATTTGTGTTCTCGCCAGGTGTGTAGAAACAAAACTAAGC
TGATACTAACACTCATGGAGAAACTGGTCTATCCAAACCCTGCTGTCTACAAGGATCAGTTGACTGCCTTTCCTCC
CTCAATGACAAAGATATTATAAGTTGGCCCTTAAAGCTAGGAAGCTTCTTGAACAAACCAAGCTTAGTGAGCTCCG
CAGAAGCATTGCAAGGAGCCTTCAGACCTTGAGATGTTTACTGAAGAAGGACGGCCATTGTGAGATCATTGGGAG
ATTTAGTGACTCCCCACGTGCAGTGCAAGATGCACTGGTTTCTTGTTTGATGCTAGCGATGAAACTCGTCAGCAG
AGGCTGATGCAGACCTACATATCCGATTATACCAGCCTCATCTTCTCAAGGATAGTATCCAGCTGAAATATCAGGA
ATCTGGTGTTATTGCTTTATGGGGATTCGCTGAAGCCCATTCAGAGAAGAGATTGGGTGCTATGGTTATTGTGAAGT
CGTTAGAATCTGTACAGCAGCAATTGGAGCTGCACTAAAGGGTACATCACGCTATGCAAGCTCTGAGGGTAACATA
ATGCATATTGCTTTATTGGGTGCTGATAATCAAATGCATGGAACTGAAGACAGTGGTGATAACGATCAAGCTCAAGT
CAGGATAGACAAACTTTCTGCGACACTGGAACAAAATACTGTCACAGCTGATCTCCGTGCTGCTGGTGTCAAGGTTA
```

FIGURE 10A (continued)

```
TTACTTGCATTGTTCAAACGGATGCACCACTCATCCCTATGCCCCATACCTCCTCTTGTCGGATGAAAAGCTTTGT
TATGAGGAAGAGCCGGTTCTCCGGCATGTGGAGCCTCCTCTTCCTGGTCTTCTTGAGTTGGGTAAGTTGAAAGTCAA
AGGATACAATGAGGTGAAGTATACACCGTCACGTGATCGTCAGTGGAACATATACACACTTAGAAATACAGAGAACC
CCAAAATGTTGCACAGGTTGTTTTTCCGGACTCTTGTTAGGCAACCCGGTGCTTCCAACAAATTCACATCAGGCAAC
ATGAGTCATGTTCAACTGGCAGGAGCTGAGCAAATCTCTTTCATTTACATGGAGCAGCATATTAAGATCGCTGATGAC
TGCTATAGAAGAGTGGGAGCTTCACGCGGATTAGGCAGGTCACTCTCATATGTTTTTGTGCATATTGAAAGAGCAAA
AGCTTCTTGATCTTCTTCCCGTTTCAAGGAACAAAGTTCTCGGATATTGGCCAAGATGAAGCTACTGCATGCTTGCTT
CTGAAAGAAATGGCTCTACAGATACATGAACTTGTGCGGTGCAAGGATGCATCATCTTTCTGTATGCCAATGGGACGT
GAAACTTAAGTTGTACAGGCATCGCCTGCCGGTGCTACCTGGAGAGTTGTAACAGGCAATGTTACTAGTCACACCT
GCACTGTGGATATCTACCCTGAGGTCGAACATACAGGATCACAGAAACTAGTCTACCACTCTCCTCCATCGTGCATCT
GGTCCTTTGCATGGCGTTCCACTGAATACTCCATATCAGCCCTTGAGTGTTATTGATCTGAAACGTTGCTCTGCTAG
AAATAGCAGGACTACATACTGCTATGATTTCCGTTGGCATTTGAAACTGCAGTGCAGAAGTCATGGTCTAACATTT
CTAGTGACACTAACCCATGTTATCTTAAACCGACCGACCTGGTGTCTGCCTCACAAGGACGGGTCATGGGGCACTCCT
GTAATTCCTATGGAGCGTCCTGCTGGCTCAATGACATTGGTATGGTAGCTTGGATCTTGGACATGTCCACTCCTGA
ATATCCGAATGGCAGGCAGATTGTTGTCATCGCAAATGATATTACTTTTAGAGCTGGATCGTTGGTCCAAGGCAAG
ATGCATTTTTTGAAACTGGTACCAACCTAGCTTGTGAGACGAAGCTTCCTCTCATCTACTTGGCAGCAAACTCTCGT
GCTCGGATCGGCATAGCACATGAAGTAAAATCTTCCTTCCGTGTTCGATGCTCTGATCATCGCAGCCCTGAACGTGG
GTTTCAATATATTTATCTGACTGAAGAAGACCATGCTTCTATTAGCCGTTCTGTTATAGCGCACAACATGCAGCTTG
ATAATGGTGAAATTAGGTGGGTTATTCATTCTGTTCTAGCGAGGAGGATGGCTAGGTGTGCAGAACATACATGGA
AGTGCTCTATTGCCAGTGCCTATTCTAGGGCCTATGCAGCAGACATTACGCTTACATTTCTGACTGGAAGGACTGT
TGGAATGGAGCATATCTTGCTCGACTTGGCATACGGTCCATACAGCGTACTGACCAGCCCATTATCCTAACTGGGT
TCTCTGCCTTGAACAAGCTTCTTGGCCGGGAAGTTTACAGCTCCCACATGCAGTTGGGTGGCCCAAAATTATGCCG
ACAAACGGTGTTGTCCATCTGACAGTTTCAGATGACCTTGAGGGTGTATCTAATATATTGAGGTGGCTCAGCTATGT
TCCTGCCAACATTGGTGGACCTCTTCCTATTACAAAATCTTTGGACCCACCTGACAGACCCCTTGCTTACATCCTG
ACAATACATGGATCCTCGTCCTGCCATCAGTGGCATTCATGATAGCCAAGCGAAATCCTTCCGCGCATGTTCGAC
AAAGACAGTTTGTGGAGACATTTGAAGGATGGGCCAAGTCAGTTGTTACTGGCAGAGCGAAACTCGGAGGGATTCC
GGTGGCTGTTATAGCTGTGGAGACACACAGACTATGAGCGATCCCTGCTGATCCAGGCCTAGCTTGATTCCCATG
AGCGATCTGTTCCTCGTGCTAGGCAAGCTCTGGTTTCCCAGCATCAGCTACTAGACAGGCAGGCAAGCTGGACTTC
AACCCTGAAGCCATTACCCTCTGTTCATCCTTGGTAACTGCAGAGCCTTCTCCGTGCACAAAGACATCTTTTTGAAGC
AATCCTTCAGGCTGGGCAACAATTGTTGAGAACCTTAGGACATACAATCAGCCTGCCTTTGTATATATCCCAAGG
CTGCAGAGCTACGTGGAGGGGCTTGCGTGCCTGCATTCATAGCCAAGATAAATCCAGATCGGCATTCAGTTCTATGCTGAG
AGGACTGCAAAGCGCATGTTCTCGAACCTCAAGGCTTGATCGAGATGAAGTTCAGGTCACAGGAACTGCTAAGAGTG
CATGCGTAGGCTTCATCCACAATTGATAAATCTGAAGCCAAACCTCCAGGCACTAAACCATGAAAATGCAACTCTAC
CTGAGTCAGAATCCCTTCAGAAGAGCATAGAAGCCGGGAAGAAACAGTTGTTGCCTTTGTATACTCAAATTGCGGTA
CGGTTCGCTGAATTGCATGACACTTCCCTTAGAATGGCTGCTAAGCGTGTGATTAAGAAGGTTGTAGACTGGGAACA
TTCTAGGTGGTTCTTCTACAAGAGATTACCGAGGACGAGATATCCGAGGATGTTCTTGCGAAGGAAATTACAGTGTAA
GTGCCAAGCAGTTTTCTCACCAATCGGCAATCCAGCCTGATCCACAAATGGTACTTGGCCTCTAACGGAGCTGAAACA
GGAAGCACTGAATGGATGATGACGATGCTTTTGTTGCCTGGACGGAAAACCTGAAAACTACCAGGAGTATATCAA
AGAACTCAGGGCTCAAAGGGTATCTCAGTTGCTGTCAGATGTTGCAGACTCCAGTCCAGATCTAGAAGCCTTGCCAC
AGGGTCTTTCTATGCTATTAGAGAAGATGGATCCTCAGGAGAGCACAGTTTGTTGAGGAAGTCAAGAAAGTCCTT
AAATGA
```

FIGURE 10B

```
>AAC39330_Triticum aestivum
MGSTHLPIVGLNASTTESLSTIRPVNSAGAAFQPSAPSRTSKKKSRRVQSLRDGGDGGVSDPWQSIRQGLAGII
DLPKEGTSAPEVDISHGSEEPRGSYQMNGILNEARNGRHASLSKVVEFCMALGGKTPIRSVLVANNGMAAAKFM
RSVRTWANETFGSERAIQLIAMATPELMRINAEHIRIADQFVEVEGGTNNNNYANVQLIVEIAVRTGVSAVWPG
NGHASEMPELPDALKANGIVPLGPPSSSMEKALGGKVGSALIAQAAGVPTLPWSGSQVEIPLEVCLDSIPAEMYR
KACVSTTEEALASCQMIGYPAMIKASWGGGGKGIRRKVNNDDGVRALPKQVQGEVPGSPIFIMRLASQSRHLEVQ
LLCDQYGNVAALHSRDCSVQRRHQKIIESGPVTVAPRETVKELEQAARRLAKAVGYVGAATVRYLYSMETGEYY
FLELRPRLQVEHPVTEWIAEVNLPAAQVAVGMGIPLWQVPEIRRFYGMDNGGGYDIWRRTAALATPFNFDEVDS
QNPKGHCVAVRISSEDPDDGFKPTGGKVKEISPKSKPNVWAYFPVKSGGGIREPADSQPCHVPAYGVSRABAIT
NMSLALKEIQTRGEIHSNVDYTVDLLNASDFKENRIHTGWLDNRIAMRVQAERPPWYISVVGGALYKTITSNTD
TVSEVVSYLVKGQIPPRHISLVISTVGLNIEESKYTIETIRSGQGSYRLRMNGSVIEANVQPLCDGGLLMQLDG
NSRVIYAREEAGGTRLLIDGKTCLLQNDHDPSRLLAETPCKLLRFLVADGARVEADVEYAEVEVMKMCMPLLSP
RAGVINVLLSEGQPMQAGDLIARLDLDDPSAVKRAEPFNGSFPEMSLPIAASGQVEKRCATSLNAARMVLAGYD
HPINKVVQDLVSCLDAPELPFLQWERIMSVIATRLPRLLKSELEGKYSEYKLNVGHGNSKDFPSKMLRETIERN
LAHGSEKRIATNERLVEPIMSLLKSYESGRESHARFIVKSLFKDYLSVEELPSDGIQSDVIERLRQQHSKDLQK
VVDIVLSHQGVRNKTPLILTPIMEKLVYPNPAVYKDQLTRFPSLNEKRYYKLALKASELLEQTKLSELRTSIARS
LSELEMPTEERTAISKIMGDLVTAPLPVEDALVSLFDCSRQTLQQRVIETYISRLYQPHLVKDSIQLKYQESGV
IALWEFAEAHSEKRLGAMVIVKSLESVSAAIGAALKGTSRYASSRGNTMRIALLGADNGMHGTRDSGDNDQAQV
RIDKLSATLEQNTVTADLRAAGVKVISCIVQRKGALMPMRETPLLSDEKLCYEEPVLRHVEPPLSALLELGKL
KVKGYNEVKYTPSRDRQWNIYTLRNTENPRMLHRVFFRTLVRQPCASNKFTSGNISDVEVGGAERSLSFTSSSI
LRSLMTAIRELELHATETGHSHMPLCILKEQRLLDLVPVSGNKVVDIGQDEATACLLLKEMALQIHELVGARMH
HLSVCQMEVKLKLDSIGPASGTWRVVTTWVTSHTCTVDIYREVEDCESQKLVYESAPSESGPLHGVALNTPYQP
LSVIDLKRCSARNNRPTYCYDFPLAPETAVQKSWSNISSDTNRCYVKATELVPASKNGSWGTPVIPMERPAGLN
DIGMVAWILDMSTPRYSNGRQIVVIANDIYPRAGSEGPRSDAFPETVTNLACERMLPLIYLAANSGARICIADE
VKSCPRVGWSDDGSPERGFQYIYLTEEDHARISASVIAHRMQLDNGETRWVIDSVVGKEDSLGVENIRGSAAIA
SAYSRAYESTFTLTPVTGRTVGIGAYLARLGIRCIQRTDQPIILTGPSALNKLLGREVYSSHMQLGGPKIMATN
GVVELFVSDDLEGVSNILRWLSYVPANIGGPLPITKSLDPPSDRPVAYIPENTCDPRAAISGIDDSQGKWLGGMF
DKDSFVETFEGWAKSVVTGRAKLGGIPVGVIAVETQTMMQLIPADPGQLDSHERSVPRAGQVNFFDSATKTAQA
MLDFNREGLPLFILANWRGFSCQQRDLFEGILQAGSTIVENLRTYNQPAFVYIPKAAELRGGAWVIDSKINPD
RIEFYAERTAKGNVLEPQGLIEIKFRSEELQECMGRLDPELINLKARLQGVKHERGSLPESESLQKSIEARKKQ
LLPLYTQIAVRFAELRDTSLRMAAKGVIKKVVDWEDSRSPYKRLRRRISEDVLAKEIRGVSGKQPSHQSAIEL
IQKWYLASKGAETGSTRWDDDDAFVANKENPENYQEYIKELRAQRVSQLLSSVADSSPDLSALPQGLSMLLEKM
DPSRRAQFVEEVKKVLK
```

FIGURE 11A

```
>AY219174_Setaria italica  (foxtail millet)
ATGTCGCAACTTGGATTAGCTGCAGCTGCCTCAAAGGCGCTGCCACTAGTTCCTAATCGCCATAGAACTTCAGCTGG
AACTACATTCCCATCACCTGTATCATCGCGCGGCCCTCAAACCGGAAGGAAAAGCCGGCACTCGTTCACTTCGTCATGCAG
GAGATGGGGTATCAGATGCCAAAAAGCATAACCAGTCTGTCCGTCAAGGTCTTGCTGGCATCATCGACCTTCCCAAAT
GAGGCAACATGGAAGTGGATATTTCTCATGGATCCGAGGATCCCAGGGGGCCAAGCGATTCATATCAAATGAATGG
GATGGTAAGTGAAGCACATAAGGCCAGACATGCCTGACTGTCCAAGGTTGTTGAATTTTGTGCGGCGCTACGTGGCA
AAACACCAATTCACAGTATACTAGTGGCCAACAATGGAATGGCAGCAGCAAAGTTCATGAGGACTGTCCGACATGG
GGCTAAGATACTTTTGGATCGGAGAAGGCCATTCAGCTTCATAGCTATGGCAACTCCAGAAGACATCAGGATAAATGC
AGAACACATTAGAATTCCTGTCAATTTGTGGAGCTGCCTGGTGGAACAAACAATAACAACTATGCAAATGTTCAAC
TCATAGTGGAGGTAGCAGAAAGAATACCTGTTTCTCCTGTTCCCCTGGTTGGGTCATGCTTCTGAGAATGCTGAA
CTTCCAGATGCATTCACCGCAAAAGGAGTTGTTTTCTTGGGCCAGCTGCGGCATCAATGAATCGCATTGGGAGATAA
GGTGGTTCAGCTCTCATTGCTCAAGCAGCTGGGTCCCGACCCTTTGGTGGAGTGGATCACATGTTGAAGTTCCAT
TAGAGTGCTGCTTAGATGCGATACCTGAGGAAATGTATAGAAAAGCTTGTGTTACTACCACAGAAGAAGCTGTTGCG
AGTTGTCAGGTGGTTGGTTATCCTGCCATGATTAAGGCATCCTGGGTAGGTGGTCGTAAAGCAATAAGAAAGGTTCA
GAATGACGATGAGCGTAGAGCACTGTTTAAGCAAGTACAAGGTGAAGTCCCTGGCTCCCAATATTTATCATGAGGC
TTGCATCCAGAGTGGTCATCTTGAAGTTCAGTTGCTTTGTGATCAATAGGCAATGTGGCAGCACTTCACAGTCGT
GATTGCAGTGTGCAACGGCGACACCAAAAGATTATTGACGAAGCCCAGTTACTGTTGCTCCTGGTGAGACAGTTAA
AGCGCTTGAGCAGGCAGCAAGAGGCCTTGCTAGGCTGTGGTTATGTTGGTGCTGCTACTGTTCAATACCTTTACA
GCATGGAGACTGGGCAATACTATTTCTGGAGCTTAATCCCGGATTACAGGTCGAGCATCCAGTCACTGAGTGGATT
GGTGAAGTAAAGCTTCCATCAACGCAAGCTGGAGCCCATAGGCATACCTCTGCAGATTCCAGAAATCAGCGC
TTCCATGTATGCACTATCGCGCGGCATATGACATTTGGAGGCAAAAGGCAGCTGTTGCCACACCATTAATTTG
ATGAAGTAGATTCTCAATGGCCAAAGGCCATTGTGTAGCAGTTAGAATTACTAGCGAGGATCCAGATTGATGCTTTC
AAACCTACTGGTGGAAAGTGAAGCAGATAAGTTTTAAAGCAAGCCTAATGTTTGGGCCTACTTCTCAGTAAGTTC
TGGTGGAGGCATTCATGAATTTGTTGATCTCAGTTTGGGCATGTTTTTGATATGGCGCTCTAGATCAGCAGCAA
TAACGAACATGGCTCTTGCATTAAAACAGATTCAATTTCCTGAGAAATTCATTCAAATCTGCATTACAGTTGAT
CTCTTAAATGCTTCGACTTCAGGAAAATAAGATTCGATACTGGCTGCTTGATACCAGAATAGCTATGCGTGTTCA
AGCTGAGAGGCCTCATGGTATATTCAGTGGTTGGAGGAGCTCTATATAAAACAGTAACTCCCAATGTAGCCACTG
TTTCTGATTATGTCAGTTATGTCACCAAGGCCCATTGAGACAGATATATCCCTTGTCGTTCAACAGTTAAT
GTGAATATGAAGCGGGCAAATACACAGTTGAAACGTGAAGCACTGGACATGCTAGCTACACATTACGAATGAATGA
TTGAGCAATGAAGCGAATGTACAATCCTTATGGATGGAGGCCCTCTTAATGCAGTTGGATGCAAATGCGATGAA
TTACGCGGAAGAAGAAGCTGGTGCTACACGACTTCTGATTGATGGAAAGACATGCTTGTTACAGAATGATCATGAT
GCATCAAAGTTATTAGCTGAGACACCCTGCAAACTTCTTCCGTTCTTGGTTGCTGATGGTGCCCATGTTGATGCTGA
TGTACCATATGCCGAAGTTGAAGTTATGAAAATGTGCATGCCCTCTTGTCGCCTGCTTCTGGTGCATTCGTGTTA
TGATGTCTGAGGCCAGGCATTGCAGGCTGGTGATCTTATAGCAACGCTGGATCTTGATGACCCTTCTGCTGTGAAA
AGAGCTGAACCATTTCATGGAATATTCCACAAATGGACCTTCCTGTTGCTGCCTCTAGCCAAGTAGACAAAAGATA
TGTTGCAAGTTGGAATGTCTCTTTAATGTCTTGCAAGATACGAGTATAATATCAATGAAGTTCTACAAGATTGG
TATGCTGCCTCGGATCAGTCCCCACCTTCCCTTCCTACAGTGGGATGAACTTATGTCAGTTCTAGCAACTAGGCTTTCA
AGAAATCTTAAAGTGACTTGAGGCATAAACATGGACAAGTTGAACTTTTACTATCCAAAAACAAGGCACTT
CCCGTCCAAGCTGCTGAGAGACATCATTGAGGCAAATCTTGCATATGGTTCAGAGAAGGGAAAAGCTACGAATGAGA
GGCTTATTGAGTCTCTTATGAGCCTACTTAAGTCATATGAGGGTTGGAGAGAAAGCCATGCTCATTTTGTTGTCAAG
TCCCTTTTCAAGGAGTACCTTTGCTGTGGAAGAACTTTTCAGTGATGGCATTCAGTCTGATGTGATTGAAACCCTGCG
TCATCAGCACAGTAAAGACTTGTGAGAAGGTTGTAGACATTGTTGTCTCACCAGGGTGTGAGGAACAAAGCTAAGC
TTGTAACAGCACTTATGGAAAGCTGGTTTATCCAAATCCTGCTGCTACAGGGATCTGTTGGTTGCTTTTCTTCA
CTCAATCATAAAGATATTATAAGTTGGCCCTTAAAGCAAGCAACTTCTTGAACAAACTAAACTAAGTGAACTCCG
TGCAAGCATCGCAAGAAGCCTTCTGATCTGGGACGCATAAGGAAGAAATGACTATTGAAGATAGCATGGAAGATT
TAGTCTCGCGCCCATTACCTGTCGAAGATGCACTTATTTCTTTGTTGCATTACAGTGCATCAACTGTTGACCAGAAA
GTGATCGAGACATACATATCCGATTGTATCAGGCTCTTCTTGTGAAAGTAGCATCCAAGTGAAATTTAAGGAATC
TGGTGGCCTTGCTTTATGGAATTTTCTGAGGGCATGTTGATACTAAAAATGGACAAGGACCGTTCTTGCTCAAA
CAAGATGGGTGCCATGGTAGCTGTCAAATCAGTTGAATCTGCAGAACAGCCATTGTAGCTGCATTAAAGGATCG
GCACAGGCATGCCAGCTCTGAGGGTCAACATGATGCACATTGCCCTATTGAGTGCTGAAAATGAAATAATATCAGTGA
TGATCAAGCTCAACATAGGATGCAAAAACTTAACAGGATACTCAAGGATACTAGTGTCGCAAATGATCTTCGAGCTG
CTTCGTTGAAGGTTATAGGTTCATTGTTCAAAGAGATGAAGCAGCCATGCCAATGTCACACATTACTCTGGTCA
GATGAAAGATTCTTATGAGCAAGAGCAGATCTTCCGGATGTGCAGCCTTCCCCTCTTCATGCTTCTTGAAATGGA
TAAGTTGAAAGTGAAAGGATACAATGAAATGAAGTATACTCCATCACGTGATCGTCAATGGCATATCTACACACTAA
```

FIGURE 11A (continued)

FIGURE 11B

```
>AA062902_Setaria italica (foxtail millet)
MSQLGLAAAASKALPLLFNRHRTSAGTTFPSPVSSRPSMRRKSRTRSLRDGGOGVSDAKKSNQSVRQGLAGIID
LPNEATSEVDISHGSEDPRGPTDSYQMNGIVSEAHNGRRASVSKVVEFCAALGGKTPIRSILWANNGMAAAKFM
RSVRTWANDTFGSEKAIQLIAMATPEDMRINAEHIRIADQFVEVFGGTNNNYANVQLIVEVAERIGVSAVKPG
WGHASENPELPDALTAKGVVFLGPPAASMNALGDRVGSALIAQAAGVPTLSWSGSHVEVPLECCLDAIPEEMYR
KACVFTTEEAVASCQVVGYPAMIKASWGGGGKGIEKVENDDSVRALEKQVQGEVPGSPIPIMRLASQSRHLEVQ
LLCDQYGNVAALSSRDCSVQRRFQKIIEEGPVTVAFRETVKALEQAARRLAKAVGYVGAATVEYLYSMETGEYY
FLELNPRLQVEHPVTEWIAEVNLPAAQVAVGMGIPLMQIPEIRRFDGMDYGGGYDIWRKTAALATPFNFDEVDS
QNPKGHCVAVRITSEDPDDGPKFTGGKVREISFKSKPNVWAYFSVKSGGGIREPVDSQFGEVFAYGLSRSAAIT
NMALALREIQIRSEIHSNVDYTVDLLNASDFRENKIHTGNLDTRIAMRVQAERFPWYISVVGGALYKTVTANAA
TVSDYVSYLTKGQIPSKHISLVESTVNLNIEGSKYTVETVSTCHGSYRLPMNDSAIEANVQSLCDGGLIMQLLG
NSHVIYAEEEAGGTRLLIDGKTCILQNDHDPSKLLAETFCKLLRFLVADGAEVDADVFYASVEVMKMCMPLLSP
ASGVIHVMMSDGQALQAGDLTARLDLDDPSAVKRAEFFHGIFPQMDLPVAASSQVNKRYAASWNAARMVLAGYE
HNINEVVQDLVOCLDDPELPFIQWDELMSVLATRLFRNLKSELEDKYMEYKLNPYNGKNKDFPSKLLRDIIEAN
LAYGSEKEKATNERLIEPLMSLLKSYEGGRESHAHPVVKSLFKEYLAVEELFSDGIQSDVIETLREQHSKDLQK
VVDIVLSHQGVRNKAKIVTAIMEKLVYPNPAAYRDLLVRFSSLNEKRYYKLALKASELLEQTKLSERLRASIARS
LSDLSMHKGKMTIEDSMEDLVSAFLPVEDALISLPDYSDPTVQQKVIETYISRLYQPLLVKDSIQVKFKESGAF
ALWSFSEGHVDTKNGQGTVLGRIRWGAMVAVKSVEBARTAIVAALKDSAQHASSEGNMMHIALLSAENENNISD
DQAQHRMEKLSKILKDTSVANDLRAAGLKVISCIVQRDEARMPKRSTLLWSDEKSCYEEEQILREVEPPLSMLL
EMDRLKVKGYNEMKYTESRDRQWHIYTLRNTENPKMLRVFFRTIVRQPNAGNKFISAQIGDTEVGGPEESLSF
ISKNSILRAIMTAIEELELHAIRTDESENYLCILKEQKLLDLIPFSGSTIVDVVQDEATACSILKSMALKIHELV
GRQMHRLSVCQMEVKLKLYCDGPASGTWRVVTDNVTSRTCTVDIYREVEDTESQKLVYRSASPSASPLHGVALD
NFYQPLSVIDLKHCSARNNRTTYCYDFPLAFETALQKSWQSNGSSVSEGSENSRSYVKATELVFAEKEGSWGTP
IISMRRPAGLNDIGMVAWILRMSTPEFPNGRQIIVIANDITFRAGSFGPREDAFFEAVTNLACERKLPLIYLAA
NSQARIGIADEVKSCFRVGWSDEGSPERGFQYIYLTDEDYARISLSVIAHRIQLDNGEIRWIIDSVVSKEDGLG
VENIHGSAAIASAYSRAYESTFTLTFVIGRTVGIGAYLARLGIRCIQRLDQPIILTGFSALNKLLGREVYSSRM
QLGGPKIMATNGVVRLTVSDDLEGVSNILRWLSYVPANIGGPLFITKPLDPPORPVAYIPENTCDFRAAIRGVD
DSQGKWLGGMFDKDSFVETFEGWAKTVVTGRAKLGGIPVGVAVETQTMMQLIPADPGQLDSHERSVPRAGQVW
FPDSATETAQALLDFNREGLPLFILANWRGFSGGQRDLFEGIILQAGSTIVEMLRTYNQPAPVYIPMAGELRGGA
WVVVDSKINPDRIECYAERTAKGNVLRPQGLIEIKFRSEELQDCMGRLDFGLINLKAKLQGAKLGNGSLTDVES
LQRSIDARTKQLLPLYTQEIAIRFAELRDTSLRMAAMGVIRKVVDWEESRSFFYRRLARRISEDVLAKEIRGIAG
DNFTHQSAVELIKEWYIASQATIGSTENDDDDAPVAWKENPENYRGYIQELRAQKVSQSLSDLADSSSDLEAFS
QSLSTLLDKMDPSQRAKFIQEVKKVLG
```

```
>AA062903_Setaria italica (foxtail millet)
MSQLGLAAAASKALPLLPNREKTSAGTTPPSPVSSRPSNRRKSRTRSLPLQGDGVSDAKKHNQSVPQGLAGIID
LPNEATSEVDISRGSEDPRGPTDSYQMNGIVNEAHNGREASVSKVVEFCAALGGFTPIESILVANNGMAAAKFM
NSVRTWANDTFGSEKAIQLIAMATFEIXRINAERIRIAPQFVEVPGGTNNNNYASVQLIVEVAERIGVSAVWPG
NQHASENPELPDALTAKGIVFLGPPAASMNALGDKVGSALIAQAAGVPTLSWSGSHVEVPLECCLDAIPEEMYR
KAQVTTTEEAVASCQVVGYPAMIRASWGGGGKGIRKVRHDDEVRALFKQVQGEVPGSPIFIMRLASQSRHLEVQ
LLCDQYGNVAALHSRUCSVQRRHQKIIEEGPVTVAPRETVKALEQAARRLAKAVGYVGAATVEYLYSMETQEYY
FLELNFRLQVEHPVTEWIAEVNLEAAQVAVGMGIPLNQIPEIRRFYGMDYGGGYDIWRKTAALATPFNFDEVDS
QWPKSRCVAVRITSEDPDDGPRPTGGKVKEISFKSKPNVNAYFSVKSGGGIBEFADSQFGHVFAYGLSRSAAIT
NMALALKEIQIRGEIRSNVDYTVDLLNASDFRENKIRIGWLDPRIAMRVQAERPPWYISVYGGALYKTVTANAA
TVSDYVSYLTKGQIPPKBISLVSSTVNLNIEGSKYPVETVRTGNGSYRIRMNDSAIEANVQSLCDGGLIMQLDG
NSRVIYARESAGGTRLLIDGKTCLIQNDMDFSKILAETPCKLLRFLVADGAHVDADVPYAEVEVMKKCMFLLSP
ASGVINVMRSEGQALQAGDLIARLDLDDPSAVKRAEFFRGIPFQMDLPVAASSQVHKRYAASLNAARMVLAGYE
HNINEVVQDLVCCLDDPELPFLQWDELMSVLATRLPRNLKSELEDKYMEYKLNFYRGKNKDFPSKLLRDIIKAN
LAYGSEKEKATNERLIEPLMSLLKSYEGGRESKAHPVVKSLFKEYLAVEELFSDGIQSDVIETIRHQHSKDLQK
VVDIVLSHQGVRNKAKLVTALMEKLVYPRPAAYROLLVRFSSLNHKRYYKIALKASELIEQTKLSELRASIARS
LSDLGMHKGEMTIEDSMEDLVSAPLPVEDALISLFDYSDPTVQQKVIETYTSRLYQPLLVKDSIQVKFKESGAF
AIWEFSEGHVDTKNQQQTVLGRTRWGAMVAVKSVESARTAIVAALKDSAQRASSEGNMMRIALLSAENENNISD
DQAQHRMEKLNKILRDTSVANDLRAAGLKVISCTVQRDEARMPMRNTLLNSDEKSCYESEQILRHVEPPLSMLL
EMDKLKVEGYNEMKYTESRDRQWHIYTLRNTENPKMLHEVFFRTIVRQPNAGNKFISAQIGDTEVGGPRESLSF
TPNSILRALNTAIKEIELKAIRTGHSRMYLCIILKEQKILDLIPFSGSTIVDVGQDEATACSLLKSMALKIRELV
GAQMHELSVCQWEVKLKLYCDGFASGTWRVVTTNVTSHTCTIDIYREVEDTESQKLVYKSASPSASPLRGVALD
NPYQPLSVIDLKRCSARNHRTTYCYDFPLAPETAIQKSWQSNGSSVSEGSENSRSYVKATELVFAEKHGSWGTP
IISMERPAGLNDIGMVANILEMSTPEFPNGRQIIVIANDITFRAGSFGPREDAFFEAVTNLACERKLPLIYLAA
NSGARIGIADEVKSCFRVGWSDEGSPERGFQYIYLTDEDYARISLSVIAHKLQLDNSEIRWIIDSVVGKEDGLG
VENLHGSAAIASAYBRAYEETFTLTFVTGRTVGIGAYLAELGIRCIQRLDQPIILTGFSALNKLLGREVYSSHM
QLGGSFKIMATNGVVRLTVSDDLEGVSNILRWLSYVPANIGGPLFFTKPLDPPDRPVAYIPENTCDPRAAIRGVD
DSQGKWLGGMFDKDSFVETFEGWAKTVVTGRAKLGGIFVGVIAVETQTMNKQLIPADVGQLDSHEKSVPRAGQVW
FPDSATKFAQALLDFNREGIPLFILANWRGFSGGQRDLFEGTILQAGSTIYEKLRTYNQPAFVYIPMAGELRGGA
WVVVDSKINFDRIECYAERTAKNVIEFQGLIEIKFRSEELQDXMGRLDPELINLKAKLQGAKLGNGSLTDVES
LQKSIDANTKQLLPLYTQIAIRFAELHDTSLEMAARGVIKKVVDWEESRSFFYRRIRRRISEDVLAKEIRGIAG
DHFTRQSAVELIKEWYLASQATTGSTEWDDDDAFVANKENFENYKGYIQELRAQKVSQSLSDLADSSSDLEAFS
QGLSTLLDKMDPSQRAKFIQEVKKVLG
```

FIGURE 13A

```
>AF294805 Setaria italica (Foxtail millet)
ATGTCGAACTTGGATTAGCTGCAGCTGCCTCAAAGGCGCTGCCACTACTTCCTAATCGCCRTAGRACTTCAGCTGG
AACTACATTCCATCACCTGTATCATCGCGRCCTCAAACGAAGRAAAGCCGCACTCCTTCACTTCGTGATGGAG
GAGATGGGGTATCRGATCCCAAAAAGCACAACCAGTCTGTCCGTCAAGGTCTTGCTGGCRTGATCGACCTCCCAAAT
CAGGCAACATCGGAAGTGGATATTTCTCATGGATCCRAGGATCCCAGGGGGCCAACCGATTCATATCAAATGAATGG
GATTGTAAATGAAGCACATAATGGCAGACATGCCTCAGTGTCCAAGGTTGTTGAATTTGTGCGGCGCTAGGTGGCA
AAACACCAATTCACRGTATACTARTGGCCAACAATGGAATGGCAGCAGCAAATTCATGACGAGTGTCCRGACATGG
GCTAATGATACTTTTGGATCGGAGAAGGCGATTCAGCTCATAGCTATGGCAACTCCAGAAGACATGAGGATAAATGC
AGAACACATTAGAATTGCTGAICAATTTGTAGAGGTGCCTGGTCGACAAACAATAACAACTATCCAAATGTTCRAC
TCATAGTGGAGGTAGCAGAAAGAATAGGTGTTTCTGCTGTTTGGCCTGGTTGGGGTCATGCTTCTGAGAATCCTGAA
CTTCCAGATGCATTGACCCCAAAAGCRAATTGTTTCCTTGGGCCACCTGCCGCATCAAATGAATCATTCCGAGATAA
GGTCGGTTCAGCTCTCATTGCTCAAGCAGCTGGGTCCCGACCCTTTCGTGGAGTGGATCACATGTTGAAGTTCCAT
TAGAGTGCTGCTTAGATGCGATACCTGAGGAAATGTATAGAAAAGCTTGTGTTACTACCACAGAAGAAGCTGTTGCG
AGTTGTCAGGTCGTTGGTTATCCTGCCATGATTAAGGCATCCTGGGGAGGTGGTGGTAAAGGAATAAGAAAGGTTCA
TAATGACGATGAGGTTAGAGCCACTGTTTAAGCAAGTACAAGGTGAAGTCCCTGGCTCCCAATATTTATCATCAGGC
TTGCATCCAGAGTCGTCATCTTGAAGTTCAGTTGCTTGTGATCAATATGGCRATGTGCAGCACTTCRCAGTCGT
GATTGCAGTGTGCAACGGCGACACCAAAAGATTATTGAGGAAGGCCCAGTTACTGTTCCTCCTCGTGAGACAGTTAA
AGCGCTGAGCAGGCAGCAAGGAGGCTTGCTAAGGCTGTGGGTTATGTTGGTGCTGCTACTGTTGAATACCTTTACA
GCATGGAGACTCGGGGAATACTATTTTCCTGGAGCTTAATCCCAGATTACAGGTCGAGCATCCAGTCACTGAGTGGATT
CCTGAAGTAAATCTTCCTCCAGCTCRAGTTGCAGTTGGAATGGGCATAACCTCTTTGGCAGATTCCAGAAATCGGACG
TTTCTATGGAATGGACTATGAGGACGATATGACATTGGAGGAAAACAGCAGCTCTTGCCACACCATTTAATTTTG
ATGAAGTAGATTCCAATGCCAAAGGGCCATTGTGTAGCAGTTAGAATTACTAGCGAGCATCCAGATGATGGTTTC
AAACCTACTGGTGGAAAGTGAAGGAGATAAGTTTAAAAGCAAGCCTAATGTTTGGGCCTACTTCTCAGTAAAGTC
TGGTGCAAGGCATTCATGAATTTGCTGATTCTCAGTTTCGCCATCTTTTCCATATGGGCTCTCTAGATCAGCAGCAA
TAACGAACATGGCTCTTGCCATTAAAAGAGATTCAAATTCGTGGAGAAATTCATTCAAATGTTCATTACACAGTTCAT
CTCTTAAATGCTTCAGACTTCAGAGAAAATAAGATTCATACTGGCTGGCTTGATACCAGAATAGCTATGCGTGTTCA
AGCTGAGAGGCCCCCATGGTATATTCAGTGGTGAGCTTCTATATAAAACAGTAACTTGCTAATCGCAGCCACTG
TTTCTGATTATGTCAGTTATCTCACCAGCGCCAGATCCACCAAAGCATATATCCCTTGTCAGTTCAACAGTTAAT
CTGAATATCGAAGGAGCAAATACACAGTTGAAACTGTAAGGACTCGACATGGTAGCTACAGATTACCAATGAATGA
TTCAGCAATTGAAGCGATGTACAATCTTTATGTGATGGAGGCCTCTTAATGCAGTTGGATGGAAATAGCCATGTAA
TTTACGCGGAAGAAGAACTGGTGGTCACGGACTTCTGATTGATGGAAAGCATGCTTGTTACAGAATGATCATGAT
CCATCAAAGTTATTAGCTGAGACACCCTGCRAACTTCTTCGGTTCTTGGTTGCTGATGGTGCTCATGTTGATGCTGA
TGTACCATATGCGGAAGTTGAGGTTATCAAAATGTGCATGCCCTCTTGTCGCCTGCTTCTGGTGTCATTCATGTTA
TGATGTCTGAGGCCAGGCATTGCAGGCTGGTGATCTTATAGCAAGGCTGGATCTTGATGACCCTTCTGCTGTGAAA
AGAGCTGAACCATTTCATGGAATATTTCCACAAATGGACCTTCCTGTTGCTGCCTCTAGCCAAGTACAAGAGATA
TGCTGCAAGTTTCAAGCTCCTCGAAATGGCCCTTGCACCATACGAGCAGCATAATATCAATGAACTTGTACAAGATTTGG
TATGCTGCCCTGGATGATCCCCGAGCTTCCCTTCCTACAGTGGGATGAACTTATGTCAGTTCTAGCAACTAGGCTTCCA
AGAAATCTTAAGCAGTGAGTTAGAGGATAAATACATGGAATACAAGTTGAACTTTTTACCATGGGAAAACAAGGGACTT
GCTTTCCRAGCTGCTTAGACAGATCATGAGGCAAATCTTGCRTATGGTTCAGAGAAGGCAAAAGCTACGAATGAGA
GGCTTATTGAGCCTCTTATGAGCCTACTTAAGTGATATGAGGGTGGGAGAAAGCCATGCTCATTTGTTGTCAAG
TCCCTTTTCAAGGAGTACCTTGCTGTGGAAGAACTTTCAGTGATGGGATTCAGTCTGATGTGATTGAAACCCTGCG
TCATCAGCACAGTAAAGACTTGCAGAAGGTTGTAGACATTGTGTTCTCACCAGCGTCTGAGGAACAAAGCTAAGC
TTGTAACAGCACTTATGGAAAAGCTGCTTTATCCAAATCCTGCTGCTACAGGGATCTGTTGGTTCGCTTTCTTCA
CTCAATCATAAAAGATATTATAAGTTGGCCCTTAAAGCAAGCGAACTTCTTCAACAAACTAAACTAAGTGAACTCCG
TGCAAGCATCGCAAGAAGCCTTTCTGATCTGGGATGCATAAGGGAGAAATGACTATTGAACATAGCATGAAGATT
TAGTCTCTGCCCCATTCCCTTGCGRAATGCACTTATTTCTTTGTTTGATTAATACAGTACCRACTGTTCAGCAGAAA
GTGATCGAGACATACATATCTCGATTGTATCAGCCTCTTCTTGTGAAAGATAAGCATCCAAGTGAAATTAAGGAATC
TGGTGCCTTTGCTTTATGGCAATTTTCTGAAGGGCATGTTGATACTAAAAATGGACAAGGGACCGTTCTTGGTCGAA
CAAGATGGGGTGCCATGGTAGCTGTCAATCAGTTGAATCTGCACGAACAGCCATTGTAGTGCATTAAGGATTCG
GCACAGCATGCCAGCTCTGAGGCAACATGATGCCATTGCCTTATTGAGTGCTGAAAATGAAATAATATCAGTGA
TGATCAAGCTCAACATAGGATGGAAAACTTAACAAGATACTCAAGGATACTATTGTCCAAATGATCTTCGAGCTG
CTGCTTTGAAGGTTATAAGTTGCATTGTTCAAAGAGATGAAGCACGCATGCCAATGCGCCACACATTACTCGGGTCA
```

FIGURE 13A (continued)

```
GATGAAAACAGTTGTTATCAGGAAGAGCAGATTCTTCGGCATGTGGAGCCTCCCTCTCCATGCTTCTTGAAATGGA
TAAGTTCAAACTGAAACCATACAATGAAATCAACTATACTCCATCACCTCTCCTCAATCCCATATCTACACACTAA
GAAATACTGAAAACCCCAAAATGTTGCATAGGGTATTTTTCCGAACTATTGTCAGGGCAACCCAATGCAGGCAACAAG
TTTATATCAGCCCAAATTGGCGCACACTGAAGTAGGAGGTCCTGAGGAATCTTTGTCATTTACATCTAATAGCATTTT
AAGAGCCTTGATGACTGCTATTGAAGAATTAGAGCCTCATGCAATTAGGACTGGTCATTCTCACATGTATTTGTGCA
TATTGAAAGAACAAAAGCTTCTTGATCTCATTCCGTTTTCAGGGAGCACAATCGTGGATGTTGGCCAAGACGAAGCT
ACTGCTTGTTCACTTTTAAAATCAATGGCTTTGAAGATACACGAACTTGTTGGTGCACAGATGCATCATCTTTCTGT
ATGCCAGTGGGAGGTGAAACTCAAGTTCTACTGTGATGGGCCTGCCAGTGGCACCTGGAGAGTTGTAACTACAAATG
TTACTAGTCACACTTGCACCGTTGATATCTACCGGGAAGTGGAAGATACTGAATCGCAGAAGTTAGTATACCATTCA
GCTTCTCCGTCAGCTAGTCCTTTGCATGGTGTGGCCCTGGATAATCCGTATCAACCTTTCACTGTCATTGATCTAAA
ACGCTGCTCTGCTAGGAACAACAGAACTACATATTGCTATGATTTTCCACTGGCATTGAAACTGCCCTGCAGAAGT
CATTGCAGTCCAATGGCTGCCAGTGTTTCTGAAGGCAGTGAAAATAGTAGGTCTTTATGTGAAAAGCAACAGAGCTGGTG
TTTGCTGAAAAACATGGGTCCTGGGGCACTGCTATAATTTCCATGGAGCGTCCCGCTGGGCTCAATGACATTGGCAT
GGTAGCTTGGATCTTACAGATCTCCACTCCTGAATTTCCAATGCCAGCCACATTATTGTCGTAGGCAAATGATATTA
CTTTCAGAGCTGGATCATTTGGCCTAAGCGAAGATGCGTTTTTTGAAGCTGTCACGAACCTGGCCTGCCAGAGGAAG
CTTCCCTCTTATATACTTGGCAGCAAACTCCGTGCTAGGATTGGCATAGCCGATGAAGTGAAATCTTGCTTCCGTGT
TGGGTGGTCCGATGAAGGTAGCCTTGAACGGCGTTTTCAGTACATTATCTGACTGACGAAGACTATGCCTGTATTA
GCTTGTCTGTATAGCACACAAGCTCCAGCTGCATAATGCTGAAATACGTCCATTATTCACTCTGTTGTGGGCAAG
GAGGATGGGCTTGGTGTTGAGAATATACATGGAAGTGCTGCTATTGCCAGTGCTTATTCTAGGGCATATGAGGAGAC
ATTTACACTTACATTTGTGACTGGGGGGACTGTTGGAATAGGAGCATATCTTGCTCGGCTCGTATACGGTGCATAC
AGCGTTCTTGACCAGCCTATTATTTAACTGGGTTTTCTGCCCCGAACAAGCTTCTTGGGCGGGAAGTGTACAGCTCC
CACATGCAGTTGCGTGCTCCTAAGATCATCGCGACCAAGGGTCTTGTCCACTTGTGTTTCACATGACCCTTCAACG
TGTTTCCAATATATTCAGGTGGCTCAGCTATGTTCCTGCCAACACTGGTGGACCTCTTCCTATTACAAAACTTTGG
ACCCACCAGACAGACCTGTTGCATACATCCCTGAGAACACATGTGATCCGCGCAGCCATTCGTGGTGTAGATGAC
AGCCAAGGGAAATGGTTGGCTGGTATGTTTGACAAAGACAGCCTTCGTCGAGACATTTGAAAGGATGGCCGAAAACAGT
GGTTACGGGCAGAGCAAAGCTTGGAGGAATTCCTGTTGGTGTCATAGCTGTGGAGACACAAACCATGATGCAGCTTA
TCCCTGCTGATCTAGGCCAGCTTGATTCCGATGAGCGATCTGTTCCTCGGGCTGGACAAGTGTGGTGCCCAGATTCT
GCAACCAAGACAGCTCAGGCATTGTTGCACTTCAACCGTAAGCATTGCCGCTGTTCATCCTTGCTAACTGAGAGG
ATTCTCTGGTGGACAAAGAGATCTGTTTGAAGGAATTCTTCAGGCTGGGCAACAATTGTTGCAGAACCTTAGGACAT
ACAATCAGCCTGCTTTTGTCTACATTCCTATGGCTGAGAGCTGCGTGGAGGCAGCTTGGGTTGTGGTTGATAGCAAA
ATAAATCCAGACCCAATTGAGTGTTATGCTCAGAGGCGTGCTAAAGGCAATGTTCTGGAACCTGCAAGGGTTAATTGA
AATCAAATTCAGATCAGAGCGCTCCAAGCACTGGTATGCTAGGCTTGACTTACAGTTTGATAAATCTGAAAGCAAAAC
TCCAGGCTGCAAAGCTTGGAAATGGAAGCCTAACAGATGTAGAATCCGTTCAGAAGAGTATAGATGCTCGTACGAAA
CAGTTCTTGCCTTTATACAGCCAGATTGCAATACGGTTTTGCTGAATTGCATGATACTTCCCTCACAATGGCAGCTAA
AGGTCTGATTAAGAAAGTTGTAGATTGCGAAGAATTACGTTCTTTCTTCTACAGAAGGCTACCGAGGAGGATCTCTG
AAGATGTTCTTTCAAAAGAAATAATAGCGAATAGCTGGTGACTACTTCACTTACCAATCAGCACTTGAGCTGATCAAG
GAATGGTACTTGCTTCTCAAGCCACAACAGGAAGCACTGAATGGGATGATGATGCTTTTGTTGCCTGGAAGGA
CAATCCTGAAAACTATAAGGGATATATCCAAGAGTTAAGGGCTCAAAAGGTGTCTCAGTCGCTCTCCATCTTGCAG
ACTCCAGTTCAGATCTAGAAGCATTCTCACAGGGTCTTTCCACATTATTAGATAAGATGGATCCCTCTCAGAGAGCC
AAGTTCATTCAGGAAGTCAAGAAGGTCCTGGGTTGA
```

FIGURE 13B

```
>AAL02056_Setaria italica (foxtail millet)
MSQLGLAAAASKALPLLPNREPTSAGTTFPSPVSSRPSNRRKSRTRSLRDGGDGVSDARRHNQSVRQGLAGIID
LPNEATSEVDISHESEDPRGPTDSYQMNGIVNEAHNGRRASVSKVVEFCAALGGKTPIHSILVANNGMAAAKEM
RSVRTWANDTFGSERAIQLIAMATPEDMRINAEHIRIADQFVSVPGGTNNNNYANVQLIVEVAERIGVSAVWPG
WGRASENPELPDALTARGIVFLGPPAASMNALGDKVGSALIAQAAGVPTLSWSGSHVEVPLECCLDAIPEEMYR
KACVTTTEKAVASCQVVGYPAMIKASWGSSGKGIRKVEHDDERVRALFKQVQGEVPGSPIFIMRLASQSRHLEVQ
LLCDQYGNVAALHSRDCSVQRREQKIIEEGPVTVAPRETVKALEQAARRLAKAVGTVGAATVEYLYSNETGEYY
FLELNPRLQVEEPVTEWIAEVSLPAAQVAVGMGIPLRQIPEIRRFYGMDYGGYDINRKTAALATPPNFDRVDS
QWPKGHCVAVRITSEDFDDGFKPTGGKVKEISFKSKPNVWAYFSVRSGGGIREFADSQFGHVFAYGLSRSAAIT
NMALALKEIQIRGEIHSNVDYTVDLLNASDFRENKIHTGWLDFRIAMRVQAERPPWYISVVGGALYKTVTANAA
TVSDYVSFLTKGQIPFRHISLVSSTVNLNTBGSKYTVEFVRTGHGSYRLRMNDSAIEANVQSLCDGGLLMQLDG
NSHVIYAEREAGGTRLLIDGKTCLLQNDHDFSKLLAETPCKLLRFLVADGAHVCADVFYAEVEVNRMCMPLLSP
ASGVIRVMMSEGQALQAGDLIARLDLDDPSAVKRAEFFHGIFFQMDLPVAAESQVHEKRYAASLNAARMVLAGYE
SNINEVVQDLVQCLDDPELPFLQWDELMSVLATRLPRNLKSELEDKYMEYRLNFYHGKNRDFPSKLLRDIIEAN
LAYGSSEKEKATNERLIEPLMSLLKSYEGGRESHAHFVVKSLFKEYLAVEELFSCGIQSDVIETLRHQHSKDLQK
VVDIVLSBQEVRNKAKLVTALMERLVYPNPAAYRDLLVRFSSINHRRYYKLALEASELIBQTRLSKLRASIARS
LSDIGMERKGEMTIEDSMEDLVSAPLPVEDALISLFDYSDPTVQQKVIETYIERLYQPLLVKDSIQVKFKESGAF
ALWEFSEGHVDIKNGQETVLGRTRWGAMVAVKSVESARTAIVAARLKDSAQHASSEGNMMRIALLSAENENNISD
DQAQHRMERKLNKILRDTSVANDLRAAGLKVISCIVQRDRARMPMRHTLLWSDRKSCYERERQIILRHVEPPLSMLL
EMDKLSVKGYNEMKYTFSRDRQWHIYTLRNTENPKMLERVFFRTIVRQPNAGNKPISAQIGDTEVGGPERSLSF
TSNSILRALMTATEELELHAIPTGHSEMYLCILKRQKLLDLIPFSGSTIVDVGQDEATACSLLKSMALKIHELV
GAQMEHLSVCQREVRLKLYCDGFASGTWRVVTTNVISETCTVDIYREVEDTESQKLVYRSASPSASPLEGVALD
NFYQPLSVIDLKRCSAPNNRTTYCYDFFLAFETALQKSWQSNGESVSEGSENSRSYVKSTELVFAERHGSWGFP
IISNERFAGLNDIGMVAWILEMSTPSFPNGRQIIVIANDITFRAGSFGPREDAFFEAVINLACERKLPLIYLAA
NSGARISIADEVKSCFRVGWSDEGSPERGFQYIYLTDEDYARISLSVIASRKLQLDNGEIRWIIDSVVGKSDGLG
VENIRGSAAIASAYSRAYEETFTLTFVTGRTVGIGAVLARLGTRCIQRLDQPIILPGFSALNKLLGREVYSSHM
QLGGFKIMATNGVVHLTVSDDLEGVSNILRWLSYVPAKIGGPLPITKPLDPPDRPVAYIPENTCDPRAAIRGVD
DSQGKNLGCMFDKDSFVETFEGWARTVVTGRAKLGGIPVGVIAVETQTMMQLIPADPGQLDSRERSVPRAGQVW
FPDSATEKTAQALLDFWREGLPLFILANWRGFSGGQRDLFEGILQAGSTIVENLRTYNQEAFVYIPMAGELRGGA
NVVVDSKINPDRIECYAERTAKGNVLEPQGLIEIKFRSEELQDCMCSLDPELINLKARLQGAKLGNGSLTDVES
LQKSIDARTKQLLPLYTQIAIRFASLEDTSLRMAAKGVIKKVVDWEELRSFFYRRLRRRISEDVLAKEIRGIAG
DHFTHQSAVELIKEWYLASQATTGSTEWDDDDAFVANKENPENYKGYIQELRAQKVSQSLSDLADSSEDLEAPS
QGLSTLLDRNDPSQRAKFIQEVRKVLG
```

FIGURE 14A

```
>AJ310767_Alopecurus_myosuroides (black-grass)
ATGGGATCCACAACATCTGCCCATTGTCGGGTTTAATGCATCCACAACACCATCGCTATCCACTCTTCGCCAGATAAA
CTCAGCTGCTGCTGCATTCCAATCTTCGTCCCTTCAAGGTCATCCAAGAAGAAAAGCCGACGTGTTAAGTCAATAA
GGGATGATGGCGATGGAAGCGTGTCAGACCTGGAGGATGGGAGTCTATTCGTAAGGTCTCGCTGGGATCATC
GACCTCCCAAAGGAGGGCGATCAGCTCCAGAGGTGGACATTCAATGGGTCTGAAGACCACAAGCCCTCCTACCA
AATGAATGGATACTGATGAATCACATAACGGGAGGCACGCCTCTCTGTCTAAAGTTTATCAATTTTGCACCGAAT
TGGGTGGAAAAACACCAATTCACAGTGTATTAGTGGCCAACAATGGAATGGCAGCAGCTAAGTTCATCGGAGTGTC
CGAGCATGGCTAATGATACATTGGGTCAGAGAAGCGATTCAGTTGATAGCTATGGCAACTCCGGAAGACATGAG
AATAAATCCACACCACATTACAATTCCTCATCAGTTTGTTGAAGTACCTGGTCGAACAAACAATAACAACTATGCAA
ATGTCCAACTCATAGTGCAGATAGCACAGAGAACTGGTGTCTCCGCCGTTTGGCCTGGGTTGGGGCCATCCATCTCAG
AATCCTGAACTTCCAGATGGCACTAACTGCAAAAGGAATTGTTTTCTTGGGCCACCAGCATCATCAATGAACGCACT
AGGCGACAAGGTTGGTTCAGCTCTCATTGCTCAAGCAGGAGGGGTTCCCACTCTTGCTTGGAGTGGATCACATGTGG
AAATTCCATTAGAACTTTGTTTGGACTCGATACCTCAGGACGGTGTATAGGAAAGCCTGTGTTACAACGCTGATGAA
GCAGTTGCAAGTTGTCAGATGATTGGTTACCCTGCCATGATCAAGGCATCCTGGGGTGGTGGTGGTAAAGCGATTAG
AAAGGTTAATAATGATGCGAGGGTGAAGCACTGTTTAAGCAAGTACAGGGTCAAGTTCCTGGCTCGCCGATATTTA
TCATGAGACTTGCATCTCAGAGTCCTCATCCTGAAGTCCAGCTGCTTTGTCATGAATATGGCAATGTAGCAGCACTT
CACCGTCGTGATTGCAGTGTGCAACGACGACACCAAAAGATTATCGAGGCACGACCAGTTACTCTTGCTCCTCCTCA
AACAGTGAAGAATCTAGAGCAAGCAGCAAGGAGGCTTGCTAAGGCCGTGGGTTACGTCGGTGCTGCTACTGTTGAAT
ATCTCTACAGCATGGAGACTGATGAATACTATTTCTGCCAGCTTAATGGACGGTTGCAGGTTGAGCACCCAGTCACC
GAGTGCATAGCTGAAGCTAAATTTGCCTGCAGCCGAAGTTGCAGTTTGGCATGGTATAGCTTTGCCAGATTCCAGAA
GATCAGACGTTTCTACGGAATGGACAATGGAGGAGCCTATGATATTTGGAGGAAAACAGCAGCTCTCGCTACTCCAT
TCAACTTTGATGAAGTAGATTCTCAATGGCCGAAGGGTCATTGTGTGGCAGTTAGGATAACCAGTGAGAATCCAGAT
GATGGATTCAAGCCTACTGGTGGAAAGTAAGGCACATAAGTTTTAAAAGTAAGCCCAAATGTCTGGGGATATTTCTC
AGTTAAGTCTGGTCGAGCCCATTCATCGAATTTGCCCATTCTCAGTTTTCGACACGTTTTTGCCTATGGAGAGACTAGAT
CAGCAGCAATAACCAGCATGTCTCTTGCACTAAAGAGATTCAAATTCGTGGAGAAATCATACAAACGTTGATTAC
ACGGTTGATCTCTTGAATGCCCAGACTTCAGAGAAAACACGATCCATACCGGTTGGCTGGATACCAGAATAGCTAT
GGGTGTTCAAGCTGAGAGGCCTCCCTGGTATATTTCAGTGGTTGGAGGAGCCTCTATATAAACAATAACCACCAATG
CGGAGACCGTTTCTGAATATGTTAGCTATCTCATCAAGGGTCAGATTCCACCAAAGCACACATATCCCTTGTCATTCA
ACTATTTCTTTGGAATATAGACGAAACCAAATATACAATTGAGATGTCGAGGAGTGGACAGGGTACCTACAGATTGAG
ACTGAATGGATCACTTATTGAAGCCAATGTACAAACATTATGTGATGGAGGCCTTTAATGCAGCTGGATGGAAATA
GCCATGTTATTTATGCTGAAGAGGAAGCGGGTGGTACACGGCTTCTTATTGATGGAAAACATGCTTGCTACAGAAT
GACCATGATCGGTCAAGGTTATTAGCTGAGACACCCTGCAAACTTCTTCGTTTCTTGATTGCCGATGGTGCTCATGT
TGATCCTGATCTACCATACGCCGGAGCTTGAGGTTATGAAGATGTCCATCCCCCTCTTGTCGCCTGCTGCGGGTGACA
TTAATGTTTTGTTCTCTGAGGGGCAGGCGATGCAGGCTGGGGATCTTATAGCGAGACTTGATCTGATGAACCTTCT
GCTGTGAAGAGAGCCGAGCCATTTGAAGGATCTTTCCAGAAATGAGCCTTCCTATTGCTGCTTCTGGCCAAGTTCA
CAAAAGATGTGCTGCAGCTTTGAAACGCTGCTCGAATGTCCTTGCAGGATATGACCATGTGGCCAACAAAGTTGTGC
AAGATTTGGTATGCTGCCTTGATACACCTGCTCTCCTTCCTACAATGGGAAACAGCTTATGTCTGTTTTAGCAACT
AGACTTCCAAGACCTCTTAAGACCCAGTTGCAGGGCAAATACAATGAATACAAGTTAAGTTGTCAGCCATGTGAAGAT
CAAGGATTTCCTACCGGACGATGCTTAGAGAGACAATGCAGGGAAAATCTTGCCATGTGTTCCCAGAAGCAAATGGTGA
CAATTGAGAGGCTTGTTGACCCCTCTGATGACCTGCTCAAGTCATACGAGGTGGAGAGAAASCCATGCCCACTTT
ATTCGCAAGTCCTTTTTGAGGACTATCTCGCGTTCACGAACTATTCAGTGATGCCATTCAGTCTGACGTGATTGA
ACGCCTGCGCCTACAATATAGTAAGACCTCCAGAAGGTTGTAGACATTGTTTTGTCTCACCAGGGTGTGAGAAACA
AAACAAAGCTGATACTGCGCTCATGGAGAAACGGTCTATCCAAACCCTGCTGCCTACAGAGATCAGTTAATCGC
TTTTCTTCCCTCAACCATAAAAGATATTATAAGTTGCCTCTTAAAGCTAGTGAACTTCTTGAACAAACCAAGCTCAG
CGGACTCCGCACAAGCATTGCAAGGAACCTTTCAGCGCTGGATATGTTCACCGAGGAAAAGGCAGATTCTCCTTGC
AAGACAGAAAATTGGCCATTAATGAGAGCATGGAGATTTAGTCACTGCCCACTGCCAGTGAAGATGCACTTGTT
TCTTTGTTTGATTGTACTGATCAAACTCTTCAACAGAGTGAATCAGACATACATATGCTCCATTATACCCGCCTCA
ACTTGTGAAGGAATAGCATCCAAGCTGAAATATCAGGATTCTGGTGTTATTGCTTTATGGGAATTCACTGAAGGAAATC
ATGAAGAGAGATTGGGTGCTATGGTTATCCTGAAGCTCACTAGAAACTGTGTCAACAGGCCATGGAGCTGCTCTAAAG
GATGCATCACATTATGCAAGCTCTGCGGGCAACACGGTGCATATTGCTTTGTTGGATGCTGATACCCAACTGAATAC
AACTGAAGATAGTGGTGATAAAGACCAAGCTCAAGACAAGATGGATAAACTTTCTTTTGTACTGAAACAAGATGTTG
TCATGGCTGATCTACCTGCTGCTGATGTCAAGCTTGTTACTGCATTGTTCAAACACATGGCAGCAATCATGCCTATG
CGGCGTACCTTCCTCTTGTCAGAGGAAAAACTTTGTTACGAGGAAGAGCCGATCTTCGGCATGTGGAGCCTCCACT
TTCTGCACTTCTTGAGTTGGATAAATTCAAAGTCAAAGCATACAATGAGATGAAGTATACACCGTCACGTGATCGTC
```

FIGURE 14A (continued)

FIGURE 14B

```
>CAC84161 Alopecurus myosuroides (black-grass)
MGSTELPIVGFNASTTPSLSTLRQINSAAAAFQSSSPSRSSKKKSRRVKSIRDDGDGSVPDPAGHGQSIRQGLA
GIIDLPKRGASAPDVDISHGSEDHKASYQMNGILNESHNGRHASLSKVYEFCTELGGKTDIRSVLVANNGMAAA
KFMRSVRTWANDTFGSEKAIQLTAMATPRDMRINAEHIBIADQFVEVPGGTNNNNYANVQLIVEIAERTGVSAV
WPGWGHASENPELPDALTAKGIVFLGPPASSMNALGDKVGSALIAQAAGVPTLAWSGSHVEIPLELCLDSIPEE
MYRKACVTTADEAVASCQMISYPAMIKASWGGGGKGIRKVNNDEVKALFKQVQGEVPGSPIFIMRLASQSRRL
RVQLLCDRYGNVAALHSRDCSVQRREHQKIIERGPVTVAPRETVKELEQAAKRLAKAVGYVGAATVEYLYSMETG
RYYPLEINERLQVEHPVTESIAEVNLPAAQVAVGMGIPLWQIPEIRRFYGMDNGGGYDIWRRTAALATPSNFDR
VDSQWFKGHCVAVRITSENPDCGFKPTGGRVKEISFKSKPNVWGYFSVKSGGGIHEFADSQFGHVFAYGETRSA
AITSMSLAIKEIQIRGEIHPNVDYTVDLLNAPDFRENTIETGWLDTRIAMRVQAERPPWYISVVGGALYKTITE
NAETVSEYVSYLIKGQIPPKEISLVESTISLNIEESKYTIEIVRSGQGSYRLRLMGSLIEANVQTLCDGGLIMQ
LDGNSHVIYAEEEAGGTRLLIDGRTCLLQNDHDPSRLLAETPCKLLRFLIADGAHVDADVPYAEVEVMFMCMPL
LSPAAGVINVLLSEGQAMQAGDLIARLDLDDPSAVKRAEPFFGSFPEMSLPTAASGQVEKRCAARSLNAARMVLA
GYDRAAMKVVQDLVWCLDTPALPFLQWEELMSVLATRLPRRLKSELEGKYNEYKLNVDEVKIKQEPTEMLRETI
EENLACVSEKEMVTIERLVDPIMSLLKSYEGGRESHAEFIVKSLFEEYLSVEELFSDGIQSDVIERLRLQYSKD
LQKVVDIVLSRQGVRNRTKLILALMEKLVYPSPAAYRDQLIRFSSLNHKRYYKLALKASELLEQTKLSELPTSI
ARNLSALSMFTEEKADFSLQDPHIAINESMGDLVTAPLFVEDALVSLFTKTDQTLQQRVIQTYISRLYQPQLVK
DSIQLKYQDSGVIALWRFTESNHEKRLGAMVILKSIESVSTAIGAALKDASHYASSAGNTVHIALLDADTQLNT
TEDSGDNDQAQDKMDKLSFVLKQDVVMADLRAADVKVVSCIVQRDGAIMPMKRTFLLSEEKLCYEEEPILRHVE
PPLSALLELDKLKVKGYNEMKYTPSRDRQWHIYTLRNTENPKMLSSVFFRTLVRQPSAGNRFTSDHITDVEVGH
AEEPLSPTSSSILKSLKIAKEELELRAIRTGHSRMTLCILKEQKLLIDLVPVSGNTVVDVGQDEATACSLLKEMA
LRIRRLVGAPMHELSVCQWEVKLKLVSDGPASGSWRVVTTNVTGETCTVDIYREVEDTESQKLVYHSTALSSGP
LRGVALNTSYQPLSVIDLKRCSABNNKTTYCYDFPLTFEAAVQKSWSNISSENNQCYVKATELVFAERNGSWGT
PIIPMQRAAGLNDIGMVAWILDMSTPRFPSGRQIIVIANDITFRAGSFGPREDAFFEAVTNLACEKKLPLIYLA
ANSGARIGIADEVKSCFRVGNTDDSSPERGFRYIYMTDEDHDRIGSSVIANKMQLDSGEIRANVIDSVVGREDGL
GVENIHGSARIASAYSRAYRRTFTLTFVTGRTVGIGAYLAPLGIRCIQRIDQPIILTGFSALNKLLGREVYSSH
MQLGGPKIMATNGVVHLTVPDDLEGVSNILRWLSYVPANIGGPLFIEKSLDPIDRPVAYIPENTCDPRAAISGI
DDSQQKWLGGMFDKDSFVETFRGWAKTVVTGRAKLSGIPVGVIAVETQTMMQLVPADFGQPDSHERSVPRAGQV
WFPDSAFKTAQAMLDFNREGLPLFILANWRGFSGGQRDLPEGILQAGSTIVENLRTYNQPAFVYIPKAARLRGG
ANVVIDSKINFDRIECYAERTAKGNVLRPQGLIEIKFRSEELKECMGRLDPELIDLKARLQGANGSLSDGRSLQ
KSIEARKKQLLFLYTQIAVRPAELHDTSLRMAAKGVIRRVVDWEDSRSFYKRLRRKLSEDVLAKEIRGVIGEK
FPHKSAIELIKKWYLASEAAAGSTDWDDQDAFVARRENPENYKEYIKELPAQRVSRLLSDVAGSSSDLQALPQ
GLSMLLDRMDPSKRAQFIEEVMKVLK
```

FIGURE 15A

>EU660897 Aegilops tauschii (jointed goatgrass)

FIGURE 15A (continued)

FIGURE 15B

```
>ACD46679_Aegilops tauschii (jointed goatgrass)
MGSTRLPIVGLNASTTPSLSTIRPVNSAGRAFQPSAPSRTSRKKSRRVQSLRDGGDGGVSDPNQSIRQGLAGII
DLPKEGTSAPEVDISHGSERPRGSYQMSNGILNEAHNGRHASLSKVVEPCMALGGKTPIRSVLVANNGMAAAKEM
RSVRTWANETPGSEKAIQLIAMATPEDMRINAERIPIADQSVEVPGGTNNNNYANVQLIVEIAVRTGVSAVWPG
WGHASENPELPDALNANGIVELGPPSSSMNALGDHVGSALIAQAAGVPTLPWSGSQVEIPLEVCLDSIPADMYR
MACVSTTEEALASCQMIGYPAMIKASWGGGKGIRSVNNDDDVRALFKQVQGEVFGSPIFIMRLASQSRHLEVQ
LLCDQYGNVAALHSRDCSVQRRHQKIIERGPVTVAPRETVKELRQAARRLAKAVGYVGAATVEYLYSMETGEYY
PLELNPRLQVEHPVTEWIAEVNLPAAQVAVGMGIPLWQVPEIRRFYGNINGGGYDIWRKTAALATPPNFDEVDS
QWPKGHCVAVRITSEDPDDGFKPTGGKVKEISFKSKPNVWAYFSVKSGGGIHEFADSQFGRVFAYGVSBAAAIT
NMSLALKEIQIRGEIHSNVDYTVDLLNASDFKNNRIHTGWLINRIAMRVQAERPPWYISVVGGALYKTITSNTD
TVSEYVSYLVKQQIPPMHISLVHSTVSLNIEESRYTIETIRSGQGSYRISMNCSVIRANVQTLCDGGLLMQLDG
NSHVIYAEEEAGGTPRLLIDGRTCLLQNDHDPSRLLAETPCKLLRFLVADGAHVEADVPYAEVEVMRMCMPLLSP
AAGVINVLLSEGQPMQAGDLIARLDLDDFSAVKRAEPPNGSPFMSLPIAASGQVHRKCATSLNAARMVLAGYD
HPINKVVQDLVSCLDAPELPFLQWEELMSVLATRLPRLLKSELEGKYSEYKLNVGHGRSKDFPSKNLREITEEN
LARGSEKEIATNERLVEPLMSLLKSVEGGRESHAHFIVKSLFEDYLSVEELFSDGIQSDVIERLRQQHSKDLQK
VVDIVLSHQGVRNKUKLILTIMEKLVYPNPAAYKDQLTRFSSLNEKRYYKLALKASELLRQTKLSELRTSIARS
LSELEMFTEERTAISEIMGDLVTAPLPVEDALVSLFDCSDQTLQQRVIETYISRLYQPRLVKDSIQLKYQESGV
IALWRFAEAHSERKLGAMVTVKSLESVSAAIGAALRGTSRYASSEGNIMRIALLGAIKQMHGTEDSGDNDQAQV
RIDKLSATLEQNTVTADLRAAGVKVISCIVQRDGALMPMRHTPLLSDEKLCYEEEPVLRAVEPPLSALLELGKL
KVKGYNEVKYTPSRDRQWNIYTLRNTRNFKMLRSVFPRTLVRQPGASNKFTSGNISCVEVQGAEESLSFTSCSI
LRSLMTAIEELELRAIATGRSHMFLCILREQKLLDLVPVSGNKVVDTGQDEATACLLLRKMALQIRELVGARMH
HLSVCQWEVELKLDSDGPASGTWRVVTTNVTSHTCFVDIYREVEDTESQKLVYHSAPSSGPLHGVALNTPTQP
LSVTDLKRCSARNNETTYCYDFPLAFETAVQKSWSNISSDTNRCYVKATELVPARKNGSWGTPVIPKERPAGLN
DIGMVANILDMSTPEYPNGRQIVVIANDITPRAGSPGPREDAFEETVTNLACERKLFLIYLAANSGARIGIADE
VKSCEPVGWSDDGSPRRGFQYIYLTEEDHARISASVIAHKMQLINGEIRWVIDSVVGKEDGLGVENIHGSAAIA
SAYSRAYEFFPTLTFVTGRTVGTGAYLARLGIRCIQRFSQPIILTGFSAINKLLGREVYSSHMQLGGPKIMATN
GVVELTVSDDLEGVSNILRWLSYVPANIGGPLPITKSLDPPDRPVAYIPENTCSPRAAISGIDESQGKWLGSMP
DKDSPVETPEGWAKSVVTGRAKLGGIPVGVIAVETQTMMQLIPADPGQLDSRERSVPRAGQVWFPDSAPKTAQA
MLDFNRECLPLPILANWRGFSGSQRDLPEGILQAGSTIVENLRTYNQPAFVYIFKAAELRGGANVVIDSKINPD
RIEFYAERTAKGNVLEPQGLIEIKFRSEELQECMGELDPELINLRAKLLGAKRENGSLSESESIQRSIEARKKQ
LLPLYTQIAVRFAELHDTSLRMAAKCVIRKVVDWEDSRSFFYKELRRRYSEDYLAKEIRGVSGKQFSRQSAIEL
IQKWYLASKGAETGNTEWDDDDAFVANRENPENYQRYIKELRAQRVSQLLSDVADSSPDLEALPQGLSMLLEKN
DPSRRAQFVEEVKKALK
```

FIGURE 16

| ACCase Mutation | Selections Agent | #exp | # ies | # Putative events | Putative TE | # Confirmed events | Confirmed TE | % escapes |
|---|---|---|---|---|---|---|---|---|
| RLM185 | pursuit | 2 | 27 | 15 | 56% | 14 | 52% | 4% |
| | cycloxydim | 2 | 29 | 0 | 0% | 0 | 0% | 0% |
| | tepraloxydim | 2 | 29 | 0 | 0% | 0 | 0% | 0% |
| I7831L | pursuit | 2 | 40 | 22 | 55% | 21 | 53% | 3% |
| | cycloxydim | 2 | 50 | 16 | 32% | 15 | 30% | 2% |
| | tepraloxydim | 2 | 50 | 0 | 0% | 0 | 0% | 0% |
| I1781L, W202C | pursuit | 2 | 40 | 10 | 25% | 9 | 23% | 3% |
| | cycloxydim | 2 | 50 | 20 | 40% | 20 | 40% | 0% |
| | tepraloxydim | 2 | 50 | 11 | 22% | 11 | 22% | 0% |
| I1781L, I2041N | pursuit | 2 | 40 | 10 | 25% | 9 | 23% | 3% |
| | cycloxydim | 2 | 50 | 12 | 24% | 12 | 24% | 0% |
| | tepraloxydim | 2 | 50 | 14 | 28% | 14 | 28% | 0% |
| I7831A | pursuit | 2 | 35 | 16 | 46% | 14 | 40% | 6% |
| | cycloxydim | 2 | 50 | 0 | 0% | 0 | 0% | 0% |
| | tepraloxydim | 2 | 50 | 0 | 0% | 0 | 0% | 0% |
| Wild Type | pursuit | 2 | 30 | 16 | 53% | 15 | 50% | 3% |
| | cycloxydim | 2 | 50 | 0 | 0% | 0 | 0% | 0% |
| | tepraloxydim | 2 | 50 | 0 | 0% | 0 | 0% | 0% |

FIGURE 18

```
   1 MGSTHLFIVG FNASTTFSLS TLRQINSAAA AFQSSSFSKS SKKKSRRVKS IRDDGDGSVP
  61 DPAGHGQSIR QGLAGIIDLF KEGASAFDVD ISHGSEDHKA SYQMNGILNE SHNGPHASLS
 121 KVYEFCTRLG GKTFIHSVLV ANNGMAAAKF MRSVRTWAND TFGSEKRIQL IAMATPEDMR
 181 INAEHIRIAD QFVEVPGGTN NNNYANVQLI VEIAERTGVS AVWPGWGHAS ENPELPDALT
 241 AKGIVFLGPF ASSMNALGDK VGSALIAQAA GVPTLAWSGS HVEIPLELCL DSIPEEMYRK
 301 ACVTTADEAV ASCQMIGYPA MIKASWGGGG KGIRKVNNDD EVKALFKQVQ GEVPGSFIFI
 361 MRLASQSRHL EVQLICDRYG NVAALHSRDC SVQRRHQKII EEGFVTVAPR STVKELSQRA
 421 RRLAKAVGYV GAATVEYLYS METGEYYFLE LNPRIQVERP VTESIAEVNL PAAQVAVGMG
 481 IPLWQIPEIR RFYGMDNGGG YDINRKTAAL ATPFNFDEVD SQWPKGHCVA VRITSENPDD
 541 GFKPTGGKVK RISFKSKPNV WGYFSVKSGG GIREFADSQF GKVFAYGETR SAAITSMSLA
 601 LKRIQIRGEI HTNVDYTVDL LNAPCFRENT IHTGWLDTRI AMRVQAERFP WYISVVGGAL
 661 YKTIITNAST VSEYVSYLIK GQIPPKHISL VHSTISLNIE ESKYTIEIVR SGQGSYRLRL
 721 NGSLIEANVQ TLCDGGLLMQ LDGNSHVIYA SSBAGGTRLL IDGKTCLLQN DHDPSRLLAS
 781 TPCKLLRFLI ADGAHVDADV PYAEVEVMSM CMPLLSPAAG VINVLLSECQ AMQRGDLIAS
 841 LDLDDPSAVK RAEFFEGSFP SMSLPIAASC QVHKRCAASL NAARMVLAGY DHAANKVVQD
 901 LVWCLDTFAL PFLQWERLMS VLATRLFRRL KSELEGKYNR YMLNVDBVKI KDFPTEMLRE
 961 TIEENLACVS EKEMVTIRRL VDPLMSLLKS YEGGRESHAH FIVKSLFEEY LSVERLFSDG
1021 IQSDVIERLR LQYSKELQKV VDIVLSHQGV RNKTKLILAL MEKLVYPNPA AYRDQLIRFS
1081 SLNHKRYYKL ALKASELLEQ TKLSEIRTSI ARNLSALDMF SEEKADFSLQ DRKLAINESM
1141 GDLVTAFLFV SDALVSLFDC TSQTLQQRVI QTYISRLYQP QLVKDSIQLK YQDSGVIALW
1201 EFTEGNHEKR LGAMVILKSL ESVSTAIGAA LKDASHYASS AGNTVHIALL DADTQLNTTE
1261 DSGDNDQAQD KMDKLSFVLK QDVVMADLRA ADVKVVSCIV QRDGAIMPMR RTFLLSEEKL
1321 CYRREFILRH VEPPLSALLE LDKLKVRGYN SMKYTPSRDR QWHIYTLRNT ENPKMLHRVF
1381 FRTLVRQFSA GNBFTSDHIT DVSVGNAEEP LSFTSSSILK SLKIAKEELE LHAIRTGNSH
1441 MYLCILKEQK LLDLVFVSGN TVVDVGQDEA TACSLLKEMA LKIHELVGAR MHHLSVCQWE
1501 VKLKLVSDGP ASGSWRVVFT NVTGHTCTVD IYREVEDTES QKLVYHSTAL SSGPLHGVAL
1561 NTSYQFLSVI DLKRCSARNN KPTYCYDFPL TFEAAVQKSW SNISSENNQC YVKATELVFA
1621 EKNGSWGTPI IPMQRAAGLN DIGMVAWILD MSTPEFPSGR QIIVIANDIT FRAGSPCPRE
1681 DAFFEAVTNL ACEKKLPEIY LAANSGARIG IADEVKSCFR VGWTDDSSFE RGFRYIYMTD
1741 EDHERIGSSV IAHKMQLDSG RIBWVIDSVV GKEDGLGVEN IHGSAAIASA YSRAYRETFT
1801 LTFVTGRTVG IGAYLAPLGI RCIQRIDQPI ILTGFSALMK LLGRRVYSSH MQLGGPKIMA
1861 TNGVVHLTVP DDLSGVSNIL RWLSYVPARI GGPLPITKSL DFIDRFVAYI PENTCDFRAA
1921 ISGIDDSQGK WLGGMFDKDS FVETFEGWAK IVVTGRAKLG GIPVGVIAVE TQTMMQLVFA
1981 DPGQPDSHER SVPRAGQVWF PDSATKTAQA MLDFNREGLP LFILAMWRGF SGGQRDLFEG
2041 ILQAGSTIVE NLRTYNQFAF VYIPKAAELR GGAWVIDSK INPDRISCYA ERTAKGNVLE
2101 PQGLIEIKFR SSELRRCMGR LDFELIDLKA RLQGANGSLS DGSSLQKSIE ARKKQLLPLY
2161 TQIAVRFAEL HDTSLRMAAK GVIRKVVDWE DSRSFFYKRL RRRLSEDVLA KEIRGVIGEK
2221 FPHKSAIELI KKWYLASERA AAGSTDWDDD DAFVAWRENP ENYKEYIKEL RAQRVSRLLS
2281 DVAGSSSDLQ ALPQGLSMLL DKMDPSKRAQ FIEEVMKVLK
```

FIGURE 19

```
                                      1                                                          60
        AmACCI [CAC84161]       (1)   MGSTHLPIVGFNASTTPSLSTLRQINSAAAAFQSSSPSRSSKKKSRRVKSIRDDGDGSVP
   OSIACCI [BGIOSIBCE018385]    (1)   MTSTHVATLGVGAQAPPRHQ---KKSAGTAFVSSGSSRPSYRKNGQRTRSLREESNGGVS
        OSJACCI [EAZ33685]      (1)   MTSTHVATLGVGAQAPPRHQ---KKSAGTAFVSSGSSRPSYRKNGQRTRSLREESNGGVS 61                                                         120
        AmACCI [CAC84161]      (61)   DPAGHGQSIRQGLAGIIDLPKEGASAPDVDISHGSEDHKA-----SYQMNGILNESHNGR
   OSIACCI [BGIOSIBCE018385]   (58)   DSKKLNHSIRQGLAGIIDLPNDAAS--EVDISHGSEDPRGPTVPGSYQMNGIINETHNGR
        OSJACCI [EAZ33685]     (58)   DSKKLNHSIRQGLAGIIDLPNDAAS--EVDISHGSEDPRGPTVPGSYQMNGIINETHNGR 121                                                        180
        AmACCI [CAC84161]     (116)   HASLSKVYEFCTELGGKTPIHSVLVANNGMAAAKFMRSVRTWANDTFGSEKAIQLIAMAT
   OSIACCI [BGIOSIBCE018385]  (116)   HASVSKVVEFCTALGGKTPIHSVLVANNGMAAAKFMRSVRTWANDTFGSEKAIQLIAMAT
        OSJACCI [EAZ33685]    (116)   HASVSKVVEFCTALGGKTPIHSVLVANNGMAAAKFMRSVRTWANDTFGSEKAIQLIAMAT 181                                                        240
        AmACCI [CAC84161]     (176)   PEDMRINAEHIRIADQFVEVPGGTNNNNYANVQLIVEIAERTGVSAVWPGWGHASENPEL
   OSIACCI [BGIOSIBCE018385]  (176)   PEDLRINAEHIRIADQFVEVPGGTNNNNYANVQLIVEIAERTGVSAVWPGWGHASENPEL
        OSJACCI [EAZ33685]    (176)   PEDLRINAEHIRIADQFVEVPGGTNNNNYANVQLIVEIAERTGVSAVWPGWGHASENPEL 241                                                        300
        AmACCI [CAC84161]     (236)   PDALTAKGIVFLGPPASSMNALGDKVGSALIAQAAGVPTLAWSGSHVEIPLELCLDSIPE
   OSIACCI [BGIOSIBCE018385]  (236)   PDALTAKGIVFLGPPASSMHALGDKVGSALIAQAAGVPTLAWSGSHVEVPLECCLDSIPD
        OSJACCI [EAZ33685]    (236)   PDALTAKGIVFLGPPASSMHALGDKVGSALIAQAAGVPTLAWSGSHVEVPLECCLDSIPD 301                                                        360
        AmACCI [CAC84161]     (296)   EMYRKACVTTADEAVASCQMIGYPAMIKASWGGGGKGIRKVNNDDEVKALFKQVQGEVPG
   OSIACCI [BGIOSIBCE018385]  (296)   EMYRKACVTTTEEAVASCQVVGYPAMIKASWGGGGKGIRKVHNDDEVRTLFKQVQGEVPG
        OSJACCI [EAZ33685]    (296)   EMYRKACVTTTEEAVASCQVVGYPAMIKASWGGGGKGIRKVHNDDEVRTLFKQVQGEVPG 361                                                        420
        AmACCI [CAC84161]     (356)   SPIFIMRLASQSRHLEVQLLCDEYGNVAALHSRDCSVQRRHQKIIEEGPVTVAPRETVKE
   OSIACCI [BGIOSIBCE018385]  (356)   SPIFIMRLAAQSRHLEVQLLCDQYGNVAALHSRDCSVQRRHQKIIEEGPVTVAPRETVKE
        OSJACCI [EAZ33685]    (356)   SPIFIMRLAAQSRHLEVQLLCDQYGNVAALHSRDCSVQRRHQKIIEEGPVTVAPRETVKE 421                                                        480
        AmACCI [CAC84161]     (416)   LEQAARRLAKAVGYVGAATVEYLYSMETGEYYFLELNPRLQVEHPVTESIAEVNLPAAQV
   OSIACCI [BGIOSIBCE018385]  (416)   LEQAARRLAKAVGYVGAATVEYLYSMETGEYYFLELNPRLQVEHPVTEWIAEVNLPAAQV
        OSJACCI [EAZ33685]    (416)   LEQAARRLAKAVGYVGAATVEYLYSMETGEYYFLELNPRLQVEHPVTEWIAEVNLPAAQV 481                                                        540
        AmACCI [CAC84161]     (476)   AVGMGIPLWQIPEIRRFYGMDNGGGYDIWRKTAALATPFNFDEVDSQWPKGHCVAVRITS
   OSIACCI [BGIOSIBCE018385]  (476)   AVGMGIPLWQIPEIRRFYGMNHGGGYDLWRKTAALATPFNFDEVDSKWPKGHCVAVRITS
        OSJACCI [EAZ33685]    (476)   AVGMGIPLWQIPEIRRFYGMNHGGGYDLWRKTAALATPFNFDEVDSKWPKGHCVAVRITS 541                                                        600
        AmACCI [CAC84161]     (536)   ENPDDGFKPTGGKVKEISFKSKPNVWGYFSVKSGGGIHEFADSQFGHVFAYGETRSAAIT
   OSIACCI [BGIOSIBCE018385]  (536)   EDPDDGFKPTGGKVKEISFKSKPNVWAYFSVKSGGGIHEFADSQFGHVFAYGTTRSAAIT
        OSJACCI [EAZ33685]    (536)   EDPDDGFKPTGGKVKEISFKSKPNVWAYFSVKSGGGIHEFADSQFGHVFAYGTTRSAAIT 601                                                        660
        AmACCI [CAC84161]     (596)   SMSLALKEIQIRGEIHTNVDYTVDLLNAPDFRENTIHTGWLDTRIAMRVQAERPPWYISV
   OSIACCI [BGIOSIBCE018385]  (596)   TMALALKEVQIRGEIHSNVDYTVDLLNASDFRENKIHTGWLDTRIAMRVQAERPPWYISV
        OSJACCI [EAZ33685]    (596)   TMALALKEVQIRGEIHSNVDYTVDLLNASDFRENKIHTGWLDTRIAMRVQAERPPWYISV 661                                                        720
        AmACCI [CAC84161]     (656)   VGGALYKTITTNAETVSEYVSYLIKGQIPPKHISLVHSTISLNIEESKYTIEIVRSGQGS
   OSIACCI [BGIOSIBCE018385]  (656)   VGGALYKTVTANTATVSDYVGYLTKGQIPPKHISLVYTTVALNIDGKKYTIDTVRSGHGS
        OSJACCI [EAZ33685]    (656)   VGGALYKTVTANTATVSDYVGYLTKGQIPPKHISLVYTTVALNIDGKKYTIDTVRSGHGS 721                                                        780
        AmACCI [CAC84161]     (716)   YRLRLNGSLIEANVQTLCDGGLLMQLDGNSHVIYAEEEAGGTRLLIDGKTCLLQNDHDPS
   OSIACCI [BGIOSIBCE018385]  (716)   YRLRMNGSTVDANVQILCDGGLLMQLDGNSHVIYAEEEASGTRLLIDGKTCMLQNDHDPS
        OSJACCI [EAZ33685]    (716)   YRLRMNGSTVDANVQILCDGGLLMQLDGNSHVIYAEEEASGTRLLIDGKTCMLQNDHDPS 781                                                        840
```

FIGURE 19 (continued)

```
      AmACCI [CAC84161]   (776)  RLLAETPCKLLRFLIADGAHVDADVPYAEVEVMKMCMPLLSPAAGVINVLLSEGQAMQAG
OSIACCI [BGI0SIBCE018385]  (776)  KLLAETPCKLLRFLVADGAHVDADVPYAEVEVMKMCMPLLSPASGVIHVVMSEGQAMQAG
     OSJACCI [EAZ33685]   (776)  KLLAETPCKLLRFLVADGAHVDADVPYAEVEVMKMCMPLLSPASGVIHVVMSEGQAMQAG 841                                                         900
      AmACCI [CAC84161]   (836)  DLIARLDLDDPSAVKRAEPFEGSFPEMSLPIAASGQVHKRCAASLNAARMVLAGYDHAAN
OSIACCI [BGI0SIBCE018385]  (836)  DLIARLDLDDPSAVKRAEPFEDTFPQMGLPIAASGQVHKLCAASLNACRMILAGYEHDID
     OSJACCI [EAZ33685]   (836)  DLIARLDLDDPSAVKRAEPFEDTFPQMGLPIAASGQVHKLCAASLNACRMILAGYEHDID 901                                                         960
      AmACCI [CAC84161]   (896)  KVVQDLVWCLDTPALPFLQWEELMSVLATRLPRRLKSELEGKYNEYKLNVDHVKIKDFPT
OSIACCI [BGI0SIBCE018385]  (896)  KVVPELVYCLDTPELPFLQWEELMSVLATRLPRNLKSELEGKYEEYKVKFDSGIINDFPA
     OSJACCI [EAZ33685]   (896)  KVVPELVYCLDTPELPFLQWEELMSVLATRLPRNLKSELEGKYEEYKVKFDSGIINDFPA 961                                                        1020
      AmACCI [CAC84161]   (956)  EMLRETIEENLACVSEKEMVTIERLVDPLMSLLKSYEGGRESHAHFIVKSLFEEYLSVEE
OSIACCI [BGI0SIBCE018385]  (956)  NMLRVIIEENLACGSEKEKATNERLVEPLMSLLKSYEGGRESHAHFVVKSLFEEYLYVEE
     OSJACCI [EAZ33685]   (956)  NMLRVIIEENLACGSEKEKATNERLVEPLMSLLKSYEGGRESHAHFVVKSLFEEYLYVEE 1021                                                       1080
      AmACCI [CAC84161]  (1016)  LFSDGIQSDVIERLRLQYSKDLQKVVDIVLSHQGVRNKTKLILALMEKLVYPNPAAYRDQ
OSIACCI [BGI0SIBCE018385] (1016)  LFSDGIQSDVIERLRLQHSKDLQKVVDIVLSHQSVRNKTKLILKLMESLVYPNPAAYRDQ
     OSJACCI [EAZ33685]  (1016)  LFSDGIQSDVIERLRLQHSKDLQKVVDIVLSHQSVRNKTKLILKLMESLVYPNPAAYRDQ 1081                                                       1140
      AmACCI [CAC84161]  (1076)  LIRFSSLNHKRYYKLALKASELLEQTKLSELRTSIARNLSALDMFTEEKADFSLQDRKLA
OSIACCI [BGI0SIBCE018385] (1076)  LIRFSSLNHKAYYKLALKASELLEQTKLSELRARIARSLSELEMFTEESKGLSMHKREIA
     OSJACCI [EAZ33685]  (1076)  LIRFSSLNHKAYYKLALKASELLEQTKLSELRARIARSLSELEMFTEESKGLSMHKREIA 1141                                                       1200
      AmACCI [CAC84161]  (1136)  INESMGDLVTAPLPVEDALVSLFDCTDQTLQQRVIQTYISRLYQPQLVKDSIQLKYQDSG
OSIACCI [BGI0SIBCE018385] (1136)  IKESMEDLVTAPLPVEDALISLFDCSDTTVQQRVIETYIARLYQPHLVKDSIKMKWIESG
     OSJACCI [EAZ33685]  (1136)  IKESMEDLVTAPLPVEDALISLFDCSDTTVQQRVIETYIARLYQPHLVKDSIKMKWIESG 1201                                                       1260
      AmACCI [CAC84161]  (1196)  VIALWEFTEGNHEKR----------LGAMVILKSLESVSTAIGAALKDASHYASSAGNTV
OSIACCI [BGI0SIBCE018385] (1196)  VIALWEFPEGHFDARNGGAVLGDKRWGAMVIVKSLESLSMAIRFALKETSHYTSSEGNMM
     OSJACCI [EAZ33685]  (1196)  VIALWEFPEGHFDARNGGAVLGDKRWGAMVIVKSLESLSMAIRFALKETSHYTSSEGNMM 1261                                                       1320
      AmACCI [CAC84161]  (1246)  HIALLDADTQLNTTEDSGDNDQAQDKMDKLSFVLKQDVVMADLRAADVKVVSCIVQRDGA
OSIACCI [BGI0SIBCE018385] (1256)  HIALLGADNKMHIIQESG---DDADRIAKLPLILKDN--VTDLHASGVKTISFIVQRDEA
     OSJACCI [EAZ33685]  (1256)  HIALLGADNKMHIIQESG---DDADRIAKLPLILKDN--VTDLHASGVKTISFIVQRDEA 1321                                                       1380
      AmACCI [CAC84161]  (1306)  IMPMRRTFLLSEEKLCYEEEPILRHVEPPLSALLELDKLKVKGYNEMKYTPSRDRQWHIY
OSIACCI [BGI0SIBCE018385] (1311)  RMTMRRTFLWSDEKLSYEEEPILRHVEPPLSALLELDKLKVKGYNEMKYTPSRDRQWHIY
     OSJACCI [EAZ33685]  (1311)  RMTMRRTFLWSDEKLSYEEEPILRHVEPPLSALLELDKLKVKGYNEMKYTPSRDRQWHIY 1381                                                       1440
      AmACCI [CAC84161]  (1366)  TLRNTENPKMLHRVFFRTLVRQPSAGNRFTSDHITDVEVGHAEEPLSFTSSSILKSLKIA
OSIACCI [BGI0SIBCE018385] (1371)  TLRNTENPKMLHRVFFRTLVRQPSVSNKFSSGQIGDMEVGSAEEPLSFTSTSILRSLMTA
     OSJACCI [EAZ33685]  (1371)  TLRNTENPKMLHRVFFRTLVRQPSVSNKFSSGQIGDMEVGSAEEPLSFTSTSILRSLMTA 1441                                                       1500
      AmACCI [CAC84161]  (1426)  KEELELHAIRTGHSHMYLCILKEQKLLDLVPVSGNTVVDVGQDEATACSLLKEMALKIHE
OSIACCI [BGI0SIBCE018385] (1431)  IEELELHAIRTGHSHMYLHVLKEQKLLDLVPVSGNTVLDVGQDEATAYSLLKEMAMKIHE
     OSJACCI [EAZ33685]  (1431)  IEELELHAIRTGHSHMYLHVLKEQKLLDLVPVSGNTVLDVGQDEATAYSLLKEMAMKIHE 1501                                                       1560
      AmACCI [CAC84161]  (1486)  LVGARMHHLSVCQWEVKLKLVSDGPASGSWRVVTTNVTGHTCTVDIYREVEDTESQKLVY
OSIACCI [BGI0SIBCE018385] (1491)  LVGARMHHLSVCQWEVKLKLDCDGPASGTWRIVTTNVTSHTCTVDIYREMEDKESRKLVY
     OSJACCI [EAZ33685]  (1491)  LVGARMHHLSVCQWEVKLKLDCDGPASGTWRIVTTNVTSHTCTVDIYREMEDKESRKLVY 1561                                                       1620
      AmACCI [CAC84161]  (1546)  HSTALSSGPLHGVALNTSYQPLSVIDLKRCSARNNKTTYCYDFPLTFEAAVQKSWSNISS
OSIACCI [BGI0SIBCE018385] (1551)  HPATPAAGPLHGVALNNPYQPLSVIDLKRCSARNNRTTYCYDFPLAFETAVRKSWSSSTS
     OSJACCI [EAZ33685]  (1551)  HPATPAAGPLHGVALNNPYQPLSVIDLKRCSARNNRTTYCYDFPLAFETAVRKSWSSSTS 1621                                                       1680
      AmACCI [CAC84161]  (1606)  ------ENNQCYVKATELVFAEKNGSWGTPIIPMQRAAGLNDIGMVAWILDMSTPEFPSG
```

FIGURE 19 (continued)

```
OSIACCI [BGIOSIBCE018385]   (1611) GASKGVENAQCYVKATELVFADKHGSWGTPLVQMDRPAGLNDIGMVAWTLKMSTPEFPSG
    OSJACCI [EAZ33685]      (1611) GASKGVENAQCYVKATELVFADKHGSWGTPLVQMDRPAGLNDIGMVAWTLKMSTPEFPSG 1681                                                       1740
       AmACCI [CAC84161]    (1660) RQIIVIANDITFRAGSFGPREDAFFEAVTNLACEKKLPLIYLAANSGARIGIADEVKSCF
OSIACCI [BGIOSIBCE018385]   (1671) REIIVVANDITFRAGSFGPREDAFFEAVTNLACEKKLPLIYLAANSGARIGIADEVKSCF
    OSJACCI [EAZ33685]      (1671) REIIVVANDITFRAGSFGPREDAFFEAVTNLACEKKLPLIYLAANSGARIGIADEVKSCF 1741                                                       1800
       AmACCI [CAC84161]    (1720) RVGWTDDSSPERGFRYIYMTDEDHDRIGSSVIAHKMQLDSGEIRWVIDSVVGKEDGLGVE
OSIACCI [BGIOSIBCE018385]   (1731) RVGWSDDGSPERGFQYIYLSEEDYARIGTSVIAHKMQLDSGEIRWVIDSVVGKEDGLGVE
    OSJACCI [EAZ33685]      (1731) RVGWSDDGSPERGFQYIYLSEEDYARIGTSVIAHKMQLDSGEIRWVIDSVVGKEDGLGVE 1801                                                       1860
       AmACCI [CAC84161]    (1780) NIHGSAAIASAYSRAYEETFTLTFVTGRTVGIGAYLARLGIRCIQRIDQPIILTGFSALN
OSIACCI [BGIOSIBCE018385]   (1791) NIHGSAAIASAYSRAYKETFTLTFVTGRTVGIGAYLARLGIRCIQRLDQPIILTGYSALN
    OSJACCI [EAZ33685]      (1791) NIHGSAAIASAYSRAYKETFTLTFVTGRTVGIGAYLARLGIRCIQRLDQPIILTGYSALN 1861                                                       1920
       AmACCI [CAC84161]    (1840) KLLGREVYSSHMQLGGPKIMATNGVVHLTVPDDLEGVSNILRWLSYVPANIGGPLPITKS
OSIACCI [BGIOSIBCE018385]   (1851) KLLGREVYSSHMQLGGPKIMATNGVVHLTVSDDLEGVSNILRWLSYVPAYIGGPLPVTTP
    OSJACCI [EAZ33685]      (1851) KLLGREVYSSHMQLGGPKIMATNGVVHLTVSDDLEGVSNILRWLSYVPAYIGGPLPVTTP 1921                                                       1980
       AmACCI [CAC84161]    (1900) LDPIDRPVAYIPENTCDPRAAISGIDDSQGKWLGGMFDKDSFVETFEGWAKTVVTGRAKL
OSIACCI [BGIOSIBCE018385]   (1911) LDPPDRPVAYIPENSCDPRAAIRGVDDSQGKWLGGMFDKDSFVETFEGWAKTVVTGRAKL
    OSJACCI [EAZ33685]      (1911) LDPPDRPVAYIPENSCDPRAAIRGVDDSQGKWLGGMFDKDSFVETFEGWAKTVVTGRAKL 1981                                                       2040
       AmACCI [CAC84161]    (1960) GGIPVGVIAVETQTMMQLVPADPGQPDSHERSVPRAGQVWFPDSATKTAQAMLDFNREGL
OSIACCI [BGIOSIBCE018385]   (1971) GGIPVGVIAVETQTMMQTIPADPGQLDSREQSVPRAGQVWFPDSATKTAQALLDFNREGL
    OSJACCI [EAZ33685]      (1971) GGIPVGVIAVETQTMMQTIPADPGQLDSREQSVPRAGQVWFPDSATKTAQALLDFNREGL 2041                                                       2100
       AmACCI [CAC84161]    (2020) PLFILANWRGFSGGQRDLFEGILQAGSTIVENLRTYNQPAFVYIPKAAELRGGAWVVIDS
OSIACCI [BGIOSIBCE018385]   (2031) PLFILANWRGFSGGQRDLFEGILQAGSTIVENLRTYNQPAFVYIPMAAELRGGAWVVVDS
    OSJACCI [EAZ33685]      (2031) PLFILANWRGFSGGQRDLFEGILQAGSTIVENLRTYNQPAFVYIPMAAELRGGAWVVVDS 2101                                                       2160
       AmACCI [CAC84161]    (2080) KINPDRIECYAERTAKGNVLEPQGLIEIKFRSEELKECMGRLDPELIDLKARLQGAN-GS
OSIACCI [BGIOSIBCE018385]   (2091) KINPDRIECYAERTAKGNVLEPQGLIEIKFRSEELQDCMSRLDPTLIDLKAKLEVANKNG
    OSJACCI [EAZ33685]      (2091) KINPDRIECYAERTAKGNVLEPQGLIEIKFRSEELQDCMSRLDPTLIDLKAKLEVANKNG 2161                                                       2220
       AmACCI [CAC84161]    (2139) LSDGESLQKSIEARKKQLLPLYTQIAVRFAELHDTSLRMAAKGVIRKVVDWEDSRSFFYK
OSIACCI [BGIOSIBCE018385]   (2151) SADTKSLQENIEARTKQLMPLYTQIAIRFAELHDTSLRMAAKGVIKKVVDWEESRSFFYK
    OSJACCI [EAZ33685]      (2151) SADTKSLQENIEARTKQLMPLYTQIAIRFAELHDTSLRMAAKGVIKKVVDWEESRSFFYK 2221                                                       2280
       AmACCI [CAC84161]    (2199) RLRRRLSEDVLAKEIRGVIGEKFPHKSAIELIKKWYLASEAAAAGSTDWDDDDAFVAWRE
OSIACCI [BGIOSIBCE018385]   (2211) RLRRRISEDVLAKEIRAVAGEQFSHQPAIELIKKWYSASHAA-----EWDDDDAFVAWMD
    OSJACCI [EAZ33685]      (2211) RLRRRISEDVLAKEIRAVAGEQFSHQPAIELIKKWYSASHAA-----EWDDDDAFVAWMD 2281                                                       2340
       AmACCI [CAC84161]    (2259) NPENYKEYIKELRAQRVSRLLSDVAGSSSDLQALPQGLSMLLDKMDPSKRAQFIEEVMKV
OSIACCI [BGIOSIBCE018385]   (2266) NPENYKDYIQYLKAQRVSQSLSSLSDSSSDLQALPQGLSMLLDKMDPSRRAQLVEEIRKV
    OSJACCI [EAZ33685]      (2266) NPENYKDYIQYLKAQRVSQSLSSLSDSSSDLQALPQGLSMLLDKMDPSRRAQLVEEIRKV

2341
       AmACCI [CAC84161]    (2319) LK
OSIACCI [BGIOSIBCE018385]   (2326) LG
    OSJACCI [EAZ33685]      (2326) LG
```

METHOD FOR TREATING POST-EMERGENT RICE

RELATED APPLICATIONS

This application is a Continuation of U.S. application Ser. No. 15/395,832, filed on Dec. 30, 2016; which is a Continuation-in-Part of U.S. application Ser. No. 14/357,691, filed on May 12, 2014; which is a 35 U.S.C. 371 National Stage entry of PCT/US12/64831, filed on Nov. 13, 2012; which claims priority of U.S. Provisional Application Ser. No. 61/559,618, filed on Nov. 14, 2011; all of which are hereby incorporated herein in their entirety by reference. U.S. application Ser. No. 15/395,832, filed on Dec. 30, 2016; is also a Continuation-in-Part of U.S. patent application Ser. No. 15/156,671, filed May 17, 2016; which is a Continuation of U.S. application Ser. No. 13/393,780, filed Jan. 7, 2013; which is a 35 U.S.C. 371 National Stage entry of PCT/US10/47571, filed on Sep. 1, 2010; which claims priority of U.S. Provisional Application Ser. No. 61/365,298, filed Jul. 16, 2010, and 61/238,906, filed Sep. 1, 2009; all of which are hereby incorporated herein in their entirety by reference.

FIELD

The present disclosure generally relates to treatment of domestic rice crop plants for the control of weeds.

BACKGROUND

Rice is one of the most important food crops in the world, particularly in Asia. Rice is a cereal grain produced by plants in the genus *Oryza*. The two most frequently cultivated species are *Oryza sativa* and *Oryza glaberrima*, with *O. sativa* being the most frequently cultivated domestic rice. In addition to the two domestic species, the genus *Oryza* contains more than 20 wild species. One of these wild species, *Oryza rufipogon* ("red rice" also referred to as *Oryza sativa* subsp. *rufipogon*) presents a major problem in commercial cultivation. Red rice produces red coated seeds. After harvest, rice seeds are milled to remove their hull. After milling, domestic rice is white while wild red rice appears discolored. The presence of discolored seeds reduces the value of the rice crop. Since red rice belongs to the same species as cultivated rice (*Oryza sativa*), their genetic makeup is very similar. This genetic similarity has made herbicidal control of red rice difficult.

Domestic rice tolerant to imidazolinone herbicides have been developed and are currently marketed under the tradename CLEARFIELD®. Imidazolinone herbicides inhibit a plant's acetohydroxyacid synthase (AHAS) enzyme. When cultivating CLEARFIELD® rice, it is possible to control red rice and other weeds by application of imidazolinone herbicides. Unfortunately, imidazolinone herbicide-tolerant red rice and weeds have developed.

Acetyl-Coenzyme A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homomeric protein, likely a homodimer.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

A number of ACCase-inhibitor-tolerance (AIT) mutations have been found in monocot weed species exhibiting tolerance toward one or more DIM or FOP herbicides. Further, an AIT maize has been marketed by BASF. All such mutations are found in the carboxyltransferase domain of the ACCase enzyme, and these appear to be located in a substrate binding pocket, altering access to the catalytic site.

DIMs and FOPs are important herbicides and it would be advantageous if rice could be provided that exhibits tolerance to these classes of herbicide. Currently, these classes of herbicide are of limited value in rice agriculture. In some cases, herbicide-tolerance-inducing mutations create a severe fitness penalty in the tolerant plant. Therefore, there remains a need in the art for an AIT rice that also exhibits no fitness penalty. This need and others are met by the present invention.

SUMMARY

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. In some further embodiments, the effective amount of quizalofop or an ester thereof is at least 14 g AI/Ha.

In even other embodiments, the aryloxyphenoxypropanoate herbicide is fluazifop or an ester thereof. In some further embodiments, the effective amount of fluazifop or an ester thereof is at least 56 g AI/Ha.

In some other embodiments, the aryloxyphenoxypropanoate herbicide is clodinafop or clodinafop-propargyl. In some further embodiments, the effective amount of clodinafop or clodinafop-propargyl is at least 11 g AI/Ha.

In still other embodiments, the aryloxyphenoxypropanoate herbicide is diclofop or diclofop-methyl. In some further embodiments, the effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona*, *Echinochloa crus-galli*, *Echinochloa crus-pavonis*, *Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis*, *Leptochloa fascicularis*, *Leptochloa panacea*, and *Leptochloa panicoides*.

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

BRIEF DESCRIPTION OF THE DRAWINGS

The present disclosure can be better understood by reference to the following drawings. The drawings are merely exemplary to illustrate certain features that may be used singularly or in combination with other features and the aspects of the present disclosure should not be limited to the embodiments shown.

FIG. 1 is a bar graph showing relative growth rice calli derived from *Oryza sativa* subsp. *indica* grown in the presence of difference selection levels of herbicide. FIG. 1A shows the results obtained with tepraloxydim, FIG. 1B shows the results obtained with sethoxydim, and FIG. 1C shows the results obtained with cycloxydim.

FIG. 2 is a diagram of the selection process used to produce herbicide-tolerant rice plants.

FIG. 3 shows photographs of plants taken one week after treatment with herbicide.

FIG. 4 shows photographs of plants taken two weeks after treatment with herbicide.

FIG. 5 provides the amino acid sequence of acetyl-coenzyme A carboxylase from *Alopecurus myosuroides* (GenBank accession number CAC84161) (SEQ ID NO. 24).

FIG. 6 provides the mRNA encoding acetyl-coenzyme A carboxylase from *Alopecurus myosuroides* (GenBank accession number AJ310767 region: 157 . . . 7119).

Figure 7A:
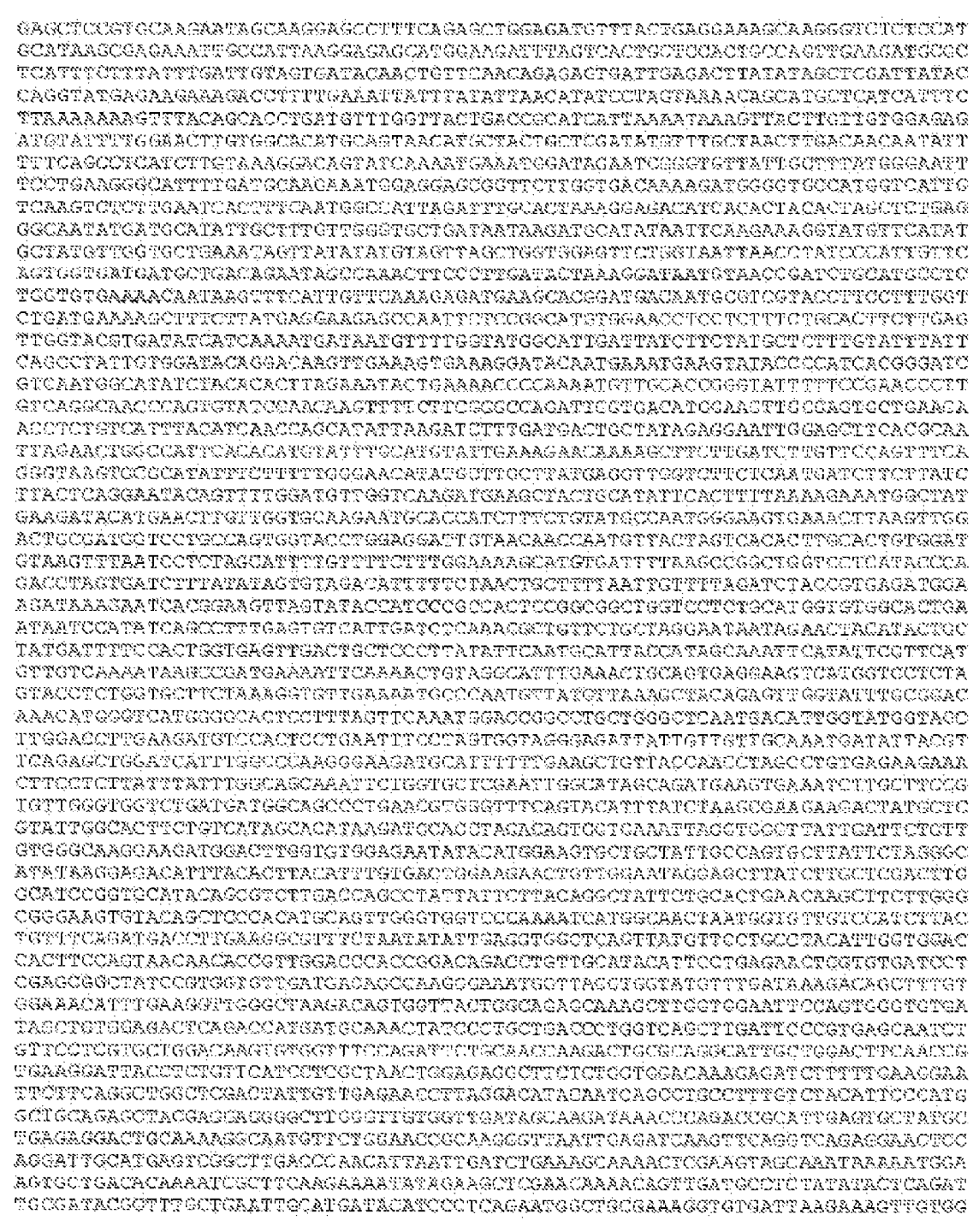

FIG. 7A provides the genomic nucleotide sequence for *Oryza sativa indica* & *japonica* acetyl-Coenzyme A carboxylase gene (SEQ ID NO:5).

FIG. 7B provides the nucleotide sequence encoding *Oryza sativa indica* & *japonica* acetyl-Coenzyme A carboxylase (SEQ ID NO:6).

FIG. 7C provides the amino acid sequence of *Oryza sativa indica* acetyl-Coenzyme A carboxylase (SEQ ID NO:3).

FIG. 8A provides the nucleotide sequence encoding *Zea mays* acetyl-Coenzyme A carboxylase (SEQ ID NO:11).

FIG. 8B provides the amino acid sequence of *Zea mays* acetyl-Coenzyme A carboxylase (SEQ ID NO:12).

Figure 9A:
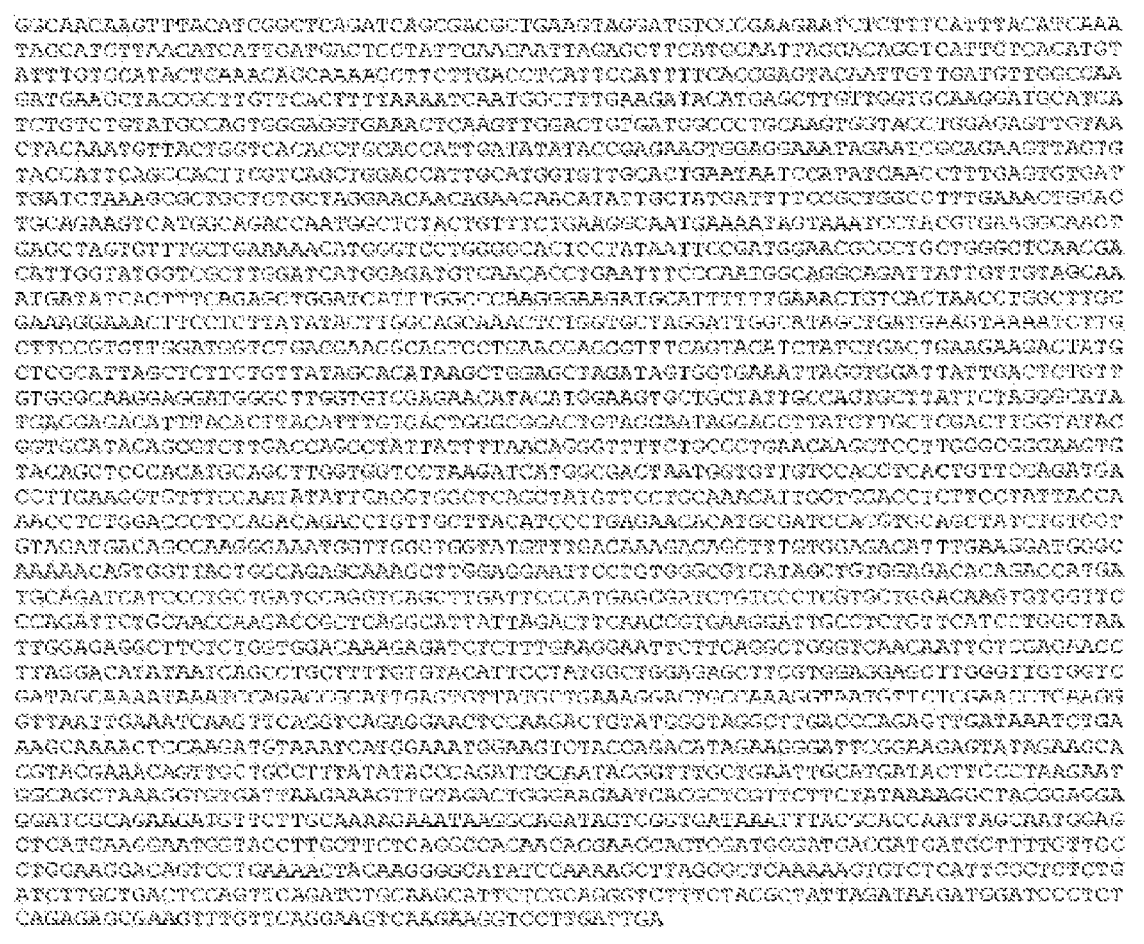

FIG. 9A provides the nucleotide sequence encoding *Zea mays* acetyl-Coenzyme A carboxylase (SEQ ID NO:13).

FIG. 9B provides the amino acid sequence of *Zea mays* acetyl-Coenzyme A carboxylase (SEQ ID NO:14).

FIG. 10A provides the nucleotide sequence encoding *Triticum aestivum* acetyl-Coenzyme A carboxylase (SEQ ID NO:15).

FIG. 10B provides the amino acid sequence of *Triticum aestivum* acetyl-Coenzyme A carboxylase (SEQ ID NO:16).

Figure 11A:
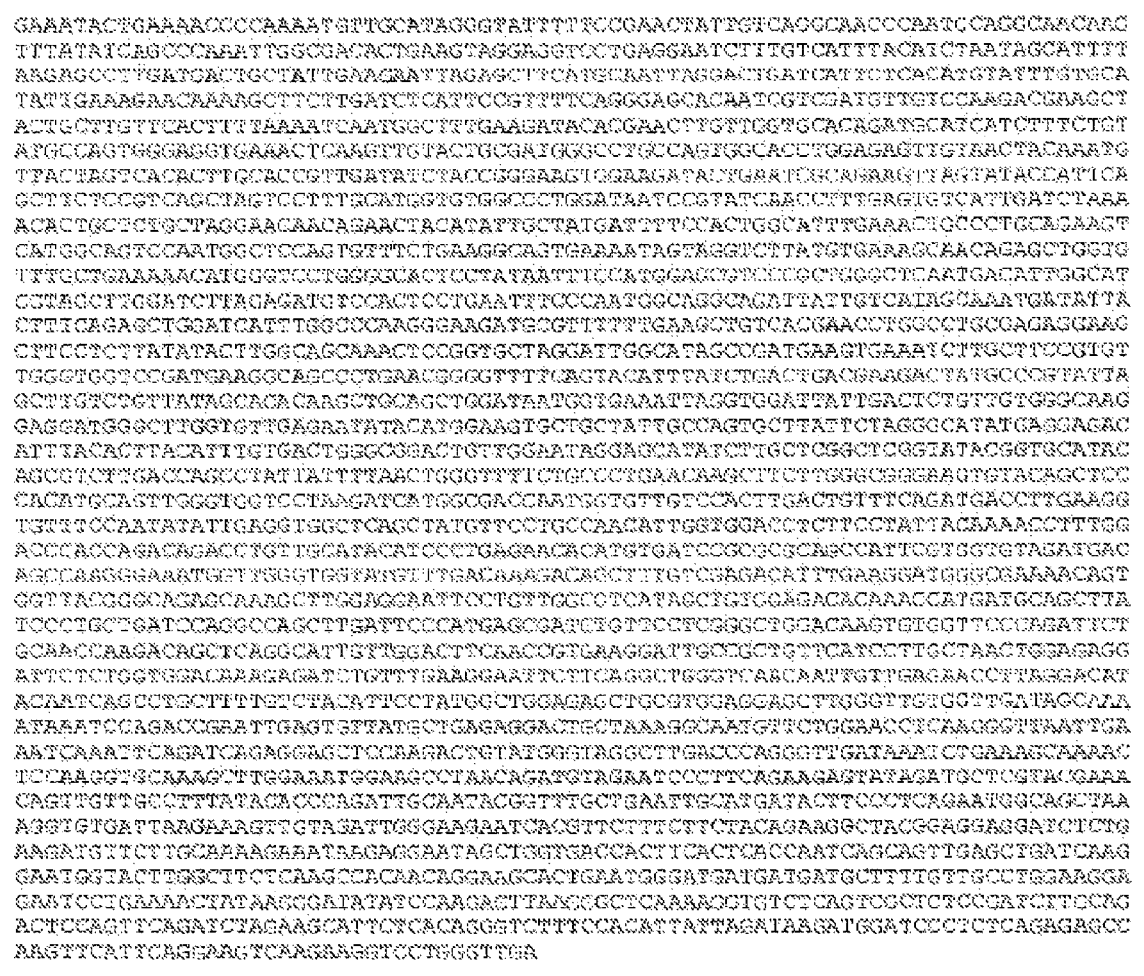

FIG. 11A provides the nucleotide sequence encoding *Setaria italica* acetyl-Coenzyme A carboxylase (SEQ ID NO:17).

FIG. 11B provides the amino acid sequence of *Setaria italica* acetyl-Coenzyme A carboxylase (SEQ ID NO:18).

Figure 12A:
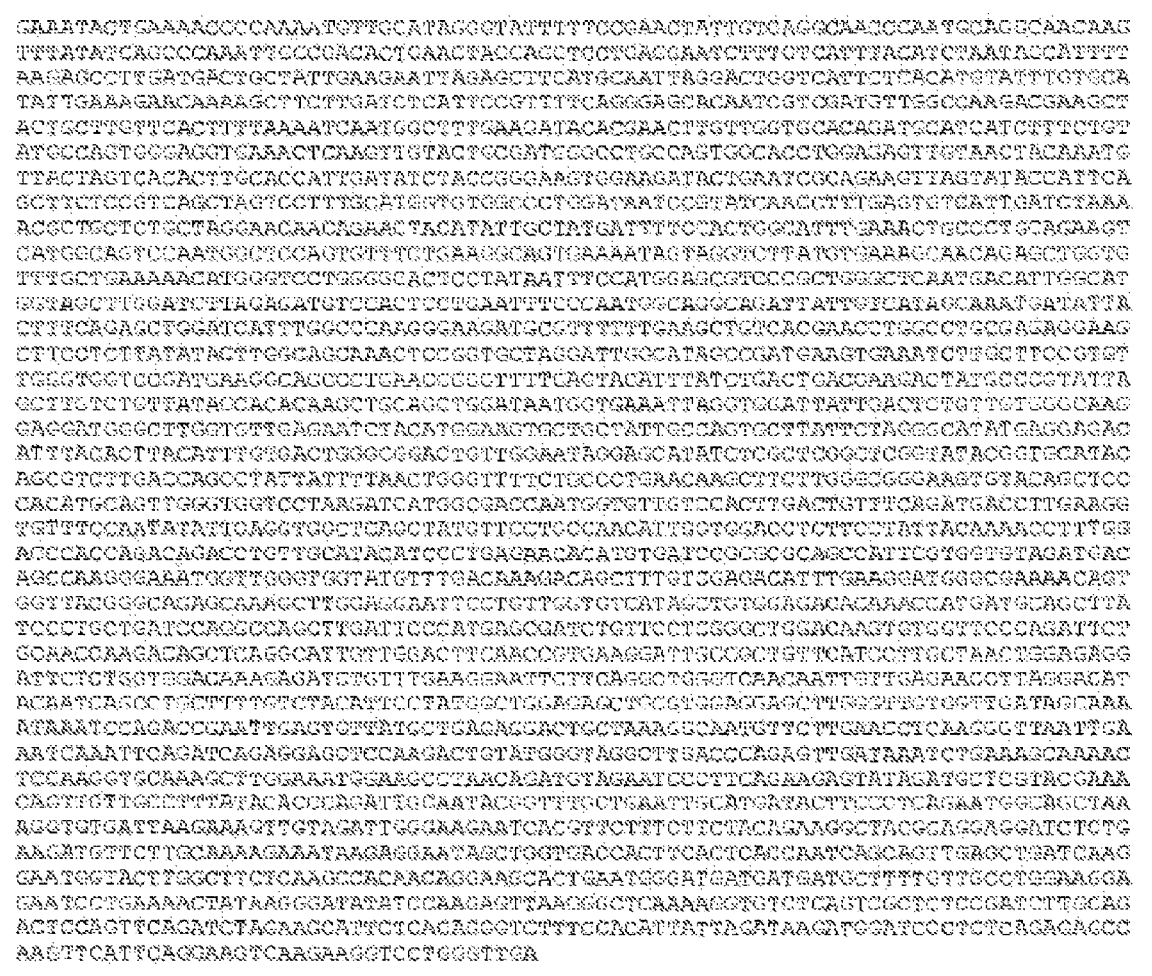

FIG. 12A provides the nucleotide sequence encoding *Setaria italica* acetyl-Coenzyme A carboxylase (SEQ ID NO:19).

FIG. 12B provides the amino acid sequence of *Setaria italica* acetyl-Coenzyme A carboxylase (SEQ ID NO:20).

FIG. 13A provides the nucleotide sequence encoding *Setaria italica* acetyl-Coenzyme A carboxylase (SEQ ID NO:21).

FIG. 13B provides the amino acid sequence of *Setaria italica* acetyl-Coenzyme A carboxylase (SEQ ID NO:22).

Figure 14A:
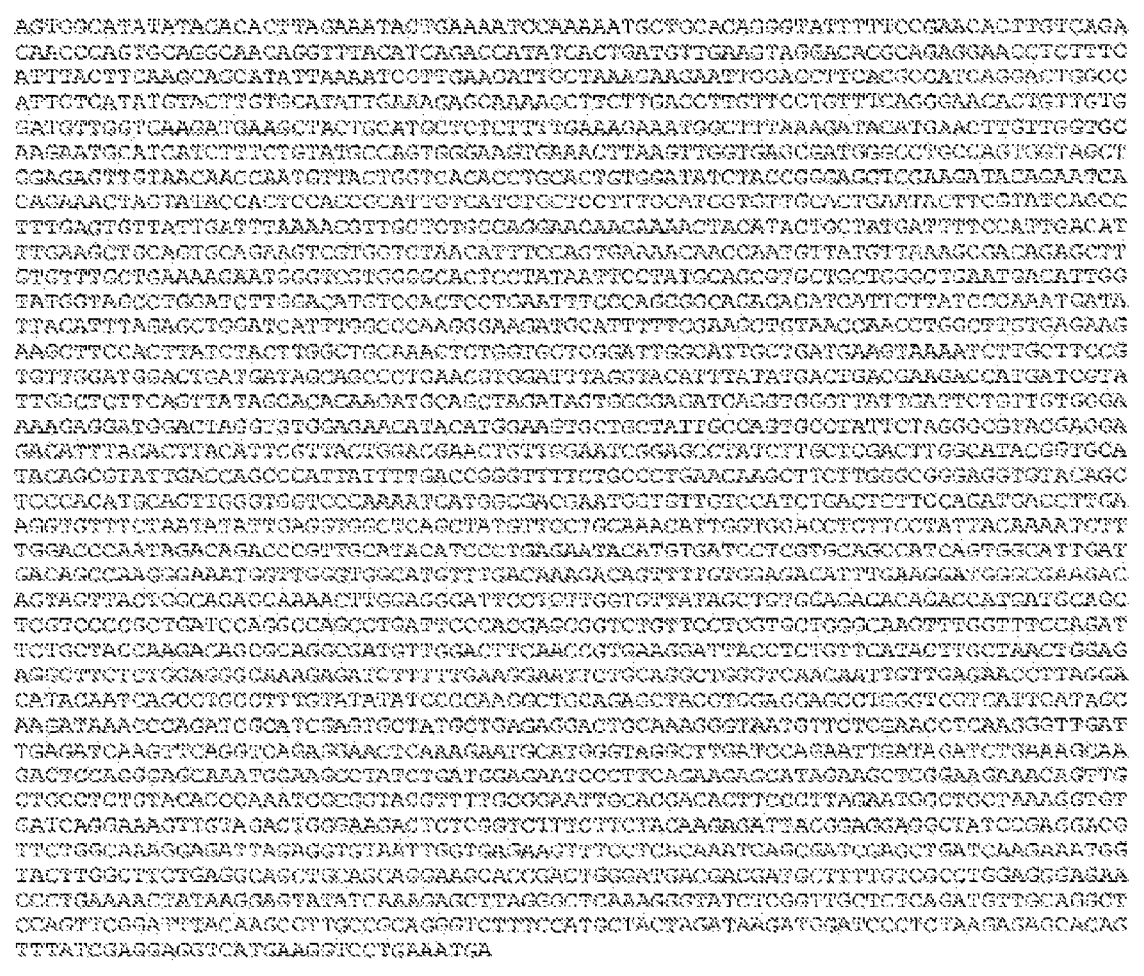

FIG. 14A provides the nucleotide sequence encoding *Alopecurus myosuroides* acetyl-Coenzyme A carboxylase (SEQ ID NO:23).

FIG. 14B provides the amino acid sequence of *Alopecurus myosuroides* acetyl-Coenzyme A carboxylase (SEQ ID NO:24).

Figure 15A:
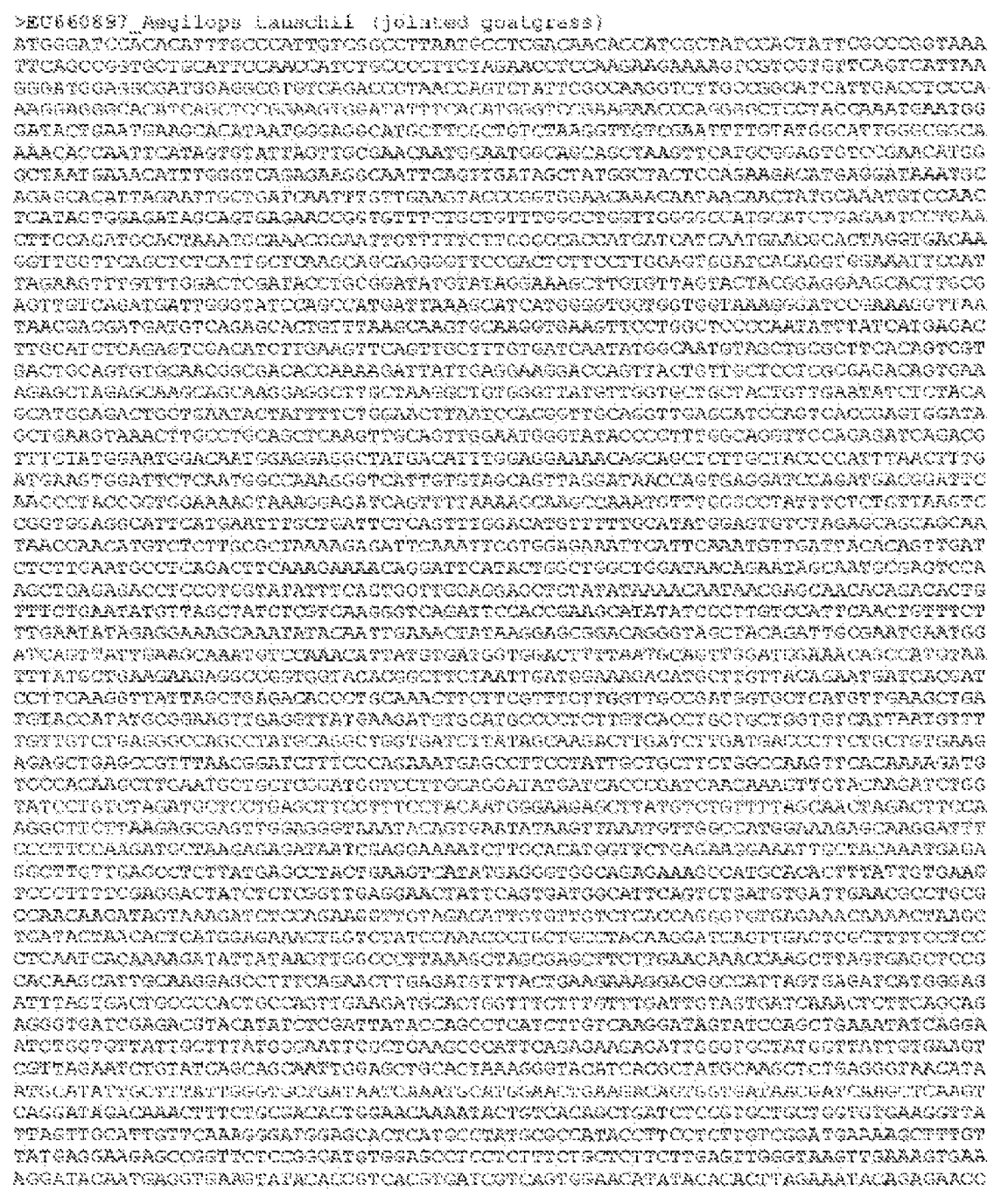
Figure 15A:
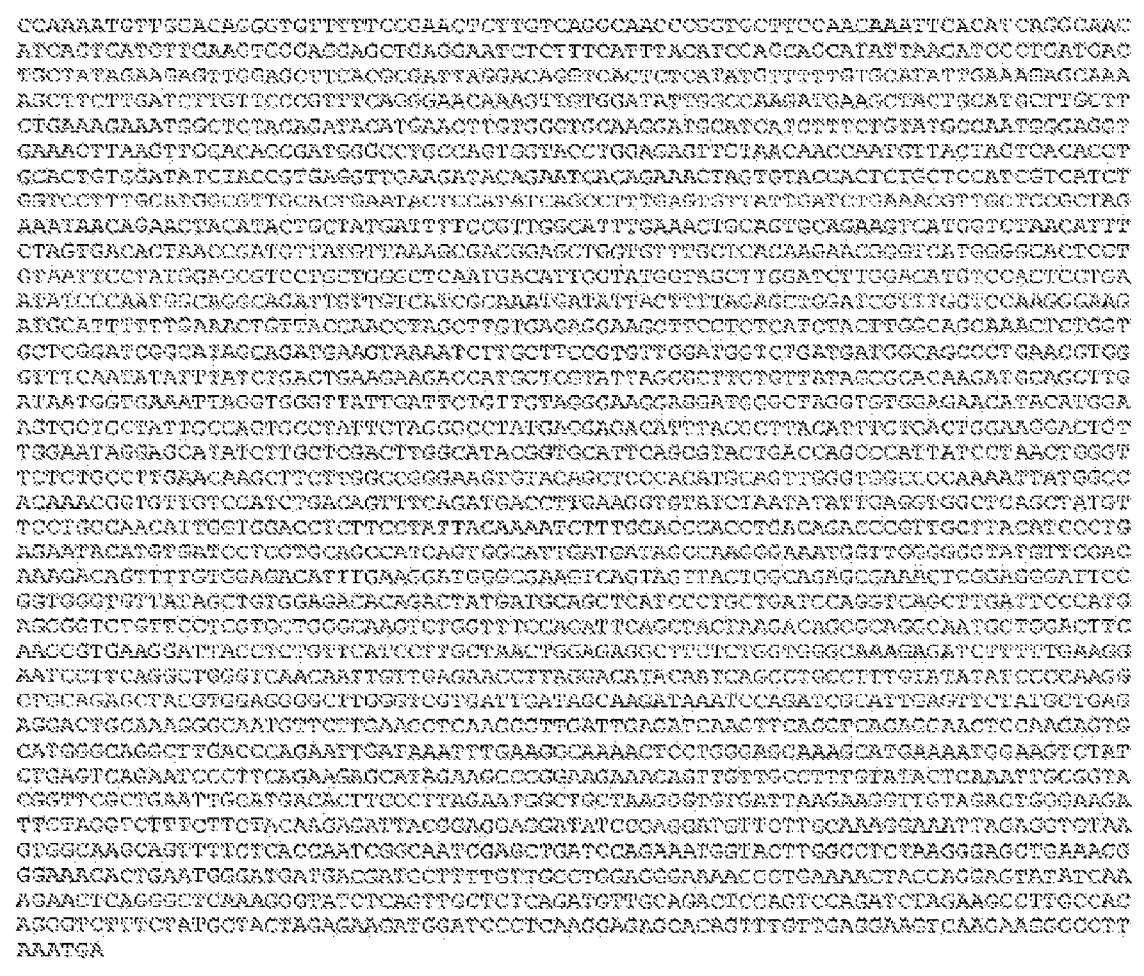

FIG. 15A provides the nucleotide sequence encoding *Aegilops tauschii* acetyl-Coenzyme A carboxylase (SEQ ID NO:25).

FIG. 15B provides the amino acid sequence of *Aegilops tauschii* acetyl-Coenzyme A carboxylase (SEQ ID NO:26).

FIG. 16 provides a comparison of single and double mutants.

FIG. 17 provides a graph showing results for mutant rice versus various ACCase inhibitors.

FIG. 18 provides *Alopecurus myosuroides* acetyl-Coenzyme A carboxylase amino acid sequence (GenBank accession no. CAC84161) (SEQ ID NO. 24). Amino acids that may be altered in the acetyl-Coenzyme A carboxylase enzymes of the disclosure are indicated in bold double underline.

FIG. 19 provides amino acid sequence of wild-type *Oryza sativa* acetyl-Coenzyme A carboxylases (SEQ ID NOs. 2, 3) aligned with *Alopecurus myosuroides* acetyl-Coenzyme A carboxylase (SEQ ID NO. 24) with some critical residues denoted.

FIG. 20A shows the effect of post-emergent application of herbicides on Red rice.

FIG. 20B shows the effect of post-emergent application of herbicides on AIT rice.

DETAILED DESCRIPTION

The following detailed description is presented to enable any person skilled in the art to make and use the objectives of the present disclosure. For purposes of explanation, specific nomenclature is set forth to provide a thorough understanding of the objectives of the present disclosure. However, it will be apparent to one skilled in the art that these specific details are not required to practice the objectives of the present disclosure. Descriptions of specific applications are provided only as representative examples. The presently claimed disclosure is not intended to be limited to the embodiments shown, but is to be accorded the widest possible scope consistent with the principles and features disclosed herein.

Definitions

As used herein, "tolerant" or "herbicide-tolerant" indicates a plant or portion thereof capable of growing in the presence of an amount of herbicide that normally causes growth inhibition in a non-tolerant (e.g., a wild-type) plant or portion thereof. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant.

As used herein, "recombinant" refers to an organism having genetic material from different sources.

As used herein, "mutagenized" refers to an organism having an altered genetic material as compared to the genetic material of a corresponding wild-type organism, wherein the alterations in genetic material were induced and/or selected by human action. Examples of human action that can be used to produce a mutagenized organism include, but are not limited to, tissue culture of plant cells (e.g., calli) in sub-lethal concentrations of herbicides (e.g., acetyl-Coenzyme A carboxylase inhibitors such as cycloxydim or sethoxydim), treatment of plant cells with a chemical mutagen and subsequent selection with herbicides (e.g., acetyl-Coenzyme A carboxylase inhibitors such as cycloxydim or sethoxydim); or by treatment of plant cells with x-rays and subsequent selection with herbicides (e.g., acetyl-Coenzyme A carboxylase inhibitors such as cycloxydim or sethoxydim). Any method known in the art may be used to induce mutations. Methods of inducing mutations may induce mutations in random positions in the genetic material or may induce mutations in specific locations in the genetic material (i.e., may be directed mutagenesis techniques).

As used herein, a "genetically modified organism" (GMO) is an organism whose genetic characteristics have been altered by insertion of genetic material from another source organism or progeny thereof that retain the inserted genetic material. The source organism may be of a different type of organism (e.g., a GMO plant may contain bacterial genetic material) or from the same type of organism (e.g., a GMO plant may contain genetic material from another plant). As used herein, recombinant and GMO are considered synonyms and indicate the presence of genetic material from a different source whereas mutagenized indicates altered genetic material from a corresponding wild-type organism but no genetic material from another source organism.

As used herein, "wild-type" or "corresponding wild-type plant" means the typical form of an organism or its genetic material, as it normally occurs, as distinguished from mutagenized and/or recombinant forms.

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope.

As used herein in regard to herbicides useful in various embodiments hereof, terms such as auxinic herbicide, AHAS inhibitor, acetyl-Coenzyme A carboxylase (ACCase) inhibitor, PPO inhibitor, EPSPS inhibitor, imidazolinone, sulfonylurea, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide tolerant (HT) and herbicide tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to an AHAS enzyme, or AHASL polypeptide, it refers specifically to the ability to tolerate an AHAS-inhibitor. Classes of AHAS-inhibitors include sulfonylureas, imidazolinones, triazolopyrimidines, sulfonylaminocarbonyltriazolinones, and pyrimidinyloxy[thio]benzoates.

As used herein, "descendant" refers to any generation plant.

As used herein, "progeny" refers to a first generation plant.

As used herein, an "effective amount" refers to the amount of an herbicide required to achieve at least about 65% phytotoxicity of conventional rice (e.g., red rice) in field applications. In some embodiments, an effective amount may be further defined as an amount of an herbicide required to achieve at least about 70, 75, 80, 85, 90, 95 or 99% phytotoxicity of conventional rice (e.g., red rice) in field applications. In other embodiments, an effective amount may be further defined as an amount of an herbicide required to achieve at least about 65, 70, 75, 80, 85, 90, 95 or 99% phytotoxicity of *Echinochloa* or *Leptochloa* species weeds in field applications. Typically, an effective amount for post-emergent application will be at least 0.5× the standard application rate of a given herbicide. 1× rates of herbicides listed herein are within the knowledge of one of ordinary skill in the art and it understood herein that for any herbicide not having a published 1× application rate, a 1× rate is one that causes at least 90% phytotoxicity in *Echinochloa crus-galli*.

As used herein, the amino acid numbering, and the associated DNA sequence numbering are based on the numbering of the ACCase in *Alopercurus myosuroides* (blackgrass) (Genbank CAC84161.1) and denoted with an (Am). The reference positions cited within are intended to correspond to the actual recited positional equivalent in the ACCase of *Alopercurus myosuroides*.

As used herein, a "non-selective" or "rice-non-selective" ACCase-inhibiting herbicide relates to an herbicide of the DIM or FOP class that, at a given rate of application, of active ingredient causes both at least about 90% phytotoxicity in *Echinochloa crus-galli* and more than 10% phytotoxicity in domestic rice (*Oryza sativa*). Conversely, "selective" means any ACCase-inhibiting DIM or FOP herbicide that, at a given rate of application causes both at least 90% phytotoxicity in *Echinochloa crus-galli* and not more than 10% phytotoxicity in domestic rice (*Oryza sativa*).

As used herein, the terms "post-emergence" and "postemergent" refer to a time period encompassing the post-germination emergence of a seedling through the soil surface to the maturity of the plant.

As used herein in regard to mutant or mutagenized nucleic acids that encode herbicide-tolerant ACCase enzymes, the term "endogenous non-transfected" is defined to mean:

(1) that the nucleic acid is endogenous to the respective cell, seed, plant, or plant part and (2) that its nucleotide sequence is "non-transfected" in that (a) it contains herbicide-tolerance mutation(s) produced randomly by a technique involving no step of introducing exogenous nucleic acid(s) or nucleic acid analog(s), into a plant cell or into other plant material, and (b) it contains no mutation(s) produced by a technique involving a step of introducing exogenous nucleic acid(s) or nucleic acid analog(s), into a plant cell or into other plant material.

Thus, techniques useful to produce such "non-transfected" nucleic acid sequences, as defined herein, include, e.g., traditional chemical mutagenesis using a chemical (i.e. non-nucleic-acid- or -analog-containing) mutagen, tissue culture mutagenesis involving somaclonal variation, radiation exposure, and other techniques for inducing mutations in endogenous plant gene(s) in a random or non-directed manner.

Accordingly, as defined herein, "endogenous non-transfected" nucleic acids exclude both those mutant or mutagenized nucleic acids whose mutation-containing sequences have resulted without an applied technique and those that were produced by use of a technique involving introduction into a plant cell or into other plant material of an exogenous nucleic acid or nucleic acid analog, whether per se or as part of a heteromolecular construct or complex. Examples of techniques excluded under this definition include: genetic engineering, oligonucleotide-directed mutagenesis, DNA mismatch-repair oligonucleotide-based mutagenesis, and other mutation-producing processes in which exogenous nucleic acid (or nucleic acid analog) has been transiently or stably introduced into a plant cell or other plant material.

As used in this definition of "endogenous non-transfected," the term "non-transfected" is analogous to the term "non-infected" used to describe a physician's patient who, not having been infected with or exposed to a pathogen, is not a carrier of it. Thus, by analogy, a "non-transfected" nucleic acid is one that is not a carrier of any "transfection product," i.e. of any mutation caused by a technique involving transient or stable introduction of exogenous nucleic acid or its analog.

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. The 1× application rate for quizalofop or an ester thereof is 28 g AI/ha. In some further embodiments, an effective amount of quizalofop or an ester thereof is at least 14 g AI/Ha.

In even other embodiments, the aryloxyphenoxypropanoate herbicide is fluazifop or an ester thereof. The 1× application rate for fluazifop or an ester thereof is 112 g AI/ha. In some further embodiments, an effective amount of fluazifop or an ester thereof is at least 56 g AI/Ha.

In some other embodiments, the aryloxyphenoxypropanoate herbicide is clodinafop or clodinafop-propargyl. The 1× application rate for clodinafop or clodinafop-propargyl is 22 g AI/ha. In some further embodiments, an effective amount of clodinafop or clodinafop-propargyl is at least 11 g AI/Ha.

In still other embodiments, the aryloxyphenoxypropanoate herbicide is diclofop or diclofop-methyl. The 1× application rate for diclofop or diclofop-methyl is 452 g AI/ha. In some further embodiments, an effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona*, *Echinochloa crus-galli*, *Echinochloa crus-pavonis*, *Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis*, *Leptochloa fascicularis*, *Leptochloa panacea*, and *Leptochloa panicoides*.

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

Yet another aspect of the present disclosure relates to a method for treating rice comprising providing a domestic rice crop plant and at least one rice-non-selective ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is at least 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, said effective amount is at least 0.5× and less than 1× of an amount that causes both at least about 90% phytotoxicity in wild type *Echinochloa crus-galli* and more than 10% phytotoxicity in wild-type *Oryza sativa*; thereby creating a treated rice plant.

In other embodiments, said effective amount is at least 0.5× and less than 0.95× of an amount that causes both at least about 90% phytotoxicity in wild type *Echinochloa crus-galli* and more than 10% phytotoxicity in wild-type *Oryza sativa*; thereby creating a treated rice plant.

In still other embodiments, said effective amount is at least 0.5× and less than 0.9× of an amount that causes both at least about 90% phytotoxicity in wild type *Echinochloa crus-galli* and more than 10% phytotoxicity in wild-type *Oryza sativa*; thereby creating a treated rice plant.

In yet other embodiments, said effective amount is at least 0.5× and less than 0.85× of an amount that causes both at least about 90% phytotoxicity in wild type *Echinochloa crus-galli* and more than 10% phytotoxicity in wild-type *Oryza sativa*; thereby creating a treated rice plant.

In even other embodiments, said effective amount is at least 0.5× and less than 0.8× of an amount that causes both at least about 90% phytotoxicity in wild type *Echinochloa crus-galli* and more than 10% phytotoxicity in wild-type *Oryza sativa*; thereby creating a treated rice plant.

In still even other embodiments, said effective amount is at least 0.5× and less than 0.75× of an amount that causes both at least about 90% phytotoxicity in wild type *Echinochloa crus-galli* and more than 10% phytotoxicity in wild-type *Oryza sativa*; thereby creating a treated rice plant.

In some embodiments, postemergent application of herbicides in the present methods can take place at the time of seedling emergence. In some embodiments, postemergent application of herbicides in the present methods can take place at the 2-, 3-, and/or 4-leaf stage. In some embodiments, postemergent application of herbicides in the present methods can take place at the 1st, 2nd, 3rd, and/or 4th tiller stage. In some embodiments, postemergent application of herbicides in the present methods can take place at the panicle initiation and/or panicle differentiation stage. In some embodiments, postemergent application of herbicides in the present methods can take place at the 2-, 3-, and/or 4-leaf stage. In some embodiments, postemergent application of herbicides in the present methods can take place at the heading, milk, or dough stages. In some embodiments, postemergent application of herbicides in the present methods can take place on mature plants.

Plants

The present disclosure provides herbicide-tolerant monocotyledonous plants of the grass family Poaceae. The family Poaceae may be divided into two major clades, the clade containing the subfamilies Bambusoideae, Ehrhartoideae, and Pooideae (the BEP clade) and the clade containing the subfamilies Panicoideae, Arundinoideae, Chloridoideae, Centothecoideae, Micrairoideae, Aristidoideae, and Danthonioideae (the PACCMAD clade). The subfamily Bambusoideae includes tribe Oryzeae. The present disclosure relates to plants of the BEP clade, in particular plants of the subfamilies Bambusoideae and Ehrhartoideae. Plants of the disclosure are typically tolerant to at least one herbicide that inhibits acetyl-Coenzyme A carboxylase activity as a result of expressing an acetyl-Coenzyme A carboxylase enzyme as described below. The BET clade includes subfamilies Bambusoideae, Ehrhartoideae, and group Triticodae and no other subfamily Pooideae groups. BET crop plants are plants grown for food or forage that are members of BET subclade, for example barley, corn, etc.

The present disclosure also provides commercially important herbicide-tolerant monocots, including Sugarcane (*Saccharum* spp.), as well as Turfgrasses, e.g., *Poa pratensis* (Bluegrass), *Agrostis* spp. (Bentgrass), *Lolium* spp. (Ryegrasses), *Festuca* spp. (Fescues), *Zoysia* spp. (*Zoysia* grass), *Cynodon* spp. (Bermudagrass), *Stenotaphrum secundatum* (St. Augustine grass), *Paspalum* spp. (Bahiagrass), *Eremochloa ophiuroides* (Centipedegrass), *Axonopus* spp. (Carpetgrass), *Bouteloua dactyloides* (Buffalograss), and *Bouteloua* var. spp. (Grama grass).

In one embodiment, the present disclosure provides herbicide-tolerant plants of the Bambusoideae subfamily. Such plants are typically tolerant to one or more herbicides that inhibit acetyl-Coenzyme A carboxylase activity. Examples of herbicide-tolerant plants of the subfamily Bambusoideae include, but are not limited to, those of the genera *Arundinaria*, *Bambusa*, *Chusquea*, *Guadua*, and *Shibataea*.

In one embodiment, the present disclosure provides herbicide-tolerant plants of the Ehrhartoideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Erharta*, *Leersia*, *Microlaena*, *Oryza*, and *Zizania*.

In one embodiment, the present disclosure provides herbicide-tolerant plants of the Pooideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Triticeae*, *Aveneae*, and *Poeae*.

In one embodiment, herbicide-tolerant plants of the disclosure are rice plants. Two species of rice are most frequently cultivated, *Oryza sativa* and *Oryza glaberrima*. Numerous subspecies of *Oryza sativa* are commercially important including *Oryza sativa* subsp. *indica*, *Oryza sativa* subsp. *japonica*, *Oryza sativa* subsp. *javanica*, *Oryza sativa* subsp. *glutinosa* (glutinous rice), *Oryza sativa* Aromatica group (e.g., basmati), and *Oryza sativa* (Floating rice group). The present disclosure encompasses herbicide-tolerant plants in all of the aforementioned species and subspecies.

In addition to being able to tolerate herbicides that inhibit acetyl-Coenzyme A carboxylase activity, plants of the disclosure may also be able to tolerate herbicides that work on other physiological processes. For example, plants of the disclosure may be tolerant to acetyl-Coenzyme A carboxylase inhibitors and also tolerant to other herbicides, for example, enzyme inhibitors. Examples of other enzyme inhibitors to which plants of the disclosure may be tolerant include, but are not limited to, inhibitors of 5-enolpyruvyl-shikimate-3-phosphate synthase (EPSPS) such as glyphosate, inhibitors of acetohydroxyacid synthase (AHAS) such as imidazolinones, sulfonylureas and sulfonamide herbicides, and inhibitors of glutamine synthase such as glufosinate. In addition to enzyme inhibitors, plants of the disclosure may also be tolerant of herbicides having other modes of action, for example, auxinic herbicides such as 2,4-D or dicamba, chlorophyll/carotenoid pigment inhibitors such as hydroxyphenylpyruvate dioxygenase (HPPD) inhibitors or phytoene desaturase (PDS) inhibitors, protoporphyrinogen-IX oxidase inhibitors, cell membrane destroyers, photosynthetic inhibitors such as bromoxynil or ioxynil, cell division inhibitors, root inhibitors, shoot inhibitors, and combinations thereof. Thus, plants of the disclosure tolerant to acetyl-Coenzyme A carboxylase inhibitors can be made resistant to multiple classes of herbicides.

For example, plants of the present disclosure are tolerant to acetyl-Coenzyme A carboxylase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden), in some embodiments, may be auxinic-herbicide tolerant, tolerant to EPSPS inhibitors, such as glyphosate; to PPO inhibitors, such as pyrimidinedione, such as saflufenacil, triazolinone, such as sulfentrazone, carfentrazone, flumioxazin, diphenylethers, such as acifluorfen, fomesafen, lactofen, oxyfluorfen, N-phenylphthalamides, such as flumiclorac, CGA-248757, and/or to GS inhibitors, such as glufosinate. In addition to these classes of inhibitors, plants of the disclosure tolerant to acetyl-Coenzyme A carboxylase inhibitors may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof. Such tolerance traits may be expressed, e.g., as mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) proteins having an herbicide-degrading activity. Plants tolerant to acetyl-Coenzyme A carboxylase inhibitors hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, plants are also covered that, in addition to being able to tolerate herbicides that inhibit acetyl-Coenzyme A carboxylase activity, are by the use of recombinant DNA techniques capable to synthesize one or more insecticidal proteins, especially those known from the bacterial genus Bacillus, particularly from Bacillus thuringiensis, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present disclosure these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coleoptera), two-winged insects (Diptera), and moths (Lepidoptera) and to nematodes (Nematoda).

Furthermore, in one embodiment, plants are also covered that are, e.g., by the use of recombinant DNA techniques and/or by breeding and/or otherwise selected for such traits, able to synthesize one or more proteins to increase the resistance or tolerance of those plants to bacterial, viral or fungal pathogens. The methods for producing such genetically modified plants are generally known to the person skilled in the art. The plants produced as described herein can also be stacked with other traits including, but not limited to, disease resistance, enhanced mineral profile, enhanced vitamin profile, enhanced oil profile (e.g., high oleic acid content), amino acid profile (e.g., high lysine corn), and other trait types known in the art.

Furthermore, in one embodiment, plants are also covered that are, e.g., by the use of recombinant DNA techniques and/or by breeding and/or by other means of selection, able to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, in one embodiment, plants are also covered that contain, e.g., by the use of recombinant DNA techniques and/or by breeding and/or by other means of selection, a modified amount of substances of content or new substances of content, specifically to improve human or animal nutrition. Furthermore, plants are also covered that contain by the use of recombinant DNA techniques a modified amount of substances of content or new substances of content, specifically to improve raw material production.

Furthermore, in some embodiments, plants of the disclosure are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, plants of the disclosure tolerant to acetyl-Coenzyme A carboxylase inhibitors, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, plants of the disclosure tolerant to acetyl-Coenzyme A carboxylase inhibitors, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g., genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, plants of the disclosure tolerant to acetyl-Coenzyme A carboxylase inhibitors, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

The present disclosure also encompasses progeny of the plants of the disclosure as well as seeds derived from the herbicide-tolerant plants of the disclosure and cells derived from the herbicide-tolerant plants of the invention.

In various embodiments, plants hereof can be used to produce plant products. Thus, a method for preparing a descendant seed comprises planting a seed of a capable of producing a plant hereof, growing the resulting plant, and harvesting descendant seed thereof. In some embodiments, such a method can further comprise applying an ACCase-inhibiting herbicide composition to the resulting plant. Similarly, a method for producing a derived product from a plant hereof can comprise processing a plant part thereof to obtain a derived product. In some embodiments, such a method can be used to obtain a derived product that is any of, e.g., fodder, feed, seed meal, oil, or seed-treatment-coated seeds. Seeds, treated seeds, and other plant products obtained by such methods are useful products that can be commercialized.

In various embodiments, the present disclosure provides production of food products, consumer products, industrial products, and veterinary products from any of the plants described herein.

Acetyl-Coenzyme A Carboxylase Enzymes

The present disclosure provides plants expressing acetyl-Coenzyme A carboxylase enzymes with amino acid sequences that differ from the amino acid sequence of the acetyl-Coenzyme A carboxylase enzyme found in the corresponding wild-type plant. For ease of understanding, the amino acid numbering system used herein will be the numbering system used for the acetyl-Coenzyme A carboxylase from *Alopecurus myosuroides* [Huds.] (also referred to as black grass). The mRNA sequence encoding the *A. myosuroides* acetyl-Coenzyme A carboxylase is available at GenBank accession number AJ310767 and the protein sequence is available at GenBank accession no. CAC84161 both of which are specifically incorporated herein by reference. The number of the amino acid referred to will be followed with (Am) to indicate the amino acid in the *Alopecurus myosuroides* sequence to which the amino acid corresponds. FIG. 18 provides *Alopecurus myosuroides* acetyl-Coenzyme A carboxylase amino acid sequence (GenBank accession no. CAC84161). Amino acids that may be altered in the acetyl-Coenzyme A carboxylase enzymes of the disclosure are indicated in bold double underline, and FIG. 19 depicts the amino acid sequence of wild-type *Oryza sativa* acetyl-Coenzyme A carboxylases aligned with *Alopecurus myosuroides* acetyl-Coenzyme A carboxylase with some critical residues denoted.

In one embodiment, an acetyl-Coenzyme A carboxylase of the present disclosure differs from the corresponding wild-type acetyl-Coenzyme A carboxylase at amino acid position 1,781(Am). Wild-type *A. myosuroides* acetyl-Coenzyme A carboxylase has an isoleucine at position 1,781 (Am) (I1781). The 1,781(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, leucine (I1781L), valine (I1781V), threonine (I1781T) and alanine (I1781A). In one embodiment, an acetyl-Coenzyme A carboxylase enzyme of the disclosure will have a leucine at position 1,781(Am).

In one embodiment, an acetyl-Coenzyme A carboxylase of the present disclosure differs from the corresponding wild-type acetyl-Coenzyme A carboxylase at amino acid position 1,785(Am). Wild-type *A. myosuroides* acetyl-Coenzyme A carboxylase has an alanine at position 1,785(Am) (A1785). The 1,785(Am) ACCase mutants of the disclosure will have an amino acid other than alanine at this position. Suitable examples of amino acids that may be found at this position in the acetyl-Coenzyme A carboxylase enzymes of the disclosure include, but are not limited to, glycine (A1785G). In one embodiment, an acetyl-Coenzyme A carboxylase enzyme of the disclosure will have a glycine at position 1,785(Am).

In one embodiment, an acetyl-Coenzyme A carboxylase of the present disclosure differs from the corresponding wild-type acetyl-Coenzyme A carboxylase at amino acid position 1,786(Am). Wild-type *A. myosuroides* acetyl-Coenzyme A carboxylase has an alanine at position 1,786(Am) (A1786). The 1,786(Am) ACCase mutants of the disclosure will have an amino acid other than alanine at this position. Suitable examples of amino acids that may be found at this position in the acetyl-Coenzyme A carboxylase enzymes of the disclosure include, but are not limited to, proline (A1786P). In one embodiment, an acetyl-Coenzyme A carboxylase enzyme of the disclosure will have a proline at position 1,786(Am).

In one embodiment, an acetyl-Coenzyme A carboxylase of the present disclosure differs from the corresponding wild-type acetyl-Coenzyme A carboxylase at amino acid position 1,811(Am). Wild-type *A. myosuroides* acetyl-Coenzyme A carboxylase has an isoleucine at position 1,811 (Am) (I1811). The 1,811(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (I1811N). In one embodiment, an acetyl-Coenzyme A carboxylase enzyme of the disclosure will have an asparagine at position 1,811(Am).

In one embodiment, an acetyl-Coenzyme A carboxylase of the present disclosure differs from the corresponding wild-type acetyl-Coenzyme A carboxylase at amino acid position 1,824(Am). Wild-type *A. myosuroides* acetyl-Coenzyme A carboxylase has a glutamine at position 1,824 (Am) (Q1824). The 1,824(Am) ACCase mutants of the disclosure will have an amino acid other than glutamine at this position. Suitable examples of amino acids that may be found at this position in the acetyl-Coenzyme A carboxylase enzymes of the disclosure include, but are not limited to, proline (Q1824P). In one embodiment, an acetyl-Coenzyme A carboxylase enzyme of the disclosure will have a proline at position 1,824(Am).

In one embodiment, an acetyl-Coenzyme A carboxylase of the present disclosure differs from the corresponding wild-type acetyl-Coenzyme A carboxylase at amino acid position 1,864(Am). Wild-type *A. myosuroides* acetyl-Coenzyme A carboxylase has a valine at position 1,864(Am) (V1864). The 1,864(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V1864F). In one embodiment, an acetyl-Coenzyme A carboxylase enzyme of the disclosure will have a phenylalanine at position 1,864(Am).

In one embodiment, an acetyl-Coenzyme A carboxylase of the present disclosure differs from the corresponding wild-type acetyl-Coenzyme A carboxylase at amino acid position 1,999(Am). Wild-type *A. myosuroides* acetyl-Coenzyme A carboxylase has a tryptophan at position 1,999 (Am) (W1999). The 1,999(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W1999C) and glycine (W1999G). In one embodiment, an acetyl-Coenzyme A carboxylase enzyme of the disclosure will have a glycine at position 1,999(Am).

In one embodiment, an acetyl-Coenzyme A carboxylase of the present disclosure differs from the corresponding wild-type acetyl-Coenzyme A carboxylase at amino acid position 2,027(Am). Wild-type *A. myosuroides* acetyl-Coenzyme A carboxylase has a tryptophan at position 2,027 (Am)(W2027). The 2,027(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W2027C) and arginine (W2027R). In one embodiment, an acetyl-Coenzyme A carboxylase enzyme of the disclosure will have a cysteine at position 2,027(Am).

In one embodiment, an acetyl-Coenzyme A carboxylase of the present disclosure differs from the corresponding wild-type acetyl-Coenzyme A carboxylase at amino acid position 2,039(Am). Wild-type *A. myosuroides* acetyl-Coenzyme A carboxylase has a glutamic acid at position 2,039(Am) (E2039). The 2,039(Am) ACCase mutants of the disclosure will have an amino acid other than glutamic acid at this position. Suitable examples of amino acids that may be found at this position in the acetyl-Coenzyme A carboxylase enzymes of the disclosure include, but are not limited to, glycine (E2039G). In one embodiment, an acetyl-Coenzyme A carboxylase enzyme of the disclosure will have an glycine at position 2,039(Am).

In one embodiment, an acetyl-Coenzyme A carboxylase of the present disclosure differs from the corresponding wild-type acetyl-Coenzyme A carboxylase at amino acid position 2,041(Am). Wild-type *A. myosuroides* acetyl-Coenzyme A carboxylase has an isoleucine at position 2,041 (Am) (I2041). The 2,041(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (I2041N), or valine (I2041V). In one embodiment, an acetyl-Coenzyme A carboxylase enzyme of the disclosure will have an asparagine at position 2,041(Am).

In one embodiment, an acetyl-Coenzyme A carboxylase of the present disclosure differs from the corresponding wild-type acetyl-Coenzyme A carboxylase at amino acid position 2,049(Am). Wild-type *A. myosuroides* acetyl-Coenzyme A carboxylase has an valine at position 2,049(Am) (V2049). The 2,049(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V2049F), isoleucine (V2049I) and leucine (V2049L). In one embodiment, an acetyl-Coenzyme A carboxylase enzyme of the disclosure will have an phenylalanine at position 2,049(Am).

In one embodiment, an acetyl-Coenzyme A carboxylase of the present disclosure differs from the corresponding wild-type acetyl-Coenzyme A carboxylase at amino acid position 2,059(Am). Wild-type *A. myosuroides* acetyl-Coenzyme A carboxylase has an alanine at position 2,059(Am) (A2059). The 2,059(Am) ACCase mutants of the disclosure will have an amino acid other than an alanine at this position. Suitable examples of amino acids that may be found at this position in the acetyl-Coenzyme A carboxylase enzymes of the disclosure include, but are not limited to, valine (A2059V). In one embodiment, an acetyl-Coenzyme A carboxylase enzyme of the disclosure will have a valine at position 2,059(Am).

In one embodiment, an acetyl-Coenzyme A carboxylase of the present disclosure differs from the corresponding wild-type acetyl-Coenzyme A carboxylase at amino acid position 2074(Am). Wild-type *A. myosuroides* acetyl-Coenzyme A carboxylase has a tryptophan at position 2074(Am) (W2074). The 2,074(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, leucine (W2074L). In one embodiment, an acetyl-Coenzyme A carboxylase enzyme of the disclosure will have a leucine at 2074(Am).

In one embodiment, an acetyl-Coenzyme A carboxylase of the present disclosure differs from the corresponding wild-type acetyl-Coenzyme A carboxylase at amino acid position 2,075(Am). Wild-type *A. myosuroides* acetyl-Coenzyme A carboxylase has a valine at position 2,075(Am) (V2075). The 2,075(Am) ACCase mutants of the disclosure will have an amino acid other than valine at this position. Suitable examples of amino acids that may be found at this position in the acetyl-Coenzyme A carboxylase enzymes of the disclosure include, but are not limited to, methionine (V2075M), leucine (V2075L) and isoleucine (V2075I). In one embodiment, an acetyl-Coenzyme A carboxylase enzyme of the disclosure will have a leucine at position 2,075(Am). In some embodiments, an acetyl-Coenzyme A carboxylase enzyme of the disclosure will have a valine at position 2075(Am) and an additional valine immediately after position 2075(Am) and before the valine at position 2076(Am), i.e., may have three consecutive valines where the wild-type enzyme has two.

In one embodiment, an acetyl-Coenzyme A carboxylase of the present disclosure differs from the corresponding wild-type acetyl-Coenzyme A carboxylase at amino acid position 2,078(Am). Wild-type *A. myosuroides* acetyl-Coenzyme A carboxylase has an aspartate at position 2,078 (Am) (D2078). The 2,078(Am) ACCase mutants of the disclosure will have an amino acid other than aspartate at this position. Suitable examples of amino acids that may be found at this position in the acetyl-Coenzyme A carboxylase enzymes of the disclosure include, but are not limited to, lysine (D2,078K), glycine (D2078G), or threonine (D2078T). In one embodiment, an acetyl-Coenzyme A carboxylase enzyme of the disclosure will have a glycine at position 2,078(Am).

In one embodiment, an acetyl-Coenzyme A carboxylase of the present disclosure differs from the corresponding wild-type acetyl-Coenzyme A carboxylase at amino acid position 2,079(Am). Wild-type *A. myosuroides* acetyl-Coenzyme A carboxylase has a serine at position 2,079(Am) (S2079). The 2,079(Am) ACCase mutants of the disclosure will have an amino acid other than serine at this position. Suitable examples of amino acids that may be found at this position in the acetyl-Coenzyme A carboxylase enzymes of the disclosure include, but are not limited to, phenylalanine (S2079F). In one embodiment, an acetyl-Coenzyme A carboxylase enzyme of the disclosure will have a phenylalanine at position 2,079(Am).

In one embodiment, an acetyl-Coenzyme A carboxylase of the present disclosure differs from the corresponding wild-type acetyl-Coenzyme A carboxylase at amino acid position 2,080(Am). Wild-type *A. myosuroides* acetyl-Coenzyme A carboxylase has a lysine at position 2,080(Am) (K2080). The 2,080(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2080E). In one embodiment, an acetyl-Coenzyme A carboxylase enzyme of the disclosure will have a glutamic acid at position 2,080(Am). In another embodiment, acetyl-Coenzyme A carboxylase enzymes of the disclosure will typically have a deletion of this position (42080).

In one embodiment, an acetyl-Coenzyme A carboxylase of the present disclosure differs from the corresponding wild-type acetyl-Coenzyme A carboxylase at amino acid position 2,081(Am). Wild-type *A. myosuroides* acetyl-Coenzyme A carboxylase has a isoleucine at position 2,081 (Am) (I2081). The 2,081(Am) ACCase mutants of the disclosure will have an amino acid other than isoleucine at this position. In one embodiment, acetyl-Coenzyme A carboxylase enzymes of the disclosure will typically have a deletion of this position (A2081).

In one embodiment, an acetyl-Coenzyme A carboxylase of the present disclosure differs from the corresponding wild-type acetyl-Coenzyme A carboxylase at amino acid position 2,088(Am). Wild-type *A. myosuroides* acetyl-Coenzyme A carboxylase has a cysteine at position 2,088(Am) (C2088). The 2,088(Am) ACCase mutants of the disclosure will have an amino acid other than cysteine at this position. Suitable examples of amino acids that may be found at this position in the acetyl-Coenzyme A carboxylase enzymes of the disclosure include, but are not limited to, arginine (C2088R), tryptophan (C2088W), phenylalanine (C2088F), glycine (C2088G), histidine (C2088H), lysine (C2088K), serine (C2088S), threonine (C2088T), leucine (C2088L) or valine (C2088V). In one embodiment, an acetyl-Coenzyme A carboxylase enzyme of the disclosure will have an arginine at position 2,088(Am).

In one embodiment, an acetyl-Coenzyme A carboxylase of the present disclosure differs from the corresponding wild-type acetyl-Coenzyme A carboxylase at amino acid position 2,095(Am). Wild-type *A. myosuroides* acetyl-Coenzyme A carboxylase has a lysine at position 2,095(Am) (K2095). The 2,095(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2095E). In one embodiment, an acetyl-Coenzyme A carboxylase enzyme of the disclosure will have a glutamic acid at position 2,095(Am).

In one embodiment, an acetyl-Coenzyme A carboxylase of the present disclosure differs from the corresponding wild-type acetyl-Coenzyme A carboxylase at amino acid position 2,096(Am). Wild-type *A. myosuroides* acetyl-Coenzyme A carboxylase has a glycine at position 2,096(Am) (G2096). The 2,096(Am) ACCase mutants of the disclosure will have an amino acid other than glycine at this position. Suitable examples of amino acids that may be found at this position in the acetyl-Coenzyme A carboxylase enzymes of the disclosure include, but are not limited to, alanine (G2096A), or serine (G2096S). In one embodiment, an acetyl-Coenzyme A carboxylase enzyme of the disclosure will have an alanine at position 2,096(Am).

In one embodiment, an acetyl-Coenzyme A carboxylase of the present disclosure differs from the corresponding wild-type acetyl-Coenzyme A carboxylase at amino acid position 2,098(Am). Wild-type *A. myosuroides* acetyl-Coenzyme A carboxylase has a valine at position 2,098(Am) (V2098). The 2,098(Am) ACCase mutants of the disclosure will have an amino acid other than valine at this position. Suitable examples of amino acids that may be found at this position in the acetyl-Coenzyme A carboxylase enzymes of the disclosure include, but are not limited to, alanine (V2098A), glycine (V2098G), proline (V2098P), histidine (V2098H), serine (V2098S) or cysteine (V2098C). In one embodiment, an acetyl-Coenzyme A carboxylase enzyme of the disclosure will have an alanine at position 2,098(Am).

In one embodiment, the present disclosure encompasses acetyl-Coenzyme A carboxylase of an herbicide-tolerant plant of the disclosure which differs from the acetyl-Coenzyme A carboxylase of the corresponding wild-type plant at only one of the following positions: 1,781(Am), 1,785(Am), 1,786(Am), 1,811(Am), 1,824(Am), 1,864(Am), 1,999 (Am), 2,027(Am), 2,039(Am), 2,041(Am), 2,049(Am), 2,059(Am), 2,074(Am), 2,075(Am), 2,078(Am), 2,079 (Am), 2,080(Am), 2,081(Am), 2,088(Am), 2,095(Am), 2,096(Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080(Am), or 2,095(Am). In a more preferred embodiment the acetyl-Coenzyme A carboxylase of a herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, Acetyl-Coenzyme A carboxylase enzymes of the disclosure will have only one of the following substitutions: an isoleucine at position 2,075(Am), glycine at position 2,078(Am), or arginine at position 2,088 (Am). In a preferred embodiment, Acetyl-Coenzyme A carboxylase enzymes of the disclosure will have only one of the following substitutions: a glycine at position 2,039(Am), valine at position 2,059(Am), methionine at position 2,075 (Am), duplication of position 2,075(Am) (i.e., an insertion of valine between 2,074(Am) and 2,075(Am), or an insertion of valine between position 2,075(Am) and 2,076(Am)), deletion of amino acid position 2,080(Am), glutamic acid at position 2,080(Am), deletion of position 2,081(Am), or glutamic acid at position 2,095(Am). In a more preferred embodiment, Acetyl-Coenzyme A carboxylase enzymes of the disclosure will have only one of the following substitutions: a glycine at position 1,785(Am), a proline at position 1,786(Am), an asparagine at position 1,811(Am), a leucine at position 2,075(Am), a methionine at position 2,075(Am), a threonine at position 2,078(Am), a deletion at position 2,080(Am), a deletion at position 2,081(Am), a tryptophan, phenylalanine, glycine, histidine, lysine, leucine, serine, threonine, or valine at position 2,088(Am), a serine at position 2,096(Am), an alanine at position 2,096(Am), an alanine at position 2,098(Am), a glycine at position 2,098 (Am), an histidine at position 2,098(Am), a proline at position 2,098(Am), or a serine at position 2,098(Am). In a most preferred embodiment, Acetyl-Coenzyme A carboxylase enzymes of the disclosure will have only one of the following substitutions: a leucine at position 1,781(Am), a threonine at position 1,781(Am), a valine at position 1,781 (Am), an alanine at position 1,781(Am), a glycine at position 1,999(Am), a cysteine or arginine at position 2,027(Am), an arginine at position 2,027(Am), an asparagine at position 2,041(Am), a valine at position 2,041(Am), an alanine at position 2,096(Am), and a serine at position 2,096(Am).

In one embodiment, nucleic acids encoding Acetyl-Coenzyme A carboxylase polypeptide having only one of the following substitutions: isoleucine at position 2,075(Am), glycine at position 2,078(Am), or arginine at position 2,088 (Am) are used transgenically. In another embodiment, a monocot plant cell is transformed with an expression vector construct comprising the nucleic acid encoding Acetyl-Coenzyme A carboxylase polypeptide having only one of the following substitutions: isoleucine at position 2,075(Am), glycine at position 2,078(Am), or arginine at position 2,088 (Am).

In one embodiment, the present disclosure provides rice plants comprising nucleic acids encoding Acetyl-Coenzyme A carboxylase polypeptides having a substitution at only one amino acid position as described above.

In one embodiment, the present disclosure provides BEP clade plants comprising nucleic acids encoding Acetyl-Coenzyme A carboxylase polypeptides having a substitution at only one amino acid position as described above.

In one embodiment, the present disclosure provides BET subclade plants comprising nucleic acids encoding Acetyl-Coenzyme A carboxylase polypeptides having a substitution at only one amino acid position as described above.

In one embodiment, the present disclosure provides BET crop plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at amino acid position 1,781(Am), wherein the amino acid at position 1,781(Am) differs from that of wild type and is not leucine.

In one embodiment, the present disclosure provides monocot plants comprising nucleic acids encoding Acetyl-Coenzyme A carboxylase polypeptides having a substitution at amino acid position 1,999(Am), wherein the amino acid at position 1,999(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,027 (Am), wherein the amino acid at position 2,027(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,041(Am), wherein the amino acid at position 2,041(Am) differs from that of wild type and is not valine or asparagine.

In one embodiment, the present disclosure provides monocot plants comprising nucleic acids encoding Acetyl-Coenzyme A carboxylase polypeptides having a substitution at amino acid position 2,096(Am), wherein the amino acid at position 2,096(Am) differs from that of wild type and is not alanine.

The present disclosure also provides acetyl-Coenzyme A carboxylase enzymes with an amino acid sequence that differs in more than one amino acid position from that of the acetyl-Coenzyme A carboxylase enzyme found in the corresponding wild-type plant. For example, an acetyl-Coenzyme A carboxylase of the present disclosure may differ in 2, 3, 4, 5, 6, or 7 positions from that of the acetyl-Coenzyme A carboxylase enzyme found in the corresponding wild-type plant.

In one embodiment, an acetyl-Coenzyme A carboxylase of the present disclosure differs from the corresponding wild-type acetyl-Coenzyme A carboxylase at amino acid position 1,781(Am) and at one or more additional amino acid positions. Acetyl-Coenzyme A carboxylase enzymes of the present disclosure will typically have a leucine, a threonine, a valine, or an alanine at position 1,781(Am). In addition, enzymes of this embodiment will also comprise one or more of a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine, or an additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine tryptophan, phenylalanine, glycine, histidine, lysine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am) and a glycine at position 1,785(Am). In one embodiment, an acetyl-Coenzyme A carboxylase of the present disclosure will have a leucine, a threonine, a valine, or an alanine at position 1,781(Am) and a proline at position 1,786(Am). In one embodiment, an acetyl-Coenzyme A carboxylase of the present disclosure will have a leucine, a threonine, a valine, or an alanine at position 1,781(Am) and an asparagine at position 1,811(Am). In one embodiment, an acetyl-Coenzyme A carboxylase of the present disclosure will have a leucine, a threonine, a valine, or an alanine at position 1,781(Am) and a proline at position 1824(Am). In one embodiment, an acetyl-Coenzyme A carboxylase of the present disclosure will have a leucine, a threonine, a valine, or an alanine at position 1,781(Am) and a phenylalanine at position 1864(Am). In one embodiment, an acetyl-Coenzyme A carboxylase of the present disclosure will have a leucine, a threonine, a valine, or an alanine at position 1,781(Am) and a cysteine or glycine at position 1,999(Am). In one embodiment, an acetyl-Coenzyme A carboxylase of the present disclosure will have a leucine, a threonine, a valine, or an alanine at position 1,781(Am) and a cysteine or an arginine at position 2,027(Am). In one embodiment, an acetyl-Coenzyme A carboxylase of the present disclosure will have a leucine, a threonine, a valine, or an alanine at position 1,781(Am) and a glycine at position 2039(Am). In one embodiment, an acetyl-Coenzyme A carboxylase of the present disclosure will have a leucine, a threonine, a valine, or an alanine at position 1,781(Am) and an asparagine at position 2,041(Am). In one embodiment, an acetyl-Coenzyme A carboxylase of the present disclosure will have a leucine, a threonine, a valine, or an alanine at position 1,781(Am) and a phenylalanine, leucine or isoleucine at position 2,049(Am). In one embodiment, an acetyl-Coenzyme A carboxylase of the present disclosure will have a leucine, a threonine, a valine, or an alanine at position 1,781(Am) and a valine at position 2059(Am). In one embodiment, an acetyl-Coenzyme A carboxylase of the present disclosure will have a leucine, a threonine, a valine, or an alanine at position 1,781(Am) and a leucine at position 2,074(Am). In one embodiment, an acetyl-Coenzyme A carboxylase of the present disclosure will have a leucine, a threonine, a valine, or an alanine at position 1,781(Am) and a leucine, isoleucine methionine, or additional valine at position 2,075(Am). In one embodiment, an acetyl-Coenzyme A carboxylase of the present disclosure will have a leucine, a threonine, a valine, or an alanine at position 1,781(Am) and a glycine or threonine at position 2,078 (Am). In one embodiment, an acetyl-Coenzyme A carboxylase of the present disclosure will have a leucine, a threonine, a valine, or an alanine at position 1,781(Am) and a phenylalanine at position 2079(Am). In one embodiment, an acetyl-Coenzyme A carboxylase of the present disclosure will have a leucine, a threonine, a valine, or an alanine at position 1,781(Am) and a glutamic acid or a deletion at position 2080(Am). In one embodiment, an acetyl-Coenzyme A carboxylase of the present disclosure will have a leucine, a threonine, a valine, or an alanine at position 1,781(Am) and a deletion at position 2081(Am). In one embodiment, an acetyl-Coenzyme A carboxylase of the present disclosure will have a leucine, a threonine, a valine, or an alanine at position 1,781(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a leucine, a threonine, a valine, or an alanine at position 1,781(Am) and a glutamic acid at position 2,095(Am). In one embodiment, an acetyl-Coenzyme A carboxylase of the present disclosure will have a leucine, a threonine, a valine, or an alanine at position 1,781(Am) and an alanine or serine at position 2,096(Am). In one embodiment, an acetyl-Coenzyme A carboxylase of the present disclosure will have a leucine, a threonine, a valine, or an alanine at position 1,781(Am) and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am), a cysteine or arginine at position 2,027(Am), and an asparagine at position 2,041(Am). In one embodiment, an acetyl-Coenzyme A carboxylase of the present disclosure will have a leucine, a threonine, a valine, or an alanine at position 1,781(Am), a cysteine or arginine at position 2,027(Am), an asparagine at position 2,041(Am), and an alanine at position 2,096(Am).

In one embodiment, an acetyl-Coenzyme A carboxylase of the present disclosure differs from the corresponding wild-type acetyl-Coenzyme A carboxylase at amino acid position 1,785(Am) and at one or more additional amino acid positions. Acetyl-Coenzyme A carboxylase enzymes of the disclosure will typically have a glycine at position 1,785(Am). In addition, enzymes of this embodiment will also comprise one or more of a leucine, threonine, a valine, or alanine at position 1,781(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a glycine at position 1,785(Am)

and a leucine, a threonine, a valine, or an alanine at position 1,781(Am). In one embodiment, an acetyl-Coenzyme A carboxylase of the present disclosure will have a glycine at position 1,785(Am) and a proline at position 1,786(Am). In one embodiment, an acetyl-Coenzyme A carboxylase of the present disclosure will have a glycine at position 1,785(Am) and an asparagine at position 1,811(Am). In one embodiment, an acetyl-Coenzyme A carboxylase of the present disclosure will have a glycine at position 1,785(Am) and a proline at position 1,824(Am). In one embodiment, an acetyl-Coenzyme A carboxylase of the present disclosure will have a glycine at position 1,785(Am) and a phenylalanine at position 1,864(Am). In one embodiment, an acetyl-Coenzyme A carboxylase of the present disclosure will have a glycine at position 1,785(Am) and a cysteine or glycine at position 1,999(Am). In one embodiment, an acetyl-Coenzyme A carboxylase of the present disclosure will have a glycine at position 1,785(Am) and a cysteine or an arginine at position 2,027(Am). In one embodiment, an acetyl-Coenzyme A carboxylase of the present disclosure will have a glycine at position 1,785(Am) and a glycine at position 2,039(Am). In one embodiment, an acetyl-Coenzyme A carboxylase of the present disclosure will have a glycine at position 1,785(Am) and an asparagine at position 2,041(Am). In one embodiment, an acetyl-Coenzyme A carboxylase of the present disclosure will have a glycine at position 1,785(Am) and a phenylalanine, isoleucine or leucine at position 2,049(Am). In one embodiment, an acetyl-Coenzyme A carboxylase of the present disclosure will have a glycine at position 1,785(Am) and a valine at position 2,059(Am). In one embodiment, an acetyl-Coenzyme A carboxylase of the present disclosure will have a glycine at position 1,785(Am) and a leucine at position 2,074(Am). In one embodiment, an acetyl-Coenzyme A carboxylase of the present disclosure will have a glycine at position 1,785(Am) and a leucine, isoleucine, methionine or additional valine at position 2,075(Am). In one embodiment, an acetyl-Coenzyme A carboxylase of the present disclosure will have a glycine at position 1,785(Am) and a glycine or threonine at position 2,078(Am). In one embodiment, an acetyl-Coenzyme A carboxylase of the present disclosure will have a glycine at position 1,785(Am) and a phenylalanine at position 2,079(Am). In one embodiment, an acetyl-Coenzyme A carboxylase of the present disclosure will have a glycine at position 1,785(Am) and a glutamic acid or deletion at position 2,080(Am). In one embodiment, an acetyl-Coenzyme A carboxylase of the present disclosure will have a glycine at position 1,785(Am) and a deletion at position 2,081(Am). In one embodiment, an acetyl-Coenzyme A carboxylase of the present disclosure will have a glycine at position 1,785(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine at position 1,785(Am) and a glutamic acid at position 2,095(Am). In one embodiment, an acetyl-Coenzyme A carboxylase of the present disclosure will have a glycine at position 1,785(Am) and an alanine or serine at position 2,096(Am). In one embodiment, an acetyl-Coenzyme A carboxylase of the present disclosure will have a glycine at position 1,785(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,786(Am) and at one or more additional amino acid positions. Acetyl-Coenzyme A carboxylase enzymes of the disclosure will typically have a proline at position 1,786(Am). In addition, enzymes of this embodiment will also comprise one or more of a leucine, threonine, a valine, or alanine at position 1,781(Am), a glycine at position 1,785(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid or deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a proline at position 1,786(Am) and a leucine, a threonine, a valine, or an alanine at position 1,781(Am). In one embodiment, an acetyl-Coenzyme A carboxylase of the present disclosure will have a proline at position 1,786(Am) and a glycine at position 1,785(Am). In one embodiment, an acetyl-Coenzyme A carboxylase of the present disclosure will have a proline at position 1,786(Am) and an asparagine at position 1,811(Am). In one embodiment, an acetyl-Coenzyme A carboxylase of the present disclosure will have a proline at position 1,786(Am) and a proline at position 1,824(Am). In one embodiment, an acetyl-Coenzyme A carboxylase of the present disclosure will have a proline at position 1,786(Am) and phenylalanine at position 1,864(Am). In one embodiment, an acetyl-Coenzyme A carboxylase of the present disclosure will have a proline at position 1,786(Am) and a cysteine or glycine at position 1,999(Am). In one embodiment, an acetyl-Coenzyme A carboxylase of the present disclosure will have a proline at position 1,786(Am) and a cysteine or an arginine at position 2,027(Am). In one embodiment, an acetyl-Coenzyme A carboxylase of the present disclosure will have a proline at position 1,786(Am) and a glycine at position 2,039(Am). In one embodiment, an acetyl-Coenzyme A carboxylase of the present disclosure will have a proline at position 1,786(Am) and an asparagine at position 2,041(Am). In one embodiment, an acetyl-Coenzyme A carboxylase of the present disclosure will have a proline at position 1,786(Am) and phenylalanine, isoleucine or leucine at position 2,049(Am) In one embodiment, an acetyl-Coenzyme A carboxylase of the present disclosure will have a proline at position 1,786(Am) and a valine at position 2,059(Am). In one embodiment, an acetyl-Coenzyme A carboxylase of the present disclosure will have a proline at position 1,786(Am) and a leucine at position 2,074(Am). In one embodiment, an acetyl-Coenzyme A carboxylase of the present disclosure will have a proline at position 1,786(Am) and a leucine, isoleucine, methionine or additional valine at position 2,075(Am). In one embodiment, an acetyl-Coenzyme A carboxylase of the present disclosure will have a proline at position 1,786(Am) and a glycine or threonine at position 2,078(Am). In one embodiment, an acetyl-Coenzyme A carboxylase of the present disclosure will have a proline at position 1,786(Am) and a phenylalanine at position 2,079(Am). In one embodiment, an acetyl-Coenzyme A carboxylase of the present disclosure will have a proline at position 1,786(Am) and a glutamic acid or deletion at position 2,080(Am). In one embodiment, an acetyl-Coenzyme A carboxylase of the present disclosure will have a proline at position 1,786(Am) and a deletion at position 2,081(Am). In one embodiment, an acetyl-Coenzyme A carboxylase of the present disclosure will have a proline at position 1,786(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a proline at position 1,786(Am) and a glutamic acid at position 2,095(Am). In one embodiment, an acetyl-Coenzyme A carboxylase of the present disclosure will have a proline at position 1,786(Am) and an alanine or serine at position 2,096(Am). In one embodiment, an acetyl-Coenzyme A carboxylase of the present disclosure will have a proline at position 1,786(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,811(Am) and at one or more additional amino acid positions. Acetyl-Coenzyme A carboxylase enzymes of the disclosure will typically have an asparagine at position 1,811(Am). In addition, enzymes of this embodiment will also comprise one or more of a leucine, threonine, a valine, or alanine at position 1,781(Am), a glycine at position 1,785(Am), a proline at position 1,786(Am), a proline at position 1,824(Am), a phenylalanine at position 1,864(Am), a cysteine or glycine at position 1,999(Am), a cysteine or arginine at position 2,027(Am), a glycine at position 2,039 (Am), an asparagine at position 2,041(Am), a a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an asparagine at position 1,811 (Am) and a leucine, a threonine, a valine, or an alanine at position 1,781(Am). In one embodiment, an acetyl-Coenzyme A carboxylase of the present disclosure will have an asparagine at position 1,811(Am) and a glycine at position 1,785(Am). In one embodiment, an acetyl-Coenzyme A carboxylase of the present disclosure will have an asparagine at position 1,811(Am) and a proline at position 1,786 (Am). In one embodiment, an acetyl-Coenzyme A carboxylase of the present disclosure will have an asparagine at position 1,811(Am) and a proline at position 1,824(Am). In one embodiment, an acetyl-Coenzyme A carboxylase of the present disclosure will have an asparagine at position 1,811 (Am) and phenylalanine at position 1,864(Am). In one embodiment, an acetyl-Coenzyme A carboxylase of the present disclosure will have an asparagine at position 1,811 (Am) and a cysteine or glycine at position 1,999(Am). In one embodiment, an acetyl-Coenzyme A carboxylase of the present disclosure will have an asparagine at position 1,811 (Am) and a cysteine or an arginine at position 2,027(Am). In one embodiment, an acetyl-Coenzyme A carboxylase of the present disclosure will have an asparagine at position 1,811 (Am) and a glycine at position 2,039(Am). In one embodiment, an acetyl-Coenzyme A carboxylase of the present disclosure will have an asparagine at position 1,811(Am) and an asparagine at position 2,041(Am). In one embodiment, an acetyl-Coenzyme A carboxylase of the present disclosure will have an asparagine at position 1,811(Am) and phenylalanine, isoleucine or leucine at position 2,049 (Am). In one embodiment, an acetyl-Coenzyme A carboxylase of the present disclosure will have an asparagine at position 1,811(Am) and a valine at position 2,059(Am). In one embodiment, an acetyl-Coenzyme A carboxylase of the present disclosure will have an asparagine at position 1,811 (Am) and a leucine at position 2,074(Am). In one embodiment, an acetyl-Coenzyme A carboxylase of the present disclosure will have an asparagine at position 1,811(Am) and a leucine, isoleucine, methionine or additional valine at position 2,075(Am). In one embodiment, an acetyl-Coenzyme A carboxylase of the present disclosure will have an asparagine at position 1,811(Am) and a glycine or threonine at position 2,078(Am). In one embodiment, an acetyl-Coenzyme A carboxylase of the present disclosure will have an asparagine at position 1,811(Am) and a phenylalanine at position 2,079(Am). In one embodiment, an acetyl-Coenzyme A carboxylase of the present disclosure will have an asparagine at position 1,811(Am) and a glutamic acid or deletion at position 2,080(Am). In one embodiment, an acetyl-Coenzyme A carboxylase of the present disclosure will have an asparagine at position 1,811(Am) and a deletion at position 2,081(Am). In one embodiment, an acetyl-Coenzyme A carboxylase of the present disclosure will have an asparagine at position 1,811(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an asparagine at position 1,811 (Am) and a glutamic acid at position 2,095(Am). In one embodiment, an acetyl-Coenzyme A carboxylase of the present disclosure will have an asparagine at position 1,811 (Am) and an alanine or serine at position 2,096(Am). In one embodiment, an acetyl-Coenzyme A carboxylase of the present disclosure will have an asparagine at position 1,811 (Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,824(Am) and at one or more additional amino acid positions. Acetyl-Coenzyme A carboxylase enzymes of the disclosure will typically have a proline at position 1,824(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,864(Am) and at one or more additional amino acid positions. Acetyl-Coenzyme A carboxylase enzymes of the disclosure will typically have a phenylalanine at position 1,864(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a cysteine or glycine at position 1,999(Am), a cysteine or arginine at position 2,027(Am), a glycine at position 2,039 (Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,999(Am) and at one or more additional amino acid positions. Acetyl-Coenzyme A carboxylase enzymes of the disclosure will typically have a cysteine or glycine at position 1,999(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or glycine at position 1,999(Am) and a leucine, a threonine, a valine, or an alanine at position 1,781(Am). In one embodiment, an acetyl-Coenzyme A carboxylase of the present disclosure will have a cysteine or glycine at position 1,999(Am) and a glycine at position 1,785(Am). In one embodiment, an acetyl-Coenzyme A carboxylase of the present disclosure will have a cysteine or glycine at position 1,999(Am) and a proline at position 1,786(Am). In one embodiment, an acetyl-Coenzyme A carboxylase of the present disclosure will have a cysteine or glycine at position 1,999(Am) and have an asparagine at position 1,811(Am). In one embodiment, an acetyl-Coenzyme A carboxylase of the present disclosure will have a cysteine or glycine at position 1,999(Am) and a proline at position 1,824(Am). In one embodiment, an acetyl-Coenzyme A carboxylase of the present disclosure will have a cysteine or glycine at position 1,999(Am) and phenylalanine at position 1,864(Am). In one embodiment, an acetyl-Coenzyme A carboxylase of the present disclosure will have a cysteine or glycine at position 1,999(Am) and a cysteine or an arginine at position 2,027(Am). In one embodiment, an acetyl-Coenzyme A carboxylase of the present disclosure will have a cysteine or glycine at position 1,999(Am) and a glycine at position 2,039(Am). In one embodiment, an acetyl-Coenzyme A carboxylase of the present disclosure will have a cysteine or glycine at position 1,999(Am) and an asparagine at position 2,041(Am). In one embodiment, an acetyl-Coenzyme A carboxylase of the present disclosure will have a cysteine or glycine at position 1,999(Am) and a phenylalanine, isoleucine or leucine at position 2,049(Am). In one embodiment, an acetyl-Coenzyme A carboxylase of the present disclosure will have a cysteine or glycine at position 1,999(Am) and a cysteine or a valine at position 2,059(Am). In one embodiment, an acetyl-Coenzyme A carboxylase of the present disclosure will have a cysteine or glycine at position 1,999(Am) and a leucine at position 2,074(Am). In one embodiment, an acetyl-Coenzyme A carboxylase of the present disclosure will have a cysteine or glycine at position 1,999(Am) and a leucine, isoleucine, methionine or additional valine at position 2,075(Am). In one embodiment, an acetyl-Coenzyme A carboxylase of the present disclosure will have a cysteine or glycine at position 1,999(Am) and a glycine or threonine at position 2,078 (Am). In one embodiment, an acetyl-Coenzyme A carboxylase of the present disclosure will have a cysteine or glycine at position 1,999(Am) and a phenylalanine at position 2,079 (Am). In one embodiment, an acetyl-Coenzyme A carboxylase of the present disclosure will have a cysteine or glycine at position 1,999(Am) and a glutamic acid or deletion at position 2,080(Am). In one embodiment, an acetyl-Coenzyme A carboxylase of the present disclosure will have a cysteine or glycine at position 1,999(Am) and a deletion at position 2,081(Am). In one embodiment, an acetyl-Coenzyme A carboxylase of the present disclosure will have a cysteine or glycine at position 1,999(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or glycine at position 1,999(Am) and a glutamic acid at position 2,095(Am). In one embodiment, an acetyl-Coenzyme A carboxylase of the present disclosure will have a cysteine or glycine at position 1,999(Am) and an alanine or serine at position 2,096(Am). In one embodiment, an acetyl-Coenzyme A carboxylase of the present disclosure will have a cysteine or glycine at position 1,999(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,027(Am) and at one or more additional amino acid positions. Acetyl-Coenzyme A carboxylase enzymes of the disclosure will typically have a cysteine or arginine at position 2,027(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or arginine at position 2,027(Am) and a leucine, a threonine, a valine, or an alanine at position 1,781(Am). In one embodiment, an acetyl-Coenzyme A carboxylase of the present disclosure will have a cysteine or arginine at position 2,027(Am) and a glycine at position 1,785(Am). In one embodiment, an acetyl-Coenzyme A carboxylase of the present disclosure will have a cysteine or arginine at position 2,027(Am) and a proline at position 1,786(Am). In one embodiment, an acetyl-Coenzyme A carboxylase of the present disclosure will have a cysteine or arginine at position 2,027(Am) and have an asparagine at position 1,811(Am). In one embodiment, an acetyl-Coenzyme A carboxylase of the present disclosure will have a cysteine or arginine at position 2,027(Am) and have a proline at position 1,824(Am). In one embodiment, an acetyl-Coenzyme A carboxylase of the present disclosure will have a cysteine or arginine at position 2,027(Am) and have a phenylalanine at position 1,864(Am). In one embodiment, an acetyl-Coenzyme A carboxylase of the present disclosure will have a cysteine or arginine at position 2,027(Am) and a cysteine or glycine at position 1,999(Am). In one embodiment, an acetyl-Coenzyme A carboxylase of the present disclosure will have a cysteine or arginine at position 2,027(Am) and have a glycine at position 2,039 (Am). In one embodiment, an acetyl-Coenzyme A carboxylase of the present disclosure will have a cysteine or arginine at position 2,027(Am) and an asparagine at position 2,041 (Am). In one embodiment, an acetyl-Coenzyme A carboxylase of the present disclosure will have a cysteine or arginine at position 2,027(Am) and a phenylalanine, isoleucine or leucine at position 2,049(Am). In one embodiment, an acetyl-Coenzyme A carboxylase of the present disclosure will have a cysteine or arginine at position 2,027(Am) and have a valine at position 2,059(Am). In one embodiment, an acetyl-Coenzyme A carboxylase of the present disclosure will have a cysteine or arginine at position 2,027(Am) and a leucine at position 2,074(Am). In one embodiment, an acetyl-Coenzyme A carboxylase of the present disclosure will have a cysteine or arginine at position 2,027(Am) and a leucine, isoleucine, methionine or additional valine at position 2,075(Am). In one embodiment, an acetyl-Coenzyme A carboxylase of the present disclosure will have a cysteine or arginine at position 2,027(Am) and a glycine or threonine at position 2,078(Am). In one embodiment, an acetyl-Coenzyme A carboxylase of the present disclosure will have a cysteine or arginine at position 2,027(Am) and a phenylalanine at position 2,079(Am). In one embodiment, an acetyl-Coenzyme A carboxylase of the present disclosure will have a cysteine or arginine at position 2,027(Am) and a glutamic acid or deletion at position 2,080(Am). In one embodiment, an acetyl-Coenzyme A carboxylase of the present disclosure will have a cysteine or arginine at position 2,027(Am) and a deletion at position 2,081(Am). In one embodiment, an acetyl-Coenzyme A carboxylase of the present disclosure will have a cysteine or arginine at position 2,027(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or arginine at position 2,027(Am) and a glutamic acid at position 2,095(Am). In one embodiment, an acetyl-Coenzyme A carboxylase of the present disclosure will have a cysteine or arginine at position 2,027(Am) and an alanine or serine at position 2,096(Am). In one embodiment, an acetyl-Coenzyme A carboxylase of the present disclosure will have a cysteine or arginine at position 2,027(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,039(Am) and at one or more additional amino acid positions. Acetyl-Coenzyme A carboxylase enzymes of the disclosure will typically have a glycine at position 2,039(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,041(Am) and at one or more additional amino acid positions. Acetyl-Coenzyme A carboxylase enzymes of the disclosure will typically have an asparagine at position 2,041(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081 (Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have an asparagine at position 2,041(Am) and a leucine, a threonine, a valine, or an alanine at position 1,781(Am). In one embodiment, an acetyl-Coenzyme A carboxylase of the present disclosure will have an asparagine at position 2,041(Am) and a glycine at position 1,785(Am). In one embodiment, an acetyl-Coenzyme A carboxylase of the present disclosure will have an asparagine at position 2,041(Am) and a proline at position 1,786(Am). In one embodiment, an acetyl-Coenzyme A carboxylase of the present disclosure will have an asparagine at position 2,041(Am) and have an asparagine at position 1,811(Am). In one embodiment, an acetyl-Coenzyme A carboxylase of the present disclosure will have an asparagine at position 2,041(Am) and a proline at position 1824(Am). In one embodiment, an acetyl-Coenzyme A carboxylase of the present disclosure will have an asparagine at position 2,041(Am) and a phenylalanine at position 1864(Am). In one embodiment, an acetyl-Coenzyme A carboxylase of the present disclosure will have an asparagine at position 2,041(Am) and a cysteine or glycine at position 1,999(Am). In one embodiment, an acetyl-Coenzyme A carboxylase of the present disclosure will have an asparagine at position 2,041(Am) and a cysteine or arginine at position 2,027(Am). In one embodiment, an acetyl-Coenzyme A carboxylase of the present disclosure will have an asparagine at position 2,041(Am) and a glycine at position 2039(Am). In one embodiment, an acetyl-Coenzyme A carboxylase of the present disclosure will have an asparagine at position 2,041(Am) and an asparagine at position 2,041(Am). In one embodiment, an acetyl-Coenzyme A carboxylase of the present disclosure will have an asparagine at position 2,041(Am) and a phenylalanine, isoleucine or leucine at position 2,049(Am) In one embodiment, an acetyl-Coenzyme A carboxylase of the present disclosure will have an asparagine at position 2,041(Am) and a valine at position 2,059(Am). In one embodiment, an acetyl-Coenzyme A carboxylase of the present disclosure will have an asparagine at position 2,041(Am) and a leucine at position 2,074(Am). In one embodiment, an acetyl-Coenzyme A carboxylase of the present disclosure will have an asparagine at position 2,041(Am) and a leucine, isoleucine, methionine or additional valine at position 2,075(Am). In one embodiment, an acetyl-Coenzyme A carboxylase of the present disclosure will have an asparagine at position 2,041 (Am) and a glycine or threonine at position 2,078(Am). In one embodiment, an acetyl-Coenzyme A carboxylase of the present disclosure will have an asparagine at position 2,041 (Am) and a phenylalanine at position 2079(Am). In one embodiment, an acetyl-Coenzyme A carboxylase of the present disclosure will have an asparagine at position 2,041 (Am) and a glutamic acid or a deletion at position 2080 (Am). In one embodiment, an acetyl-Coenzyme A carboxylase of the present disclosure will have an asparagine at position 2,041(Am) and a deletion at position 2081(Am). In one embodiment, an acetyl-Coenzyme A carboxylase of the present disclosure will have an isoleucine at position 2,041 (Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an isoleucine at position 2,041(Am) and a glutamic acid at position 2,095(Am). In one embodiment, an acetyl-Coenzyme A carboxylase of the present disclosure will have an isoleucine at position 2,041(Am) and an alanine or serine at position 2,096(Am). In one embodiment, an acetyl-Coenzyme A carboxylase of the present disclosure will have an isoleucine at position 2,041(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,049(Am) and at one or more additional amino acid positions. Acetyl-Coenzyme A carboxylase enzymes of the disclosure will typically have a phenylalanine, isoleucine or leucine at position 2,049(Am). In addition, enzymes of this embodiment will also comprise one or more of a leucine, threonine, a valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a phenylalanine, isoleucine or leucine at position 2,049(Am) and a leucine, a threonine, a valine, or an alanine at position 1,781(Am). In one embodiment, an acetyl-Coenzyme A carboxylase of the present disclosure will have a phenylalanine, isoleucine or leucine at position 2,049(Am) and a glycine at position 1,785(Am). In one embodiment, an acetyl-Coenzyme A carboxylase of the present disclosure will have a phenylalanine, isoleucine or leucine at position 2,049(Am) and a proline at position 1,786(Am). In one embodiment, an acetyl-Coenzyme A carboxylase of the present disclosure will have a phenylalanine, isoleucine or leucine at position 2,049(Am) and have an asparagine at position 1,811(Am). In one embodiment, an acetyl-Coenzyme A carboxylase of the present disclosure will have a phenylalanine, isoleucine or leucine at position 2,049(Am) and a proline at position 1824(Am). In one embodiment, an acetyl-Coenzyme A carboxylase of the present disclosure will have a phenylalanine, isoleucine or leucine at position 2,049(Am) and a phenylalanine at position 1864(Am). In one embodiment, an acetyl-Coenzyme A carboxylase of the present disclosure will have a phenylalanine, isoleucine or leucine at position 2,049(Am) and a cysteine or glycine at position 1,999(Am). In one embodiment, an acetyl-Coenzyme A carboxylase of the present disclosure will have a phenylalanine, isoleucine or leucine at position 2,049(Am) and a cysteine or an arginine at position 2,027(Am). In one embodiment, an acetyl-Coenzyme A carboxylase of the present disclosure will have a phenylalanine, isoleucine or leucine at position 2,049(Am) and a glycine at position 2039(Am). In one embodiment, an acetyl-Coenzyme A carboxylase of the present disclosure will have a phenylalanine, isoleucine or leucine at position 2,049(Am) and an asparagine at position 2,041(Am). In one embodiment, an acetyl-Coenzyme A carboxylase of the present disclosure will have a phenylalanine, isoleucine or leucine at position 2,049(Am) and a valine at position 2059(Am). In one embodiment, an acetyl-Coenzyme A carboxylase of the present disclosure will have a phenylalanine, isoleucine or leucine at position 2,049(Am) and a leucine at position 2,074(Am). In one embodiment, an acetyl-Coenzyme A carboxylase of the present disclosure will have a phenylalanine, isoleucine or leucine at position 2,049(Am) and a leucine, isoleucine methionine, or additional valine at position 2,075(Am). In one embodiment, an acetyl-Coenzyme A carboxylase of the present disclosure will have a phenylalanine, isoleucine or leucine at position 2,049(Am) and a glycine or threonine at position 2,078 (Am). In one embodiment, an acetyl-Coenzyme A carboxylase of the present disclosure will have a phenylalanine, isoleucine or leucine at position 2,049(Am) and a phenylalanine at position 2079(Am). In one embodiment, an acetyl-Coenzyme A carboxylase of the present disclosure will have a phenylalanine, isoleucine or leucine at position 2,049(Am) and a glutamic acid or a deletion at position 2080(Am). In one embodiment, an acetyl-Coenzyme A carboxylase of the present disclosure will have a phenylalanine, isoleucine or leucine at position 2,049(Am) and a deletion at position 2081(Am). In one embodiment, an acetyl-Coenzyme A carboxylase of the present disclosure will have a phenylalanine, isoleucine or leucine at position 2,049(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a phenylalanine, isoleucine or leucine at position 2,049(Am) and a glutamic acid at position 2,095(Am). In one embodiment, an acetyl-Coenzyme A carboxylase of the present disclosure will have a phenylalanine, isoleucine or leucine at position 2,049(Am) and an alanine or serine at position 2,096(Am). In one embodiment, an acetyl-Coenzyme A carboxylase of the present disclosure will have a phenylalanine, isoleucine or leucine at position 2,049(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,059(Am) and at one or more additional amino acid positions. Acetyl-Coenzyme A carboxylase enzymes of the disclosure will typically have a valine at position 2,059 (Am). In addition, enzymes of this embodiment will also comprise one or more of a leucine, threonine, a valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine or tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,074(Am) and at one or more additional amino acid positions. Acetyl-Coenzyme A carboxylase enzymes of the disclosure will typically have a leucine at position 2,074(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine at position 2,074(Am) and a leucine, a threonine, a valine, or an alanine at position 1,781(Am). In one embodiment, an acetyl-Coenzyme A carboxylase of the present disclosure will have a leucine at position 2,074(Am) and a glycine at position 1,785(Am). In one embodiment, an acetyl-Coenzyme A carboxylase of the present disclosure will have a leucine at position 2,074(Am) and a proline at position 1,786(Am). In one embodiment, an acetyl-Coenzyme A carboxylase of the present disclosure will have a leucine at position 2,074(Am) and have an asparagine at position 1,811(Am). In one embodiment, an acetyl-Coenzyme A carboxylase of the present disclosure will have a leucine at position 2,074(Am) and a proline at position 1824(Am). In one embodiment, an acetyl-Coenzyme A carboxylase of the present disclosure will have a leucine at position 2,074(Am) and a phenylalanine at position 1864(Am). In one embodiment, an acetyl-Coenzyme A carboxylase of the present disclosure will have a leucine at position 2,074(Am) and a cysteine or glycine at position 1,999(Am). In one embodiment, an acetyl-Coenzyme A carboxylase of the present disclosure will have a leucine at position 2,074(Am) and a cysteine or an arginine at position 2,027(Am). In one embodiment, an acetyl-Coenzyme A carboxylase of the present disclosure will have a leucine at position 2,074(Am) and a glycine at position 2039(Am). In one embodiment, an acetyl-Coenzyme A carboxylase of the present disclosure will have a leucine at position 2,074(Am) and an asparagine at position 2,041(Am). In one embodiment, an acetyl-Coenzyme A carboxylase of the present disclosure will have a leucine at position 2,074(Am) and a phenylalanine, leucine or isoleucine at position 2,049(Am). In one embodiment, an acetyl-Coenzyme A carboxylase of the present disclosure will have a leucine at position 2,074 (Am) and a valine at position 2059(Am). In one embodiment, an acetyl-Coenzyme A carboxylase of the present disclosure will have a leucine at position 2,074(Am) and a leucine, isoleucine methionine, or additional valine at position 2,075(Am). In one embodiment, an acetyl-Coenzyme A carboxylase of the present disclosure will have a leucine at position 2,074(Am) and a glycine or threonine at position 2,078(Am). In one embodiment, an acetyl-Coenzyme A carboxylase of the present disclosure will have a leucine at position 2,074(Am) and a phenylalanine at position 2079 (Am). In one embodiment, an acetyl-Coenzyme A carboxylase of the present disclosure will have a leucine at position 2,074(Am) and a glutamic acid or a deletion at position 2080(Am). In one embodiment, an acetyl-Coenzyme A carboxylase of the present disclosure will have a leucine at position 2,074(Am) and a deletion at position 2081(Am). In one embodiment, an acetyl-Coenzyme A carboxylase of the present disclosure will have a leucine at position 2,074(Am) and an arginine, tryptophan, phenylalanine, glycine, histidine, lysine, serine, threonine, or valine at position 2,088 (Am). In one embodiment, an acetyl-Coenzyme A carboxylase of the present disclosure will have a leucine at position 2,074(Am) and a glutamic acid at position 2,095(Am). In one embodiment, an acetyl-Coenzyme A carboxylase of the present disclosure will have a leucine at position 2,074(Am) and an alanine or serine at position 2,096(Am). In one embodiment, an acetyl-Coenzyme A carboxylase of the present disclosure will have a leucine at position 2,074(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,075(Am) and at one or more additional amino acid positions. Acetyl-Coenzyme A carboxylase enzymes of the disclosure will typically have a leucine, isoleucine, methionine or additional valine at position 2,075(Am). In addition, enzymes of this embodiment will also comprise one or more of a leucine, threonine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, isoleucine, methionine or additional valine at position 2,075(Am) and a leucine, a threonine, a valine, or an alanine at position 1,781(Am). In one embodiment, an acetyl-Coenzyme A carboxylase of the present disclosure will have a leucine, isoleucine, methionine or additional valine at position 2,075(Am) and a glycine at position 1,785(Am). In one embodiment, an acetyl-Coenzyme A carboxylase of the present disclosure will have a leucine, isoleucine, methionine or additional valine at position 2,075(Am) and a proline at position 1,786(Am). In one embodiment, an acetyl-Coenzyme A carboxylase of the present disclosure will have a leucine, isoleucine, methionine or additional valine at position 2,075(Am) and have an asparagine at position 1,811(Am). In one embodiment, an acetyl-Coenzyme A carboxylase of the present disclosure will have a leucine, isoleucine, methionine or additional valine at position 2,075(Am) and a cysteine or glycine at position 1,999(Am). In one embodiment, an acetyl-Coenzyme A carboxylase of the present disclosure will have a leucine, isoleucine, methionine or additional valine at position 2,075(Am) and a cysteine or arginine at position 2,027 (Am). In one embodiment, an acetyl-Coenzyme A carboxylase of the present disclosure will have a leucine, isoleucine, methionine or additional valine at position 2,075(Am) and an isoleucine at position 2,041(Am). In one embodiment, an acetyl-Coenzyme A carboxylase of the present disclosure will have a leucine, isoleucine, methionine or additional valine at position 2,075(Am) and a phenylalanine, isoleucine or leucine at position 2,049(Am). In one embodiment, an acetyl-Coenzyme A carboxylase of the present disclosure will have a leucine, isoleucine, methionine or additional valine at position 2,075(Am) and a leucine at position 2,074(Am). In one embodiment, an acetyl-Coenzyme A carboxylase of the present disclosure will have a leucine, isoleucine, methionine or additional valine at position 2,075 (Am) and a glycine or threonine at position 2,078(Am). In one embodiment, an acetyl-Coenzyme A carboxylase of the present disclosure will have a leucine, isoleucine, methionine or additional valine at position 2,075(Am) and an arginine or tryptophan, phenylalanine, glycine, histidine, lysine, leucine, serine, threonine, or valine at position 2,088 (Am). In one embodiment, an acetyl-Coenzyme A carboxylase of the present disclosure will have a leucine, isoleucine, methionine or additional valine at position 2,075(Am) and an alanine or serine at position 2,096(Am). In one embodiment, an acetyl-Coenzyme A carboxylase of the present disclosure will have a leucine, isoleucine, methionine or additional valine at position 2,075(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,078(Am) and at one or more additional amino acid positions. Acetyl-Coenzyme A carboxylase enzymes of the disclosure will typically have a glycine or threonine at position 2,078(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have a glycine or threonine at position 2,078(Am) and a leucine, a threonine or an alanine at position 1,781(Am). In one embodiment, an acetyl-Coenzyme A carboxylase of the present disclosure will have a glycine or threonine at position 2,078(Am) and a glycine at position 1,785(Am). In one embodiment, an acetyl-Coenzyme A carboxylase of the present disclosure will have a glycine or threonine at position 2,078(Am) and a proline at position 1,786(Am). In one embodiment, an acetyl-Coenzyme A carboxylase of the present disclosure will have a glycine or threonine at position 2,078(Am) and an asparagine at position 1,811(Am). In one embodiment, an acetyl- Coenzyme A carboxylase of the present disclosure will have a glycine or threonine at position 2,078(Am) and a cysteine or glycine at position 1,999(Am). In one embodiment, an acetyl-Coenzyme A carboxylase of the present disclosure will have a glycine or threonine at position 2,078(Am) and a cysteine or arginine at position 2,027(Am). In one embodiment, an acetyl-Coenzyme A carboxylase of the present disclosure will have a glycine or threonine at position 2,078(Am) and an isoleucine at position 2,041(Am). In one embodiment, an acetyl-Coenzyme A carboxylase of the present disclosure will have a glycine or threonine at position 2,078(Am) and a phenylalanine, isoleucine or leucine at position 2,049(Am). In one embodiment, an acetyl-Coenzyme A carboxylase of the present disclosure will have a glycine or threonine at position 2,078(Am) and a leucine at position 2,074(Am). In one embodiment, an acetyl-Coenzyme A carboxylase of the present disclosure will have a glycine or threonine at position 2,078(Am) and a leucine, isoleucine, methionine or additional valine at position 2,075 (Am). In one embodiment, an acetyl-Coenzyme A carboxylase of the present disclosure will have a glycine or threonine at position 2,078(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine or threonine at position 2,078(Am) and an alanine or serine at position 2,096(Am). In one embodiment, an acetyl-Coenzyme A carboxylase of the present disclosure will have a glycine or threonine at position 2,078(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,079(Am) and at one or more additional amino acid positions. Acetyl-Coenzyme A carboxylase enzymes of the disclosure will typically have a phenylalanine at position 2,079(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,080(Am) and at one or more additional amino acid positions. Acetyl-Coenzyme A carboxylase enzymes of the disclosure will typically have a glutamic acid or a deletion at position 2,080(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,081(Am) and at one or more additional amino acid positions. Acetyl-Coenzyme A carboxylase enzymes of the disclosure will typically have a deletion at position 2,081(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,088(Am) and at one or more additional amino acid positions. Acetyl-Coenzyme A carboxylase enzymes of the disclosure will typically have an arginine, tryptophan, phenylalanine, glycine, histidine, lysine, leucine, serine, threonine, or valine at position 2,088(Am). In addition, enzymes of this embodiment will also comprise one or more of a leucine, threonine, valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, a threonine, valine, or an alanine at position 1,781(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine at position 1,785(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a proline at position 1,786(Am). In one embodiment, an acetyl-Coenzyme A carboxylase of the present disclosure will have an arginine, tryptophan, phenylalanine, glycine, histidine, lysine, leucine, serine, threonine, or valine at position 2,088 (Am) and an asparagine at position 1,811(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a cysteine or glycine at position 1,999(Am). In one embodiment, an acetyl-Coenzyme A carboxylase of the present disclosure will have an arginine or tryptophan, phenylalanine, glycine, histidine, lysine, leucine, serine, threonine, or valine at position 2,088(Am) and a cysteine or arginine at position 2,027(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an isoleucine at position 2,041(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a phenylalanine, isoleucine or leucine at position 2,049(Am). In one embodiment, an acetyl-Coenzyme A carboxylase of the present disclosure will have an arginine, tryptophan, phenylalanine, glycine, histidine, lysine, leucine, serine, threonine, or valine at position 2,088 (Am) and a leucine at position 2,074(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, isoleucine, methionine or additional valine at position 2,075(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine or threonine at position 2,078(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine or serine at position 2,096(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,095(Am) and at one or more additional amino acid positions. Acetyl-Coenzyme A carboxylase enzymes of the disclosure will typically have a glutamic acid at position 2,095(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), a deletion at position 2,081(Am), an arginine or tryptophan, phenylalanine, glycine, histidine, lysine, leucine, serine, threonine, or valine at position 2,088(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,096(Am) and at one or more additional amino acid positions. Acetyl-Coenzyme A carboxylase enzymes of the disclosure will typically have an alanine or serine at position 2,096(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095 (Am), and an alanine, glycine, proline, histidine, cysteine, or serine at position 2,098(Am). In one embodiment, an acetyl-Coenzyme A carboxylase of the present disclosure will have an alanine or serine at position 2,096(Am) and a leucine, a threonine or an alanine at position 1,781(Am). In one embodiment, an acetyl-Coenzyme A carboxylase of the present disclosure will have an alanine or serine at position 2,096(Am) and a glycine at position 1,785(Am). In one embodiment, an acetyl-Coenzyme A carboxylase of the present disclosure will have an alanine or serine at position 2,096(Am) and a proline at position 1,786(Am). In one embodiment, an acetyl-Coenzyme A carboxylase of the present disclosure will have an alanine or serine at position 2,096(Am) and an asparagine at position 1,811(Am). In one embodiment, an acetyl-Coenzyme A carboxylase of the present disclosure will have an alanine or serine at position 2,096(Am) and a cysteine or glycine at position 1,999(Am). In one embodiment, an acetyl-Coenzyme A carboxylase of the present disclosure will have an alanine or serine at position 2,096(Am) and a cysteine or arginine at position 2,027(Am). In one embodiment, an acetyl-Coenzyme A carboxylase of the present disclosure will have an alanine or serine at position 2,096(Am) and an isoleucine at position 2,041(Am). In one embodiment, an acetyl-Coenzyme A carboxylase of the present disclosure will have an alanine or serine at position 2,096(Am) and a phenylalanine, isoleucine or leucine at position 2,049(Am). In one embodiment, an acetyl-Coenzyme A carboxylase of the present disclosure will have an alanine or serine at position 2,096(Am) and a leucine at position 2,074(Am). In one embodiment, an acetyl-Coenzyme A carboxylase of the present disclosure will have an alanine or serine at position 2,096(Am) and a leucine, isoleucine, methionine or additional valine at position 2,075(Am). In one embodiment, an acetyl-Coenzyme A carboxylase of the present disclosure will have an alanine or serine at position 2,096(Am) and a glycine or threonine at position 2,078(Am). In one embodiment, an acetyl-Coenzyme A carboxylase of the present disclosure will have an alanine or serine at position 2,096(Am) and an an arginine, tryptophan, phenylalanine, glycine, histidine, lysine, leucine, serine, threonine, or valine at position 2,088(Am). In one embodiment, an acetyl-Coenzyme A carboxylase of the present disclosure will have an alanine or serine at position 2,096(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,098(Am) and at one or more additional amino acid positions. Acetyl-Coenzyme A carboxylase enzymes of the disclosure will typically have an alanine, glycine, proline, histidine, cysteine, or serine at position 2,098(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), and an alanine or serine at position 2,096(Am). In one embodiment, an acetyl-Coenzyme A carboxylase of the present disclosure will have an alanine, glycine, proline, histidine, cysteine, or serine at position 2,098(Am) and a leucine, a threonine, valine, or an alanine at position 1,781(Am). In one embodiment, an acetyl-Coenzyme A carboxylase of the present disclosure will have an alanine, glycine, proline, histidine, cysteine, or serine at position 2,098(Am) and a glycine at position 1,785(Am). In one embodiment, an acetyl-Coenzyme A carboxylase of the present disclosure will have an alanine, glycine, proline, histidine, cysteine, or serine at position 2,098(Am) and a proline at position 1,786(Am). In one embodiment, an acetyl-Coenzyme A carboxylase of the present disclosure will have an alanine, glycine, proline, histidine, cysteine, or serine at position 2,098(Am) and an asparagine at position 1,811(Am). In one embodiment, an acetyl-Coenzyme A carboxylase of the present disclosure will have an alanine, glycine, proline, histidine, cysteine, or serine at position 2,098(Am) and a cysteine or glycine at position 1,999(Am). In one embodiment, an acetyl-Coenzyme A carboxylase of the present disclosure will have an alanine, glycine, proline, histidine, cysteine, or serine at position 2,098(Am) and a cysteine or arginine at position 2,027(Am). In one embodiment, an acetyl-Coenzyme A carboxylase of the present disclosure will have an alanine, glycine, proline, histidine, cysteine, or serine at position 2,098(Am) and an isoleucine at position 2,041(Am). In one embodiment, an acetyl-Coenzyme A carboxylase of the present disclosure will have an alanine, glycine, proline, histidine, cysteine, or serine at position 2,098(Am) and a phenylalanine, isoleucine or leucine at position 2,049(Am). In one embodiment, an acetyl-Coenzyme A carboxylase of the present disclosure will have an alanine, glycine, proline, histidine, cysteine, or serine at position 2,098(Am) and a leucine at position 2,074(Am). In one embodiment, an acetyl-Coenzyme A carboxylase of the present disclosure will have an alanine, glycine, proline, histidine, cysteine, or serine at position 2,098(Am) and a leucine, isoleucine, methionine or additional valine at position 2,075(Am). In one embodiment, an acetyl-Coenzyme A carboxylase of the present disclosure will have an alanine, glycine, proline, histidine, cysteine, or serine at position 2,098(Am) and a glycine or threonine at position 2,078(Am). In one embodiment, an acetyl-Coenzyme A carboxylase of the present disclosure will have an alanine, glycine, proline, histidine, cysteine, or serine at position 2,098(Am) and an arginine or tryptophan, phenylalanine, glycine, histidine, lysine, leucine, serine, threonine, or valine at position 2,088(Am). In one embodiment, an acetyl-Coenzyme A carboxylase of the present disclosure will have an alanine, glycine, proline, histidine, cysteine, or serine at position 2,098(Am) and an alanine or serine at position 2,096(Am).

In one embodiment, the disclosure includes acetyl-Coenzyme A carboxylases having an isoleucine at position 2,075(Am) and a glycine at position 1,999(Am); acetyl-Coenzyme A carboxylases having a methionine at position 2,075(Am) and a glutamic acid at position 2,080(Am); acetyl-Coenzyme A carboxylases having a methionine at position 2,075(Am) and a glutamic acid at position 2,095(Am); acetyl-Coenzyme A carboxylases having a glycine at position 2,078(Am) and a valine at position 2,041(Am); acetyl-Coenzyme A carboxylases having a glycine at position 2,078(Am) and a glycine at position 2,039(Am); acetyl-Coenzyme A carboxylases having a glycine at position 2,078(Am) and an alanine at position 2,049(Am); acetyl-Coenzyme A carboxylases having a glycine at position 2,078(Am) and a cysteine at position 2,049(Am); acetyl-Coenzyme A carboxylases having a glycine at position 2,078(Am) and a serine at position 2,049(Am); acetyl-Coenzyme A carboxylases having a glycine at position 2,078(Am) and a threonine at position 2,049(Am); acetyl-Coenzyme A carboxylases having a glycine at position 2,078(Am) and a valine at position 2,059(Am); acetyl-Coenzyme A carboxylases having a glycine at position 2,078(Am) and a phenylalanine at position 2,079(Am); acetyl-Coenzyme A carboxylases having a glycine at position 2,078(Am) and a proline at position at position 2,079(Am); and acetyl-Coenzyme A carboxylases having a glycine at position 2,078(Am) and a glycine at position 2,088(Am).

In a preferred embodiment, the disclosure includes acetyl-Coenzyme A carboxylases having a leucine at position 1,781(Am) and a proline at position 1,824(Am); acetyl-Coenzyme A carboxylases having a leucine at position 1,781(Am) and an arginine at position 2027(Am); and acetyl-Coenzyme A carboxylases having a glycine at position 2,078(Am) and a proline at position 1,824(Am).

In a more preferred embodiment, the disclosure includes acetyl-Coenzyme A carboxylases having a leucine at position 1,781(Am) and a phenylalanine at position 2,049(Am); acetyl-Coenzyme A carboxylases having an alanine at position 2,098(Am) and a leucine at position 2,049(Am); acetyl-Coenzyme A carboxylases having an alanine at position 2,098(Am) and a histidine at position 2088(Am); acetyl-Coenzyme A carboxylases having an alanine at position 2,098(Am) and a phenylalanine at position 2,088(Am); acetyl-Coenzyme A carboxylases having an alanine at position 2,098(Am) and a lysine at position 2,088(Am); acetyl-Coenzyme A carboxylases having an alanine at position 2,098(Am) and a leucine at position 2,088(Am); acetyl-Coenzyme A carboxylases having an alanine at position 2,098(Am) and a threonine at position 2,088(Am); acetyl-Coenzyme A carboxylases having a glycine at position 2,098(Am) and a glycine at position 2,088(Am); acetyl-Coenzyme A carboxylases having a glycine at position 2,098(Am) and a histidine at position 2,088(Am); acetyl-Coenzyme A carboxylases having a glycine at position 2,098(Am) and leucine at position 2,088(Am); acetyl-Coenzyme A carboxylases having a glycine at position 2,098(Am) and a serine at position 2,088(Am); acetyl-Coenzyme A carboxylases having a glycine at position 2,098(Am) and threonine at position 2,088(Am); acetyl-Coenzyme A carboxylases having a glycine at position 2,098(Am) and a valine at position 2,088(Am); acetyl-Coenzyme A carboxylases having a cysteine at position 2,098(Am) and a tryptophan at position 2088(Am); acetyl-Coenzyme A carboxylases having a serine at position 2,098(Am) and a tryptophan at position 2088(Am); and acetyl-Coenzyme A carboxylases having a deletion at position 2,080(Am) and a deletion at position 2081(Am).

In a most preferred embodiment, the disclosure includes acetyl-Coenzyme A carboxylases having a leucine at position 1,781(Am) and a asparagine at position 2,041(Am); acetyl-Coenzyme A carboxylases having a leucine at position 1,781(Am) and a cysteine at position 2,027(Am); acetyl-Coenzyme A carboxylases having a leucine at position 1,781(Am) and a leucine at position 2,075(Am); acetyl-Coenzyme A carboxylases having a leucine at position 1,781(Am) and a phenylalanine at position 1,864(Am); acetyl-Coenzyme A carboxylases having a leucine at position 1,781(Am) and an alanine at position 2098(Am); acetyl-Coenzyme A carboxylases having a leucine at position 1,781(Am) and a glycine at position 2,098(Am); acetyl-Coenzyme A carboxylases having a leucine at position 1,781(Am) and a duplication 2,075(Am); acetyl-Coenzyme A carboxylases having a glycine at position 1,999(Am) and a phenylalanine at position 1,864(Am); acetyl-Coenzyme A carboxylases having a glycine at position 1,999(Am) and isoleucine at position 2,049(Am); acetyl-Coenzyme A carboxylases having a glycine at position 1,999(Am) and leucine at position 2,075(Am); and acetyl-Coenzyme A carboxylases having a glycine at position 1,999(Am) and alanine at position 2,098(Am).

Nucleic Acid Molecules

The present disclosure also encompasses nucleic acid molecules that encode all or a portion of the acetyl-Coenzyme A carboxylase enzymes described above. Nucleic acid molecules of the disclosure may comprise a nucleic acid sequence encoding an amino acid sequence comprising a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine, methionine or additional valine; the amino acid at position 2,078(Am) is glycine, or threonine; the amino acid at position 2,079(Am) is phenylalanine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences. In some embodiments, a nucleic acid molecule of the disclosure may encode an acetyl-Coenzyme A carboxylase having multiple differences from the wild type acetyl-Coenzyme A carboxylase as described above.

In one embodiment, the present disclosure encompasses a nucleic acid molecule encoding an acetyl-Coenzyme A carboxylase which differs from the acetyl-Coenzyme A carboxylase of the corresponding wild-type plant at only one of the following positions: 1,781(Am), 1,785(Am), 1,786 (Am), 1,811(Am), 1,824(Am), 1,864(Am), 1,999(Am), 2,027(Am), 2,039(Am), 2,041(Am), 2,049(Am), 2,059 (Am), 2,074(Am), 2,075(Am), 2,078(Am), 2,079(Am), 2,080(Am), 2,081(Am), 2,088(Am), 2,095(Am), 2,096 (Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080 (Am), or 2,095(Am). In a more preferred embodiment the acetyl-Coenzyme A carboxylase of an herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, the present disclosure encompasses a nucleic acid molecule encoding an acetyl-Coenzyme A carboxylase having only one of the following substitutions: isoleucine at position 2,075(Am), glycine at position 2,078 (Am), or arginine at position 2,088(Am). In a preferred embodiment, the present disclosure encompasses a nucleic acid molecule encoding an acetyl-Coenzyme A carboxylase having only one of the following substitutions: glycine at position 2,039(Am), valine at position 2,059(Am), methionine at position 2,075(Am), duplication of position 2,075 (Am) (i.e., an insertion of valine between 2,074(Am) and 2,075(Am), or an insertion of valine between position 2,075 (Am) and 2,076(Am), deletion of amino acid position 2,088

(Am), glutamic acid at position 2,080(Am), deletion of position 2,088(Am), or glutamic acid at position 2,095(Am). In a more preferred embodiment, the present disclosure encompasses a nucleic acid molecule encoding an acetyl-Coenzyme A carboxylase having only one of the following substitutions: a glycine at position 1,785(Am), a proline at position 1,786(Am), an asparagine at position 1,811(Am), a leucine at position 2,075(Am), a methionine at position 2,075(Am), a threonine at position 2,078(Am), a deletion at position 2,080(Am), a deletion at position 2,081(Am), a tryptophan at position 2,088(Am), a serine at position 2,096 (Am), an alanine at position 2,096(Am), an alanine at position 2,098(Am), a glycine at position 2,098(Am), an histidine at position 2,098(Am), a proline at position 2,098 (Am), or a serine at position 2,098(Am). In a most preferred embodiment, the present disclosure encompasses a nucleic acid molecule encoding an acetyl-Coenzyme A carboxylase having only one of the following substitutions: a leucine at position 1,781(Am), a threonine at position 1,781(Am), a valine at position 1,781(Am), an alanine at position 1,781 (Am), a glycine at position 1,999(Am), a cysteine at position 2,027(Am), an arginine at position 2,027(Am), an asparagine at position 2,041(Am), a valine at position 2,041(Am), an alanine at position 2,096(Am), and a serine at position 2,096(Am).

In one embodiment, a nucleic acid molecule of the disclosure may encode an acetyl-Coenzyme A carboxylase comprising a leucine, threonine, valine, or an alanine at position 1,781(Am) and a cysteine or glycine at position 1,999(Am). In one embodiment, a nucleic acid molecule of the disclosure may encode an acetyl-Coenzyme A carboxylase comprising a leucine, threonine, valine, or an alanine at position 1,781(Am) and a cysteine or arginine at position 2,027(Am). In one embodiment, a nucleic acid molecule of the disclosure may encode an acetyl-Coenzyme A carboxylase comprising a leucine, threonine, valine, or an alanine at position 1,781(Am) and an asparagine at position 2,041 (Am). In one embodiment, a nucleic acid molecule of the disclosure may encode an acetyl-Coenzyme A carboxylase comprising a leucine, threonine, valine, or an alanine at position 1,781(Am) and a phenylalanine, isoleucine or leucine at position 2,049(Am). In one embodiment, a nucleic acid molecule of the disclosure may encode an acetyl-Coenzyme A carboxylase comprising a leucine, threonine, valine, or an alanine at position 1,781(Am) and a leucine or isoleucine at position 2,075(Am). In one embodiment, a nucleic acid molecule of the disclosure may encode an acetyl-Coenzyme A carboxylase comprising a leucine, threonine, valine, or an alanine at position 1,781(Am) and a glycine at position 2,078(Am). In one embodiment, a nucleic acid molecule of the disclosure may encode an acetyl-Coenzyme A carboxylase comprising a leucine, threonine, valine, or an alanine at position 1,781(Am) and an arginine at position 2,088(Am). In one embodiment, a nucleic acid molecule of the disclosure may encode an acetyl-Coenzyme A carboxylase comprising a leucine, threonine, valine, or an alanine at position 1,781(Am) and an alanine at position 2,096(Am). In one embodiment, a nucleic acid molecule of the disclosure may encode an acetyl-Coenzyme A carboxylase comprising a leucine, threonine, valine, or an alanine at position 1,781(Am) and an alanine at position 2,098(Am). In one embodiment, a nucleic acid molecule of the disclosure may encode an acetyl-Coenzyme A carboxylase comprising a leucine, threonine, valine, or an alanine at position 1,781(Am), a cysteine at position 2,027 (Am), and an asparagine at position 2,041(Am). In one embodiment, a nucleic acid molecule of the disclosure may encode an acetyl-Coenzyme A carboxylase comprising a leucine, threonine, valine, or an alanine at position 1,781 (Am), a cysteine at position 2,027(Am), an asparagine at position 2,041(Am), and an alanine at position 2,096(Am).

In one embodiment, the disclosure includes a nucleic acid molecule encoding an acetyl-Coenzyme A carboxylase having an isoleucine at position 2,075(Am) and a glycine at position 1,999(Am); a nucleic acid molecule encoding an acetyl-Coenzyme A carboxylase having a methionine at position 2,075(Am) and a glutamic acid at position 2,080 (Am); a nucleic acid molecule encoding an acetyl-Coenzyme A carboxylase having a methionine at position 2,075 (Am) and a glutamic acid at position 2,095(Am); a nucleic acid molecule encoding an acetyl-Coenzyme A carboxylase having a glycine at position 2,078(Am) and a valine at position 2,041(Am); a nucleic acid molecule encoding an acetyl-Coenzyme A carboxylase having a glycine at position 2,078(Am) and a glycine at position 2,039(Am); a nucleic acid molecule encoding an acetyl-Coenzyme A carboxylase having a glycine at position 2,078(Am) and an alanine at position 2,049(Am); a nucleic acid molecule encoding an acetyl-Coenzyme A carboxylase having a glycine at position 2,078(Am) and a cysteine at position 2,049(Am); a nucleic acid molecule encoding an acetyl-Coenzyme A carboxylase having a glycine at position 2,078(Am) and a serine at position 2,049(Am); a nucleic acid molecule encoding an acetyl-Coenzyme A carboxylase having a glycine at position 2,078(Am) and a threonine at position 2,049(Am); a nucleic acid molecule encoding an acetyl-Coenzyme A carboxylase having a glycine at position 2,078(Am) and a valine at position 2,059(Am); a nucleic acid molecule encoding an acetyl-Coenzyme A carboxylase having a glycine at position 2,078(Am) and a phenylalanine at position 2,079(Am); a nucleic acid molecule encoding an acetyl-Coenzyme A carboxylase having a glycine at position 2,078(Am) and a proline at position at position 2,079(Am); or a nucleic acid molecule encoding an acetyl-Coenzyme A carboxylase having a glycine at position 2,078(Am) and a glycine at position 2,088(Am).

In a preferred embodiment, the disclosure includes a nucleic acid molecule encoding an acetyl-Coenzyme A carboxylase having a leucine at position 1,781(Am) and a proline at position 1,824(Am); a nucleic acid molecule encoding an acetyl-Coenzyme A carboxylase having a leucine at position 1,781(Am) and an arginine at position 2027(Am); or a nucleic acid molecule encoding an acetyl-Coenzyme A carboxylase having a glycine at position 2,078 (Am) and a proline at position 1,824(Am).

In a more preferred embodiment, the disclosure includes a nucleic acid molecule encoding an acetyl-Coenzyme A carboxylase having a leucine at position 1,781(Am) and a phenylalanine at position 2,049(Am); a nucleic acid molecule encoding an acetyl-Coenzyme A carboxylase having an alanine at position 2,098(Am) and a leucine at position 2,049(Am); a nucleic acid molecule encoding an acetyl-Coenzyme A carboxylase having an alanine at position 2,098(Am) and a histidine at position 2088(Am); a nucleic acid molecule encoding an acetyl-Coenzyme A carboxylase having an alanine at position 2,098(Am) and a phenylalanine at position 2,088(Am); a nucleic acid molecule encoding an acetyl-Coenzyme A carboxylase having an alanine at position 2,098(Am) and a lysine at position 2,088(Am); a nucleic acid molecule encoding an acetyl-Coenzyme A carboxylase having an alanine at position 2,098(Am) and a leucine at position 2,088(Am); a nucleic acid molecule encoding an acetyl-Coenzyme A carboxylase having an alanine at position 2,098(Am) and a threonine at position 2,088(Am); a nucleic acid molecule encoding an acetyl-Coenzyme A carboxylase having a glycine at position 2,098 (Am) and a glycine at position 2,088(Am); a nucleic acid molecule encoding an acetyl-Coenzyme A carboxylase having a glycine at position 2,098(Am) and a histidine at position 2,088(Am); a nucleic acid molecule encoding an acetyl-Coenzyme A carboxylase having a glycine at position 2,098(Am) and leucine at position 2,088(Am); a nucleic acid molecule encoding an acetyl-Coenzyme A carboxylase having a glycine at position 2,098(Am) and a serine at position 2,088(Am); a nucleic acid molecule encoding an acetyl-Coenzyme A carboxylase having a glycine at position 2,098 (Am) and threonine at position 2,088(Am); a nucleic acid molecule encoding an acetyl-Coenzyme A carboxylase having a glycine at position 2,098(Am) and a valine at position 2,088(Am); a nucleic acid molecule encoding an acetyl-Coenzyme A carboxylase having a cysteine at position 2,098(Am) and a tryptophan at position 2088(Am); a nucleic acid molecule encoding an acetyl-Coenzyme A carboxylase having a serine at position 2,098(Am) and a tryptophan at position 2088(Am); or a nucleic acid molecule encoding an acetyl-Coenzyme A carboxylase having a deletion at position 2,080(Am) and a deletion at position 2081(Am).

In a most preferred embodiment, the disclosure includes a nucleic acid molecule encoding an acetyl-Coenzyme A carboxylase having a leucine at position 1,781(Am) and a asparagine at position 2,041(Am); a nucleic acid molecule encoding an acetyl-Coenzyme A carboxylase having a leucine at position 1,781(Am) and a cysteine at position 2,027 (Am); a nucleic acid molecule encoding an acetyl-Coenzyme A carboxylase having a leucine at position 1,781(Am) and a leucine at position 2,075(Am); a nucleic acid molecule encoding an acetyl-Coenzyme A carboxylase having a leucine at position 1,781(Am) and a phenylalanine at position 1,864(Am); a nucleic acid molecule encoding an acetyl-Coenzyme A carboxylase having a leucine at position 1,781 (Am) and an alanine at position 2098(Am); a nucleic acid molecule encoding an acetyl-Coenzyme A carboxylase having a leucine at position 1,781(Am) and a glycine at position 2,098(Am); a nucleic acid molecule encoding an acetyl-Coenzyme A carboxylase having a leucine at position 1,781 (Am) and a duplication 2,075(Am); a nucleic acid molecule encoding an acetyl-Coenzyme A carboxylase having a glycine at position 1,999(Am) and a phenylalanine at position 1,864(Am); a nucleic acid molecule encoding an acetyl-Coenzyme A carboxylase having a glycine at position 1,999 (Am) and isoleucine at position 2,049(Am); a nucleic acid molecule encoding an acetyl-Coenzyme A carboxylase having a glycine at position 1,999(Am) and leucine at position 2,075(Am); or a nucleic acid molecule encoding an acetyl-Coenzyme A carboxylase having a glycine at position 1,999 (Am) and alanine at position 2,098(Am).

In one embodiment, the disclosure provides rice plants comprising nucleic acids encoding Acetyl-Coenzyme A carboxylase polypeptide having one or more substitutions as described above.

In one embodiment, the disclosure provides BEP clade plants comprising nucleic acids encoding Acetyl-Coenzyme A carboxylase polypeptide having one or more substitutions as described above.

In one embodiment, the disclosure provides BET subclade plant comprising nucleic acids encoding Acetyl-Coenzyme A carboxylase polypeptide having one or more substitutions as described above.

In one embodiment, the disclosure provides BET crop plants comprising nucleic acids encoding Acetyl-Coenzyme A carboxylase polypeptide having one or more substitutions as described above.

In one embodiment, the disclosure provides monocot plants comprising nucleic acids encoding Acetyl-Coenzyme A carboxylase polypeptide having one or more substitutions as described above.

A nucleic acid molecule of the disclosure may be DNA, derived from genomic DNA or cDNA, or RNA. A nucleic acid molecule of the disclosure may be naturally occurring or may be synthetic. A nucleic acid molecule of the disclosure may be isolated, recombinant and/or mutagenized.

In one embodiment, a nucleic acid molecule of the disclosure encodes an acetyl-Coenzyme A carboxylase enzyme in which the amino acid at position 1,781(Am) is leucine or alanine or is complementary to such a nucleic acid molecule. Such nucleic acid molecules include, but are not limited to, genomic DNA that serves as a template for a primary RNA transcription, a plasmid molecule encoding the acetyl-Coenzyme A carboxylase, as well as an mRNA encoding such an acetyl-Coenzyme A carboxylase.

Nucleic acid molecules of the disclosure may comprise non-coding sequences, which may or may not be transcribed. Non-coding sequences that may be included in the nucleic acid molecules of the disclosure include, but are not limited to, 5' and 3' UTRs, polyadenylation signals and regulatory sequences that control gene expression (e.g., promoters). Nucleic acid molecules of the disclosure may also comprise sequences encoding transit peptides, protease cleavage sites, covalent modification sites and the like. In one embodiment, nucleic acid molecules of the disclosure encode a chloroplast transit peptide sequence in addition to a sequence encoding an acetyl-Coenzyme A carboxylase enzyme.

In another embodiment, nucleic acid molecules of the disclosure may encode an acetyl-Coenzyme A carboxylase enzyme having at least 50%, 60%, 70%, 75%, 80%, 85%, 90%, 95% or more sequence identity to a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, leucine or isoleucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalanine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences.

As used herein, "percent (%) sequence identity" is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program BLAST available at http://blast.ncbi.nlm.nih.gov/Blast.cgi with search parameters set to default values.

The present disclosure also encompasses nucleic acid molecules that hybridize to nucleic acid molecules encoding acetyl-Coenzyme A carboxylase of the present disclosure as well as nucleic acid molecules that hybridize to the reverse complement of nucleic acid molecules encoding an acetyl-Coenzyme A carboxylase of the present disclosure. In one embodiment, nucleic acid molecules of the disclosure comprise nucleic acid molecules that hybridize to a nucleic acid molecule encoding one or more of a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalanine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences, or the reverse complement of such nucleic acid molecules under stringent conditions. The stringency of hybridization can be controlled by temperature, ionic strength, pH, and the presence of denaturing agents such as formamide during hybridization and washing. Stringent conditions that may be used include those defined in *Current Protocols in Molecular Biology*, Vol. 1, Chap. 2.10, John Wiley & Sons, Publishers (1994) and Sambrook et al., *Molecular Cloning*, Cold Spring Harbor (1989) which are specifically incorporated herein as they relate to teaching stringent conditions.

Any of the mutants described above in a plasmid with a combination of the gene of interest can be used in transformation.

In one embodiment, the present disclosure provides expression vectors comprising nucleic acid molecules encoding any of the ACCase mutants described above.

In one embodiment, the present disclosure provides for the use of mutant ACCase nucleic acids and proteins encoded by such mutant ACCase nucleic acids as described above as selectable markers.

In one embodiment, nucleic acid molecules of the disclosure encompass oligonucleotides that may be used as hybridization probes, sequencing primers, and/or PCR primers. Such oligonucleotides may be used, for example, to determine a codon sequence at a particular position in a nucleic acid molecule encoding an acetyl-Coenzyme A carboxylase, for example, by allele specific PCR. Such oligonucleotides may be from about 15 to about 30, from about 20 to about 30, or from about 20-25 nucleotides in length.

Test for double mutant ACCase genes "DBLM Assay":

(1) In a test population (of, e.g., at least 12 and preferably at least 20) whole rice plants containing 1 or 2 copies of a transgenic ACCase gene encoding an at-least-double-mutant ACCase (i.e. 1 min. and 2 max. chromosomal insertions of the transgenic ACCase gene to be tested),
wherein the rice plants are T0 ("T-zero") regenerates
and in parallel with a control population of such plants to be used as untreated check plants;

(2) Application to the test population at 200 L/ha spray volume of a composition comprising Tepraloxydim (AI) and 1% Crop Oil Concentrate (COC), to provide an AI application rate equivalent to 50 g/ha of Tepraloxydim (AI);

(3) Determining a phytotoxicity score for each test and check plant, based on a traditional plant injury rating system (e.g., evaluating visual evidence of herbicide burn, leaf morphology changes, wilt, yellowing, and other morphological characteristics, preferably according to a typical, at-least-5-level injury rating scale);

(4) Analyzing the collected data to determine whether at least 75% of the plants in the test population exhibit an average phytotoxicity, i.e. increase in injury relative to check plants, of less than 10%; and (5) Identifying a positive result so determined as demonstrating that the double-mutant ACCase provides an acceptable AIT.

Herbicides

The present disclosure provides plants, e.g., rice plants, that are tolerant of concentrations of herbicide that normally inhibit the growth of wild-type plants. The plants are typically resistant to herbicides that interfere with acetyl-Coenzyme A carboxylase activity. Any herbicide that inhibits acetyl-Coenzyme A carboxylase activity can be used in conjunction with the plants of the invention. Suitable examples include, but are not limited to, cyclohexanedione herbicides, aryloxyphenoxy propionate herbicides, and phenylpyrazole herbicides. In some methods of controlling weeds and/or growing herbicide-tolerant plants, at least one herbicide is selected from the group consisting of sethoxydim, cycloxydim, tepraloxydim, haloxyfop, haloxyfop-P or a derivative of any of these herbicides.

Table 1 provides a list of cyclohexanedione herbicides (DIMs, also referred to as: cyclohexene oxime cyclohexanedione oxime; and CHD) that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention. Also included in Table 1 is a list of aryloxyphenoxy propionate herbicides (also referred to as aryloxyphenoxy propanoate; aryloxyphenoxyalkanoate; oxyphenoxy; APP; AOPP; APA; APPA; FOP, note that these are sometime written with the suffix '-oic') that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention.

TABLE 1

| ACCase Inhibitor | Class | Company | Examples of Synonyms and Trade Names |
|---|---|---|---|
| alloxydim | DIM | BASF | Fervin, Kusagard, NP-48Na, BAS 9021H, Carbodimedon, Zizalon |
| butroxydim | DIM | Syngenta | Falcon, ICI-A0500, Butroxydim |
| clethodim | DIM | Valent | Select, Prism, Centurion, RE-45601, Motsa |
| Clodinafop-propargyl | FOP | Syngenta | Discover, Topik, CGA 184 927 |
| clofop | FOP | | Fenofibric Acid, Alopex |
| cloproxydim | FOP | | |
| chlorazifop | FOP | | |
| cycloxydim | DIM | BASF | Focus, Laser, Stratos, BAS 517H |
| cyhalofop-butyl | FOP | Dow | Clincher, XDE 537, DEH 112, Barnstorm |
| diclofop-methyl | FOP | Bayer | Hoegrass, Hoelon, Illoxan, HOE 23408, Dichlorfop, Illoxan |
| fenoxaprop-P-ethyl | FOP | Bayer | Super Whip, Option Super, Exel Super, HOE-46360, Aclaim, Puma S, Fusion |
| fenthiaprop | FOP | | Taifun; Joker |
| fluazifop-P-butyl | FOP | Syngenta | Fusilade, Fusilade 2000, Fusilade DX, ICI-A 0009, ICI-A 0005, SL-236, IH-773B, TF-1169, Fusion |
| haloxyfop-etotyl | FOP | Dow | Gallant, DOWCO 453EE |
| haloxyfop-methyl | FOP | Dow | Verdict, DOWCO 453ME |
| haloxyfop-P-methyl | FOP | Dow | Edge, DE 535 |
| isoxapyrifop | FOP | | |
| Metamifop | FOP | Dongbu | NA |
| pinoxaden | DEN | Syngenta | Axial |
| profoxydim | DIM | BASF | Aura, Tetris, BAS 625H, Clefoxydim |
| propaquizafop | FOP | Syngenta | Agil, Shogun, Ro 17-3664, Correct |
| quizalofop-P-ethyl | FOP | DuPont | Assure, Assure II, DPX-Y6202-3, Targa Super, NC-302, Quizafop |
| quizalofop-P-tefuryl | | Uniroyal | Pantera, UBI C4874 |
| sethoxydim | DIM | BASF | Poast, Poast Plus, NABU, Fervinal, NP-55, Sertin, BAS 562H, Cyethoxydim, Rezult |
| tepraloxydim | DIM | BASF | BAS 620H, Aramo, Caloxydim |
| tralkoxydim | DIM | Syngenta | Achieve, Splendor, ICI-A0604, Tralkoxydime, Tralkoxidym |
| trifop | FOP | | |

In addition to the herbicides listed above, other ACCase-inhibitors can be used in conjunction with the herbicide-tolerant plants of the invention. For example, ACCase-inhibiting herbicides of the phenylpyrazole class, also known as DENs, can be used. An exemplary DEN is pinoxaden, which is a phenylpyrazoline-type member of this class. Herbicide compositions containing pinoxaden are sold under the brands Axial and Traxos.

The herbicidal compositions hereof comprising one or more acetyl-Coenzyme A carboxylase-inhibiting herbicides, and optionally other agronomic A.I.(s), e.g., one or more sulfonylureas (SUs) selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, or one or more imidazolinones selected from the group of imazamox, imazethapyr, imazapyr, imazapic, combinations thereof, and their agriculturally suitable salts and esters, can be used in any agronomically acceptable format. For example, these can be formulated as ready-to-spray aqueous solutions, powders, suspensions; as concentrated or highly concentrated aqueous, oily or other solutions, suspensions or dispersions; as emulsions, oil dispersions, pastes, dusts, granules, or other broadcastable formats. The herbicide compositions can be applied by any means known in the art, including, for example, spraying, atomizing, dusting, spreading, watering, seed treatment, or co-planting in admixture with the seed. The use forms depend on the intended purpose; in any case, they should ensure the finest possible distribution of the active ingredients according to the invention.

In other embodiments, where the optional A.I. includes an herbicide from a different class to which the plant(s) hereof would normally be susceptible, the plant to be used is selected from among those that further comprise a trait of tolerance to such herbicide. Such further tolerance traits can be provided to the plant by any method known in the art, e.g., including techniques of traditional breeding to obtain a tolerance trait gene by hybridization or introgression, of mutagenesis, and/or of transformation. Such plants can be described as having "stacked" traits.

In addition, any of the above acetyl-Coenzyme A carboxylase-inhibiting herbicides can be combined with one or more herbicides of another class, for example, any of the acetohydroxyacid synthase-inhibiting herbicides, EPSP synthase-inhibiting herbicides, glutamine synthase-inhibiting herbicides, lipid- or pigment-biosynthesis inhibitor herbicides, cell-membrane disrupter herbicides, photosynthesis or respiration inhibitor herbicides, or growth regulator or growth inhibitor herbicides known in the art. Non-limiting examples include those recited in Weed Science Society of America's *Herbicide Handbook*, 9th Edition edited by S. A. Senseman, copy right 2007. An herbicidal composition herein can contain one or more agricultural active ingredient(s) selected from the agriculturally-acceptable fungicides, strobilurin fungicides, insecticides (including nematicides), miticides, and molluscicides. Non-limiting examples include those recited in 2009 Crop Protection Reference (www.greenbook.net), Vance Publications.

In one embodiment of the invention, any of the above acetyl-Coenzyme A carboxylase-inhibiting herbicides are combined with herbicides which exhibit low damage to rice, whereby the rice tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, azimsulfuron, bensulfuron, chlorimuron, cyclosulfamuron, ethoxysulfuron, flucetosulfuron, halosulfuron, imazosulfuron, metsulfuron, orthosulfamuron, propyrisulfuron, pyrazosulfuron, bispyribac, pyrimisulfan or penoxsulam, the EPSP synthase-inhibiting herbicides glyphosate or sulfosate, the glutamine synthase-inhibiting herbicides glufosinate, glufosinate-P or bialaphos, the lipid biosynthesis inhibitor herbicides benfuresate, molinate or thiobencarb, the photosynthesis inhibitor herbicides bentazon, paraquat, prometryn or propanil, the bleacher herbicides benzobicyclone, clomazone or tefuryltrione, the auxin herbicides 2,4-D, fluroxypyr, MCPA, quinclorac, quinmerac or triclopyr, the microtubule inhibitor herbicide pendimethalin, the VLCFA inhibitor herbicides anilofos, butachlor, fentrazamide, ipfencarbazone, mefenacet, pretilachlor, acetochlor, metolachlor or S-metolachlor or the protoporphyrinogen-IX-oxidase inhibitor herbicides carfentrazone, oxadiazon, oxyfluorfen, pyraclonil or saflufenacil.

In one embodiment of the invention, any of the above acetyl-Coenzyme A carboxylase-inhibiting herbicides are combined with herbicides which exhibit low damage to cereals such as wheat, barley or rye, whereby the cereals tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, amidosulfuron, chlorsulfuron, flucetosulfuron, flupyrsulfuron, iodosulfuron, mesosulfuron, metsulfuron, sulfosulfuron, thifensulfuron, triasulfuron, tribenuron, tritosulfuron, florasulam, pyroxsulam, pyrimisulfan, flucarbazone, propoxycarbazone or thiencarbazone, the EPSP synthase-inhibiting herbicides glyphosate or sulfosate, the glutamine synthase-inhibiting herbicides glufosinate, glufosinate-P or bialaphos, the lipid biosynthesis inhibitor herbicides prosulfocarb, the photosynthesis inhibitor herbicides bentazon, chlorotoluron, isoproturon, ioxynil, bromoxynil, the bleacher herbicides diflufenican, flurtamone, picolinafen or pyrasulfotole, the auxin herbicides aminocyclopyrachlor, aminopyralid, 2,4-D, dicamba, fluroxypyr, MCPA, clopyralid, MCPP, or MCPP-P, the microtubule inhibitor herbicides pendimethalin or trifluralin, the VLCFA inhibitor herbicide flufenacet, or the protoporphyrinogen-IX-oxidase inhibitor herbicides bencarbazone, carfentrazone or saflufenacil, or the herbicide difenzoquat.

In one embodiment of the invention, any of the above acetyl-Coenzyme A carboxylase-inhibiting herbicides are combined with herbicides which exhibit low damage to turf, whereby the turf tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, flazasulfuron, foramsulfuron, halosulfuron, trifloxysulfuron, bispyribac or thiencarbazone, the EPSP synthase-inhibiting herbicides glyphosate or sulfosate, the glutamine synthase-inhibiting herbicides glufosinate, glufosinate-P or bialaphos, the photosynthesis inhibitor herbicides atrazine or bentazon, the bleacher herbicides mesotrione, picolinafen, pyrasulfotole or topramezone, the auxin herbicides aminocyclopyrachlor, aminopyralid, 2,4-D, 2,4-DB, clopyralid, dicamba, dichlorprop, dichlorprop-P, fluroxypyr, MCPA, MCPB, MCPP, MCPP-P, quinclorac, quinmerac or trichlopyr, the microtubule inhibitor herbicide pendimethalin, the VLCFA inhibitor herbicides dimethenamide, dimethenamide-P or ipfencarbazone, the protoporphyrinogen-IX-oxidase inhibitor herbicides saflufenacil or sulfentrazone, or the herbicide indaziflam.

Furthermore, any of the above acetyl-Coenzyme A carboxylase-inhibiting herbicides can be combined with safeners. Safeners are chemical compounds which prevent or reduce damage on useful plants without having a major impact on the herbicidal action of the herbicides towards unwanted plants. They can be applied either before sowings (e.g. on seed treatments, shoots or seedlings) or in the pre-emergence application or post-emergence application of the useful plant. The safeners and the aforementioned herbicides can be applied simultaneously or in succession. Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates. Examples of safeners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

In some embodiments, an herbicidal composition hereof can comprise, e.g., a combination of: auxinic herbicide(s), e.g., dicamba; AHAS-inhibitor(s), e.g., imidazolinone(s) and/or sulfonylurea(s); ACCase-inhibitor(s); EPSPS inhibitor(s), e.g., glyphosate; glutamine synthetase inhibitor(s), e.g., glufosinate; protoporphyrinogen-IX oxidase (PPO) inhibitor(s), e.g., saflufenacil; fungicide(s), e.g., strobilurin fungicide(s) such as pyraclostrobin; and the like. In some embodiments, an herbicidal composition hereof can comprise, e.g., a combination of auxinic herbicide(s), e.g., dicamba; a microtubule inhibitor herbicide, e.g., pendimethalin and strobilurin fungicide(s) such as pyraclostrobin(s). An herbicidal composition will be selected according to the tolerances of a plant hereof, and the plant can be selected from among those having stacked tolerance traits.

The herbicides individually and/or in combination as described in the present disclosure can be used as pre-mixes or tank mixes. Such herbicides can also be incorporated into agronomically acceptable compositions.

Those skilled in the art will recognize that some of the above mentioned herbicides and/or safeners are capable of forming geometrical isomers, for example E/Z isomers. It is possible to use both, the pure isomers and mixtures thereof, in the compositions according to the invention. Furthermore, some of the above mentioned herbicides and/or safeners have one or more centers of chirality and, as a consequence, are present as enantiomers or diastereomers. It is possible to use both, the pure enantiomers and diastereomers and their mixtures, in the compositions according to the invention. In particular, some of the aryloxyphenoxy propionate herbicides are chiral, and some of them are commonly used in enantiomerically enriched or enantiopure form, e.g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P.

Those skilled in the art will recognize that any derivative of the above mentioned herbicides and/or safeners can be used in the practice of the invention, for example agriculturally suitable salts and esters.

The herbicides and/or safeners, or the herbicidal compositions comprising them, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one of the acetyl-Coenzyme A carboxylase-inhibiting herbicides and potentially other herbicides and/or safeners and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives. The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the herbicidal compositions, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

Rice-Non-Selective ACCase-Inhibitor Herbicides

Aspects of the present disclosure relate to methods for the treatment of rice comprising providing a domestic rice crop plant with at least one herbicide that is a rice-non-selective ACCase-inhibiting herbicide. The method comprises applying an effective amount (measured in g AI/Ha) of the at least one rice-non-selective ACCase-inhibiting herbicide to the domestic rice crop plant, post-emergence; thereby creating a treated rice plant; and growing the resulting treated rice plant. In some embodiments said rice-non-selective ACCase-inhibiting herbicide includes isomers, salts or esters of the rice-non-selective ACCase-inhibiting herbicide.

Some examples of rice-non-selective ACCase-inhibiting herbicides include, but are not limited to, those shown here in Table 2.

TABLE 2

| Herbicide Class (Synonyms) | Name of Active | Example Synonyms, Isomers, Salts, Esters | Example Products |
|---|---|---|---|
| Cyclohexene Oxime (Cyclohexanedione; Cyclohexanedione oxime; CHD; DIM) | | | |
| | alloxydim | alloxydim-sodium | Kusaguard; Fervin Clout |
| | butroxydim | butoxydim | Falcon; Factor; Fusion Super |
| | cethoxydim | CGA215684 | |
| | clethodim | | Select; Prism |
| | cloproxydim | | Selectone |
| | cycloxydim | | Focus 10 EC; Focus Ultra; Laser; Stratos Ultra |
| | sethoxydim | cyethoxydim; sethoxydime | Poast; Rezult; Vantage |
| | tepraloxydim | caloxydim | Aramo |
| | tralkoxydim | | Achieve |
| Aryloxyphenoxy Propionate (Aryloxyphenoxyalkanoate; APP; AOPP; FOP) | | | |
| | chlorazifop | chlorazifop-propargyl; chloroazifop-propynyl | |
| | clodinafop | clodinafop-propargyl | Discover; Cowboy; Dynofop; Topik |
| | clofop | clofop-isobutyl | Alopex |
| | diclofop | | Hoelon; Hoegrass |
| | fenthiaprop | fenthiaprop-ethyl | Joker |
| | fluazifop | fluazifop-P | Fusilade DX; Fusion |
| | haloxyfop | haloxyfop-P | Motsa; Verdict |
| | isoxapyrifop | | |
| | propaquizafop | | Correct; Agil 100EC; Falcon; Longhorn; Shogun; Zealot |
| | quizalofop | quizalofop-P; quizafop; quizafop-P; quizalofop-P-ethyl; quizalofop-P-tefuryl | Assure II; Targa |
| | trifop | trifop-methyl | |

Field Herbicide Application

Aspects of the present disclosure relate to methods for the treatment of rice comprising providing a domestic rice crop plant in a field and at least one ACCase-inhibiting FOP herbicide. The method comprises applying an effective amount (measured in g AI/Ha) of the at least one FOP herbicide to the domestic rice crop plant, post-emergence; thereby creating a treated rice plant; and growing the resulting treated rice plant.

In other embodiments, the FOP herbicide is quizalofop or an ester thereof quizalofop or an ester thereof (e.g., the ethyl ester thereof). In some further embodiments, the effective amount of quizalofop or an ester thereof is at least 14 g AI/Ha. In other further embodiments, the effective amount of quizalofop or an ester thereof is at least 16, 18, 20, 22, 24 or 26 g AI/Ha. In still other further embodiments, the effective amount of quizalofop or an ester thereof is at least 28 g AI/Ha. In yet other further embodiments, the effective amount of quizalofop or an ester thereof is at least 32, 36 or 40 g AI/Ha.

In some embodiments, the FOP herbicide is haloxyfop. In some further embodiments, the effective amount of haloxyfop is at least 38 g AI/Ha. In other further embodiments, the effective amount of haloxyfop is at least 44, 50, 56, 62, 66 or 72 g AI/Ha. In still other further embodiments, the effective amount of haloxyfop is at least 76 g AI/Ha. In yet other further embodiments, the effective amount of haloxyfop is at least 82, 88 or 94 g AI/Ha.

In other embodiments, the FOP herbicide is fluazifop or an ester thereof (e.g., the butyl ester thereof). In some further embodiments, the effective amount of fluazifop or an ester thereof is at least 56 g AI/Ha. In other further embodiments, the effective amount of fluazifop or an ester thereof is at least 65, 74, 83, 92 or 102 g AI/Ha. In still other further embodiments, the effective amount of fluazifop or an ester thereof is at least 112 g AI/Ha. In yet other further embodiments, the effective amount of fluazifop or an ester thereof is at least 120, 130 or 140 g AI/Ha.

In some embodiments, the FOP herbicide is clodinafop or clodinafop-propargyl. In some further embodiments, the effective amount of clodinafop or clodinafop-propargyl is at least 11 g AI/Ha. In other further embodiments, the effective amount of clodinafop or clodinafop-propargyl is at least 13, 15, 17, 19 or 20 g AI/Ha. In still other further embodiments, the effective amount of clodinafop or clodinafop-propargyl is at least 22 g AI/Ha. In yet other further embodiments, the effective amount of clodinafop or clodinafop-propargyl is at least 26, 30 or 34 g AI/Ha.

In some embodiments, the FOP herbicide is diclofop or diclofop-methyl. In some further embodiments, the effective amount of diclofop or diclofop-methyl is at least 226 g AI/Ha.

In other further embodiments, the effective amount of diclofop or diclofop-methyl is at least 260, 295, 330, 395 or 426 g AI/Ha. In still other further embodiments, the effective amount of diclofop or diclofop-methyl is at least 452 g AI/Ha. In yet other further embodiments, the effective amount of diclofop or diclofop-methyl is at least 480, 510 or 540 g AI/Ha.

In some embodiments, providing a domestic rice crop plant relates to planting a seed for the domestic rice crop plant and allowing the domestic rice crop plant to emerge prior to applying an effective amount of the at least one FOP herbicide.

In other embodiments, providing a domestic rice crop plant relates to transplanting the domestic rice crop plant prior to applying an effective amount of the at least one FOP herbicide.

In still other embodiments, providing a domestic rice crop plant relates to the domestic rice crop plant being previously established pre-emergence or post-emergence in a field prior to applying an effective amount of the at least one FOP herbicide post-emergence.

In some embodiments, the domestic rice crop plant was further treated pre-emergence or post-emergence with at least one additional herbicide. In some further embodiments, the at least one additional herbicide is a FOP, DIM, or DEN herbicide. In other further embodiments, the pre-emergence treatment with at least one additional herbicide is a seed coating. In still other further embodiments, the post-emergence treatment with at least one additional herbicide is prior to, concurrent with, or following the applying an effective amount of the at least one FOP herbicide to the domestic rice crop plant, post-emergence. In even other further embodiments, the DIM herbicide is selected from the group consisting of cycloxydim, sethoxydim, tepraloxydim, clethodim, and tralkoxydim.

In some embodiments, the field was previously used for the growth of a previous domestic rice crop plant that was not treated with an herbicide.

In other embodiments, the field was previously used for the growth of a previous herbicide-treated domestic rice crop plant. In some further embodiments, the previous herbicide-treated domestic rice crop plant was treated with at least one FOP, DIM, or DEN herbicide. In even other further embodiments, the DIM herbicide is selected from the group consisting of cycloxydim, sethoxydim, tepraloxydim, clethodim, and tralkoxydim.

Problem Weed Species

There are a number of weed species that present problems to the commercial cultivation of rice and that can be controlled according to the methods of the present disclosure including, but not limited to, weeds of the genera *Echinochloa* and *Leptochloa*.

Exemplary of problem *Echinochloa* species include, but are not limited to *E. colona* (common name Jungle rice), *E. crus-galli* (Barnyard grass), *E. crus-pavonis* (Gulf barnyard grass, or Gulf cockspur), *E. oryzicola* (Late Watergrass, or Late Barnyard grass; a.k.a., *E. phyllopogon* or *E. crus-galli* var. *oryzicola*), and *E. oryzoides* (Early Watergrass, or Early Barnyard grass).

Exemplary of problem *Leptochloa* species include, but are not limited to *L. chinensis* (Red sprangletop, Chinese sprangletop, or Asian sprangletop), *L. fascicularis* (Bearded sprangletop; a.k.a., *L. fusca* subspecies *fascicularis*), *L. panacea* (Mucronate sprangletop; a.k.a., *L. mucronata, L. panacea* subspecies *mucronata*, and *L. filiformis*), and *L. panicoides* (Amazon sprangletop).

Methods of Controlling Weeds

Herbicide-tolerant plants of the disclosure may be used in conjunction with an herbicide to which they are tolerant. Herbicides may be applied to the plants of the disclosure using any techniques known to those skilled in the art. Herbicides may be applied at any point in the plant cultivation process. For example, herbicides may be applied pre-planting, at planting, pre-emergence, post-emergence or combinations thereof.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides may be used to control the growth of weeds that may be found growing in the vicinity of the herbicide-tolerant plants invention. In embodiments of this type, an herbicide may be applied to a plot in which herbicide-tolerant plants of the disclosure are growing in vicinity to weeds. An herbicide to which the herbicide-tolerant plant of the disclosure is tolerant may then be applied to the plot at a concentration sufficient to kill or inhibit the growth of the weed. Concentrations of herbicide sufficient to kill or inhibit the growth of weeds are known in the art.

It will be readily apparent to one of ordinary skill in the relevant arts that other suitable modifications and adaptations to the methods and applications described herein are obvious and may be made without departing from the scope of the disclosure or any embodiment thereof. Having now described the present disclosure in detail, the same will be more clearly understood by reference to the following examples, which are included herewith for purposes of illustration only and are not intended to be limiting of the invention.

Use of Tissue Culture for Selection of Herbicide

Herbicide tolerant crops offer farmers additional options for weed management. Currently, there are genetically modified (GMO) solutions available in some crop systems. Additional, mutational techniques have been used to select for altered enzyme, activities or structures that confer herbicide resistance such as the current CLEARFIELD° solutions from BASF. In the US, CLEARFIELD Rice is the premier tool for managing red rice in infested areas (USDA-ARS, 2006); however, gene flow between red rice and CLEARFIELD Rice represents a considerable risk for the AHAS tolerance since out-crossing, has been reported at up to 170 F1 hybrids/ha (Shivrain et al, 2007). Stewardship guidelines including, amongst many other aspects, alternation non CLEARFIELD Rice can limit CLEARFIELD Rice market penetration. The generation of cultivated rice with tolerance to a different mode of action (MOA) graminicides would reduce these risks and provide more tools for weed management.

One enzyme that is already a target for many different graminaceous herbicides is acetyl CoA carboxylase (ACCase, EC 6.4.1.2), which catalyzes the first committed step in fatty acid (FA) biosynthesis. Aryloxyphenoxypropionate (APP or FOP) and cyclohexanedione (CHD or DIM) type herbicides are used post-emergence in dicot crops, with the exception of cyhalofop-butyl which is selective in rice to control grass weeds. Furthermore, most of these herbicides have relatively low persistence in soil and provide growers with flexibility for weed control and crop rotation. Mutations in this enzyme are known that confer tolerance to specific sets of FOPS and/or DIMS (Liu et al, 2007; Delye et al, 2003, 2005).

Tissue culture offers an alternative approach in that single clumps of callus represent hundreds or even thousands of cells, each of which can be selected for a novel trait such as herbicide resistance (Jain, 2001). Mutations arising spontaneously in tissue culture or upon some kind of induction can be directly selected in culture and mutated events selected.

The exploitation of somaclonal variation that is inherent to in vitro tissue culture techniques has been a successful approach to selectively generate mutations that confer DIM and FOP tolerance in corn (Somers, 1996; Somers et al., 1994; Marshal et al., 1992; Parker et al., 1990) and in seashore paspalum (Heckart et al, 2009). In the case of maize, the efficiencies of producing regenerable events can be calculated. In Somers et al, 1994, sethoxydim resistant maize plants were obtained using tissue culture selection. They utilized 100 g of callus and obtained 2 tolerant lines following stepwise selection at 0.5, 1.0, 2.0, 5.0 and 10 μM sethoxydim. A calculated mutation rate in their protocol would be 2 lines/100 g of callus or 0.02 lines/g.

In the case of seashore paspalum, Heckert directly utilized a high level of sethoxydim and recovered 3 regenerable lines in approx 10,000 callus pieces or, essentially, a 0.03% rate. While not comparable, these numbers will be later used for comparison with rice tissue culture mutagenesis. In the maize work, calli were constantly culled at each selection stage with only growing callus being transferred; however, in the case of seashore paspalum, all calli were transferred at each subculture. ACCase genes as selectable markers:

Plant transformation involves the use of selectable marker genes to identify the few transformed cells or individuals from the larger group of non-transformed cells or individuals. Selectable marker genes exist, but they are limited in number and availability. Alternative marker genes are required for stacking traits. In addition, the use of a selectable marker gene that confers an agronomic trait (i.e. herbicide resistance) is often desirable. The present disclosure discloses ACCase genes as selectable markers that can be added to the current limited suite of available selectable marker genes. Any of the mutants described herein can be introduced into a plasmid with a gene of interest and transformed into the whole plant, plant tissue or plant cell for use as selectable markers. A detailed method is outlined in example 7 below. The selectable markers of the inventions may be utilized to produce events that confer field tolerance to a given group of herbicides and other where cross protection has been shown (i.e., FOP's).

Modern, high throughput plant transformation systems require an effective selectable marker system; however, there is a limited number available that are acceptable in the market. Therefore, selection systems which also convey a commercial trait are always valuable. The system described herein is an effective selection system in/for plant cells which also encode for an herbicide tolerance trait suitable for use in any monocotyledonous crop.

In one embodiment, the present disclosure provides a method for selecting a transformed plant comprising introducing a nucleic acid molecule encoding a gene of interest into a plant cell, wherein the nucleic acid molecule further encodes a mutant acetyl-Coenzyme A carboxylase (ACCase) in which the amino acid sequence differs from an amino acid sequence of an ACCase of a corresponding wild-type rice plant at one amino acid position; and contacting the plant cells with an ACCase inhibitor to obtain the transformed plant, wherein said mutant ACCase confers upon the transformed plant increased herbicide tolerance as compared to the corresponding wild-type variety of the plant when expressed therein.

In one embodiment, the present disclosure provides a method of marker-assisted breeding, the method comprising breeding any plant of the disclosure with a second plant; and contacting progeny of the breeding step with an ACCase inhibitor to obtain the progeny comprising said mutant ACCase; wherein said mutant ACCase confers upon the progeny plant increased herbicide tolerance as compared to the second plant.

In one embodiment, a single ACCase gene is linked to a single gene of interest. The ACCase gene may be linked upstream or downstream of the gene of interest.

In one embodiment, the present disclosure provides for the use of ACCase nucleic acid and protein as described above in diagnostic assays. The diagnostic uses for selectable markers described herein can be employed to identify ACCase gene. Diagnostic methods can include PCR methodologies, proteins assays, labeled probes, and any other standard diagnostic methods known in the art.

EXAMPLES

Example 1: Tissue Culture Conditions

An in vitro tissue culture mutagenesis assay has been developed to isolate and characterize plant tissue (e.g., rice tissue) that is tolerant to acetyl-Coenzyme A carboxylase inhibiting herbicides, e.g., tepraloxydim, cycloxydim, and sethoxydim. The assay utilizes the somaclonal variation that is found in in vitro tissue culture. Spontaneous mutations derived from somaclonal variation can be enhanced by chemical mutagenesis and subsequent selection in a step-wise manner, on increasing concentrations of herbicide.

The present disclosure provides tissue culture conditions for encouraging growth of friable, embryogenic rice callus that is regenerable. Calli were initiated from 4 different rice cultivars encompassing both *japonica* (Taipei 309, Nipponbare, Koshihikari) and *indica* (*indica* 1) varieties. Dehusked seed were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 3.

TABLE 3

| Ingredient | Supplier | R001M | R025M | R026M | R327M | R008M | MS711R |
|---|---|---|---|---|---|---|---|
| B5 Vitamins | Sigma | | | | | 1.0X | |
| MS salts | Sigma | | | 1.0X | 1.0X | 1.0X | 1.0X |
| MS Vitamins | Sigma | | | 1.0X | 1.0X | | |
| N6 salts | Phytotech | 4.0 g/L | 4.0 g/L | | | | |
| N6 vitamins | Phytotech | 1.0X | 1.0X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 µg/L | |
| 2,4-D | Sigma | 2.0 mg/L | | | | | 1.0 mg/L |
| MgCl$_2$•6H$_2$O | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 2: Selection of Herbicide-Tolerant Calli

Once tissue culture conditions were determined, further establishment of selection conditions were established through the analysis of tissue survival in kill curves with cycloxydim, tepraloxydim, sethoxydim (FIG. 1) or haloxyfop (not shown). Careful consideration of accumulation of the herbicide in the tissue, as well as its persistence and stability in the cells and the culture media was performed. Through these experiments, a sub-lethal dose has been established for the initial selection of mutated material.

Figure 2:
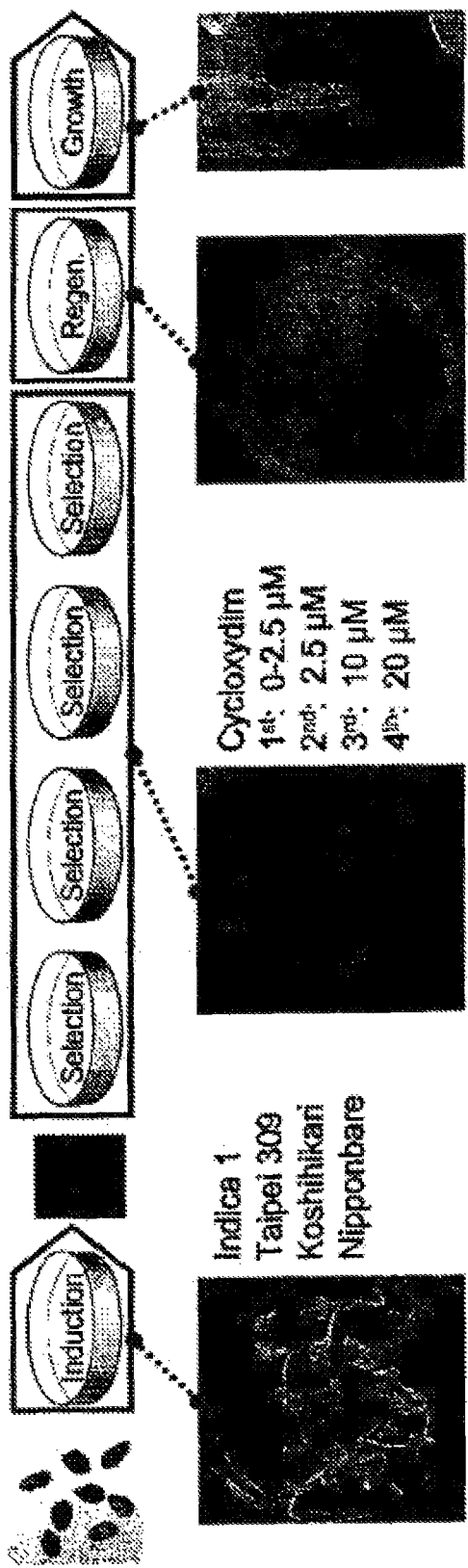

After the establishment of the starting dose of sethoxydim, cycloxydim, tepraloxydim, and haloxyfop in selection media, the tissues were selected in a step-wise fashion by increasing the concentration of the ACCase inhibitor with each transfer until cells are recovered that grew vigorously in the presence of toxic doses (see FIG. 2). The resulting calli were further subcultured every 3-4 weeks to R001M with selective agent. Over 26,000 calli were subjected to selection for 4-5 subcultures until the selective pressure was above toxic levels as determined by kill curves and observations of continued culture. Toxic levels were determined to be 50 µM sethoxydim, 20 µM cycloxydim, 2.5 µM tepraloxydim (FIG. 1) and 10 µM haloxyfop (not shown).

Alternatively, liquid cultures initiated from calli in MS711R (Table 2) with slow shaking and weekly subcultures. Once liquid cultures were established, selection agent was added directly to the flask at each subculture. Following 2-4 rounds of liquid selection, cultures were transferred to filters on solid R001M media for further growth.

Example 3: Regeneration of Plants

Tolerant tissue was regenerated and characterized molecularly for ACCase gene sequence mutations and/or biochemically for altered ACCase activity in the presence of the selective agent.

Following herbicide selection, calli were regenerated using a media regime of R025M for 10-14 days, R026M for ca. 2 weeks, R327M until well formed shoots were developed, and R0085 until shoots were well rooted for transfer to the greenhouse (Table 2). Regeneration was carried out in the light. No selection agent was included during regeneration.

Once strong roots were established, M0 regenerates were transplant to the greenhouse in 4" square pots in a mixture of sand, NC Sandhills loamy soil, and Redi-earth (2:4:6) supplemented with gypsum. Transplants were maintained under a clear plastic cup until they were adapted to greenhouse conditions (ca. 1 week). The greenhouse was set to a day/night cycle of 27° C./21° C. (80° F./70° F.) with 600W high pressure sodium lights supplementing light to maintain a 14 hour day length. Plants were watered 2-3 times a day depending in the weather and fertilized daily. Rice plants selected for seed increase were transplanted into one gallon pots. As plants approached maturity and prepared to bolt, the pots were placed in small flood flats to better maintain water and nutrient delivery. Plants were monitored for insects and plant health and managed under standard Integrated Pest Management practices.

Example 4: Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using one forward and one reverse primer.

```
Forward Primers:
                                      (SEQ ID NO:7)
OsACCpU5142: 5'-GCAAATGATATTACGTTCAGAGCTG-3'

(SEQ ID NO: 8)
OsACCpU5205: 5'-GTTACCAACCTAGCCTGTGAGAAG-3'

Reverse Primers:
                                      (SEQ ID NO: 9)
OsACCpL7100: 5'-GATTTCTTCAACAAGTTGAGCTCTTC-3'

(SEQ ID NO: 10)
OsACCpL7054: 5'-AGTAACATGGAAAGACCCTGTGGC-3'
```

PCR amplification was performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks). Chromatogram trace files (.scf) were analyzed for mutation relative to Os05g0295300 using Vector NTI Advance 10™ (Invitrogen). Based on sequence information, two mutations were identified in several individuals. I1,781(Am)L and D2,078(Am)G were present in the heterozygous state. Sequence analysis was performed on the representative chromatograms and corresponding AlignX alignment with default settings and edited to call secondary peaks.

Samples inconsistent with an ACCase mutation were spray tested for tolerance and discarded as escapes. Surprisingly, most of the recovered lines were heterozygous for the I1,781(Am)L mutation and resistant events were generated in all tested genotypes using cycloxydim or sethoxydim: Indical (≥18 lines), Taipei 309 (≥14 lines), Nipponbare (≥3 lines), and Koshihikare (≥6 lines). One line was heterozygous for a D2,078(Am)G mutation. The D2,078(Am)G heterozygote line appeared stunted with narrow leaves, while the I1,781(Am)L heterozygotes varied in appearance, but most looked normal relative to their parental genotype. Several escapes were recovered and confirmed by sequencing and spray testing; however, sequencing results of the herbicide sensitive region of ACCase revealed that most tolerant mutants were heterozygous for an I1,781(Am)L, A to T mutation (See Table 4). One line, OsARWI010, was heterozygous for a D2,078(Am)G, A to G mutation. To date, all recovered plants lacking an ACCase mutation have been sensitive to herbicide application in the greenhouse.

TABLE 4

Genotype of Rice Lines Recovered via Tissue Culture Selection

| Line | Parental Genotype | Rice Type | Mutation Identified | ATCC ® Patent Deposit Designation |
|---|---|---|---|---|
| OsARWI1 | Indica 1 | indica | I1781(Am)L | PTA-10568 |
| OsARWI3 | Indica 1 | indica | I1781(Am)L | PTA-10569 |
| OsARWI8 | Indica 1 | indica | I1781(Am)L | PTA-10570 |

TABLE 4-continued

Genotype of Rice Lines Recovered via Tissue Culture Selection

| Line | Parental Genotype | Rice Type | Mutation Identified | ATCC® Patent Deposit Designation |
|---|---|---|---|---|
| OsARWI10 | Indica 1 | indica | D2078(Am)G | NA, sterile |
| OsARWI15 | Indica 1 | indica | I1781(Am)L | NA |
| OsHPHI2 | Indica 1 | indica | I1781(Am)L | PTA-10267 |
| OsHPHI3 | Indica 1 | indica | I1781(Am)L | NA |
| OsHPHI4 | Indica 1 | indica | I1781(Am)L | NA |
| OsHPHK1 | Koshihikari | japonica | I1781(Am)L | NA |
| OsHPHK2 | Koshihikari | japonica | I1781(Am)L | NA |
| OsHPHK3 | Koshihikari | japonica | I1781(Am)L | NA |
| OsHPHK4 | Koshihikari | japonica | I1781(Am)L | NA |
| OsHPHK6 | Koshihikari | japonica | I1781(Am)L | NA |
| OsHPHN1 | Nipponbare | japonica | I1781(Am)L | PTA-10571 |
| OsHPHT1 | Taipei 309 | japonica | I1781(Am)L | NA |
| OsHPHT4 | Taipei 309 | japonica | I1781(Am)L | NA |
| OsHPHT6 | Taipei 309 | japonica | I1781(Am)L | NA |

Example 5: Demonstration of Herbicide-Tolerance

Selected mutants and escapes were transferred to small pots. Wild-type cultivars and 3 biovars of red rice were germinated from seed to serve as controls.

Figure 3:
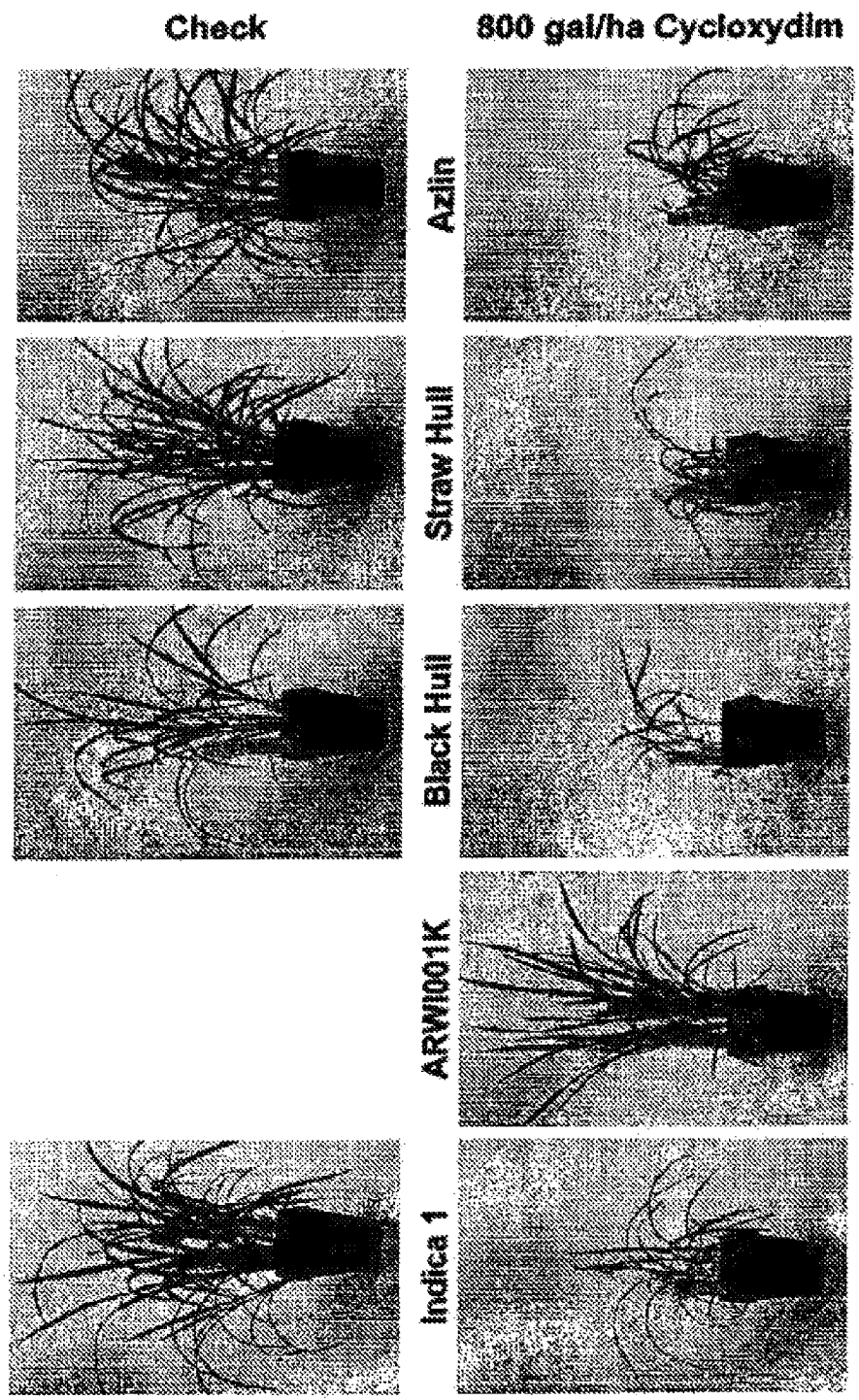
Figure 4:
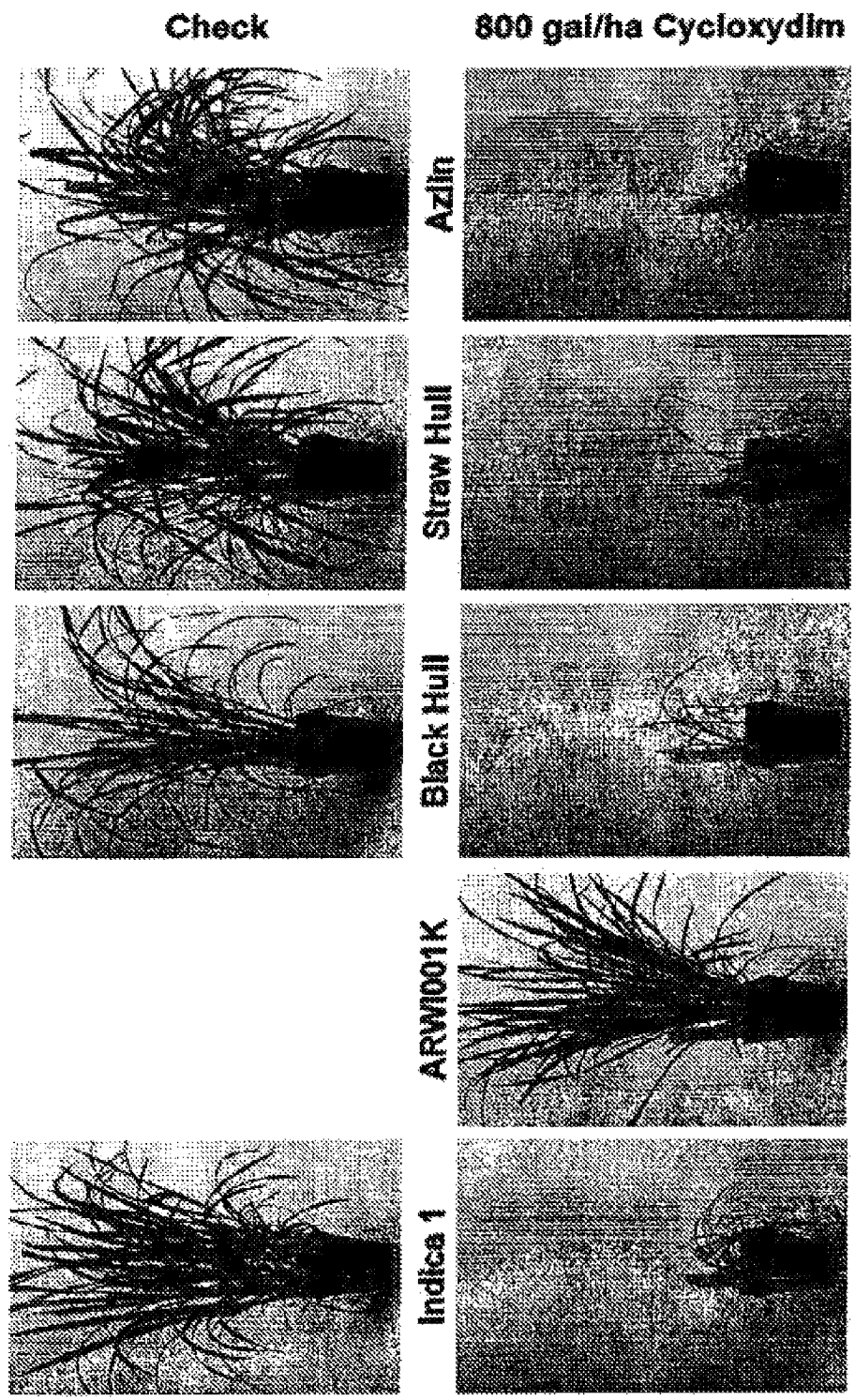
Figure 17:
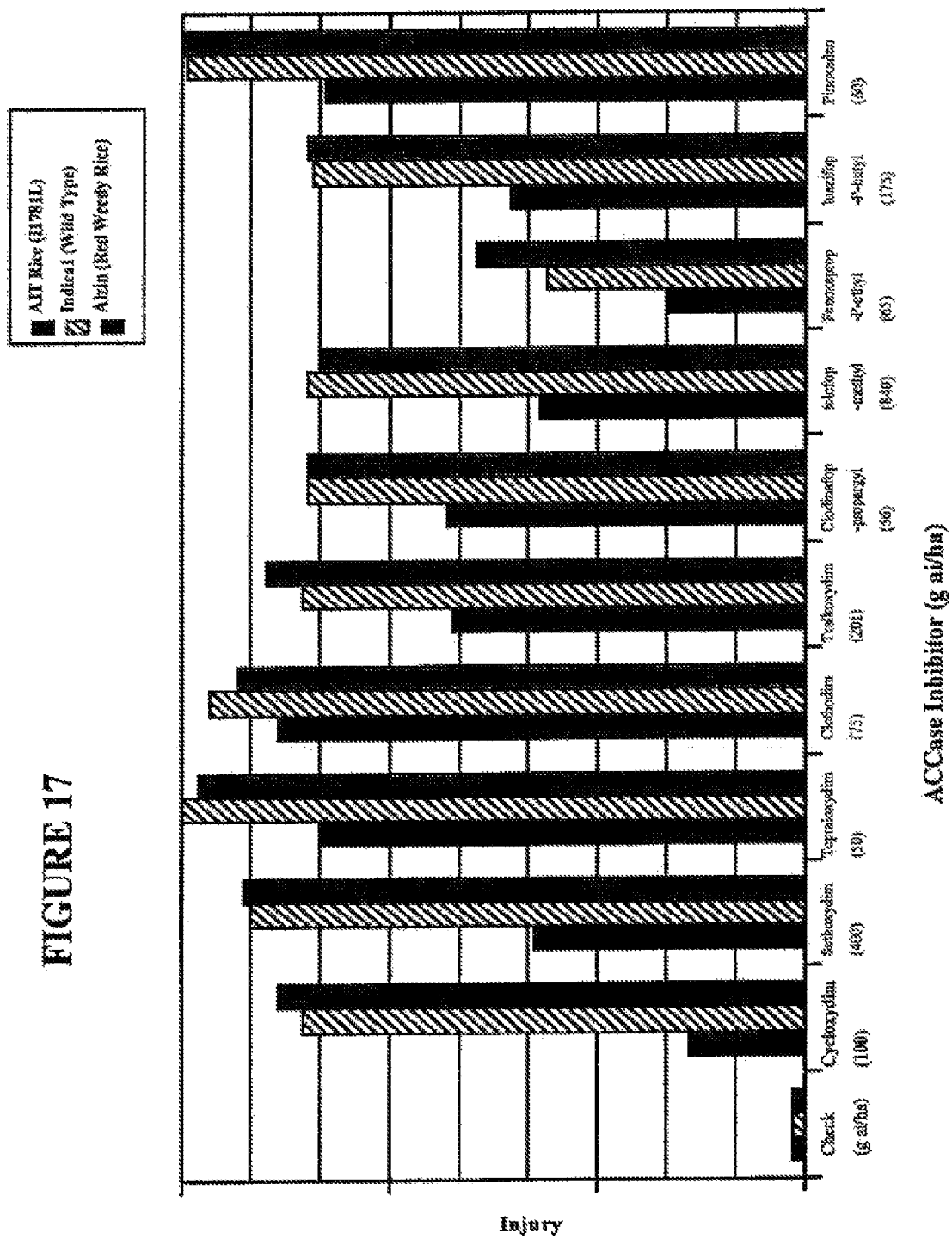

After ca. 3 weeks post-transplant, M0 regenerants were sprayed using a track sprayer with 400-1600 g ai/ha cycloxydim (BAS 517H) supplemented with 0.1% methylated seed oil. After the plants had adapted to greenhouse conditions, a subset were sprayed with 800 g ai/ha cycloxydim. Once sprayed, plants were kept on drought conditions for 24 hours before being watered and fertilized again. Sprayed plants were photographed and rated for herbicide injury at 1 (FIG. 3) and 2 weeks after treatment (FIG. 4). No injury was observed on plants containing the I1,781(Am)L heterozygous mutation while control plants and tissue culture escapes (regenerated plants negative for the sequenced mutations) were heavily damaged after treatment (FIGS. 3 & 4). FIGS. 5-15 provide nucleic acid and/or amino acid sequences of acetyl-Coenzyme A carboxylase enzymes from various plants. FIG. 17 provides a graph showing results for mutant rice versus various ACCase inhibitors.

Example 6: Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to: facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media.

Mutant lines were selected using cycloxydim or sethoxydim in 4 different rice genotypes. Efficiencies of obtaining mutants was high either based on a percentage of calli that gave rise to a regenerable, mutant line or the number of lines as determined by the gram of tissue utilized.

Overall, the mutation frequency compared to seashore paspalum is 5 fold and compared to maize is 2 fold. In some cases, this difference is much higher (>10 fold) as shown in Table 5 below.

TABLE 5

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.04 | 0.07 |
| Indica 1 | 2640 | Sethoxydim | 3 | 0.114% | 58.08 | 0.05 |
| Koshi | 1800 | Cycloxidim | 6 | 0.333% | 39.6 | 0.15 |
| NB | 3400 | Cycloxidim | 1 | 0.029% | 74.8 | 0.01 |
| NB | 725 | Sethoxydim | 0 | 0.000% | 15.95 | 0.00 |
| T309 | 1800 | Cycloxidim | 8 | 0.444% | 36.9 | 0.20 |
| T309 | 1015 | Sethoxydim | 0 | 0.000% | 22.33 | 0.00 |
| Total | 13245 | | 21 | 0.159% | 291.39 | 0.07 |

If the data is analyzed using the criteria of selection, it is possible to see that cylcoxydim selection contributes to a higher rate of mutants isolated than sethoxydim, as shown in Table 6.

TABLE 6

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.03 | 0.07 |
| Koshi | 1800 | Cycloxidim | 6 | 0.333% | 39.6 | 0.15 |
| NB | 3400 | Cycloxidim | 1 | 0.029% | 74.8 | 0.01 |
| T309 | 1800 | Cycloxidim | 8 | 0.444% | 39.6 | 0.20 |
| Total | 8865 | | 18 | 0.203% | 195.03 | 0.09 |
| Indica 1 | 2640 | Sethoxydim | 3 | 0.114% | 58.08 | 0.05 |
| NB | 725 | Sethoxydim | 0 | 0.000% | 15.95 | 0.00 |
| T309 | 1015 | Sethoxydim | 0 | 0.000% | 22.33 | 0.00 |
| Total | 4380 | | 3 | 0.068% | 96.36 | 0.03 |

Using this analysis, the rate for cycloxydim is almost 10 fold higher than either of the previous reports using sethoxydim selection, whereas rates using sethoxydim selection are similar to those previously reported. Further, 68% of the lines were confirmed as mutants when selection was on cycloxydim compared to 21% of the lines when selection was on sethoxydim. Increases seem to come from using cycloxydim instead of sethoxydim as a selection agent. Further, the use of membranes made transfer of callus significantly easier than moving each piece individually during subcultures. Over 20 mutants were obtained. Fertility appears to be high with the exception of one mutant that has a mutation known to cause a fitness penalty (D2,078(Am) G).

Example 7: Use of Mutant ACCase Genes as Selectable Markers in Plant Transformation Methods:

Indical and Nipponbare rice callus transformation was carried out essentially as described in Hiei and Komari (2008) with the exception of media substitutions as specified (see attached media table for details). Callus was induced on R001M media for 4-8 weeks prior to use in transformation. Agrobacterium utilized was LBA4404(pSB1) (Ishida et al. 1996) transformed with RLM185 (L. Mankin, unpublished; contains DsRed and a mutant AHAS for selection), ACC gene containing I1781(Am)L, ACC gene containing I1781 (Am)L and W2027C, ACC gene containing I1781(Am)L and I2041(Am)N, or ACC gene containing I1781(Am)A or wild type which also contains a mutant AHAS gene for selection. *Agrobacterium* grown for 1-3 days on solid media was suspended in M-LS-002 medium and the $OD_{660}$ adjusted to approximately 0.1. Callus was immersed in the *Agrobacterium* solution for approximately 30 minutes. Liquid was removed, and then callus was moved to filter paper for co-culture on semi-solid rice cc media. Co-culture was for 3 days in the dark at 24° C. Filters containing rice callus were directly transferred to R001M media containing Timentin for 1-2 weeks for recovery and cultured in the dark at 30° C. Callus was subdivided onto fresh R001M media with Timentin and supplemented with 100 μM Imazethapyr, 10 μM Cycloxydim or 2.5 μM Tepraloxydim. After 3-4 weeks, callus was transferred to fresh selection media. Following another 3-4 weeks, growing callus was transferred to fresh media and allowed to grow prior to Taqman analysis. Taqman analysis was for the Nos terminator and was conducted to provide for a molecular confirmation of the transgenic nature of the selected calli. Growth of transgenic calli was measured with various selection agents by subculturing calli on media containing either 10 μM Cycloxydim or Haloxyfop, 2.5 μM Tepraloxydim or 100 μM Imazethapry. Calli size was measured from scanned images following initial subculture and then after approximately 1 month of growth.

Transformation of maize immature embryos was carried out essentially as described by Lai et al (submitted). Briefly, immature embryos were co-cultured with the same *Agrobacterium* strains utilized for rice transformation suspended in M-LS-002 medium to an $OD_{660}$ of 1.0. Co-culture was on Maize CC medium for 3 days in the dark at 22° C. Embryos were removed from co-culture and transferred to M-MS-101 medium for 4-7 days at 27° C. Responding embryos were transferred to M-LS-202 medium for Imazethapyr selection or M-LS-213 media supplemented with either 1 μM Cycloxydim or 0.75 μM Tepraloxydim. Embryos were cultured for 2 weeks and growing callus was transferred to a second round of selection using the same media as previous except that Cycloxydim selection was increased to 5 μM. Selected calli were transferred to M-LS-504 or M-LS-513 media supplemented with either 5 μM Cycloxydim or 0.75 μM of Tepraloxydim for and moved to the light (16 hr/8 hr day/night) for regeneration. Shoots appeared between 2-3 weeks and were transferred to plantcon boxes containing either M-LS-618 or M-LS-613 supplemented with either 5 μM Cycloxydim or 0.75 μM of Tepraloxydim for further shoot development and rooting. Leaf samples were submitted for Taqman analysis. Positive plants were transferred to soil for growth and seed generation. In the second set of experiments, conditions were identical except that Tepraloxydim selection was decreased to 0.5 μM during regeneration and shoot and root formation. In the third set of experiments, Haloxyfop was also tested as a selection agent. In these experiments, 1 μM was used throughout for selection.

Results and Discussion:

Transgenic calli were obtained from Indical rice transformation experiments using ACC gene containing I1781 (Am)L and W2027(Am)C, and ACC gene containing I1781 (Am)L and I2041(Am)N. One callus was obtained from ACC gene containing I1781(Am)L and W2027(Am)C following Tepraloxydim selection and 3 calli were obtained from ACC gene containing I1781(Am)L and I2041(Am)N. One callus was obtained from ACC gene containing I1781 (Am)L and I2041(Am)N using Cycloxydim selection. Nos Taqman showed that all of these calli were transgenic. Calli were screened for growth under various selection agents including Imazethapry (Pursuit—P) for the mutant AHAS selectable marker.

As can be observed in Table 7, the double mutant constructs allowed for growth on both Cycloxydim and Tepraloxydim in addition to Haloxyfop. The levels utilized in these growth experiments are inhibitory for wild type material. Growth was measured as a % change in size following 1 month of culture on the selection media.

TABLE 7

Growth of transgenic Indical callus on various selection media.

| Construct | Selection μM | | | |
|---|---|---|---|---|
| | H10 | C10 | T2.5 | P100 |
| I1781(Am)L, W2027(Am)C | 1669% | 867% | 1416% | 739% |
| I1781(Am)L, I2041(Am)N | 1613% | 884% | 1360% | 634% |

Results from the first set of maize experiments reveal that both the single of the double mutant can be used to select for Cycloxydim resistance or both Cylcoxydim or Tepraloxydim resistance at a relatively high efficiency (FIG. 16).

Efficiencies between selection agents was relatively comparable in these experiments with maybe a slight decrease in the overall efficiency with the single mutant on Cycloxydim compared to Pursuit selection. However, the double mutant may have a slight increased efficiency. The escape rate—the percentage of non-confirmed putative events—was lower for Cycloxydim or Tepraloxydim. Further, under the conditions described, it was possible to differentiate between the single and double mutants using Tepraloxydim selection.

Similar results have been obtained in the second set of experiments (not shown). In the third set of experiments, Haloxyfop is also an efficient selectable marker for use in transformation with either the single or the double mutant (not shown).

The single mutant is useful for high efficiency transformation using Cycloxydim or Haloxyfop selection. It should also be useful for other related compounds such as Sethoxydim. The double mutant is useful for these selection agents with the addition that Tepraloxydim can be used. The single and the double mutant can be used in a two stage transformation in that the single mutant can be differentiated from the double with Tepraloxydim selection. In combination with other current BASF selection markers, these give two more options for high efficiency transformations of monocots and maize in particular.

Herbicide tolerance phenotypes as described herein have also been exhibited by ACCase-inhibitor tolerant rice plants hereof, in the field under 600 g/ha cycloxydim treatment (data not shown).

Example 8: AIT Rice Tolerance to Herbicide Versus Red Rice

The tolerance of AIT rice to a variety of FOP, DIM and DEN herbicides was evaluated and compared to the tolerance of wild-type red rice to the same herbicides.

Methods:

Untreated AIT rice and red rice seeds were sown into fields in three separate locations and allowed to emerge. At the 3-4 leaf growth stage, plots at each location were treated with single applications of varying concentrations of herbicide. All herbicides were suspended in solutions comprising 1% methylated seed oil.

Cycloxydim was applied at a rate of 300 g AI/Ha.
Sethoxydim was applied at a rate of 600 g AI/Ha.
Tepraloxydim was applied at a rate of 50 g AI/Ha.
Clethodim was applied at a rate of 100 200 g AI/Ha.
Quizalofop-P-ethyl was applied at rates of 35, 70 and 140 g AI/Ha.
Pinoxaden was applied at rates of 30, 60 and 120 g AI/Ha.
Clodinafop-propargyl was applied at rates of 35, 70 and 140 g AI/Ha.

Percent injury to treated plants was evaluated two weeks after herbicide treatment according to procedures standard in the art.

Results:

Results are shown as the average percent injury of the three plots for each plant type treated with the given application rate of herbicide.

Figure 20A:
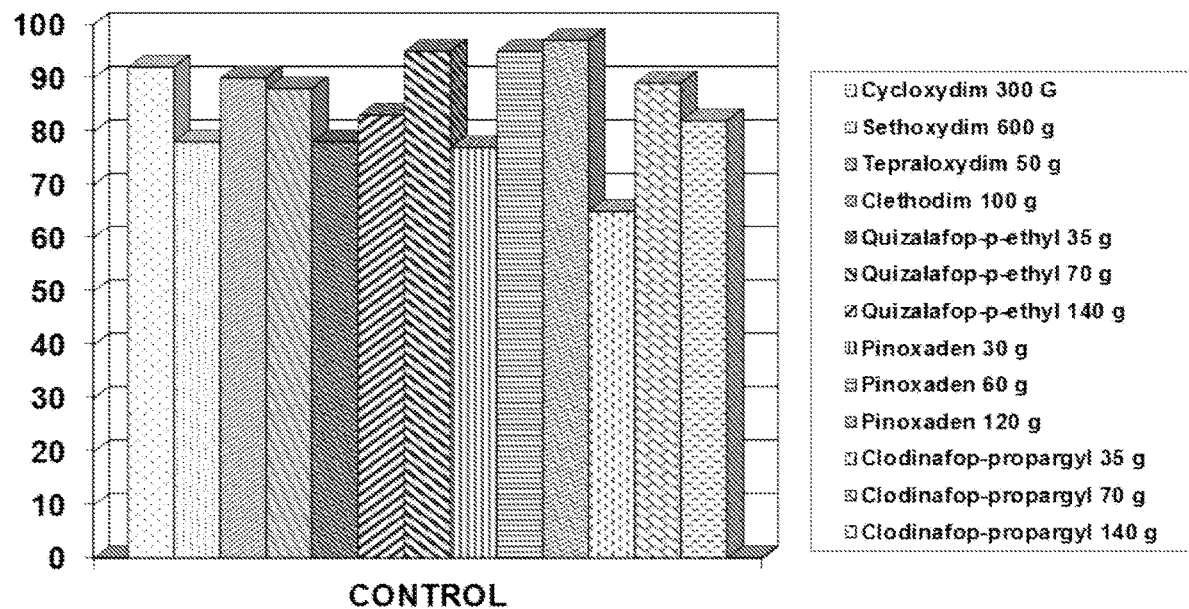
Figure 20B:
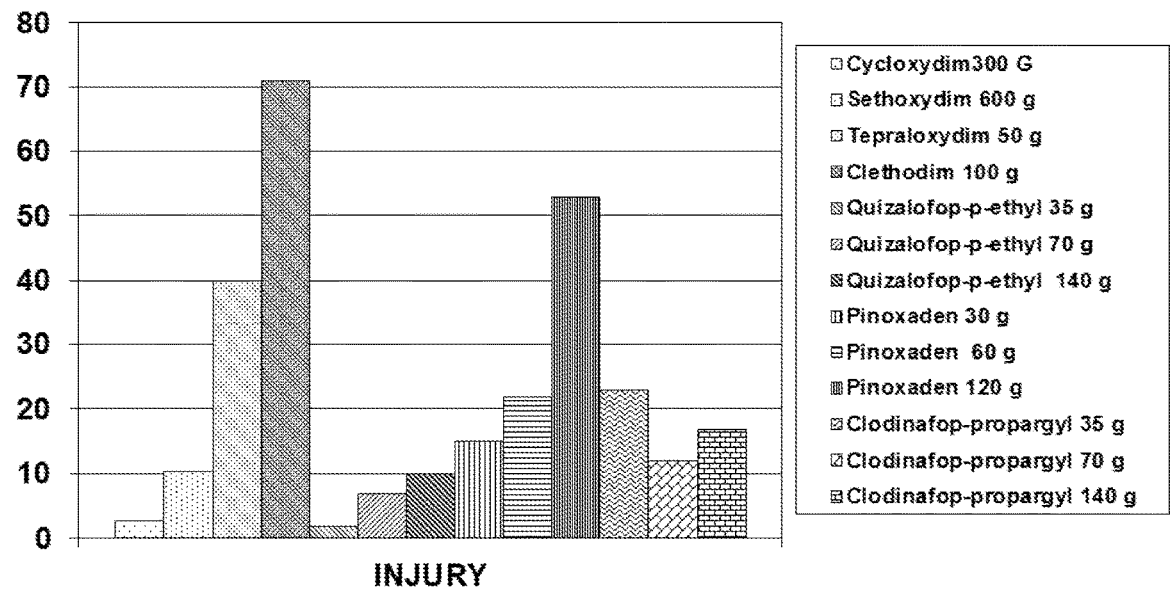

As shown in FIG. 20A, red rice suffered more injury to each herbicide at each concentration that the corresponding plots of AIT rice as shown in FIG. 20B.

The above description is for the purpose of teaching the person of ordinary skill in the art how to practice the claimed aspects of the disclosure and embodiments thereof, and it is not intended to detail all those obvious modifications and variations of it which will become apparent to the skilled worker upon reading the description. It is intended, however, that all such obvious modifications and variations be included within the scope of the present disclosure. The disclosure is intended to cover the components and steps in any sequence which is effective to meet the objectives there intended, unless the context specifically indicates the contrary. All patents and publications cited herein are entirely incorporated herein by reference.

What is claimed is:

1. A method for treating rice, comprising:
(i) providing at least one ACCase-inhibiting aryloxyphenoxypropanoate herbicide selected from the group consisting of quizalofop, an ester of quizalofop, an enantiomer of quizalofop, and an agriculturally acceptable salt of quizalofop;
(ii) providing a domestic rice crop plant grown from seed, the domestic rice crop plant comprising and expressing an endogenous non-transfected mutant ACCase nucleic acid whose sequence encodes a multi-functional, plastidic ACCase containing a mutation selected from the group consisting of I1781L (Am), G2096S (Am), and W2027C (Am) that causes the ACCase to be tolerant to the herbicide, the nucleic acid thereby providing to the plant tolerance to the aryloxyphenoxypropanoate herbicide;
(iii) applying an effective amount (measured in grams of active ingredient per hectare (g AI/Ha)) of the at least one aryloxyphenoxypropanoate herbicide to the domestic rice crop plant, post-emergence; thereby creating a treated rice plant; and
(iv) growing the treated rice plant,
wherein the effective amount of the at least one ACCase-inhibiting aryloxyphenoxypropanoate herbicide is 14 g AI/Ha to 40 g AI/Ha of quizalofop or an ester of quizalofop, or an amount equivalent to 14 g AI/Ha to 40 g AI/Ha of quizalofop or an ester of quizalofop, and wherein the effective amount of the aryloxyphenoxypropanoate herbicide causes less than 10% injury to the rice plant in field applications, wherein the injury to the rice plant is evaluated 2-3 weeks after herbicide treatment.

2. The method of claim 1, further comprising harvesting seed from the treated rice plant.

3. The method of claim 1, wherein the at least one aryloxyphenoxypropanoate herbicide comprises quizalofop.

4. The method of claim 3, wherein the effective amount of quizalofop is 14 g AI/Ha.

5. The method of claim 1, wherein the at least one aryloxyphenoxypropanoate herbicide comprises an ester of quizalofop.

6. The method of claim 5, wherein the effective amount of an ester of quizalofop is 14 g AI/Ha.

7. The method of claim 5, wherein the ester of quizalofop is selected from the group consisting of quizalofop-P-ethyl and quizalofop-P-tefuryl.

8. The method of claim 1, wherein the at least one aryloxyphenoxypropanoate herbicide comprises an enantiomer of quizalofop.

9. The method of claim 8, wherein the effective amount of an enantiomer of quizalofop is 14 g AI/Ha.

10. The method of claim 8, wherein the enantiomer of quizalofop is quizalofop-P.

11. The method of claim 1, wherein the effective amount is effective for killing a weed of the genus *Echinochloa*.

12. The method of claim 11, wherein the weed of the genus *Echinochloa* is selected from the group consisting of *Echinochloa colona, Echinochloa crus-galli, Echinochloa crus-pavonis, Echinochloa oryzicola*, and *Echinochloa oryzoides*.

13. The method of claim 1, wherein the effective amount is effective for killing a weed of the genus *Leptochloa*.

14. The method of claim 13, wherein the weed of the genus *Leptochloa* is selected from the group consisting of *Leptochloa chinensis, Leptochloa fascicularis, Leptochloa panacea*, and *Leptochloa panicoides*.

15. The domestic rice crop plant treated by the method of claim 1.

16. The domestic rice crop plant of claim 15, wherein the rice plant exhibits less than 10% injury when treated with 14 g AI/Ha to 40 g AI/Ha of quizalofop or an ester of quizalofop, or an amount equivalent to 14 g AI/Ha to 40 g AI/Ha of quizalofop or an ester of quizalofop in field applications, wherein the injury to the rice plant is evaluated 2-3 weeks after herbicide treatment.

17. The seed harvested by the method of claim 2.

* * * * *

(12) POST-GRANT REVIEW CERTIFICATE (258th)
United States Patent
Mankin et al.

(10) Number: US 11,096,346 J1
(45) Certificate Issued: Jun. 5, 2023

(54) METHOD FOR TREATING POST-EMERGENT RICE

(71) Applicants: S. Luke Mankin; Sherry R. Whitt; Haiping Hong; Dale R. Carlson; Jill M. Stevenson-Paulik; Leon Neuteboom; Ulrich Schofl; Allan Wenck; John A. McElver

(72) Inventors: S. Luke Mankin; Sherry R. Whitt; Haiping Hong; Dale R. Carlson; Jill M. Stevenson-Paulik; Leon Neuteboom; Ulrich Schofl; Allan Wenck; John A. McElver

(73) Assignee: BASF SE

Trial Number:

PGR2021-00114 filed Aug. 24, 2021

Post-Grant Review Certificate for:

Patent No.: 11,096,346
Issued: Aug. 24, 2021
Appl. No.: 15/443,714
Filed: Feb. 27, 2017

The results of PGR2021-00114 are reflected in this post-grant review certificate under 35 U.S.C. 328(b).

POST-GRANT REVIEW CERTIFICATE
U.S. Patent 11,096,346 J1
Trial No. PGR2021-00114
Certificate Issued Jun. 5, 2023

AS A RESULT OF THE POST-GRANT REVIEW PROCEEDING, IT HAS BEEN DETERMINED THAT:

Claims 1-17 are cancelled.

\* \* \* \* \*

SEQUENCE LISTING

```
<160> NUMBER OF SEQ ID NOS: 26

<210> SEQ ID NO 1
<211> LENGTH: 2320
<212> TYPE: PRT
<213> ORGANISM: Alopecurus myosuroides

<400> SEQUENCE: 1

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255
```

```
Leu Gly Asp Lys Val Gly Ser Ala Leu Ile Ala Gln Ala Ala Gly Val
                260                 265                 270
Pro Thr Leu Ala Trp Ser Gly Ser His Val Glu Ile Pro Leu Glu Leu
                275                 280                 285
Cys Leu Asp Ser Ile Pro Glu Glu Met Tyr Arg Lys Ala Cys Val Thr
290                 295                 300
Thr Ala Asp Glu Ala Val Ala Ser Cys Gln Met Ile Gly Tyr Pro Ala
305                 310                 315                 320
Met Ile Lys Ala Ser Trp Gly Gly Gly Lys Gly Ile Arg Lys Val
                325                 330                 335
Asn Asn Asp Asp Glu Val Lys Ala Leu Phe Lys Gln Val Gln Gly Glu
                340                 345                 350
Val Pro Gly Ser Pro Ile Phe Ile Met Arg Leu Ala Ser Gln Ser Arg
                355                 360                 365
His Leu Glu Val Gln Leu Leu Cys Asp Glu Tyr Gly Asn Val Ala Ala
                370                 375                 380
Leu His Ser Arg Asp Cys Ser Val Gln Arg Arg His Gln Lys Ile Ile
385                 390                 395                 400
Glu Glu Gly Pro Val Thr Val Ala Pro Arg Glu Thr Val Lys Glu Leu
                405                 410                 415
Glu Gln Ala Ala Arg Arg Leu Ala Lys Ala Val Gly Tyr Val Gly Ala
                420                 425                 430
Ala Thr Val Glu Tyr Leu Tyr Ser Met Glu Thr Gly Glu Tyr Tyr Phe
                435                 440                 445
Leu Glu Leu Asn Pro Arg Leu Gln Val Glu His Pro Val Thr Glu Ser
450                 455                 460
Ile Ala Glu Val Asn Leu Pro Ala Ala Gln Val Ala Val Gly Met Gly
465                 470                 475                 480
Ile Pro Leu Trp Gln Ile Pro Glu Ile Arg Arg Phe Tyr Gly Met Asp
                485                 490                 495
Asn Gly Gly Gly Tyr Asp Ile Trp Arg Lys Thr Ala Ala Leu Ala Thr
                500                 505                 510
Pro Phe Asn Phe Asp Glu Val Asp Ser Gln Trp Pro Lys Gly His Cys
                515                 520                 525
Val Ala Val Arg Ile Thr Ser Glu Asn Pro Asp Asp Gly Phe Lys Pro
530                 535                 540
Thr Gly Gly Lys Val Lys Glu Ile Ser Phe Lys Ser Lys Pro Asn Val
545                 550                 555                 560
Trp Gly Tyr Phe Ser Val Lys Ser Gly Gly Gly Ile His Glu Phe Ala
                565                 570                 575
Asp Ser Gln Phe Gly His Val Phe Ala Tyr Gly Glu Thr Arg Ser Ala
                580                 585                 590
Ala Ile Thr Ser Met Ser Leu Ala Leu Lys Glu Ile Gln Ile Arg Gly
                595                 600                 605
Glu Ile His Thr Asn Val Asp Tyr Thr Val Asp Leu Leu Asn Ala Pro
                610                 615                 620
Asp Phe Arg Glu Asn Thr Ile His Thr Gly Trp Leu Asp Thr Arg Ile
625                 630                 635                 640
Ala Met Arg Val Gln Ala Glu Arg Pro Pro Trp Tyr Ile Ser Val Val
                645                 650                 655
Gly Gly Ala Leu Tyr Lys Thr Ile Thr Thr Asn Ala Glu Thr Val Ser
                660                 665                 670
Glu Tyr Val Ser Tyr Leu Ile Lys Gly Gln Ile Pro Pro Lys His Ile
```

-continued

```
            675                 680                 685
Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
    850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His  Phe Ile Val Lys Ser  Leu Phe Glu
        995                 1000                1005

Glu Tyr  Leu Ser Val Glu Glu  Leu Phe Ser Asp Gly  Ile Gln Ser
    1010                1015                1020

Asp Val  Ile Glu Arg Leu Arg  Leu Gln Tyr Ser Lys  Asp Leu Gln
    1025                1030                1035

Lys Val  Val Asp Ile Val Leu  Ser His Gln Gly Val  Arg Asn Lys
    1040                1045                1050

Thr Lys  Leu Ile Leu Ala Leu  Met Glu Lys Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Arg Tyr Tyr Lys Leu  Ala Leu Lys Ala Ser  Glu Leu Leu
    1085                1090                1095
```

```
Glu Gln Thr Lys Leu Ser Glu Leu Arg Thr Ser Ile Ala Arg Asn
    1100            1105                1110

Leu Ser Ala Leu Asp Met Phe Thr Glu Glu Lys Ala Asp Phe Ser
    1115            1120                1125

Leu Gln Asp Arg Lys Leu Ala Ile Asn Glu Ser Met Gly Asp Leu
    1130            1135                1140

Val Thr Ala Pro Leu Pro Val Glu Asp Ala Leu Val Ser Leu Phe
    1145            1150                1155

Asp Cys Thr Asp Gln Thr Leu Gln Gln Arg Val Ile Gln Thr Tyr
    1160            1165                1170

Ile Ser Arg Leu Tyr Gln Pro Gln Leu Val Lys Asp Ser Ile Gln
    1175            1180                1185

Leu Lys Tyr Gln Asp Ser Gly Val Ile Ala Leu Trp Glu Phe Thr
    1190            1195                1200

Glu Gly Asn His Glu Lys Arg Leu Gly Ala Met Val Ile Leu Lys
    1205            1210                1215

Ser Leu Glu Ser Val Ser Thr Ala Ile Gly Ala Ala Leu Lys Asp
    1220            1225                1230

Ala Ser His Tyr Ala Ser Ser Ala Gly Asn Thr Val His Ile Ala
    1235            1240                1245

Leu Leu Asp Ala Asp Thr Gln Leu Asn Thr Thr Glu Asp Ser Gly
    1250            1255                1260

Asp Asn Asp Gln Ala Gln Asp Lys Met Asp Lys Leu Ser Phe Val
    1265            1270                1275

Leu Lys Gln Asp Val Val Met Ala Asp Leu Arg Ala Ala Asp Val
    1280            1285                1290

Lys Val Val Ser Cys Ile Val Gln Arg Asp Gly Ala Ile Met Pro
    1295            1300                1305

Met Arg Arg Thr Phe Leu Leu Ser Glu Glu Lys Leu Cys Tyr Glu
    1310            1315                1320

Glu Glu Pro Ile Leu Arg His Val Glu Pro Pro Leu Ser Ala Leu
    1325            1330                1335

Leu Glu Leu Asp Lys Leu Lys Val Lys Gly Tyr Asn Glu Met Lys
    1340            1345                1350

Tyr Thr Pro Ser Arg Asp Arg Gln Trp His Ile Tyr Thr Leu Arg
    1355            1360                1365

Asn Thr Glu Asn Pro Lys Met Leu His Arg Val Phe Phe Arg Thr
    1370            1375                1380

Leu Val Arg Gln Pro Ser Ala Gly Asn Arg Phe Thr Ser Asp His
    1385            1390                1395

Ile Thr Asp Val Glu Val Gly His Ala Glu Glu Pro Leu Ser Phe
    1400            1405                1410

Thr Ser Ser Ser Ile Leu Lys Ser Leu Lys Ile Ala Lys Glu Glu
    1415            1420                1425

Leu Glu Leu His Ala Ile Arg Thr Gly His Ser His Met Tyr Leu
    1430            1435                1440

Cys Ile Leu Lys Glu Gln Lys Leu Leu Asp Leu Val Pro Val Ser
    1445            1450                1455

Gly Asn Thr Val Val Asp Val Gly Gln Asp Glu Ala Thr Ala Cys
    1460            1465                1470

Ser Leu Leu Lys Glu Met Ala Leu Lys Ile His Glu Leu Val Gly
    1475            1480                1485
```

-continued

```
Ala Arg Met His His Leu Ser Val Cys Gln Trp Glu Val Lys Leu
    1490                1495                1500

Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560

Tyr Gln Pro Leu Ser Val Ile Asp Leu Lys Arg Cys Ser Ala Arg
    1565                1570                1575

Asn Asn Lys Thr Thr Tyr Cys Tyr Asp Phe Pro Leu Thr Phe Glu
    1580                1585                1590

Ala Ala Val Gln Lys Ser Trp Ser Asn Ile Ser Ser Glu Asn Asn
    1595                1600                1605

Gln Cys Tyr Val Lys Ala Thr Glu Leu Val Phe Ala Glu Lys Asn
    1610                1615                1620

Gly Ser Trp Gly Thr Pro Ile Ile Pro Met Gln Arg Ala Ala Gly
    1625                1630                1635

Leu Asn Asp Ile Gly Met Val Ala Trp Ile Leu Asp Met Ser Thr
    1640                1645                1650

Pro Glu Phe Pro Ser Gly Arg Gln Ile Ile Val Ile Ala Asn Asp
    1655                1660                1665

Ile Thr Phe Arg Ala Gly Ser Phe Gly Pro Arg Glu Asp Ala Phe
    1670                1675                1680

Phe Glu Ala Val Thr Asn Leu Ala Cys Glu Lys Lys Leu Pro Leu
    1685                1690                1695

Ile Tyr Leu Ala Ala Asn Ser Gly Ala Arg Ile Gly Ile Ala Asp
    1700                1705                1710

Glu Val Lys Ser Cys Phe Arg Val Gly Trp Thr Asp Asp Ser Ser
    1715                1720                1725

Pro Glu Arg Gly Phe Arg Tyr Ile Tyr Met Thr Asp Glu Asp His
    1730                1735                1740

Asp Arg Ile Gly Ser Ser Val Ile Ala His Lys Met Gln Leu Asp
    1745                1750                1755

Ser Gly Glu Ile Arg Trp Val Ile Asp Ser Val Val Gly Lys Glu
    1760                1765                1770

Asp Gly Leu Gly Val Glu Asn Ile His Gly Ser Ala Ala Ile Ala
    1775                1780                1785

Ser Ala Tyr Ser Arg Ala Tyr Glu Glu Thr Phe Thr Leu Thr Phe
    1790                1795                1800

Val Thr Gly Arg Thr Val Gly Ile Gly Ala Tyr Leu Ala Arg Leu
    1805                1810                1815

Gly Ile Arg Cys Ile Gln Arg Ile Asp Gln Pro Ile Ile Leu Thr
    1820                1825                1830

Gly Phe Ser Ala Leu Asn Lys Leu Leu Gly Arg Glu Val Tyr Ser
    1835                1840                1845

Ser His Met Gln Leu Gly Gly Pro Lys Ile Met Ala Thr Asn Gly
    1850                1855                1860

Val Val His Leu Thr Val Pro Asp Asp Leu Glu Gly Val Ser Asn
    1865                1870                1875

Ile Leu Arg Trp Leu Ser Tyr Val Pro Ala Asn Ile Gly Gly Pro
```

```
              1880                1885                1890
     Leu Pro Ile Thr Lys Ser Leu Asp Pro Ile Asp Arg Pro Val Ala
              1895                1900                1905

Tyr Ile Pro Glu Asn Thr Cys Asp Pro Arg Ala Ala Ile Ser Gly
              1910                1915                1920

Ile Asp Asp Ser Gln Gly Lys Trp Leu Gly Gly Met Phe Asp Lys
              1925                1930                1935

Asp Ser Phe Val Glu Thr Phe Glu Gly Trp Ala Lys Thr Val Val
              1940                1945                1950

Thr Gly Arg Ala Lys Leu Gly Gly Ile Pro Val Gly Val Ile Ala
              1955                1960                1965

Val Glu Thr Gln Thr Met Met Gln Leu Val Pro Ala Asp Pro Gly
              1970                1975                1980

Gln Pro Asp Ser His Glu Arg Ser Val Pro Arg Ala Gly Gln Val
              1985                1990                1995

Trp Phe Pro Asp Ser Ala Thr Lys Thr Ala Gln Ala Met Leu Asp
              2000                2005                2010

Phe Asn Arg Glu Gly Leu Pro Leu Phe Ile Leu Ala Asn Trp Arg
              2015                2020                2025

Gly Phe Ser Gly Gly Gln Arg Asp Leu Phe Glu Gly Ile Leu Gln
              2030                2035                2040

Ala Gly Ser Thr Ile Val Glu Asn Leu Arg Thr Tyr Asn Gln Pro
              2045                2050                2055

Ala Phe Val Tyr Ile Pro Lys Ala Ala Glu Leu Arg Gly Gly Ala
              2060                2065                2070

Trp Val Val Ile Asp Ser Lys Ile Asn Pro Asp Arg Ile Glu Cys
              2075                2080                2085

Tyr Ala Glu Arg Thr Ala Lys Gly Asn Val Leu Glu Pro Gln Gly
              2090                2095                2100

Leu Ile Glu Ile Lys Phe Arg Ser Glu Glu Leu Lys Glu Cys Met
              2105                2110                2115

Gly Arg Leu Asp Pro Glu Leu Ile Asp Leu Lys Ala Arg Leu Gln
              2120                2125                2130

Gly Ala Asn Gly Ser Leu Ser Asp Gly Glu Ser Leu Gln Lys Ser
              2135                2140                2145

Ile Glu Ala Arg Lys Lys Gln Leu Leu Pro Leu Tyr Thr Gln Ile
              2150                2155                2160

Ala Val Arg Phe Ala Glu Leu His Asp Thr Ser Leu Arg Met Ala
              2165                2170                2175

Ala Lys Gly Val Ile Arg Lys Val Val Asp Trp Glu Asp Ser Arg
              2180                2185                2190

Ser Phe Phe Tyr Lys Arg Leu Arg Arg Arg Leu Ser Glu Asp Val
              2195                2200                2205

Leu Ala Lys Glu Ile Arg Gly Val Ile Gly Glu Lys Phe Pro His
              2210                2215                2220

Lys Ser Ala Ile Glu Leu Ile Lys Lys Trp Tyr Leu Ala Ser Glu
              2225                2230                2235

Ala Ala Ala Ala Gly Ser Thr Asp Trp Asp Asp Asp Ala Phe
              2240                2245                2250

Val Ala Trp Arg Glu Asn Pro Glu Asn Tyr Lys Glu Tyr Ile Lys
              2255                2260                2265

Glu Leu Arg Ala Gln Arg Val Ser Arg Leu Leu Ser Asp Val Ala
              2270                2275                2280
```

```
Gly Ser  Ser Ser Asp Leu Gln  Ala Leu Pro Gln Gly  Leu Ser Met
    2285         2290              2295

Leu Leu  Asp Lys Met Asp Pro  Ser Lys Arg Ala Gln  Phe Ile Glu
    2300         2305              2310

Glu Val  Met Lys Val Leu Lys
    2315         2320
```

<210> SEQ ID NO 2
<211> LENGTH: 2327
<212> TYPE: PRT
<213> ORGANISM: Oryza sativa

<400> SEQUENCE: 2

```
Met Thr Ser Thr His Val Ala Thr Leu Gly Val Gly Ala Gln Ala Pro
 1               5                  10                  15

Pro Arg His Gln Lys Lys Ser Ala Gly Thr Ala Phe Val Ser Ser Gly
             20                  25                  30

Ser Ser Arg Pro Ser Tyr Arg Lys Asn Gly Gln Arg Thr Arg Ser Leu
         35                  40                  45

Arg Glu Glu Ser Asn Gly Gly Val Ser Asp Ser Lys Lys Leu Asn His
 50                  55                  60

Ser Ile Arg Gln Gly Leu Ala Gly Ile Ile Asp Leu Pro Asn Asp Ala
 65                  70                  75                  80

Ala Ser Glu Val Asp Ile Ser His Gly Ser Glu Asp Pro Arg Gly Pro
             85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Gly Lys Gly Ile Arg Lys Val
```

```
                325                 330                 335
His Asn Asp Asp Glu Val Arg Thr Leu Phe Lys Gln Val Gln Gly Glu
            340                 345                 350
Val Pro Gly Ser Pro Ile Phe Ile Met Arg Leu Ala Ala Gln Ser Arg
            355                 360                 365
His Leu Glu Val Gln Leu Leu Cys Asp Gln Tyr Gly Asn Val Ala Ala
            370                 375                 380
Leu His Ser Arg Asp Cys Ser Val Gln Arg Arg His Gln Lys Ile Ile
385                 390                 395                 400
Glu Glu Gly Pro Val Thr Val Ala Pro Arg Glu Thr Val Lys Glu Leu
            405                 410                 415
Glu Gln Ala Ala Arg Arg Leu Ala Lys Ala Val Gly Tyr Val Gly Ala
            420                 425                 430
Ala Thr Val Glu Tyr Leu Tyr Ser Met Glu Thr Gly Glu Tyr Tyr Phe
            435                 440                 445
Leu Glu Leu Asn Pro Arg Leu Gln Val Glu His Pro Val Thr Glu Trp
            450                 455                 460
Ile Ala Glu Val Asn Leu Pro Ala Ala Gln Val Ala Val Gly Met Gly
465                 470                 475                 480
Ile Pro Leu Trp Gln Ile Pro Glu Ile Arg Arg Phe Tyr Gly Met Asn
            485                 490                 495
His Gly Gly Gly Tyr Asp Leu Trp Arg Lys Thr Ala Ala Leu Ala Thr
            500                 505                 510
Pro Phe Asn Phe Asp Glu Val Asp Ser Lys Trp Pro Lys Gly His Cys
            515                 520                 525
Val Ala Val Arg Ile Thr Ser Glu Asp Pro Asp Asp Gly Phe Lys Pro
            530                 535                 540
Thr Gly Gly Lys Val Lys Glu Ile Ser Phe Lys Ser Lys Pro Asn Val
545                 550                 555                 560
Trp Ala Tyr Phe Ser Val Lys Ser Gly Gly Gly Ile His Glu Phe Ala
            565                 570                 575
Asp Ser Gln Phe Gly His Val Phe Ala Tyr Gly Thr Thr Arg Ser Ala
            580                 585                 590
Ala Ile Thr Thr Met Ala Leu Ala Leu Lys Glu Val Gln Ile Arg Gly
            595                 600                 605
Glu Ile His Ser Asn Val Asp Tyr Thr Val Asp Leu Leu Asn Ala Ser
            610                 615                 620
Asp Phe Arg Glu Asn Lys Ile His Thr Gly Trp Leu Asp Thr Arg Ile
625                 630                 635                 640
Ala Met Arg Val Gln Ala Glu Arg Pro Pro Trp Tyr Ile Ser Val Val
            645                 650                 655
Gly Gly Ala Leu Tyr Lys Thr Val Thr Ala Asn Thr Ala Thr Val Ser
            660                 665                 670
Asp Tyr Val Gly Tyr Leu Thr Lys Gly Gln Ile Pro Pro Lys His Ile
            675                 680                 685
Ser Leu Val Tyr Thr Thr Val Ala Leu Asn Ile Asp Gly Lys Lys Tyr
            690                 695                 700
Thr Ile Asp Thr Val Arg Ser Gly His Gly Ser Tyr Arg Leu Arg Met
705                 710                 715                 720
Asn Gly Ser Thr Val Asp Ala Asn Val Gln Ile Leu Cys Asp Gly Gly
            725                 730                 735
Leu Leu Met Gln Leu Asp Gly Asn Ser His Val Ile Tyr Ala Glu Glu
            740                 745                 750
```

```
Glu Ala Ser Gly Thr Arg Leu Leu Ile Asp Gly Lys Thr Cys Met Leu
        755                 760                 765

Gln Asn Asp His Asp Pro Ser Lys Leu Leu Ala Glu Thr Pro Cys Lys
770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ser Gly Val Ile His Val Val Met Ser Glu Gly Gln Ala Met
                820                 825                 830

Gln Ala Gly Asp Leu Ile Ala Arg Leu Asp Leu Asp Asp Pro Ser Ala
                835                 840                 845

Val Lys Arg Ala Glu Pro Phe Glu Asp Thr Phe Pro Gln Met Gly Leu
850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
                900                 905                 910

Leu Gln Trp Glu Glu Leu Met Ser Val Leu Ala Thr Arg Leu Pro Arg
                915                 920                 925

Asn Leu Lys Ser Glu Leu Glu Gly Lys Tyr Glu Glu Tyr Lys Val Lys
                930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Lys Glu Lys Ala Thr
                965                 970                 975

Asn Glu Arg Leu Val Glu Pro Leu Met Ser Leu Leu Lys Ser Tyr Glu
                980                 985                 990

Gly Gly Arg Glu Ser His Ala His Phe Val Val Lys Ser Leu Phe Glu
                995                 1000                1005

Glu Tyr  Leu Tyr Val Glu  Leu Phe Ser Asp Gly  Ile Gln Ser
    1010                 1015                 1020

Asp Val  Ile Glu Arg Leu Arg  Leu Gln His Ser Lys  Asp Leu Gln
    1025                 1030                 1035

Lys Val  Val Asp Ile Val Leu  Ser His Gln Ser Val  Arg Asn Lys
    1040                 1045                 1050

Thr Lys  Leu Ile Leu Lys Leu  Met Glu Ser Leu Val  Tyr Pro Asn
    1055                 1060                 1065

Pro Ala  Ala Tyr Arg Asp Gln  Leu Ile Arg Phe Ser  Ser Leu Asn
    1070                 1075                 1080

His Lys  Ala Tyr Tyr Lys Leu  Ala Leu Lys Ala Ser  Glu Leu Leu
    1085                 1090                 1095

Glu Gln  Thr Lys Leu Ser Glu  Leu Arg Ala Arg Ile  Ala Arg Ser
    1100                 1105                 1110

Leu Ser  Glu Leu Glu Met Phe  Thr Glu Glu Ser Lys  Gly Leu Ser
    1115                 1120                 1125

Met His  Lys Arg Glu Ile Ala  Ile Lys Glu Ser Met  Glu Asp Leu
    1130                 1135                 1140

Val Thr  Ala Pro Leu Pro Val  Glu Asp Ala Leu Ile  Ser Leu Phe
    1145                 1150                 1155
```

```
Asp Cys Ser Asp Thr Thr Val Gln Gln Arg Val Ile Glu Thr Tyr
    1160                1165                1170

Ile Ala Arg Leu Tyr Gln Pro His Leu Val Lys Asp Ser Ile Lys
    1175                1180                1185

Met Lys Trp Ile Glu Ser Gly Val Ile Ala Leu Trp Glu Phe Pro
    1190                1195                1200

Glu Gly His Phe Asp Ala Arg Asn Gly Gly Ala Val Leu Gly Asp
    1205                1210                1215

Lys Arg Trp Gly Ala Met Val Ile Val Lys Ser Leu Glu Ser Leu
    1220                1225                1230

Ser Met Ala Ile Arg Phe Ala Leu Lys Glu Thr Ser His Tyr Thr
    1235                1240                1245

Ser Ser Glu Gly Asn Met Met His Ile Ala Leu Leu Gly Ala Asp
    1250                1255                1260

Asn Lys Met His Ile Ile Gln Glu Ser Gly Asp Asp Ala Asp Arg
    1265                1270                1275

Ile Ala Lys Leu Pro Leu Ile Leu Lys Asp Asn Val Thr Asp Leu
    1280                1285                1290

His Ala Ser Gly Val Lys Thr Ile Ser Phe Ile Val Gln Arg Asp
    1295                1300                1305

Glu Ala Arg Met Thr Met Arg Arg Thr Phe Leu Trp Ser Asp Glu
    1310                1315                1320

Lys Leu Ser Tyr Glu Glu Glu Pro Ile Leu Arg His Val Glu Pro
    1325                1330                1335

Pro Leu Ser Ala Leu Leu Glu Leu Asp Lys Leu Lys Val Lys Gly
    1340                1345                1350

Tyr Asn Glu Met Lys Tyr Thr Pro Ser Arg Asp Arg Gln Trp His
    1355                1360                1365

Ile Tyr Thr Leu Arg Asn Thr Glu Asn Pro Lys Met Leu His Arg
    1370                1375                1380

Val Phe Phe Arg Thr Leu Val Arg Gln Pro Ser Val Ser Asn Lys
    1385                1390                1395

Phe Ser Ser Gly Gln Ile Gly Asp Met Glu Val Gly Ser Ala Glu
    1400                1405                1410

Glu Pro Leu Ser Phe Thr Ser Thr Ser Ile Leu Arg Ser Leu Met
    1415                1420                1425

Thr Ala Ile Glu Glu Leu Glu Leu His Ala Ile Arg Thr Gly His
    1430                1435                1440

Ser His Met Tyr Leu His Val Leu Lys Glu Gln Lys Leu Leu Asp
    1445                1450                1455

Leu Val Pro Val Ser Gly Asn Thr Val Leu Asp Val Gly Gln Asp
    1460                1465                1470

Glu Ala Thr Ala Tyr Ser Leu Leu Lys Glu Met Ala Met Lys Ile
    1475                1480                1485

His Glu Leu Val Gly Ala Arg Met His His Leu Ser Val Cys Gln
    1490                1495                1500

Trp Glu Val Lys Leu Lys Leu Asp Cys Asp Gly Pro Ala Ser Gly
    1505                1510                1515

Thr Trp Arg Ile Val Thr Thr Asn Val Thr Ser His Thr Cys Thr
    1520                1525                1530

Val Asp Ile Tyr Arg Glu Met Glu Asp Lys Glu Ser Arg Lys Leu
    1535                1540                1545

Val Tyr His Pro Ala Thr Pro Ala Ala Gly Pro Leu His Gly Val
```

```
              1550                1555                1560

Ala Leu Asn Asn Pro Tyr Gln Pro Leu Ser Val Ile Asp Leu Lys
    1565                1570                1575

Arg Cys Ser Ala Arg Asn Asn Arg Thr Thr Tyr Cys Tyr Asp Phe
    1580                1585                1590

Pro Leu Ala Phe Glu Thr Ala Val Arg Lys Ser Trp Ser Ser Ser
    1595                1600                1605

Thr Ser Gly Ala Ser Lys Gly Val Glu Asn Ala Gln Cys Tyr Val
    1610                1615                1620

Lys Ala Thr Glu Leu Val Phe Ala Asp Lys His Gly Ser Trp Gly
    1625                1630                1635

Thr Pro Leu Val Gln Met Asp Arg Pro Ala Gly Leu Asn Asp Ile
    1640                1645                1650

Gly Met Val Ala Trp Thr Leu Lys Met Ser Thr Pro Glu Phe Pro
    1655                1660                1665

Ser Gly Arg Glu Ile Ile Val Val Ala Asn Asp Ile Thr Phe Arg
    1670                1675                1680

Ala Gly Ser Phe Gly Pro Arg Glu Asp Ala Phe Phe Glu Ala Val
    1685                1690                1695

Thr Asn Leu Ala Cys Glu Lys Lys Leu Pro Leu Ile Tyr Leu Ala
    1700                1705                1710

Ala Asn Ser Gly Ala Arg Ile Gly Ile Ala Asp Glu Val Lys Ser
    1715                1720                1725

Cys Phe Arg Val Gly Trp Ser Asp Asp Gly Ser Pro Glu Arg Gly
    1730                1735                1740

Phe Gln Tyr Ile Tyr Leu Ser Glu Glu Asp Tyr Ala Arg Ile Gly
    1745                1750                1755

Thr Ser Val Ile Ala His Lys Met Gln Leu Asp Ser Gly Glu Ile
    1760                1765                1770

Arg Trp Val Ile Asp Ser Val Val Gly Lys Glu Asp Gly Leu Gly
    1775                1780                1785

Val Glu Asn Ile His Gly Ser Ala Ala Ile Ala Ser Ala Tyr Ser
    1790                1795                1800

Arg Ala Tyr Lys Glu Thr Phe Thr Leu Thr Phe Val Thr Gly Arg
    1805                1810                1815

Thr Val Gly Ile Gly Ala Tyr Leu Ala Arg Leu Gly Ile Arg Cys
    1820                1825                1830

Ile Gln Arg Leu Asp Gln Pro Ile Ile Leu Thr Gly Tyr Ser Ala
    1835                1840                1845

Leu Asn Lys Leu Leu Gly Arg Glu Val Tyr Ser Ser His Met Gln
    1850                1855                1860

Leu Gly Gly Pro Lys Ile Met Ala Thr Asn Gly Val Val His Leu
    1865                1870                1875

Thr Val Ser Asp Asp Leu Glu Gly Val Ser Asn Ile Leu Arg Trp
    1880                1885                1890

Leu Ser Tyr Val Pro Ala Tyr Ile Gly Gly Pro Leu Pro Val Thr
    1895                1900                1905

Thr Pro Leu Asp Pro Pro Asp Arg Pro Val Ala Tyr Ile Pro Glu
    1910                1915                1920

Asn Ser Cys Asp Pro Arg Ala Ala Ile Arg Gly Val Asp Asp Ser
    1925                1930                1935

Gln Gly Lys Trp Leu Gly Gly Met Phe Asp Lys Asp Ser Phe Val
    1940                1945                1950
```

```
Glu Thr Phe Glu Gly Trp Ala Lys Thr Val Val Thr Gly Arg Ala
    1955                1960                1965

Lys Leu Gly Gly Ile Pro Val Gly Val Ile Ala Val Glu Thr Gln
    1970                1975                1980

Thr Met Met Gln Thr Ile Pro Ala Asp Pro Gly Gln Leu Asp Ser
    1985                1990                1995

Arg Glu Gln Ser Val Pro Arg Ala Gly Gln Val Trp Phe Pro Asp
    2000                2005                2010

Ser Ala Thr Lys Thr Ala Gln Ala Leu Leu Asp Phe Asn Arg Glu
    2015                2020                2025

Gly Leu Pro Leu Phe Ile Leu Ala Asn Trp Arg Gly Phe Ser Gly
    2030                2035                2040

Gly Gln Arg Asp Leu Phe Glu Gly Ile Leu Gln Ala Gly Ser Thr
    2045                2050                2055

Ile Val Glu Asn Leu Arg Thr Tyr Asn Gln Pro Ala Phe Val Tyr
    2060                2065                2070

Ile Pro Met Ala Ala Glu Leu Arg Gly Gly Ala Trp Val Val Val
    2075                2080                2085

Asp Ser Lys Ile Asn Pro Asp Arg Ile Glu Cys Tyr Ala Glu Arg
    2090                2095                2100

Thr Ala Lys Gly Asn Val Leu Glu Pro Gln Gly Leu Ile Glu Ile
    2105                2110                2115

Lys Phe Arg Ser Glu Glu Leu Gln Asp Cys Met Ser Arg Leu Asp
    2120                2125                2130

Pro Thr Leu Ile Asp Leu Lys Ala Lys Leu Glu Val Ala Asn Lys
    2135                2140                2145

Asn Gly Ser Ala Asp Thr Lys Ser Leu Gln Glu Asn Ile Glu Ala
    2150                2155                2160

Arg Thr Lys Gln Leu Met Pro Leu Tyr Thr Gln Ile Ala Ile Arg
    2165                2170                2175

Phe Ala Glu Leu His Asp Thr Ser Leu Arg Met Ala Ala Lys Gly
    2180                2185                2190

Val Ile Lys Lys Val Val Asp Trp Glu Glu Ser Arg Ser Phe Phe
    2195                2200                2205

Tyr Lys Arg Leu Arg Arg Arg Ile Ser Glu Asp Val Leu Ala Lys
    2210                2215                2220

Glu Ile Arg Ala Val Ala Gly Glu Gln Phe Ser His Gln Pro Ala
    2225                2230                2235

Ile Glu Leu Ile Lys Lys Trp Tyr Ser Ala Ser His Ala Ala Glu
    2240                2245                2250

Trp Asp Asp Asp Ala Phe Val Ala Trp Met Asp Asn Pro Glu
    2255                2260                2265

Asn Tyr Lys Asp Tyr Ile Gln Tyr Leu Lys Ala Gln Arg Val Ser
    2270                2275                2280

Gln Ser Leu Ser Ser Leu Ser Asp Ser Ser Asp Leu Gln Ala
    2285                2290                2295

Leu Pro Gln Gly Leu Ser Met Leu Leu Asp Lys Met Asp Pro Ser
    2300                2305                2310

Arg Arg Ala Gln Leu Val Glu Glu Ile Arg Lys Val Leu Gly
    2315                2320                2325

<210> SEQ ID NO 3
<211> LENGTH: 2327
```

<212> TYPE: PRT
<213> ORGANISM: Oryza sativa

<400> SEQUENCE: 3

```
Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Gly Tyr Pro Ala
305                 310                 315                 320

Met Ile Lys Ala Ser Trp Gly Gly Gly Lys Gly Ile Arg Lys Val
                325                 330                 335

His Asn Asp Asp Glu Val Arg Thr Leu Phe Lys Gln Val Gln Gly Glu
            340                 345                 350

Val Pro Gly Ser Pro Ile Phe Ile Met Arg Leu Ala Ala Gln Ser Arg
        355                 360                 365

His Leu Glu Val Gln Leu Leu Cys Asp Gln Tyr Gly Asn Val Ala Ala
    370                 375                 380

Leu His Ser Arg Asp Cys Ser Val Gln Arg Arg His Gln Lys Ile Ile
385                 390                 395                 400
```

```
Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
            500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Ile His Glu Phe Ala
                565                 570                 575

Asp Ser Gln Phe Gly His Val Phe Ala Tyr Gly Thr Thr Arg Ser Ala
            580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
    610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
            660                 665                 670

Asp Tyr Val Gly Tyr Leu Thr Lys Gly Gln Ile Pro Pro Lys His Ile
        675                 680                 685

Ser Leu Val Tyr Thr Thr Val Ala Leu Asn Ile Asp Gly Lys Lys Tyr
    690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
        755                 760                 765

Gln Asn Asp His Asp Pro Ser Lys Leu Leu Ala Glu Thr Pro Cys Lys
    770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815
```

Pro Ala Ser Gly Val Ile His Val Val Met Ser Glu Gly Gln Ala Met
            820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Asp Thr Phe Pro Gln Met Gly Leu
850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
            885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
            915                 920                 925

Asn Leu Lys Ser Glu Leu Glu Gly Lys Tyr Glu Glu Tyr Lys Val Lys
            930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Gly Lys Glu Lys Ala Thr
            965                 970                 975

Asn Glu Arg Leu Val Glu Pro Leu Met Ser Leu Leu Lys Ser Tyr Glu
            980                 985                 990

Gly Gly Arg Glu Ser His Ala His Phe Val Val Lys Ser Leu Phe Glu
            995                 1000                1005

Glu Tyr Leu Tyr Val Glu Glu Leu Phe Ser Asp Gly Ile Gln Ser
            1010                1015                1020

Asp Val Ile Glu Arg Leu Arg Leu Gln His Ser Lys Asp Leu Gln
            1025                1030                1035

Lys Val Val Asp Ile Val Leu Ser His Gln Ser Val Arg Asn Lys
            1040                1045                1050

Thr Lys Leu Ile Leu Lys Leu Met Glu Ser Leu Val Tyr Pro Asn
            1055                1060                1065

Pro Ala Ala Tyr Arg Asp Gln Leu Ile Arg Phe Ser Ser Leu Asn
            1070                1075                1080

His Lys Ala Tyr Tyr Lys Leu Ala Leu Lys Ala Ser Glu Leu Leu
            1085                1090                1095

Glu Gln Thr Lys Leu Ser Glu Leu Arg Ala Arg Ile Ala Arg Ser
            1100                1105                1110

Leu Ser Glu Leu Glu Met Phe Thr Glu Glu Ser Lys Gly Leu Ser
            1115                1120                1125

Met His Lys Arg Glu Ile Ala Ile Lys Glu Ser Met Glu Asp Leu
            1130                1135                1140

Val Thr Ala Pro Leu Pro Val Glu Asp Ala Leu Ile Ser Leu Phe
            1145                1150                1155

Asp Cys Ser Asp Thr Thr Val Gln Gln Arg Val Ile Glu Thr Tyr
            1160                1165                1170

Ile Ala Arg Leu Tyr Gln Pro His Leu Val Lys Asp Ser Ile Lys
            1175                1180                1185

Met Lys Trp Ile Glu Ser Gly Val Ile Ala Leu Trp Glu Phe Pro
            1190                1195                1200

Glu Gly His Phe Asp Ala Arg Asn Gly Gly Ala Val Leu Gly Asp
            1205                1210                1215

Lys Arg Trp Gly Ala Met Val Ile Val Lys Ser Leu Glu Ser Leu

```
            1220                1225                1230

Ser Met Ala Ile Arg Phe Ala Leu Lys Glu Thr Ser His Tyr Thr
    1235                1240                1245

Ser Ser Glu Gly Asn Met Met His Ile Ala Leu Leu Gly Ala Asp
    1250                1255                1260

Asn Lys Met His Ile Ile Gln Glu Ser Gly Asp Asp Ala Asp Arg
    1265                1270                1275

Ile Ala Lys Leu Pro Leu Ile Leu Lys Asp Asn Val Thr Asp Leu
    1280                1285                1290

His Ala Ser Gly Val Lys Thr Ile Ser Phe Ile Val Gln Arg Asp
    1295                1300                1305

Glu Ala Arg Met Thr Met Arg Arg Thr Phe Leu Trp Ser Asp Glu
    1310                1315                1320

Lys Leu Ser Tyr Glu Glu Pro Ile Leu Arg His Val Glu Pro
    1325                1330                1335

Pro Leu Ser Ala Leu Leu Glu Leu Asp Lys Leu Lys Val Lys Gly
    1340                1345                1350

Tyr Asn Glu Met Lys Tyr Thr Pro Ser Arg Asp Arg Gln Trp His
    1355                1360                1365

Ile Tyr Thr Leu Arg Asn Thr Glu Asn Pro Lys Met Leu His Arg
    1370                1375                1380

Val Phe Phe Arg Thr Leu Val Arg Gln Pro Ser Val Ser Asn Lys
    1385                1390                1395

Phe Ser Ser Gly Gln Ile Gly Asp Met Glu Val Gly Ser Ala Glu
    1400                1405                1410

Glu Pro Leu Ser Phe Thr Ser Thr Ser Ile Leu Arg Ser Leu Met
    1415                1420                1425

Thr Ala Ile Glu Glu Leu Glu Leu His Ala Ile Arg Thr Gly His
    1430                1435                1440

Ser His Met Tyr Leu His Val Leu Lys Glu Gln Lys Leu Leu Asp
    1445                1450                1455

Leu Val Pro Val Ser Gly Asn Thr Val Leu Asp Val Gly Gln Asp
    1460                1465                1470

Glu Ala Thr Ala Tyr Ser Leu Leu Lys Glu Met Ala Met Lys Ile
    1475                1480                1485

His Glu Leu Val Gly Ala Arg Met His His Leu Ser Val Cys Gln
    1490                1495                1500

Trp Glu Val Lys Leu Lys Leu Asp Cys Asp Gly Pro Ala Ser Gly
    1505                1510                1515

Thr Trp Arg Ile Val Thr Thr Asn Val Thr Ser His Thr Cys Thr
    1520                1525                1530

Val Asp Ile Tyr Arg Glu Met Glu Asp Lys Glu Ser Arg Lys Leu
    1535                1540                1545

Val Tyr His Pro Ala Thr Pro Ala Ala Gly Pro Leu His Gly Val
    1550                1555                1560

Ala Leu Asn Asn Pro Tyr Gln Pro Leu Ser Val Ile Asp Leu Lys
    1565                1570                1575

Arg Cys Ser Ala Arg Asn Asn Arg Thr Thr Tyr Cys Tyr Asp Phe
    1580                1585                1590

Pro Leu Ala Phe Glu Thr Ala Val Arg Lys Ser Trp Ser Ser Ser
    1595                1600                1605

Thr Ser Gly Ala Ser Lys Gly Val Glu Asn Ala Gln Cys Tyr Val
    1610                1615                1620
```

```
Lys Ala Thr Glu Leu Val Phe Ala Asp Lys His Gly Ser Trp Gly
1625                1630                1635

Thr Pro Leu Val Gln Met Asp Arg Pro Ala Gly Leu Asn Asp Ile
1640                1645                1650

Gly Met Val Ala Trp Thr Leu Lys Met Ser Thr Pro Glu Phe Pro
1655                1660                1665

Ser Gly Arg Glu Ile Ile Val Val Ala Asn Asp Ile Thr Phe Arg
1670                1675                1680

Ala Gly Ser Phe Gly Pro Arg Glu Asp Ala Phe Phe Glu Ala Val
1685                1690                1695

Thr Asn Leu Ala Cys Glu Lys Lys Leu Pro Leu Ile Tyr Leu Ala
1700                1705                1710

Ala Asn Ser Gly Ala Arg Ile Gly Ile Ala Asp Glu Val Lys Ser
1715                1720                1725

Cys Phe Arg Val Gly Trp Ser Asp Asp Gly Ser Pro Glu Arg Gly
1730                1735                1740

Phe Gln Tyr Ile Tyr Leu Ser Glu Glu Asp Tyr Ala Arg Ile Gly
1745                1750                1755

Thr Ser Val Ile Ala His Lys Met Gln Leu Asp Ser Gly Glu Ile
1760                1765                1770

Arg Trp Val Ile Asp Ser Val Val Gly Lys Glu Asp Gly Leu Gly
1775                1780                1785

Val Glu Asn Ile His Gly Ser Ala Ala Ile Ala Ser Ala Tyr Ser
1790                1795                1800

Arg Ala Tyr Lys Glu Thr Phe Thr Leu Thr Phe Val Thr Gly Arg
1805                1810                1815

Thr Val Gly Ile Gly Ala Tyr Leu Ala Arg Leu Gly Ile Arg Cys
1820                1825                1830

Ile Gln Arg Leu Asp Gln Pro Ile Ile Leu Thr Gly Tyr Ser Ala
1835                1840                1845

Leu Asn Lys Leu Leu Gly Arg Glu Val Tyr Ser Ser His Met Gln
1850                1855                1860

Leu Gly Gly Pro Lys Ile Met Ala Thr Asn Gly Val Val His Leu
1865                1870                1875

Thr Val Ser Asp Asp Leu Glu Gly Val Ser Asn Ile Leu Arg Trp
1880                1885                1890

Leu Ser Tyr Val Pro Ala Tyr Ile Gly Gly Pro Leu Pro Val Thr
1895                1900                1905

Thr Pro Leu Asp Pro Pro Asp Arg Pro Val Ala Tyr Ile Pro Glu
1910                1915                1920

Asn Ser Cys Asp Pro Arg Ala Ala Ile Arg Gly Val Asp Asp Ser
1925                1930                1935

Gln Gly Lys Trp Leu Gly Gly Met Phe Asp Lys Asp Ser Phe Val
1940                1945                1950

Glu Thr Phe Glu Gly Trp Ala Lys Thr Val Val Thr Gly Arg Ala
1955                1960                1965

Lys Leu Gly Gly Ile Pro Val Gly Val Ile Ala Val Glu Thr Gln
1970                1975                1980

Thr Met Met Gln Thr Ile Pro Ala Asp Pro Gly Gln Leu Asp Ser
1985                1990                1995

Arg Glu Gln Ser Val Pro Arg Ala Gly Gln Val Trp Phe Pro Asp
2000                2005                2010
```

| | | | | | | | | | | |
|---|---|---|---|---|---|---|---|---|---|---|
|Ser|Ala|Thr|Lys|Thr|Ala|Gln|Ala|Leu|Leu|Asp|Phe|Asn|Arg|Glu|
| |2015| | | |2020| | | |2025| |

Ser Ala Thr Lys Thr Ala Gln Ala Leu Leu Asp Phe Asn Arg Glu
    2015                2020                2025

Gly Leu Pro Leu Phe Ile Leu Ala Asn Trp Arg Gly Phe Ser Gly
    2030                2035                2040

Gly Gln Arg Asp Leu Phe Glu Gly Ile Leu Gln Ala Gly Ser Thr
    2045                2050                2055

Ile Val Glu Asn Leu Arg Thr Tyr Asn Gln Pro Ala Phe Val Tyr
    2060                2065                2070

Ile Pro Met Ala Ala Glu Leu Arg Gly Gly Ala Trp Val Val Val
    2075                2080                2085

Asp Ser Lys Ile Asn Pro Asp Arg Ile Glu Cys Tyr Ala Glu Arg
    2090                2095                2100

Thr Ala Lys Gly Asn Val Leu Glu Pro Gln Gly Leu Ile Glu Ile
    2105                2110                2115

Lys Phe Arg Ser Glu Glu Leu Gln Asp Cys Met Ser Arg Leu Asp
    2120                2125                2130

Pro Thr Leu Ile Asp Leu Lys Ala Lys Leu Glu Val Ala Asn Lys
    2135                2140                2145

Asn Gly Ser Ala Asp Thr Lys Ser Leu Gln Glu Asn Ile Glu Ala
    2150                2155                2160

Arg Thr Lys Gln Leu Met Pro Leu Tyr Thr Gln Ile Ala Ile Arg
    2165                2170                2175

Phe Ala Glu Leu His Asp Thr Ser Leu Arg Met Ala Ala Lys Gly
    2180                2185                2190

Val Ile Lys Lys Val Val Asp Trp Glu Glu Ser Arg Ser Phe Phe
    2195                2200                2205

Tyr Lys Arg Leu Arg Arg Arg Ile Ser Glu Asp Val Leu Ala Lys
    2210                2215                2220

Glu Ile Arg Ala Val Ala Gly Glu Gln Phe Ser His Gln Pro Ala
    2225                2230                2235

Ile Glu Leu Ile Lys Lys Trp Tyr Ser Ala Ser His Ala Ala Glu
    2240                2245                2250

Trp Asp Asp Asp Ala Phe Val Ala Trp Met Asp Asn Pro Glu
    2255                2260                2265

Asn Tyr Lys Asp Tyr Ile Gln Tyr Leu Lys Ala Gln Arg Val Ser
    2270                2275                2280

Gln Ser Leu Ser Ser Leu Ser Asp Ser Ser Asp Leu Gln Ala
    2285                2290                2295

Leu Pro Gln Gly Leu Ser Met Leu Leu Asp Lys Met Asp Pro Ser
    2300                2305                2310

Arg Arg Ala Gln Leu Val Glu Glu Ile Arg Lys Val Leu Gly
    2315                2320                2325

<210> SEQ ID NO 4
<211> LENGTH: 6963
<212> TYPE: DNA
<213> ORGANISM: Alopecurus myosuroides

<400> SEQUENCE: 4
atgggatcca cacatctgcc cattgtcggg tttaatgcat ccacaacacc atcgctatcc    60
actcttcgcc agataaactc agctgctgct gcattccaat cttcgtcccc ttcaaggtca   120
tccaagaaga aaagccgacg tgttaagtca ataagggatg atggcgatgg aagcgtgcca   180
gaccctgcag gccatggcca gtctattcgc caaggtctcg ctggcatcat cgacctccca   240

```
aaggagggcg catcagctcc agatgtggac atttcacatg ggtctgaaga ccacaaggcc    300
tcctaccaaa tgaatgggat actgaatgaa tcacataacg ggaggcacgc ctctctgtct    360
aaagtttatg aattttgcac ggaattgggt ggaaaaacac caattcacag tgtattagtc    420
gccaacaatg gaatggcagc agctaagttc atgcggagtg tccggacatg ggctaatgat    480
acatttgggt cagagaaggc gattcagttg atagctatgg caactccgga agacatgaga    540
ataaatgcag agcacattag aattgctgat cagtttgttg aagtacctgg tggaacaaac    600
aataacaact atgcaaatgt ccaactcata gtggagatag cagagagaac tggtgtctcc    660
gccgtttggc ctggttgggg ccatgcatct gagaatcctg aacttccaga tgcactaact    720
gcaaaaggaa ttgttttttct tgggccacca gcatcatcaa tgaacgcact aggcgacaag    780
gttggttcag ctctcattgc tcaagcagca ggggttccca ctcttgcttg gagtggatca    840
catgtggaaa ttccattaga actttgtttg gactcgatac ctgaggagat gtataggaaa    900
gcctgtgtta caaccgctga tgaagcagtt gcaagttgtc agatgattgg ttaccctgcc    960
atgatcaagg catcctgggg tggtggtggt aaagggatta gaaaggttaa taatgatgac   1020
gaggtgaaag cactgtttaa gcaagtacag ggtgaagttc ctggctcccc gatatttatc   1080
atgagacttg catctcagag tcgtcatctt gaagtccagc tgctttgtga tgaatatggc   1140
aatgtagcag cacttcacag tcgtgattgc agtgtgcaac gacgacacca aaagattatc   1200
gaggaaggac cagttactgt tgctcctcgt gaaacagtga agagctaga gcaagcagca   1260
aggaggcttg ctaaggccgt gggttacgtc ggtgctgcta ctgttgaata tctctacagc   1320
atggagactg gtgaatacta ttttctggag cttaatccac ggttgcaggt tgagcaccca   1380
gtcaccgagt cgatagctga agtaaatttg cctgcagccc aagttgcagt tgggatgggt   1440
ataccccttt ggcagattcc agagatcaga cgtttctacg gaatggacaa tggaggaggc   1500
tatgatattt ggaggaaaac agcagctctc gctactccat tcaactttga tgaagtagat   1560
tctcaatggc cgaagggtca ttgtgtggca gttaggataa ccagtgagaa tccagatgat   1620
ggattcaagc ctactggtgg aaaagtaaag gagataagtt ttaaaagtaa gccaaatgtc   1680
tgggatatatt tctcagttaa gtctggtgga ggcattcatg aatttgcgga ttctcagttt   1740
ggacacgttt ttgcctatgg agagactaga tcagcagcaa taaccagcat gtctcttgca   1800
ctaaaagaga ttcaaattcg tggagaaatt catacaaacg ttgattacac ggttgatctc   1860
ttgaatgccc cagacttcag agaaaacacg atccataccg gttggctgga taccagaata   1920
gctatgcgtg ttcaagctga gaggcctccc tggtatattt cagtggttgg aggagctcta   1980
tataaaacaa taaccaccaa tgcggagacc gtttctgaat atgttagcta tctcatcaag   2040
ggtcagattc caccaaagca catatcccctt gtccattcaa ctatttctttt gaatatagag   2100
gaaagcaaat atacaattga gattgtgagg agtggacagg gtagctacag attgagactg   2160
aatggatcac ttattgaagc caatgtacaa acattatgtg atggaggcct tttaatgcag   2220
ctggatggaa atagccatgt tatttatgct gaagaagaag cgggtggtac acggcttctt   2280
attgatggaa aaacatgctt gctacagaat gaccatgatc cgtcaaggtt attagctgag   2340
acaccctgca aacttcttcg tttcttgatt gccgatggtg ctcatgttga tgctgatgta   2400
ccatacgcgg aagttgaggt tatgaagatg tgcatgcccc tcttgtcgcc tgctgctggt   2460
gtcattaatg ttttgttgtc tgagggccag gcgatgcagg ctggtgatct tatagcgaga   2520
cttgatctcg atgacccttc tgctgtgaag agagccgagc catttgaagg atcttttcca   2580
gaaatgagcc ttcctattgc tgcttctggc caagttcaca aaagatgtgc tgcaagtttg   2640
```

```
aacgctgctc gaatggtcct tgcaggatat gaccatgcgg ccaacaaagt tgtgcaagat    2700
ttggtatggt gccttgatac acctgctctt cctttcctac aatgggaaga gcttatgtct    2760
gttttagcaa ctagacttcc aagacgtctt aagagcgagt tggagggcaa atacaatgaa    2820
tacaagttaa atgttgacca tgtgaagatc aaggatttcc ctaccgagat gcttagagag    2880
acaatcgagg aaaatcttgc atgtgtttcc gagaaggaaa tggtgacaat tgagaggctt    2940
gttgaccctc tgatgagcct gctgaagtca tacgagggtg ggagagaaag ccatgcccac    3000
tttattgtca agtcccttt tgaggagtat ctctcggttg aggaactatt cagtgatggc    3060
attcagtctg acgtgattga acgcctgcgc ctacaatata gtaaagacct ccagaaggtt    3120
gtagacattg ttttgtctca ccagggtgtg agaaacaaaa caaagctgat actcgcgctc    3180
atggagaaac tggtctatcc aaaccctgct gcctacagag atcagttgat tcgcttttct    3240
tccctcaacc ataaaagata ttataagttg gctcttaaag ctagtgaact tcttgaacaa    3300
accaagctca gcgaactccg cacaagcatt gcaggaacc tttcagcgct ggatatgttc    3360
accgaggaaa aggcagattt ctccttgcaa cagaaaat tggccattaa tgagagcatg    3420
ggagatttag tcactgcccc actgccagtt gaagatgcac ttgtttcttt gtttgattgt    3480
actgatcaaa ctcttcagca gagagtgatt cagacataca tatctcgatt ataccagcct    3540
caacttgtga aggatagcat ccagctgaaa tatcaggatt ctggtgttat tgctttatgg    3600
gaattcactg aaggaaatca tgagaagaga ttgggtgcta tggttatcct gaagtcacta    3660
gaatctgtgt caacagccat tggagctgct ctaaaggatg catcacatta tgcaagctct    3720
gcgggcaaca cggtgcatat tgctttgttg gatgctgata cccaactgaa tacaactgaa    3780
gatagtggtg ataatgacca agctcaagac aagatggata aactttctt tgtactgaaa    3840 caagatgttg tcatggctga tctacgtgct gctgatgtca aggttgttag ttgcattgtt    3900
caaagagatg gagcaatcat gcctatgcgc cgtaccttcc tcttgtcaga ggaaaaactt    3960
tgttacgagg aagagccgat tcttcggcat gtggagcctc cactttctgc acttcttgag    4020
ttggataaat tgaaagtgaa aggatacaat gagatgaagt atacaccgtc acgtgatcgt    4080
cagtggcata tatacacact tagaaatact gaaaatccaa aaatgctgca cagggtattt    4140
ttccgaacac ttgtcagaca acccagtgca ggcaacaggt ttacatcaga ccatatcact    4200
gatgttgaag taggacacgc agaggaacct ctttcattta cttcaagcag catattaaaa    4260
tcgttgaaga ttgctaaaga agaattggag cttcacgcga tcaggactgg ccattctcat    4320
atgtacttgt gcatattgaa agagcaaaag cttcttgacc ttgttcctgt ttcagggaac    4380
actgttgtgg atgttggtca agatgaagct actgcatgct ctcttttgaa agaaatggct    4440
ttaaagatac atgaacttgt tggtgcaaga atgcatcatc tttctgtatg ccagtgggaa    4500
gtgaaactta agttggtgag cgatgggcct gccagtggta gctggagagt tgtaacaacc    4560
aatgttactg tcacacctg cactgtggat atctaccggg aggtcgaaga tacagaatca    4620
cagaaactag tataccactc caccgcattg tcatctggtc ctttgcatgg tgttgcactg    4680
aatacttcgt atcagccttt gagtgttatt gatttaaaac gttgctctgc caggaacaac    4740
aaaactacat actgctatga ttttccattg acatttgaag ctgcagtgca gaagtcgtgg    4800
tctaacattt ccagtgaaaa caaccaatgt tatgttaaag cgacagagct tgtgtttgct    4860
gaaaagaatg ggtcgtgggg cactcctata attcctatgc agcgtgctgc tgggctgaat    4920
gacattggta tggtagcctg gatcttggac atgtccactc ctgaatttcc cagcggcaga    4980
```

-continued

| | |
|---|---|
| cagatcattg ttatcgcaaa tgatattaca tttagagctg atcatttggg cccaagggaa | 5040 |
| gatgcattt tcgaagctgt aaccaacctg gcttgtgaga agaagcttcc acttatctac | 5100 |
| ttggctgcaa actctggtgc tcggattggc attgctgatg aagtaaaatc ttgcttccgt | 5160 |
| gttggatgga ctgatgatag cagccctgaa cgtggattta ggtacattta tatgactgac | 5220 |
| gaagaccatg atcgtattgg ctcttcagtt atagcacaca agatgcagct agatagtggc | 5280 |
| gagatcaggt gggttattga ttctgttgtg ggaaaagagg atggactagg tgtgagaac | 5340 |
| atacatggaa gtgctgctat tgccagtgcc tattctaggg cgtacgagga gacatttaca | 5400 |
| cttacattcg ttactggacg aactgttgga atcggagcct atcttgctcg acttggcata | 5460 |
| cggtgcatac agcgtattga ccagcccatt attttgaccg ggttttctgc cctgaacaag | 5520 |
| cttcttgggc gggaggtgta cagctcccac atgcagttgg gtggtcccaa aatcatggcg | 5580 |
| acgaatggtg ttgtccatct gactgttcca gatgaccttg aaggtgtttc taatatattg | 5640 |
| aggtggctca gctatgttcc tgcaaacatt ggtggacctc ttcctattac aaaatctttg | 5700 |
| gacccaatag acagacccgt tgcatacatc cctgagaata catgtgatcc tcgtgcagcc | 5760 |
| atcagtggca ttgatgacag ccaagggaaa tggttgggtg gcatgtttga caaagacagt | 5820 |
| tttgtggaga catttgaagg atgggcgaag acagtagtta ctggcagagc aaaacttgga | 5880 |
| gggattcctg ttggtgttat agctgtggag acacagacca tgatgcagct cgtccccgct | 5940 |
| gatccaggcc agcctgattc ccacgagcgg tctgttcctc gtgctgggca agtttggttt | 6000 |
| ccagattctg ctaccaagac agcgcaggcg atgttggact tcaaccgtga aggattacct | 6060 |
| ctgttcatac ttgctaactg gagaggcttc tctggagggc aaagagatct ttttgaagga | 6120 |
| attctgcagg ctgggtcaac aattgttgag aaccttagga catacaatca gcctgccttt | 6180 |
| gtatatatcc ccaaggctgc agagctacgt ggaggagcct gggtcgtgat tgatagcaag | 6240 |
| ataaacccag atcgcatcga gtgctatgct gagaggactg caaagggtaa tgttctcgaa | 6300 |
| cctcaagggt tgattgagat caagttcagg tcagaggaac tcaaagaatg catggggtagg | 6360 |
| cttgatccag aattgataga tctgaaagca agactccagg gagcaaatgg aagcctatct | 6420 |
| gatggagaat cccttcagaa gagcatagaa gctcggaaga aacagttgct gcctctgtac | 6480 |
| acccaaatcg cggtacgttt tgcggaattg cacgacactt ccctttagaat ggctgctaaa | 6540 |
| ggtgtgatca ggaaagttgt agactgggaa gactctcggt cttttcttcta caagagatta | 6600 |
| cggaggaggc tatccgagga cgttctggca aaggagatta gaggtgtaat tggtgagaag | 6660 |
| tttcctcaca aatcagcgat cgagctgatc aagaaatggt acttggcttc tgaggcagct | 6720 |
| gcagcaggaa gcaccgactg ggatgacgac gatgcttttg tcgcctggag ggagaaccct | 6780 |
| gaaaactata aggagtatat caagagcttt agggctcaaa gggtatctcg gttgctctca | 6840 |
| gatgttgcag gctccagttc ggatttacaa gccttgccgc agggtctttc catgctacta | 6900 |
| gataagatgg atccctctaa gagagcacag tttatcgagg aggtcatgaa ggtcctgaaa | 6960 |
| tga | 6963 |

<210> SEQ ID NO 5
<211> LENGTH: 11927
<212> TYPE: DNA
<213> ORGANISM: Oryza sativa

<400> SEQUENCE: 5

| | |
|---|---|
| atgacatcca cacatgtggc gacattggga gttggtgccc aggcacctcc tcgtcaccag | 60 |
| aaaaagtcag ctggcactgc atttgtatca tctgggtcat caagacccctc ataccgaaag | 120 |

```
aatggtcagc gtactcggtc acttagggaa gaaagcaatg gaggagtgtc tgattccaaa    180
aagcttaacc actctattcg ccaaggtgac cactagctac tttacatatg ctataatttg    240
tgccaaacat aaacatgcaa tggctgctat tatttaaacg ttaatgttga aatagctgct    300
ataggataca gcaaaaatat ataattgact gggcaagatg caacaattgt ttttcactaa    360
agttagttat cttttgctgt aaaagacaac tgttttttac ataaaatggt attaataacc    420
ttgtaatatt caatgcaaca tgttctcaag taaaaaaaaa cattgcctgg ttgtataagc    480
aaatgtgtcg ttgtagacat cttattaaac cttttgtga tatctattac cgtagggaac    540
aggggagctg tttaaatctg ttatcataga gtaaatgag aaaagtggat tgtgcgactt    600
tggcatgtat acctgctcaa tttcaaatat atgtctatgt gcaggtcttg ctggcatcat    660
tgacctccca aatgacgcag cttcagaagt tgatatttca cagtaaggac tttatatttt    720
ataataatta ttatataatt ttctgacatg ttttgagaac ctcaaaacat gtgattgcac    780
cttccttttt tatgtctggt tcagaaactg ataagttttg acagtgttta ggatggatct    840
ttgatgcgca cagtgctttc taatgttttc attttgaaa gtaatgtttt aggaagaaat    900
atctgattaa atttatactt tatctttaca aaagtcaaat gcgttctgta tcaattgcgg    960
tttgtaatat ggcaagaaca tgctttcaga atttgttcat acaatgcttt ctttctatta   1020
ttatgtagaa caaataccta atactttgtt cacctttttat agtggacacc tctcacagct   1080
ttttcagtaa gtgatgcaat tttgtacatt tgtaagatgt gttccagaaa ccttttctcc   1140
tgcaattcta atgtacccac tcaaactggt atcaccaaag atctccatct gattgaaaaa   1200
aagctgcgtg aagtatgctt atttatgcta accatacatg atttatactg ttttatagta   1260
caatgcttat ttatgctaac catacataat tttattctgt tttctagtac attatttgtg   1320
cccctgacca taaatgatcc tttcttttac agtggttccg aagatcccag ggggcctacg   1380
gtcccaggtt cctaccaaat gaatgggatt atcaatgaaa cacataatgg gaggcatgct   1440
tcagtctcca aggttgttga gttttgtacg gcacttggtg gcaaaacacc aattcacagt   1500
gtattagtgg ccaacaatgg aatggcagca gctaagttca tgcggagtgt ccgaacatgg   1560
gctaatgata cttttggatc agagaaggca attcagctga tagctatggc aactccggag   1620
gatctgagga taaatgcaga gcacatcaga attgccgatc aatttgtaga ggtacctggt   1680
ggaacaaaca acaacaacta tgcaaatgtc caactcatag tggaggttag ttcagctcat   1740
ccctcaacac aacattttcg tttctattta agttagggaa aaatctctac gaccctccaa   1800
tttctgaaca tccaattttc accatcaact gcaatcacag atagcagaga aacaggtgt   1860 ttctgctgtt tggcctggtt ggggtcatgc atctgagaat cctgaacttc cagatgcgct   1920
gactgcaaaa ggaattgttt tcttgggcc accagcatca tcaatgcatg cattaggaga   1980
caaggttggc tcagctctca ttgctcaagc agctggagtt ccaacacttg cttggagtgg   2040
atcacatgtg agccttgtct tctcttttt agcttatcat cttatctttt cggtgatgca   2100
ttatcccaat gacactaaac cataggtgga agttcctctg gagtgttgct tggactcaat   2160
acctgatgag atgtatagaa aagcttgtgt tactaccaca gaggaagcag ttgcaagttg   2220
tcaggtggtt ggttatcctg ccatgattaa ggcatcttgg ggtggtggtg gtaaaggaat   2280
aaggaaggtt tgttcttctt gtagttatca agagattgtt tggattgcaa gtgtttagtg   2340
cccatagtta actctggtct ttctaacatg agtaactcaa cttctcttgca ggttcataat   2400 gatgatgagg ttaggacatt atttaagcaa gttcaaggcg aagtacctgg ttccccaata   2460
```

```
tttatcatga ggctagctgc tcaggtgggg cctttatgg aagttacacc tttcccctta    2520
atgttgagtt attccggagt tattatggtt atgttctgta tgtttgatct gtaaattatt    2580
gaaattcacc tccattggtt ctccagatta gcagacctac aattctacat atggtttata    2640
ctttataaat actaggattt agggatcttc atatagttta tacatggtat ttagatttca    2700
tttgtaaccc tattgaagac atcctgattg ttgtcttatg tagagtcgac atcttgaagt    2760
tcagttgctt tgtgatcaat atggcaacgt agcagcactt cacagtcgag attgcagtgt    2820
acaacggcga caccaaaagg tctgctgtct cagttaaatc accctctga atgatctact     2880
tcttgcctgc tgcgttggtc agaggaataa tggttgtatt ctactgaaca gataatcgag    2940
gaaggaccag ttactgttgc tcctcgtgag actgtgaaag agcttgagca ggcagcacgg    3000
aggcttgcta agctgtggg ttatgttggt gctgctactg ttgaatacct ttacagcatg     3060
gaaactggtg aatattattt tctggaactt aatccacggc tacaggtcgg ctcctttgac    3120
attcttcagg aattaatttc tgttgaccac atgatttaca ttgtcaaatg gtctcacagg    3180
ttgagcatcc tgtcactgag tggatagctg aagtaaattt gcctgcggct caagttgctg    3240
ttggaatggg tatacccctt tggcagattc caggtaatgc ttcttcattt agttcctgct    3300
ctttgttaat tgaatgagct cttatacaga ccatgagaca cattctactg ttaattcata    3360
gtatccctg acttgttagt gttagagata cagagatgta tcacaaattc attgtatctc     3420
ctcaaggact gtaaaaatcc tataattaaa tttctgaaaa tttgttcttt taagcagaaa    3480
aaaaatctct aaattatctc cctgtataca gagatcaggc gcttctacgg aatgaaccat    3540
ggaggaggct atgacctttg gaggaaaaca gcagctctag cgactccatt taactttgat    3600
gaagtagatt ctaaatggcc aaaaggccac tgcgtagctg ttagaataac tagcgaggat    3660
ccagatgatg ggtttaagcc tactggtgga aagtaaagg tgcggtttcc tgatgttagg     3720
tgtatgaatt gaacacattg ctatattgca gctagtgaaa tgactggatc atggttctct    3780
tatttttcagg agataagttt caagagtaaa ccaaatgttt gggcctattt ctcagtaaag   3840
gtagtcctca atattgttgc actgccacat tatttgagtt gtcctaacaa ttgtgctgca    3900
attgttagtt ttcaactatt tgttgttctg tttggttgac tggtaccctc tctttgcagt    3960
ctggtggagg catccatgaa ttcgctgatt ctcagttcgg tatgtaaagt taaaagagta    4020
atattgtctt tgctatttat gtttgtcctc acttttaaaa gatattgcct tccattacag    4080
gacatgtttt tgcgtatgga actactagat cggcagcaat aactaccatg gctcttgcac    4140
taaaagaggt tcaaattcgt ggagaaattc attcaaacgt agactacaca gttgacctat    4200
taaatgtaag gactaaatat ctgcttattg aaccttgctt tttggttccc taatgccatt    4260
ttagtctggc tactgaagaa cttatccatc atgccatttc tgttatctta aattcaggcc    4320
tcagatttta gagaaaataa gattcatact ggttggctgg ataccaggat agccatgcgt    4380
gttcaagctg agaggcctcc atggtatatt tcagtcgttg gagggctttt atatgtaaga    4440
caaactatgc cactcattag catttatgtg aagcaaatgc ggaaaacatg atcaatatgt    4500
cgtcttattt aaatttattt attttttgtgc tgcagaaaac agtaactgcc aacacggcca    4560
ctgtttctga ttatgttggt tatcttacca agggccagat tccaccaaag gtactattct    4620
gttttttcag gatatgaatg ctgtttgaat gtgaaaacca ttgaccataa atccttgttt    4680
gcagcatata tcccttgtct atacgactgt tgctttgaat atagatggga aaaaatatac    4740
agtaagtgtg acattcttaa tggggaaact taatttgttg taaataatca atatcatatt    4800
gactcgtgta tgctgcatca tagatcgata ctgtgaggag tggacatggt agctacagat    4860
```

-continued

```
tgcgaatgaa tggatcaacg gttgacgcaa atgtacaaat attatgtgat ggtgggcttt      4920
taatgcaggt aatatcttct tcctagttaa agaagatata tcttgttcaa agaattctga      4980
ttattgatct tttaatgttt tcagctggat ggaaacagcc atgtaattta tgctgaagaa      5040
gaggccagtg gtacacgact tcttattgat ggaaagacat gcatgttaca gtaatgata       5100 gccttgttct ttttagttct agtcacggtg tttgcttgct atttgttgta tctatttaat      5160
gcattcacta attactatat tagtttgcat catcaagtta aaatggaact tctttcttgc      5220
agaatgacca tgacccatca aagttattag ctgagacacc atgcaaactt cttcgtttct      5280
tggttgctga tggtgctcat gttgatgctg atgtaccata tgcggaagtt gaggttatga      5340
agatgtgcat gcccctctta tcacccgctt ctggtgtcat acatgttgta atgtctgagg      5400
gccaagcaat gcaggtacat tcctacattc cattcattgt gctgtgctga catgaacatt      5460
tcaagtaaat acctgtaact tgtttattat tctaggctgg tgatcttata gctaggctgg      5520
atcttgatga cccttctgct gttaagagag ctgagccgtt cgaagatact tttccacaaa      5580
tgggtctccc tattgctgct tctggccaag ttcacaaatt atgtgctgca agtctgaatg      5640
cttgtcgaat gatccttgcg gggtatgagc atgatattga caaggtaaac atcatgtcct      5700 cttgttttt cttttgttta tcatgcattc ttatgttcat catgtcctct ggcaaatcta       5760
gattccgctg tcgtttcaca cagatttttc tcattctcat aatggtgcca acataaata       5820 tgctgctata ttcatcaatg ttttcactcg atttctaatt ttgcttttga gttttaaact      5880
ttagtacaat ccatatctaa tctcctttgg caacagtgaa tccattatat atatttttat      5940
taaactgctt tctttttcag gttgtgccag agttggtata ctgcctagac actccggagc      6000 ttccttttcct gcagtgggag gagcttatgt ctgttttagc aactagactt ccaagaaatc     6060
ttaaaagtga ggtatattat ggttgacaag atagctagtc tcatgctcta aggacttgta     6120
catttcgcca cataggttaa ttttccatat caagttctaa tgtacgatat aaaagtagta     6180
ctggcctaaa acagtattgg tggttgacta tctttgttgt gtaagatcaa gtatttcttt    6240
ttcatgctta gtttgtcaat acttcacatt tatcactgac ttgtcgagct aaatgagatt    6300
ttatttgatt tctgtgctcc attatttttg tatatatata tatatattta actatgacta    6360
tatgttatgc ctcaaacgtt tcaaactctt tcagttggag ggcaaatatg aggaatacaa     6420
agtaaaattt gactctggga taatcaatga tttccctgcc aatatgctac gagtgataat     6480
tgaggtcagt tattcaattt gttgtgataa tcactgcctt aactgttcgt tcttttaaca    6540
agcggtttta taggaaaatc ttgcatgtgg ttctgagaag gagaaggcta caaatgagag    6600
gcttgttgag cctcttatga gcctactgaa gtcatatgag ggtgggagag aaagtcatgc    6660
tcactttgtt gtcaagtccc ttttggagga gtatctctat gttgaagaat tgttcagtga     6720
tggaattcag gttaacttac ctattcgcat taaacaaatc atcagttgtt ttatgataaa    6780
gtcaaaatgt ttatatttcc cattcttctg tggatcaaat atatcacgga catgatatag    6840
tttccttagg ctatataatg gttcttcatc aaataatatt gcaggaaaca gtatagcaaa    6900
ctatttgtat atactcgaga tggaaattgt tagaaacatc attgactaaa tctgtccttt    6960
gttacgctgt ttttgtagtc tgatgtgatt gagcgtctgc gccttcaaca tagtaaagac    7020
ctacagaagg tcgtagacat tgtgttgtcc caccaggtaa atttcttcat ggtctgatga    7080
cttcactgcg aatggttact gaactgtctt cttgttctga caatgtgact tttctttgta    7140
gagtgttaga aataaaacta agctgatact aaaactcatg gagagtctgg tctatccaaa    7200
```

```
tcctgctgcc tacagggatc aattgattcg cttttcttcc cttaatcaca aagcgtatta    7260
caaggtgacc aggataaaca taaataaacg tgaatttttc aatgaccttt tcttctgaca    7320
tctgaatctg atgaatttct tgcatattaa tacagttggc acttaaagct agtgaacttc    7380
ttgaacaaac aaaacttagt gagctccgtg caagaatagc aaggagcctt tcagagctgg    7440
agatgtttac tgaggaaagc aagggtctct ccatgcataa gcgagaaatt gccattaagg    7500
agagcatgga agatttagtc actgctccac tgccagttga agatgcgctc atttctttat    7560
ttgattgtag tgatacaact gttcaacaga gagtgattga gacttatata gctcgattat    7620
accaggtatg agaagaaaga cctttttgaaa ttatttatat taacatatcc tagtaaaaca    7680
gcatgctcat catttcttaa aaaaagttta cagcacctga tgtttggtta ctgaccgcat    7740
cattaaaata aagttacttg ttgtggagag atgtattttg gaacttgtgg cacatgcagt    7800
aacatgctac tgctcgatat gtttgctaac ttgacaacaa tattttttcag cctcatcttg    7860 taaaggacag tatcaaaatg aaatggatag aatcgggtgt tattgcttta tgggaatttc    7920
ctgaagggca ttttgatgca agaaatggag gagcggttct tggtgacaaa agatggggtg    7980
ccatggtcat tgtcaagtct cttgaatcac tttcaatggc cattagattt gcactaaagg    8040
agacatcaca ctacactagc tctgagggca atatgatgca tattgctttg ttgggtgctg    8100
ataataagat gcatataatt caagaaaggt atgttcatat gctatgttgg tgctgaaata    8160
gttatatatg tagttagctg gtggagttct ggtaattaac ctatcccatt gttcagtggt    8220
gatgatgctg acagaatagc caaacttccc ttgatactaa aggataatgt aaccgatctg    8280
catgcctctg gtgtgaaaac aataagtttc attgttcaaa gagatgaagc acggatgaca    8340
atgcgtcgta ccttcctttg gtctgatgaa aagctttctt atgaggaaga gccaattctc    8400
cggcatgtgg aacctcctct ttctgcactt cttgagttgg tacgtgatat catcaaaatg    8460
ataatgtttt ggtatggcat tgattatctt ctatgctctt tgtatttatt cagcctattg    8520
tggatacagg acaagttgaa agtgaaagga tacaatgaaa tgaagtatac cccatcacgg    8580
gatcgtcaat ggcatatcta cacacttaga aatactgaaa accccaaaat gttgcaccgg    8640 gtattttttcc gaacccttgt caggcaaccc agtgtatcca acaagttttc ttcgggccag    8700
attggtgaca tggaagttgg gagtgctgaa gaacctctgt catttacatc aaccagcata    8760
ttaagatctt tgatgactgc tatagaggaa ttggagcttc acgcaattag aactggccat    8820
tcacacatgt atttgcatgt attgaaagaa caaaagcttc ttgatcttgt tccagtttca    8880
gggtaagtgc gcatatttct tttttgggaac atatgcttgc ttatgaggtt ggtcttctca    8940
atgatcttct tatcttactc aggaatacag ttttggatgt tggtcaagat gaagctactg    9000
catattcact tttaaaagaa atggctatga agatacatga acttgttggt gcaagaatgc    9060
accatctttc tgtatgccaa tgggaagtga aacttaagtt ggactgcgat ggtcctgcca    9120
gtggtacctg gaggattgta acaaccaatg ttactagtca cacttgcact gtggatgtaa    9180
gtttaatcct ctagcatttt gttttctttg gaaaagcatg tgattttaag ccggctggtc    9240 ctcatacccca gacctagtga tctttatata gtgtagacat ttttctaact gcttttaatt    9300
gttttagatc taccgtgaga tggaagataa agaatcacgg aagttagtat accatcccgc    9360
cactccggcg gctggtcctc tgcatggtgt ggcactgaat aatccatatc agcctttgag    9420
tgtcattgat ctcaaacgct gttctgctag gaataataga actacatact gctatgattt    9480
tccactggtg agttgactgc tcccttatat tcaatgcatt accatagcaa attcatattc    9540
gttcatgttg tcaaaataag ccgatgaaaa ttcaaaactg taggcatttg aaactgcagt    9600
```

```
gaggaagtca tggtcctcta gtacctctgg tgcttctaaa ggtgttgaaa atgcccaatg    9660
ttatgttaaa gctacagagt tggtatttgc ggacaaacat gggtcatggg gcactccttt    9720
agttcaaatg gaccggcctg ctgggctcaa tgacattggt atggtagctt ggaccttgaa    9780
gatgtccact cctgaatttc ctagtggtag ggagattatt gttgttgcaa atgatattac    9840
gttcagagct ggatcatttg gcccaaggga agatgcattt tttgaagctg ttaccaacct    9900
agcctgtgag aagaaacttc ctcttattta tttggcagca aattctggtg ctcgaattgg    9960
catagcagat gaagtgaaat cttgcttccg tgttgggtgg tctgatgatg cagccctga   10020 acgtgggttt cagtacattt atctaagcga agaagactat gctcgtattg cacttctgt   10080 catagcacat aagatgcagc tagacagtgg tgaaattagg tgggttattg attctgttgt   10140
gggcaaggaa gatggacttg gtgtggagaa atacatggaa agtgctgcta ttgccagtgc   10200
ttattctagg gcatataagg agacatttac acttacattt gtgactggaa gaactgttgg   10260
aataggagct tatcttgctc gacttggcat ccggtgcata cagcgtcttg accagcctat   10320
tattcttaca ggctattctg cactgaacaa gcttcttggg cgggaagtgt acagctccca   10380
catgcagttg ggtggtccca aaatcatggc aactaatggt gttgtccatc ttactgtttc   10440
agatgacctt gaaggcgttt ctaatatatt gaggtggctc agttatgttc ctgcctacat   10500
tggtggacca cttccagtaa caacaccgtt ggacccaccg gacagacctg ttgcatacat   10560
tcctgagaac tcgtgtgatc ctcgagcggc tatccgtggt gttgatgaca gccaagggaa   10620
atggttaggt ggtatgtttg ataaagacag ctttgtggaa acatttgaag gttgggctaa   10680
gacagtggtt actggcagag caaagcttgg tggaattcca gtgggtgtga tagctgtgga   10740
gactcagacc atgatgcaaa ctatccctgc tgaccctggt cagcttgatt cccgtgagca   10800
atctgttcct cgtgctggac aagtgtggtt tccagattct gcaaccaaga ctgcgcaggc   10860
attgctggac ttcaaccgtg aaggattacc tctgttcatc ctcgctaact ggagaggctt   10920
ctctggtgga caaagagatc tttttgaagg aattcttcag gctggctcga ctattgttga   10980
gaaccttagg acatacaatc agcctgcctt tgtctacatt cccatggctg cagagctacg   11040
aggaggggct tgggttgtgg ttgatagcaa gataaaccca gaccgcattg agtgctatgc   11100
tgagaggact gcaaaaggca atgttctgga accgcaaggg ttaattgaga tcaagttcag   11160
gtcagaggaa ctccaggatt gcatgagtcg gcttgaccca acattaattg atctgaaagc   11220
aaaactcgaa gtagcaaata aaaatggaag tgctgacaca aaatcgcttc aagaaaatat   11280
agaagctcga acaaaacagt tgatgcctct atatactcag attgcgatac ggtttgctga   11340
attgcatgat acatccctca gaatggctgc gaaaggtgtg attaagaaag ttgtggactg   11400
ggaagaatca cgatctttct tctataagag attacggagg aggatctctg aggatgttct   11460
tgcaaaagaa attagagctg tagcaggtga gcagttttcc caccaaccag caatcgagct   11520
gatcaagaaa tggtattcag cttcacatgc agctgaatgg gatgatgacg atgcttttgt   11580
tgcttggatg gataaccctg aaaactacaa ggattatatt caatatctta aggctcaaag   11640
agtatcccaa tccctctcaa gtctttcaga ttccagctca gatttgcaag ccctgccaca   11700
gggtctttcc atgttactag ataaggtaat tagcttactg atgcttatat aaattctttt   11760
tcattacata tggctggaga actatctaat caaataatga ttataattcc aatcgttctt   11820
tttatgccat tatgatcttc tgaaatttcc ttctttggac acttattcag atggatccct   11880
ctagaagagc tcaacttgtt gaagaaatca ggaaggtcct tggttga                11927
```

<210> SEQ ID NO 6
<211> LENGTH: 6984
<212> TYPE: DNA
<213> ORGANISM: Oryza sativa

<400> SEQUENCE: 6

| | | | | | |
|---|---|---|---|---|---|
| atgacatcca | cacatgtggc | gacattggga | gttggtgccc | aggcacctcc | tcgtcaccag | 60 |
| aaaaagtcag | ctggcactgc | atttgtatca | tctgggtcat | caagaccctc | ataccgaaag | 120 |
| aatggtcagc | gtactcggtc | acttagggaa | gaaagcaatg | gaggagtgtc | tgattccaaa | 180 |
| aagcttaacc | actctattcg | ccaaggtctt | gctggcatca | ttgacctccc | aaatgacgca | 240 |
| gcttcagaag | ttgatatttc | acatggttcc | gaagatccca | gggggcctac | ggtcccaggt | 300 |
| tcctaccaaa | tgaatgggat | tatcaatgaa | cacataatg | ggaggcatgc | ttcagtctcc | 360 |
| aaggttgttg | agttttgtac | ggcacttggt | ggcaaaacac | caattcacag | tgtattagtg | 420 |
| gccaacaatg | gaatggcagc | agctaagttc | atgcggagtg | tccgaacatg | gctaatgat | 480 |
| acttttggat | cagagaaggc | aattcagctg | atagctatgg | caactccgga | ggatctgagg | 540 |
| ataaatgcag | agcacatcag | aattgccgat | caatttgtag | aggtacctgg | tggaacaaac | 600 |
| aacaacaact | atgcaaatgt | ccaactcata | gtggagatag | cagagagaac | aggtgtttct | 660 |
| gctgtttggc | ctggttgggg | tcatgcatct | gagaatcctg | aacttccaga | tgcgctgact | 720 |
| gcaaaaggaa | ttgttttttct | tgggccacca | gcatcatcaa | tgcatgcatt | aggagacaag | 780 |
| gttggctcag | ctctcattgc | tcaagcagct | ggagttccaa | cacttgcttg | agtggatca | 840 |
| catgtggaag | ttcctctgga | gtgttgcttg | gactcaatac | ctgatgagat | gtatagaaaa | 900 |
| gcttgtgtta | ctaccacaga | ggaagcagtt | gcaagttgtc | aggtggttgg | ttatcctgcc | 960 |
| atgattaagg | catcttgggg | tggtggtggt | aaaggaataa | ggaaggttca | taatgatgat | 1020 |
| gaggttagga | cattatttaa | gcaagttcaa | ggcgaagtac | ctggttcccc | aatatttatc | 1080 |
| atgaggctag | ctgctcagag | tcgacatctt | gaagttcagt | tgctttgtga | tcaatatggc | 1140 |
| aacgtagcag | cacttcacag | tcgagattgc | agtgtacaac | ggcgacacca | aaagataatc | 1200 |
| gaggaaggac | cagttactgt | tgctcctcgt | gagactgtga | agagcttga | gcaggcagca | 1260 |
| cggaggcttg | ctaaagctgt | gggttatgtt | ggtgctgcta | ctgttgaata | cctttacagc | 1320 |
| atggaaactg | gtaatatta | ttttctggaa | cttaatccac | ggctacaggt | tgagcatcct | 1380 |
| gtcactgagt | ggatagctga | agtaaatttg | cctgcggctc | aagttgctgt | tggaatgggt | 1440 |
| atacccttt | ggcagattcc | agagatcagg | cgcttctacg | gaatgaacca | tggaggaggc | 1500 |
| tatgacccttt | ggaggaaaac | agcagctcta | gcgactccat | ttaactttga | tgaagtagat | 1560 |
| tctaaatggc | caaaaggcca | ctgcgtagct | gttagaataa | ctagcgagga | tccagatgat | 1620 |
| gggtttaagc | ctactggtgg | aaaagtaaag | gagataagtt | tcaagagtaa | accaaatgtt | 1680 |
| tgggcctatt | tctcagtaaa | gtctggtgga | ggcatccatg | aattcgctga | ttctcagttc | 1740 |
| ggacatgtttt | ttgcgtatgg | aactactaga | tcggcagcaa | taactaccat | ggctcttgca | 1800 |
| ctaaaagagg | ttcaaattcg | tggagaaatt | cattcaaacg | tagactacac | agttgaccta | 1860 |
| ttaaatgcct | cagattttag | agaaaataag | attcatactg | gttggctgga | taccaggata | 1920 |
| gccatgcgtg | ttcaagctga | gaggcctcca | tggtatattt | cagtcgttgg | aggggcttta | 1980 |
| tataaaacag | taactgccaa | cacggccact | gtttctgatt | atgttggtta | tcttaccaag | 2040 |
| ggccagattc | caccaaagca | tatatccctt | gtctatacga | ctgttgcttt | gaatatagat | 2100 |
| gggaaaaaat | atacaatcga | tactgtgagg | agtggacatg | gtagctacag | attgcgaatg | 2160 |

```
aatggatcaa cggttgacgc aaatgtacaa atattatgtg atggtgggct tttaatgcag    2220
ctggatggaa acagccatgt aatttatgct gaagaagagg ccagtggtac acgacttctt    2280
attgatggaa agacatgcat gttacagaat gaccatgacc catcaaagtt attagctgag    2340
acaccatgca aacttcttcg tttcttggtt gctgatggtg ctcatgttga tgctgatgta    2400
ccatatgcgg aagttgaggt tatgaagatg tgcatgcccc tcttatcacc cgcttctggt    2460
gtcatacatg ttgtaatgtc tgagggccaa gcaatgcagg ctggtgatct tatagctagg    2520
ctggatcttg atgacccttc tgctgttaag agagctgagc cgttcgaaga tacttttcca    2580
caaatgggtc tccctattgc tgcttctggc caagttcaca aattatgtgc tgcaagtctg    2640
aatgcttgtc gaatgatcct tgcggggtat gagcatgata ttgacaaggt tgtgccagag    2700
ttggtatact gcctagacac tccggagctt cctttcctgc agtgggagga gcttatgtct    2760
gttttagcaa ctagacttcc aagaaatctt aaaagtgagt tggagggcaa atatgaggaa    2820
tacaaagtaa aatttgactc tgggataatc aatgatttcc ctgccaatat gctacgagtg    2880
ataattgagg aaaatcttgc atgtggttct gagaaggaga aggctacaaa tgagaggctt    2940
gttgagcctc ttatgagcct actgaagtca tatgagggtg ggagagaaag tcatgctcac    3000
tttgttgtca agtcccttt tgaggagtat ctctatgttg aagaattgtt cagtgatgga    3060
attcagtctg atgtgattga gcgtctgcgc cttcaacata gtaaagacct acagaaggtc    3120
gtagacattg tgttgtccca ccagagtgtt agaaataaaa ctaagctgat actaaaactc    3180
atggagagtc tggtctatcc aaatcctgct gcctacaggg atcaattgat tcgcttttct    3240
tcccttaatc acaaagcgta ttacaagttg gcacttaaag ctagtgaact tcttgaacaa    3300
acaaaactta gtgagctccg tgcaagaata gcaggagcc tttcagagct ggagatgttt    3360
actgaggaaa gcaagggtct ctccatgcat aagcgagaaa ttgccattaa ggagagcatg    3420
gaagatttag tcactgctcc actgccagtt gaagatgcgc tcatttcttt atttgattgt    3480
agtgatacaa ctgttcaaca gagagtgatt gagacttata tagctcgatt ataccagcct    3540
catcttgtaa aggacagtat caaaatgaaa tggatagaat cgggtgttat tgctttatgg    3600
gaatttcctg aagggcattt tgatgcaaga aatggaggag cggttcttgg tgacaaaaga    3660
tggggtgcca tggtcattgt caagtctctt gaatcacttt caatggccat tagatttgca    3720
ctaaaggaga catcacacta cactagctct gagggcaata tgatgcatat tgctttgttg    3780
ggtgctgata taagatgca tataattcaa gaaagtggtg atgatgctga cagaatagcc    3840
aaacttccct tgatactaaa ggataatgta accgatctgc atgcctctgg tgtgaaaaca    3900
ataagtttca ttgttcaaag agatgaagca cggatgacaa tgcgtcgtac cttcctttgg    3960
tctgatgaaa agctttctta tgaggaagag ccaattctcc ggcatgtgga acctcctctt    4020
tctgcacttc ttgagttgga caagttgaaa gtgaaaggat acaatgaaat gaagtatacc    4080
ccatcacggg atcgtcaatg gcatatctac acacttagaa atactgaaaa ccccaaaatg    4140
ttgcaccggg tattttttccg aaccttgtc aggcaaccca gtgtatccaa caagttttct    4200
tcgggccaga ttggtgacat ggaagttggg agtgctgaag aacctctgtc atttacatca    4260
accagcatat taagatcttt gatgactgct atagaggaat ggagcttca cgcaattaga    4320 actggccatt cacacatgta tttgcatgta ttgaaagaac aaaagcttct tgatcttgtt    4380
ccagtttcag ggaatacagt tttggatgtt ggtcaagatg aagctactgc atattcactt    4440
ttaaaagaaa tggctatgaa gatacatgaa cttgttggtg caagaatgca ccatctttct    4500
```

```
gtatgccaat gggaagtgaa acttaagttg gactgcgatg gtcctgccag tggtacctgg     4560
aggattgtaa caaccaatgt tactagtcac acttgcactg tggatatcta ccgtgagatg     4620
gaagataaag aatcacggaa gttagtatac catcccgcca ctccggcggc tggtcctctg     4680
catggtgtgg cactgaataa tccatatcag cctttgagtg tcattgatct caaacgctgt     4740
tctgctagga ataatagaac tacatactgc tatgattttc cactggcatt tgaaactgca     4800
gtgaggaagt catggtcctc tagtacctct ggtgcttcta aggtgttga aaatgcccaa      4860 tgttatgtta aagctacaga gttggtattt gcggacaaac atgggtcatg gggcactcct     4920
ttagttcaaa tggaccggcc tgctgggctc aatgacattg gtatggtagc ttggaccttg     4980
aagatgtcca ctcctgaatt tcctagtggt agggagatta ttgttgttgc aaatgatatt     5040
acgttcagag ctggatcatt tggcccaagg gaagatgcat tttttgaagc tgttaccaac     5100
ctagcctgtg agaagaaact tcctcttatt tatttggcag caaattctgg tgctcgaatt     5160
ggcatagcag atgaagtgaa atcttgcttc cgtgttgggt ggtctgatga tggcagccct     5220
gaacgtgggt ttcagtacat ttatctaagc gaagaagact atgctcgtat tggcacttct     5280
gtcatagcac ataagatgca gctagacagt ggtgaaatta ggtgggttat tgattctgtt     5340
gtgggcaagg aagatggact tggtgtggag aatatacatg gaagtgctgc tattgccagt     5400
gcttattcta gggcatataa ggagacattt acacttacat ttgtgactgg aagaactgtt     5460
ggaataggag cttatcttgc tcgacttggc atccggtgca tacagcgtct tgaccagcct     5520
attattctta caggctattc tgcactgaac aagcttcttg ggcgggaagt gtacagctcc     5580
cacatgcagt tgggtggtcc caaaatcatg gcaactaatg tgttgtcca tcttactgtt      5640 tcagatgacc ttgaaggcgt ttctaatata ttgaggtggc tcagttatgt tcctgcctac     5700
attggtggac cacttccagt aacaacaccg ttggacccac cggacagacc tgttgcatac     5760
attcctgaga actcgtgtga tcctcgagcg gctatccgtg gtgttgatga cagccaaggg     5820
aaatggttag gtggtatgtt tgataaagac agctttgtgg aaacatttga aggttgggct     5880
aagacagtgg ttactggcag agcaaagctt ggtggaattc cagtgggtgt gatagctgtg     5940
gagactcaga ccatgatgca aactatccct gctgaccctg gtcagcttga ttcccgtgag     6000
caatctgttc ctcgtgctgg acaagtgtgg tttccagatt ctgcaaccaa gactgcgcag     6060
gcattgctgg acttcaaccg tgaaggatta cctctgttca tcctcgctaa ctggagaggc     6120
ttctctggtg gacaaagaga tctttttgaa ggaattcttc aggctggctc gactattgtt     6180
gagaacctta ggcatacaa tcagcctgcc tttgtctaca ttcccatggc tgcagagcta     6240
cgaggagggg cttgggttgt ggttgatagc aagataaacc cagaccgcat tgagtgctat     6300
gctgagagga ctgcaaaagg caatgttctg gaaccgcaag ggttaattga gatcaagttc     6360
aggtcagagg aactccagga ttgcatgagt cggcttgacc caacattaat tgatctgaaa     6420
gcaaaactcg aagtagcaaa taaaatgga agtgctgaca caaaatcgct tcaagaaaat     6480
atagaagctc gaacaaaaca gttgatgcct ctatatactc agattgcgat acggtttgct     6540
gaattgcatg atacatccct cagaatggct gcgaaaggtg tgattaagaa agttgtggac     6600
tgggaagaat cacgatcttt cttctataag agattacgga ggaggatctc tgaggatgtt     6660
cttgcaaaag aaattagagc tgtagcaggt gagcagtttt cccaccaacc agcaatcgag     6720
ctgatcaaga aatggtattc agcttcacat gcagctgaat gggatgatga cgatgctttt     6780
gttgcttgga tggataaccc tgaaaactac aaggattata ttcaatatct taaggctcaa     6840
agagtatccc aatccctctc aagtctttca gattccagct cagatttgca agccctgcca     6900
```

```
cagggtcttt ccatgttact agataagatg gatccctcta gaagagctca acttgttgaa    6960
gaaatcagga aggtccttgg ttga                                          6984
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gcaaatgata ttacgttcag agctg                                           25
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gttaccaacc tagcctgtga gaag                                            24
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gatttcttca acaagttgag ctcttc                                          26
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
agtaacatgg aaagaccctg tggc                                            24
```

<210> SEQ ID NO 11
<211> LENGTH: 6978
<212> TYPE: DNA
<213> ORGANISM: Zea mays

<400> SEQUENCE: 11

```
atgtcacagc ttggattagc cgcagctgcc tcaaaggcct tgccactact ccctaatcgc     60
cagagaagtt cagctgggac tacattctca tcatcttcat tatcgaggcc cttaaacaga    120
aggaaaagcc gtactcgttc actccgtgat ggcggagatg gggtatcaga tgccaaaaag    180
cacagccagt ctgttcgtca aggtcttgct ggcattatcg acctcccaag tgaggcacct    240
tccgaagtgg atatttcaca tggatctgag gatcctaggg ggccaacaga ttcttatcaa    300
atgaatggga ttatcaatga aacacataat ggaagacatg cctcagtgtc caaggttgtt    360
gaatttgtgt cggcactagg tggcaaaaca ccaattcaca gtatattagt ggccaacaat    420
```

| | |
|---|---|
| ggaatggcag cagcaaaatt tatgaggagt gtccggacat gggctaatga tacttttgga | 480 |
| tctgagaagg caattcaact catagctatg gcaactccgg aagacatgag gataaatgca | 540 |
| gaacacatta gaattgctga ccaattcgta gaggtgcctg gtggaacaaa caataataac | 600 |
| tacgccaatg ttcaactcat agtggagatg gcacaaaaac taggtgtttc tgctgtttgg | 660 |
| cctggttggg gtcatgcttc tgagaatcct gaactgccag atgcattgac cgcaaaaggg | 720 |
| atcgttttc ttggcccacc tgcatcatca atgaatgctt tgggagataa ggtcggctca | 780 |
| gctctcattg ctcaagcagc cggggtccca actcttgctc ggagtggatc acatgttgaa | 840 |
| gttccattag agtgctgctt agacgcgata cctgaggaga tgtatagaaa gcttgcgtt | 900 |
| actaccacag aggaagcagt tgcaagttgt caagtggttg gttatcctgc catgattaag | 960 |
| gcatcctggg gaggtggtgg taaaggaata agaaaggttc ataatgatga tgaggttaga | 1020 |
| gcgctgttta gcaagtaca aggtgaagtc cctggctccc caatatttgt catgaggctt | 1080 |
| gcatcccaga gtcggcatct tgaagttcag ttgctttgtg atcaatatgg taatgtagca | 1140 |
| gcacttcaca gtcgtgattg cagtgtgcaa cggcgacacc agaagattat tgaagaaggt | 1200 |
| ccagttactg ttgctcctcg tgagacagtt aaagcacttg agcaggcagc aaggaggctt | 1260 |
| gctaaggctg tgggttatgt tggtgctgct actgttgagt atctttacag catggaaact | 1320 |
| ggagactact attttctgga acttaatccc cgactacagg ttgagcatcc agtcaccgag | 1380 |
| tggatagctg aagtaaatct gcctgcagct caagttgctg ttggaatggg catacctctt | 1440 |
| tggcagattc cagaaatcag acgtttctat ggaatggact atggaggagg gtatgacatt | 1500 |
| tggaggaaaa cagcagctct tgctacacca tttaattttg atgaagtaga ttctcaatgg | 1560 |
| ccaaagggcc attgtgtagc agttagaatt actagtgagg acccagatga tggtttcaaa | 1620 |
| cctactggtg ggaaagtgaa ggagataagt tttaaaagca agcctaatgt ttgggcctac | 1680 |
| ttctcagtaa agtctggtgg aggcattcat gaatttgctg attctcagtt cggacatgtt | 1740 |
| tttgcatatg ggctctctag atcagcagca ataacaaaca tgactcttgc attaaaagag | 1800 |
| attcaaattc gtggagaaat tcattcaaat gttgattaca cagttgacct cttaaatgct | 1860 |
| tcagacttta gagaaaacaa gattcatact ggttggctcg acaccagaat agctatgcgt | 1920 |
| gttcaagctg agaggccccc atggtatatt tcagtggttg gaggtgctt atataaaaca | 1980 |
| gtaaccacca atgcagccac tgtttctgaa tatgttagtt atctcaccaa gggccagatt | 2040 |
| ccaccaaagc atatatccct tgtcaattct acagttaatt tgaatataga agggagcaaa | 2100 |
| tacacaattg aaactgtaag gactggacat ggtagctaca ggttgagaat gaatgattca | 2160 |
| acagttgaag cgaatgtaca atctttatgt gatggtggcc tcttaatgca gttggatgga | 2220 |
| aacagccatg taatttatgc agaagaagaa gctggtggta cacggcttca gattgatgga | 2280 |
| aagacatgtt tattgcagaa tgaccatgat ccatcaaagt tattagctga gacaccctgc | 2340 |
| aaacttcttc gtttcttggt tgctgatggt gctcatgttg atgcggatgt accatacgcg | 2400 |
| gaagttgagg ttatgaagat gtgcatgcct ctcttgtcac ctgcttctgg tgtcattcat | 2460 |
| tgtatgatgt ctgagggcca ggcattgcag gctggtgatc ttatagcaag gttggatctt | 2520 |
| gatgacccctt ctgctgtgaa aagagctgag ccatttgatg gaatatttcc acaaatggag | 2580 |
| ctccctgttg ctgtctctag tcaagtacac aaaagatatg ctgcaagttt gaatgctgct | 2640 |
| cgaatggtcc ttgcaggata tgagcacaat attaatgaag tcgttcaaga tttggtatgc | 2700 |
| tgcctggaca accctgagct tcctttccta cagtgggatg aacttatgtc tgttctagca | 2760 |
| acgaggcttc caagaaatct caagagtgag ttagaggata aatacaagga atacaagttg | 2820 |

```
aatttttacc atggaaaaaa cgaggacttt ccatccaagt tgctaagaga catcattgag   2880
gaaaatcttt cttatggttc agagaaggaa aaggctacaa atgagaggct tgttgagcct   2940
cttatgaacc tactgaagtc atatgagggt gggagagaga gccatgcaca ttttgttgtc   3000
aagtctcttt tcgaggagta tcttacagtg gaagaacttt ttagtgatgg cattcagtct   3060
gacgtgattg aaacattgcg gcatcagcac agtaaagacc tgcagaaggt tgtagacatt   3120
gtgttgtctc accagggtgt gaggaacaaa gctaagcttg taacggcact tatggaaaag   3180
ctggtttatc caaatcctgg tggttacagg gatctgttag ttcgcttttc ttccctcaat   3240
cataaaagat attataagtt ggcccttaaa gcaagtgaac ttcttgaaca aaccaaacta   3300
agtgaactcc gtgcaagcgt tgcaagaagc ctttcggatc tggggatgca aagggagaa    3360 atgagtatta aggataacat ggaagattta gtctctgccc cattacctgt tgaagatgct   3420
ctgatttctt tgtttgatta cagtgatcga actgttcagc agaaagtgat tgagacatac   3480
atatcacgat tgtaccagcc tcatcttgta aaggatagca tccaaatgaa attcaaggaa   3540
tctggtgcta ttacttttg ggaattttat gaagggcatg ttgatactag aaatggacat    3600
ggggctatta ttggtgggaa gcgatggggt gccatggtcg ttctcaaatc acttgaatct   3660
gcgtcaacag ccattgtggc tgcattaaag gattcggcac agttcaacag ctctgagggc   3720
aacatgatgc acattgcatt attgagtgct gaaaatgaaa gtaatataag tggaataagc   3780
agtgatgatc aagctcaaca taagatggaa aagcttagca agatactgaa ggatactagc   3840
gttgcaagtg atctccaagc tgctggttg aaggttataa gttgcattgt tcaaagagat    3900
gaagctcgca tgccaatgcg ccacacattc ctctggttgg atgacaagag ttgttatgaa   3960
gaagagcaga ttctccggca tgtggagcct ccctctcta cacttcttga attggataag    4020
ttgaaggtga aggatacaa tgaaatgaag tatactcctt cgcgtgaccg ccaatggcat    4080
atctacacac taagaaatac tgaaaacccc aaaatgttgc ataggggtgtt tttccgaact  4140 attgtcaggc aacccaatgc aggcaacaag tttacatcgg ctcagatcag cgacgctgaa   4200
gtaggatgtc ccgaagaatc tctttcattt acatcaaata gcatcttaag atcattgatg   4260
actgctattg aagaattaga gcttcatgca attaggacag gtcattctca catgtatttg   4320
tgcatactga aagagcaaaa gcttcttgac ctcattccat tttcagggag tacaattgtt   4380
gatgttggcc aagatgaagc taccgcttgt tcactttaa aatcaatggc tttgaagata    4440
catgagcttg ttggtgcaag gatgcatcat ctgtctgtat gccagtggga ggtgaaactc   4500
aagttggact gtgatggccc tgcaagtggt acctggagag ttgtaactac aaatgttact   4560
ggtcacacct gcaccattga tatataccga gaagtggagg aaatagaatc gcagaagtta   4620
gtgtaccatt cagccacttc gtcagctgga ccattgcatg gtgttgcact gaataatcca   4680
tatcaacctt tgagtgtgat tgatctaaag cgctgctctg ctaggaacaa cagaacaaca   4740
tattgctatg attttccgct ggcctttgaa actgcactgc agaagtcatg gcagtccaat   4800
ggctctactg tttctgaagg caatgaaaat agtaaatcct acgtgaaggc aactgagcta   4860
gtgtttgctg aaaaacatgg gtcctggggc actcctataa ttccgatgga acgccctgct   4920
gggctcaacg acattggtat ggtcgcttgg atcatggaga tgtcaacacc tgaatttccc   4980
aatggcaggc agattattgt tgtagcaaat gatatcactt tcagagctgg atcatttggc   5040
ccaagggaag atgcattttt tgaaactgtc actaacctgg cttgcgaaag gaaacttcct   5100
cttatatact tggcagcaaa actctggtgct aggattggca tagctgatga agtaaaatct  5160
```

-continued

```
tgcttccgtg ttggatggtc tgacgaaggc agtcctgaac gagggtttca gtacatctat    5220
ctgactgaag aagactatgc tcgcattagc tcttctgtta tagcacataa gctggagcta    5280
gatagtggtg aaattaggtg gattattgac tctgttgtgg gcaaggagga tgggcttggt    5340
gtcgagaaca tacatggaag tgctgctatt gccagtgctt attctagggc atatgaggag    5400
acatttacac ttacatttgt gactgggcgg actgtaggaa taggagctta tcttgctcga    5460
cttggtatac ggtgcataca gcgtcttgac cagcctatta ttttaacagg gttttctgcc    5520
ctgaacaagc tccttgggcg ggaagtgtac agctcccaca tgcagcttgg tggtcctaag    5580
atcatggcga ctaatggtgt tgtccacctc actgttccag atgaccttga aggtgtttcc    5640
aatatattga ggtggctcag ctatgttcct gcaaacattg gtggacctct tcctattacc    5700
aaacctctgg accctccaga cagacctgtt gcttacatcc ctgagaacac atgcgatcca    5760
cgtgcagcta tctgtggtgt agatgacagc caagggaaat ggttgggtgg tatgtttgac    5820
aaagacagct ttgtggagac atttgaagga tgggcaaaaa cagtggttac tggcagagca    5880
aagcttggag gaattcctgt gggcgtcata gctgtggaga cacagaccat gatgcagatc    5940
atccctgctg atccaggtca gcttgattcc catgagcgat ctgtccctcg tgctggacaa    6000
gtgtggttcc cagattctgc aaccaagacc gctcaggcat tattagactt caaccgtgaa    6060
ggattgcctc tgttcatcct ggctaattgg agaggcttct ctggtggaca aagagatctc    6120
tttgaaggaa ttcttcaggc tgggtcaaca attgtcgaga accttaggac atctaatcag    6180
cctgcttttg tgtacattcc tatggctgga gagcttcgtg gaggagcttg ggttgtggtc    6240
gatagcaaaa taaatccaga ccgcattgag tgttatgctg aaaggactgc caaaggtaat    6300
gttctcgaac ctcaagggtt aattgaaatc aagttcaggt cagaggaact ccaagactgt    6360
atgggtaggc ttgacccaga gttgataaat ctgaaagcaa aactccaaga tgtaaatcat    6420
ggaaatggaa gtctaccaga catagaaggg attcggaaga gtatagaagc acgtacgaaa    6480
cagttgctgc ctttatatac ccagattgca atacggtttg ctgaattgca tgatacttcc    6540
ctaagaatgg cagctaaagg tgtgattaag aaagttgtag actgggaaga atcacgctcg    6600
ttcttctata aaaggctacg gaggaggatc gcagaagatg ttcttgcaaa gaaataagg    6660
cagatagtcg gtgataaatt tacgcaccaa ttagcaatgg agctcatcaa ggaatggtac    6720
cttgcttctc aggccacaac aggaagcact ggatgggatg acgatgatgc ttttgttgcc    6780
tggaaggaca gtcctgaaaa ctacaagggg catatccaaa agcttagggc tcaaaaagtg    6840
tctcattcgc tctctgatct tgctgactcc agttcagatc tgcaagcatt ctcgcagggt    6900
cttttctacgc tattagataa gatggatccc tctcagagag cgaagtttgt tcaggaagtc    6960
aagaaggtcc ttgattga                                                  6978
```

<210> SEQ ID NO 12
<211> LENGTH: 2325
<212> TYPE: PRT
<213> ORGANISM: Zea mays

<400> SEQUENCE: 12

```
Met Ser Gln Leu Gly Leu Ala Ala Ala Ser Lys Ala Leu Pro Leu
1               5                   10                  15

Leu Pro Asn Arg Gln Arg Ser Ser Ala Gly Thr Thr Phe Ser Ser Ser
                20                  25                  30

Ser Leu Ser Arg Pro Leu Asn Arg Arg Lys Ser Arg Thr Arg Ser Leu
        35                  40                  45
```

```
Arg Asp Gly Gly Asp Gly Val Ser Asp Ala Lys Lys His Ser Gln Ser
    50              55                  60

Val Arg Gln Gly Leu Ala Gly Ile Ile Asp Leu Pro Ser Glu Ala Pro
65              70                  75                  80

Ser Glu Val Asp Ile Ser His Gly Ser Glu Asp Pro Arg Gly Pro Thr
            85                  90                  95

Asp Ser Tyr Gln Met Asn Gly Ile Ile Asn Glu Thr His Asn Gly Arg
            100                 105                 110

His Ala Ser Val Ser Lys Val Val Glu Phe Cys Ala Ala Leu Gly Gly
            115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
                180                 185                 190

Pro Gly Gly Thr Asn Asn Asn Asn Tyr Ala Asn Val Gln Leu Ile Val
            195                 200                 205

Glu Met Ala Gln Lys Leu Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Ala Arg Ser Gly Ser His Val Glu Val Pro Leu Glu Cys Cys Leu Asp
            275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Val Met Arg Leu Ala Ser Gln Ser Arg His Leu Glu
            355                 360                 365

Val Gln Leu Leu Cys Asp Gln Tyr Gly Asn Val Ala Ala Leu His Ser
    370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Asp Tyr Tyr Phe Leu Glu Leu
            435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
```

```
                465                 470                 475                 480
        Trp Gln Ile Pro Glu Ile Arg Arg Phe Tyr Gly Met Asp Tyr Gly Gly
                        485                 490                 495

Gly Tyr Asp Ile Trp Arg Lys Thr Ala Ala Leu Ala Thr Pro Phe Asn
                        500                 505                 510

Phe Asp Glu Val Asp Ser Gln Trp Pro Lys Gly His Cys Val Ala Val
                        515                 520                 525

Arg Ile Thr Ser Glu Asp Pro Asp Asp Gly Phe Lys Pro Thr Gly Gly
                        530                 535                 540

Lys Val Lys Glu Ile Ser Phe Lys Ser Lys Pro Asn Val Trp Ala Tyr
        545                 550                 555                 560

Phe Ser Val Lys Ser Gly Gly Ile His Glu Phe Ala Asp Ser Gln
                        565                 570                 575

Phe Gly His Val Phe Ala Tyr Gly Leu Ser Arg Ser Ala Ala Ile Thr
                        580                 585                 590

Asn Met Thr Leu Ala Leu Lys Glu Ile Gln Ile Arg Gly Glu Ile His
                        595                 600                 605

Ser Asn Val Asp Tyr Thr Val Asp Leu Leu Asn Ala Ser Asp Phe Arg
                        610                 615                 620

Glu Asn Lys Ile His Thr Gly Trp Leu Asp Thr Arg Ile Ala Met Arg
        625                 630                 635                 640

Val Gln Ala Glu Arg Pro Pro Trp Tyr Ile Ser Val Val Gly Gly Ala
                        645                 650                 655

Leu Tyr Lys Thr Val Thr Thr Asn Ala Ala Thr Val Ser Glu Tyr Val
                        660                 665                 670

Ser Tyr Leu Thr Lys Gly Gln Ile Pro Pro Lys His Ile Ser Leu Val
                        675                 680                 685

Asn Ser Thr Val Asn Leu Asn Ile Glu Gly Ser Lys Tyr Thr Ile Glu
                        690                 695                 700

Thr Val Arg Thr Gly His Gly Ser Tyr Arg Leu Arg Met Asn Asp Ser
        705                 710                 715                 720

Thr Val Glu Ala Asn Val Gln Ser Leu Cys Asp Gly Gly Leu Leu Met
                        725                 730                 735

Gln Leu Asp Gly Asn Ser His Val Ile Tyr Ala Glu Glu Ala Gly
                        740                 745                 750

Gly Thr Arg Leu Gln Ile Asp Gly Lys Thr Cys Leu Leu Gln Asn Asp
                        755                 760                 765

His Asp Pro Ser Lys Leu Leu Ala Glu Thr Pro Cys Lys Leu Leu Arg
        770                 775                 780

Phe Leu Val Ala Asp Gly Ala His Val Asp Ala Asp Val Pro Tyr Ala
        785                 790                 795                 800

Glu Val Glu Val Met Lys Met Cys Met Pro Leu Leu Ser Pro Ala Ser
                        805                 810                 815

Gly Val Ile His Cys Met Met Ser Glu Gly Gln Ala Leu Gln Ala Gly
                        820                 825                 830

Asp Leu Ile Ala Arg Leu Asp Leu Asp Asp Pro Ser Ala Val Lys Arg
                        835                 840                 845

Ala Glu Pro Phe Asp Gly Ile Phe Pro Gln Met Glu Leu Pro Val Ala
                        850                 855                 860

Val Ser Ser Gln Val His Lys Arg Tyr Ala Ala Ser Leu Asn Ala Ala
        865                 870                 875                 880

Arg Met Val Leu Ala Gly Tyr Glu His Asn Ile Asn Glu Val Val Gln
                        885                 890                 895
```

-continued

```
Asp Leu Val Cys Cys Leu Asp Asn Pro Glu Leu Pro Phe Leu Gln Trp
            900                 905                 910

Asp Glu Leu Met Ser Val Leu Ala Thr Arg Leu Pro Arg Asn Leu Lys
            915                 920                 925

Ser Glu Leu Glu Asp Lys Tyr Lys Glu Tyr Lys Leu Asn Phe Tyr His
        930                 935                 940

Gly Lys Asn Glu Asp Phe Pro Ser Lys Leu Leu Arg Asp Ile Ile Glu
945                 950                 955                 960

Glu Asn Leu Ser Tyr Gly Ser Glu Lys Glu Lys Ala Thr Asn Glu Arg
            965                 970                 975

Leu Val Glu Pro Leu Met Asn Leu Leu Lys Ser Tyr Glu Gly Gly Arg
            980                 985                 990

Glu Ser His Ala His Phe Val Val Lys Ser Leu Phe Glu Glu Tyr Leu
            995                 1000                1005

Thr Val Glu Glu Leu Phe Ser Asp Gly Ile Gln Ser Asp Val Ile
        1010                1015                1020

Glu Thr Leu Arg His Gln His Ser Lys Asp Leu Gln Lys Val Val
        1025                1030                1035

Asp Ile Val Leu Ser His Gln Gly Val Arg Asn Lys Ala Lys Leu
        1040                1045                1050

Val Thr Ala Leu Met Glu Lys Leu Val Tyr Pro Asn Pro Gly Gly
        1055                1060                1065

Tyr Arg Asp Leu Leu Val Arg Phe Ser Ser Leu Asn His Lys Arg
        1070                1075                1080

Tyr Tyr Lys Leu Ala Leu Lys Ala Ser Glu Leu Leu Glu Gln Thr
        1085                1090                1095

Lys Leu Ser Glu Leu Arg Ala Ser Val Ala Arg Ser Leu Ser Asp
        1100                1105                1110

Leu Gly Met His Lys Gly Glu Met Ser Ile Lys Asp Asn Met Glu
        1115                1120                1125

Asp Leu Val Ser Ala Pro Leu Pro Val Glu Asp Ala Leu Ile Ser
        1130                1135                1140

Leu Phe Asp Tyr Ser Asp Arg Thr Val Gln Gln Lys Val Ile Glu
        1145                1150                1155

Thr Tyr Ile Ser Arg Leu Tyr Gln Pro His Leu Val Lys Asp Ser
        1160                1165                1170

Ile Gln Met Lys Phe Lys Glu Ser Gly Ala Ile Thr Phe Trp Glu
        1175                1180                1185

Phe Tyr Glu Gly His Val Asp Thr Arg Asn Gly His Gly Ala Ile
        1190                1195                1200

Ile Gly Gly Lys Arg Trp Gly Ala Met Val Val Leu Lys Ser Leu
        1205                1210                1215

Glu Ser Ala Ser Thr Ala Ile Val Ala Ala Leu Lys Asp Ser Ala
        1220                1225                1230

Gln Phe Asn Ser Ser Glu Gly Asn Met Met His Ile Ala Leu Leu
        1235                1240                1245

Ser Ala Glu Asn Glu Ser Asn Ile Ser Gly Ile Ser Ser Asp Asp
        1250                1255                1260

Gln Ala Gln His Lys Met Glu Lys Leu Ser Lys Ile Leu Lys Asp
        1265                1270                1275

Thr Ser Val Ala Ser Asp Leu Gln Ala Ala Gly Leu Lys Val Ile
        1280                1285                1290
```

```
Ser Cys Ile Val Gln Arg Asp Glu Ala Arg Met Pro Met Arg His
    1295                1300            1305

Thr Phe Leu Trp Leu Asp Asp Lys Ser Cys Tyr Glu Glu Gln
    1310                1315            1320

Ile Leu Arg His Val Glu Pro Pro Leu Ser Thr Leu Leu Glu Leu
    1325                1330            1335

Asp Lys Leu Lys Val Lys Gly Tyr Asn Glu Met Lys Tyr Thr Pro
    1340                1345            1350

Ser Arg Asp Arg Gln Trp His Ile Tyr Thr Leu Arg Asn Thr Glu
    1355                1360            1365

Asn Pro Lys Met Leu His Arg Val Phe Phe Arg Thr Ile Val Arg
    1370                1375            1380

Gln Pro Asn Ala Gly Asn Lys Phe Thr Ser Ala Gln Ile Ser Asp
    1385                1390            1395

Ala Glu Val Gly Cys Pro Glu Glu Ser Leu Ser Phe Thr Ser Asn
    1400                1405            1410

Ser Ile Leu Arg Ser Leu Met Thr Ala Ile Glu Glu Leu Glu Leu
    1415                1420            1425

His Ala Ile Arg Thr Gly His Ser His Met Tyr Leu Cys Ile Leu
    1430                1435            1440

Lys Glu Gln Lys Leu Leu Asp Leu Ile Pro Phe Ser Gly Ser Thr
    1445                1450            1455

Ile Val Asp Val Gly Gln Asp Glu Ala Thr Ala Cys Ser Leu Leu
    1460                1465            1470

Lys Ser Met Ala Leu Lys Ile His Glu Leu Val Gly Ala Arg Met
    1475                1480            1485

His His Leu Ser Val Cys Gln Trp Glu Val Lys Leu Lys Leu Asp
    1490                1495            1500

Cys Asp Gly Pro Ala Ser Gly Thr Trp Arg Val Val Thr Thr Asn
    1505                1510            1515

Val Thr Gly His Thr Cys Thr Ile Asp Ile Tyr Arg Glu Val Glu
    1520                1525            1530

Glu Ile Glu Ser Gln Lys Leu Val Tyr His Ser Ala Thr Ser Ser
    1535                1540            1545

Ala Gly Pro Leu His Gly Val Ala Leu Asn Asn Pro Tyr Gln Pro
    1550                1555            1560

Leu Ser Val Ile Asp Leu Lys Arg Cys Ser Ala Arg Asn Asn Arg
    1565                1570            1575

Thr Thr Tyr Cys Tyr Asp Phe Pro Leu Ala Phe Glu Thr Ala Leu
    1580                1585            1590

Gln Lys Ser Trp Gln Ser Asn Gly Ser Thr Val Ser Glu Gly Asn
    1595                1600            1605

Glu Asn Ser Lys Ser Tyr Val Lys Ala Thr Glu Leu Val Phe Ala
    1610                1615            1620

Glu Lys His Gly Ser Trp Gly Thr Pro Ile Ile Pro Met Glu Arg
    1625                1630            1635

Pro Ala Gly Leu Asn Asp Ile Gly Met Val Ala Trp Ile Met Glu
    1640                1645            1650

Met Ser Thr Pro Glu Phe Pro Asn Gly Arg Gln Ile Ile Val Val
    1655                1660            1665

Ala Asn Asp Ile Thr Phe Arg Ala Gly Ser Phe Gly Pro Arg Glu
    1670                1675            1680

Asp Ala Phe Phe Glu Thr Val Thr Asn Leu Ala Cys Glu Arg Lys
```

```
            1685                1690                1695

Leu Pro Leu Ile Tyr Leu Ala Ala Asn Ser Gly Ala Arg Ile Gly
        1700                1705                1710

Ile Ala Asp Glu Val Lys Ser Cys Phe Arg Val Gly Trp Ser Asp
        1715                1720                1725

Glu Gly Ser Pro Glu Arg Gly Phe Gln Tyr Ile Tyr Leu Thr Glu
        1730                1735                1740

Glu Asp Tyr Ala Arg Ile Ser Ser Ser Val Ile Ala His Lys Leu
        1745                1750                1755

Glu Leu Asp Ser Gly Glu Ile Arg Trp Ile Ile Asp Ser Val Val
        1760                1765                1770

Gly Lys Glu Asp Gly Leu Gly Val Glu Asn Ile His Gly Ser Ala
        1775                1780                1785

Ala Ile Ala Ser Ala Tyr Ser Arg Ala Tyr Glu Glu Thr Phe Thr
        1790                1795                1800

Leu Thr Phe Val Thr Gly Arg Thr Val Gly Ile Gly Ala Tyr Leu
        1805                1810                1815

Ala Arg Leu Gly Ile Arg Cys Ile Gln Arg Leu Asp Gln Pro Ile
        1820                1825                1830

Ile Leu Thr Gly Phe Ser Ala Leu Asn Lys Leu Leu Gly Arg Glu
        1835                1840                1845

Val Tyr Ser Ser His Met Gln Leu Gly Gly Pro Lys Ile Met Ala
        1850                1855                1860

Thr Asn Gly Val Val His Leu Thr Val Pro Asp Asp Leu Glu Gly
        1865                1870                1875

Val Ser Asn Ile Leu Arg Trp Leu Ser Tyr Val Pro Ala Asn Ile
        1880                1885                1890

Gly Gly Pro Leu Pro Ile Thr Lys Pro Leu Asp Pro Pro Asp Arg
        1895                1900                1905

Pro Val Ala Tyr Ile Pro Glu Asn Thr Cys Asp Pro Arg Ala Ala
        1910                1915                1920

Ile Cys Gly Val Asp Asp Ser Gln Gly Lys Trp Leu Gly Gly Met
        1925                1930                1935

Phe Asp Lys Asp Ser Phe Val Glu Thr Phe Glu Gly Trp Ala Lys
        1940                1945                1950

Thr Val Val Thr Gly Arg Ala Lys Leu Gly Gly Ile Pro Val Gly
        1955                1960                1965

Val Ile Ala Val Glu Thr Gln Thr Met Met Gln Ile Ile Pro Ala
        1970                1975                1980

Asp Pro Gly Gln Leu Asp Ser His Glu Arg Ser Val Pro Arg Ala
        1985                1990                1995

Gly Gln Val Trp Phe Pro Asp Ser Ala Thr Lys Thr Ala Gln Ala
        2000                2005                2010

Leu Leu Asp Phe Asn Arg Glu Gly Leu Pro Leu Phe Ile Leu Ala
        2015                2020                2025

Asn Trp Arg Gly Phe Ser Gly Gly Gln Arg Asp Leu Phe Glu Gly
        2030                2035                2040

Ile Leu Gln Ala Gly Ser Thr Ile Val Glu Asn Leu Arg Thr Ser
        2045                2050                2055

Asn Gln Pro Ala Phe Val Tyr Ile Pro Met Ala Gly Glu Leu Arg
        2060                2065                2070

Gly Gly Ala Trp Val Val Val Asp Ser Lys Ile Asn Pro Asp Arg
        2075                2080                2085
```

```
Ile Glu Cys Tyr Ala Glu Arg Thr Ala Lys Gly Asn Val Leu Glu
    2090            2095                2100

Pro Gln Gly Leu Ile Glu Ile Lys Phe Arg Ser Glu Glu Leu Gln
    2105            2110                2115

Asp Cys Met Gly Arg Leu Asp Pro Glu Leu Ile Asn Leu Lys Ala
    2120            2125                2130

Lys Leu Gln Asp Val Asn His Gly Asn Gly Ser Leu Pro Asp Ile
    2135            2140                2145

Glu Gly Ile Arg Lys Ser Ile Glu Ala Arg Thr Lys Gln Leu Leu
    2150            2155                2160

Pro Leu Tyr Thr Gln Ile Ala Ile Arg Phe Ala Glu Leu His Asp
    2165            2170                2175

Thr Ser Leu Arg Met Ala Ala Lys Gly Val Ile Lys Lys Val Val
    2180            2185                2190

Asp Trp Glu Glu Ser Arg Ser Phe Phe Tyr Lys Arg Leu Arg Arg
    2195            2200                2205

Arg Ile Ala Glu Asp Val Leu Ala Lys Glu Ile Arg Gln Ile Val
    2210            2215                2220

Gly Asp Lys Phe Thr His Gln Leu Ala Met Glu Leu Ile Lys Glu
    2225            2230                2235

Trp Tyr Leu Ala Ser Gln Ala Thr Thr Gly Ser Thr Gly Trp Asp
    2240            2245                2250

Asp Asp Asp Ala Phe Val Ala Trp Lys Asp Ser Pro Glu Asn Tyr
    2255            2260                2265

Lys Gly His Ile Gln Lys Leu Arg Ala Gln Lys Val Ser His Ser
    2270            2275                2280

Leu Ser Asp Leu Ala Asp Ser Ser Ser Asp Leu Gln Ala Phe Ser
    2285            2290                2295

Gln Gly Leu Ser Thr Leu Leu Asp Lys Met Asp Pro Ser Gln Arg
    2300            2305                2310

Ala Lys Phe Val Gln Glu Val Lys Lys Val Leu Asp
    2315            2320                2325

<210> SEQ ID NO 13
<211> LENGTH: 6975
<212> TYPE: DNA
<213> ORGANISM: Zea mays

<400> SEQUENCE: 13
atgtcacagc ttggattagc cgcagctgcc tcaaaggcct tgccactact ccctaatcgc      60
cagagaagtt cagctgggac tacattctca tcatcttcat tatcgaggcc cttaaacaga     120
aggaaaagcc gtactcgttc actccgtgat ggcggagatg gggtatcaga tgccaaaaag     180
cacagccagt ctgttcgtca aggtcttgct ggcattatcg acctcccaag tgaggcacct     240
tccgaagtgg atatttcaca tggatctgag gatcctaggg ggccaacaga ttcttatcaa     300
atgaatggga ttatcaatga aacacataat ggaagacatg cctcagtgtc caaggttgtt     360
gaattttgtg cggcactagg tggcaaaaca ccaattcaca gtatattagt ggccaacaat     420
ggaatggcag cagcaaaatt tatgaggagt gtccggacat gggctaatga tactttggat     480
tctgagaagg caattcaact catagctatg caactccgg aagacatgag gataaatgca     540
gaacacatta gaattgctga ccaattcgta gaggtgcctg gtggaacaaa caataataac     600
tacgccaatg ttcaactcat agtggagatg gcacaaaaac taggtgtttc tgctgtttgg     660
```

```
cctggttggg gtcatgcttc tgagaatcct gaactgccag atgcattgac cgcaaaaggg    720
atcgtttttc ttggcccacc tgcatcatca atgaatgctt tgggagataa ggtcggctca    780
gctctcattg ctcaagcagc cggggtccca actcttgctt ggagtggatc acatgttgaa    840
gttccattag agtgctgctt agacgcgata cctgaggaga tgtatagaaa agcttgcgtt    900
actaccacag aggaagcagt tgcaagttgt caagtggttg gttatcctgc catgattaag    960
gcatcctggg gaggtggtgg taaaggaata agaaaggttc ataatgatga tgaggttaga   1020
gcgctgttta agcaagtaca aggtgaagtc cctggctccc caatatttgt catgaggctt   1080
gcatcccaga gtcggcatct tgaagttcag ttgctttgtg atcaatatgg taatgtagca   1140
gcacttcaca gtcgtgattg cagtgtgcaa cggcgacacc agaagattat tgaagaaggt   1200
ccagttactg ttgctcctcg tgagacagtt aaagcacttg agcaggcagc aaggaggctt   1260
gctaaggctg tgggttatgt tggtgctgct actgttgagt atctttacag catggaaact   1320
ggagactact attttctgga acttaatccc cgactacagg ttgagcatcc agtcaccgag   1380
tggatagctg aagtaaatct gcctgcagct caagttgctg ttggaatggg catacctctt   1440
tggcagattc cagaaatcag acgtttctat ggaatggact atggaggagg gtatgacatt   1500
tggaggaaaa cagcagctct tgctacacca tttaattttg atgaagtaga ttctcaatgg   1560
ccaaagggcc attgtgtagc agttagaatt actagtgagg acccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt cggacatgtt   1740
tttgcatatg ggctctctag atcagcagca ataacaaaca tgactcttgc attaaaagag   1800
attcaaattc gtggagaaat tcattcaaat gttgattaca cagttgaccct cttaaatgct   1860 tcagacttta gagaaaacaa gattcatact ggttggctcg acaccagaat agctatgcgt   1920
gttcaagctg agaggccccc atggtatatt tcagtggttg ggggtgcttt atataaaaca   1980
gtaaccacca atgcagccac tgtttctgaa tatgttagtt atctcaccaa gggccagatt   2040
ccaccaaagc atatatccct tgtcaattct acagttaatt tgaatataga agggagcaaa   2100
tacacaattg aaactgtaag gactggacat ggtagctaca ggttgagaat gaatgattca   2160
acagttgaag cgaatgtaca atctttatgt gatggtggcc tcttaatgca gttggatgga   2220
aacagccatg taatttatgc agaagaagaa gctggtggta cacggcttca gattgatgga   2280
aagacatgtt tattgcagaa tgaccatgat ccatcaaagt tattagctga cacaccctgc   2340
aaacttcttc gtttcttggt tgctgatggt gctcatgttg atgcggatgt accatacgcg   2400
gaagttgagg ttatgaagat gtgcatgcct ctcttgtcgc ctgcttctgg tgtcattcat   2460
tgtatgatgt ctgagggcca ggcattgcag gctggtgatc ttatagcaag gttggatctt   2520
gatgacccct ctgctgtgaa aagagctgag ccatttgatg gaatatttcc acaaatggag   2580
ctccctgttg ctgtctctag tcaagtacac aaaagatatg ctgcaagttt gaatgctgct   2640
cgaatggtcc ttgcaggata tgagcacaat attaatgaag tcgttcaaga tttggtatgc   2700
tgcctggaca accctgagct tcctttccta cagtgggatg aacttatgtc tgttctagca   2760
acgaggcttc caagaaatct caagagtgag ttagaggata aatacaagga atacaagttg   2820 aattttacc atggaaaaaa cgaggacttt ccatccaagt tgctaagaga catcattgag   2880
gaaaatcttt cttatggttc agagaaggaa aaggctacaa atgagaggct tgttgagcct   2940
cttatgaacc tactgaagtc atatgagggt gggagagaga gccatgcaca ttttgttgtc   3000
aagtctcttt tcgaggagta tcttacagtg gaagaacttt ttagtgatgg cattcagtct   3060
```

```
gacgtgattg aaacattgcg gcatcagcac agtaaagacc tgcagaaggt tgtagacatt    3120
gtgttgtctc accagggtgt gaggaacaaa gctaagcttg taacggcact tatggaaaag    3180
ctggtttatc caaatcctgg tggttacagg gatctgttag ttcgcttttc ttccctcaat    3240
cataaaagat attataagtt ggcccttaaa gcaagtgaac ttcttgaaca aaccaaacta    3300
agtgaactcc gtgcaagcgt tgcaagaagc ctttcggatc tggggatgca taagggagaa    3360
atgagtatta aggataacat ggaagattta gtctctgccc cattacctgt tgaagatgct    3420
ctgatttctt tgtttgatta cagtgatcga actgttcagc agaaagtgat tgagacatac    3480
atatcacgat tgtaccagcc tcatcttgta aaggatagca tccaaatgaa attcaaggaa    3540
tctggtgcta ttacttttg ggaattttat gaagggcatg ttgatactag aaatggacat    3600
ggggctatta ttggtgggaa gcgatggggt gccatggtcg ttctcaaatc acttgaatct    3660
gcgtcaacag ccattgtggc tgcattaaag gattcggcac agttcaacag ctctgagggc    3720
aacatgatgc acattgcatt attgagtgct gaaaatgaaa gtaatataag tggaataagt    3780
gatgatcaag ctcaacataa gatggaaaag cttagcaaga tactgaagga tactagcgtt    3840
gcaagtgatc tccaagctgc tggtttgaag gttataagtt gcattgttca aagagatgaa    3900
gctcgcatgc caatgcgcca cacattcctc tggttggatg acaagagttg ttatgaagaa    3960
gagcagattc tccggcatgt ggagcctccc ctctctacac ttcttgaatt ggataagttg    4020
aaggtgaaag gatacaatga aatgaagtat actccttcgc gtgaccgcca atggcatatc    4080
tacacactaa gaaatactga aaaccccaaa atgttgcata gggtgttttt ccgaactatt    4140
gtcaggcaac ccaatgcagg caacaagttt acatcggctc agatcagcga cgctgaagta    4200
ggatgtcccg aagaatctct ttcatttaca tcaaatagca tcttaagatc attgatgact    4260
gctattgaag aattagagct tcatgcaatt aggacaggtc attctcacat gtatttgtgc    4320
atactgaaag agcaaaagct tcttgacctc attccatttt cagggagtac aattgttgat    4380
gttggccaag atgaagctac cgcttgttca ctttttaaaat caatggcttt gaagatacat    4440
gagcttgttg gtgcaaggat gcatcatctg tctgtatgcc agtgggaggt gaaactcaag    4500
ttggactgtg atggccctgc aagtggtacc tggagagttg taactacaaa tgttactggt    4560
cacacctgca ccattgatat ataccgagaa gtggaggaaa tagaatcgca gaagttagtg    4620
taccattcag ccacttcgtc agctggacca ttgcatggtg ttgcactgaa taatccatat    4680
caacctttga gtgtgattga tctaaagcgc tgctctgcta ggaacaacag aacaacatat    4740
tgctatgatt ttccgctggc ctttgaaact gcactgcaga agtcatggca gaccaatggc    4800
tctactgttt ctgaaggcaa tgaaaatagt aaatcctacg tgaaggcaac tgagctagtg    4860
tttgctgaaa acatgggtc ctggggcact cctataattc cgatggaacg ccctgctggg    4920
ctcaacgaca ttggtatggt cgcttggatc atggagatgt caacacctga atttcccaat    4980
ggcaggcaga ttattgttgt agcaaatgat atcacttttca gagctggatc atttggccca    5040
agggaagatg cattttttga aactgtcact aacctggctt gcgaaaggaa acttcctctt    5100
atatacttgg cagcaaactc tggtgctagg attggcatag ctgatgaagt aaaatcttgc    5160
ttccgtgttg atggtctga cgaaggcagt cctgaacgag ggtttcagta catctatctg    5220
actgaagaag actatgctcg cattagctct tctgttatag cacataagct ggagctagat    5280
agtggtgaaa ttaggtggat tattgactct gttgtgggca aggaggatgg gcttggtgtc    5340
gagaacatac atggaagtgc tgctattgcc agtgcttatt ctagggcata tgaggagaca    5400
```

| | |
|---|---|
| tttacactta catttgtgac tgggcggact gtaggaatag gagcttatct tgctcgactt | 5460 |
| ggtatacggt gcatacagcg tcttgaccag cctattattt taacagggtt ttctgccctg | 5520 |
| aacaagctcc ttgggcggga agtgtacagc tcccacatgc agcttggtgg tcctaagatc | 5580 |
| atggcgacta atggtgttgt ccacctcact gttccagatg accttgaagg tgtttccaat | 5640 |
| atattgaggt ggctcagcta tgttcctgca acattggtg gacctcttcc tattaccaaa | 5700 |
| cctctggacc ctccagacag acctgttgct tacatccctg agaacacatg cgatccacgt | 5760 |
| gcagctatct gtggtgtaga tgacagccaa gggaaatggt tgggtggtat gtttgacaaa | 5820 |
| gacagctttg tggagacatt tgaaggatgg gcaaaaacag tggttactgg cagagcaaag | 5880 |
| cttggaggaa ttcctgtggg cgtcatagct gtggagacac agaccatgat gcagatcatc | 5940 |
| cctgctgatc caggtcagct tgattcccat gagcgatctg tccctcgtgc tggacaagtg | 6000 |
| tggttcccag attctgcaac caagaccgct caggcattat tagacttcaa ccgtgaagga | 6060 |
| ttgcctctgt tcatcctggc taattggaga ggcttctctg gtggacaaag agatctcttt | 6120 |
| gaaggaattc ttcaggctgg gtcaacaatt gtcgagaacc ttaggacata taatcagcct | 6180 |
| gcttttgtgt acattcctat ggctggagag cttcgtggag gagcttgggt tgtggtcgat | 6240 |
| agcaaaataa atccagaccg cattgagtgt tatgctgaaa ggactgccaa aggtaatgtt | 6300 |
| ctcgaacctc aagggttaat tgaaatcaag ttcaggtcag aggaactcca agactgtatg | 6360 |
| ggtaggcttg acccagagtt gataaatctg aaagcaaaac tccaagatgt aaatcatgga | 6420 |
| aatggaagtc taccagacat agaagggatt cggaagagta tagaagcacg tacgaaacag | 6480 |
| ttgctgcctt tatataccca gattgcaata cggtttgctg aattgcatga acttcccta | 6540 |
| agaatggcag ctaaaggtgt gattaagaaa gttgtagact gggaagaatc acgctcgttc | 6600 |
| ttctataaaa ggctacggag gaggatcgca gaagatgttc ttgcaaaaga aataaggcag | 6660 |
| atagtcggtg ataaatttac gcaccaatta gcaatggagc tcatcaagga atggtacctt | 6720 |
| gcttctcagg ccacaacagg aagcactgga tgggatgacg atgatgcttt tgttgcctgg | 6780 |
| aaggacagtc ctgaaaacta caaggggcat atccaaaagc ttagggctca aaaagtgtct | 6840 |
| cattcgctct ctgatcttgc tgactccagt tcagatctgc aagcattctc gcagggtctt | 6900 |
| tctacgctat tagataagat ggatccctct cagagagcga agtttgttca ggaagtcaag | 6960 |
| aaggtccttg attga | 6975 |

<210> SEQ ID NO 14
<211> LENGTH: 2324
<212> TYPE: PRT
<213> ORGANISM: Zea mays

<400> SEQUENCE: 14

Met Ser Gln Leu Gly Leu Ala Ala Ala Ser Lys Ala Leu Pro Leu
1               5                   10                  15

Leu Pro Asn Arg Gln Arg Ser Ser Ala Gly Thr Thr Phe Ser Ser Ser
            20                  25                  30

Ser Leu Ser Arg Pro Leu Asn Arg Arg Lys Ser Arg Thr Arg Ser Leu
        35                  40                  45

Arg Asp Gly Gly Asp Gly Val Ser Asp Ala Lys Lys His Ser Gln Ser
    50                  55                  60

Val Arg Gln Gly Leu Ala Gly Ile Ile Asp Leu Pro Ser Glu Ala Pro
65                  70                  75                  80

Ser Glu Val Asp Ile Ser His Gly Ser Glu Asp Pro Arg Gly Pro Thr
                85                  90                  95

-continued

```
Asp Ser Tyr Gln Met Asn Gly Ile Ile Asn Glu Thr His Asn Gly Arg
                100                 105                 110

His Ala Ser Val Ser Lys Val Val Glu Phe Cys Ala Ala Leu Gly Gly
            115                 120                 125

Lys Thr Pro Ile His Ser Ile Leu Val Ala Asn Asn Gly Met Ala Ala
130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
                195                 200                 205

Glu Met Ala Gln Lys Leu Gly Val Ser Ala Val Trp Pro Gly Trp Gly
210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Ala Trp Ser Gly Ser His Val Glu Val Pro Leu Glu Cys Cys Leu Asp
                275                 280                 285

Ala Ile Pro Glu Glu Met Tyr Arg Lys Ala Cys Val Thr Thr Thr Glu
            290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Val Met Arg Leu Ala Ser Gln Ser Arg His Leu Glu
                355                 360                 365

Val Gln Leu Leu Cys Asp Gln Tyr Gly Asn Val Ala Ala Leu His Ser
370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Asp Tyr Tyr Phe Leu Glu Leu
                435                 440                 445

Asn Pro Arg Leu Gln Val Glu His Pro Val Thr Glu Trp Ile Ala Glu
            450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510
```

```
Phe Asp Glu Val Asp Ser Gln Trp Pro Lys Gly His Cys Val Ala Val
            515                 520                 525

Arg Ile Thr Ser Glu Asp Pro Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
            565                 570                 575

Phe Gly His Val Phe Ala Tyr Gly Leu Ser Arg Ser Ala Ala Ile Thr
            580                 585                 590

Asn Met Thr Leu Ala Leu Lys Glu Ile Gln Ile Arg Gly Glu Ile His
    595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Thr Asn Ala Ala Thr Val Ser Glu Tyr Val
                660                 665                 670

Ser Tyr Leu Thr Lys Gly Gln Ile Pro Pro Lys His Ile Ser Leu Val
    675                 680                 685

Asn Ser Thr Val Asn Leu Asn Ile Glu Gly Ser Lys Tyr Thr Ile Glu
    690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
                725                 730                 735

Gln Leu Asp Gly Asn Ser His Val Ile Tyr Ala Glu Glu Ala Gly
                740                 745                 750

Gly Thr Arg Leu Gln Ile Asp Gly Lys Thr Cys Leu Leu Gln Asn Asp
    755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Cys Met Met Ser Glu Gly Gln Ala Leu Gln Ala Gly
                820                 825                 830

Asp Leu Ile Ala Arg Leu Asp Leu Asp Asp Pro Ser Ala Val Lys Arg
    835                 840                 845

Ala Glu Pro Phe Asp Gly Ile Phe Pro Gln Met Glu Leu Pro Val Ala
    850                 855                 860

Val Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asn Pro Glu Leu Pro Phe Leu Gln Trp
                900                 905                 910

Asp Glu Leu Met Ser Val Leu Ala Thr Arg Leu Pro Arg Asn Leu Lys
    915                 920                 925

Ser Glu Leu Glu Asp Lys Tyr Lys Glu Tyr Lys Leu Asn Phe Tyr His
```

```
                930             935             940
Gly Lys Asn Glu Asp Phe Pro Ser Lys Leu Leu Arg Asp Ile Ile Glu
945             950             955             960
Glu Asn Leu Ser Tyr Gly Ser Glu Lys Glu Lys Ala Thr Asn Glu Arg
                965             970             975
Leu Val Glu Pro Leu Met Asn Leu Leu Lys Ser Tyr Glu Gly Gly Arg
            980             985             990
Glu Ser His Ala His Phe Val Val Lys Ser Leu Phe Glu Glu Tyr Leu
        995             1000            1005
Thr Val Glu Glu Leu Phe Ser Asp Gly Ile Gln Ser Asp Val Ile
1010            1015            1020
Glu Thr Leu Arg His Gln His Ser Lys Asp Leu Gln Lys Val Val
1025            1030            1035
Asp Ile Val Leu Ser His Gln Gly Val Arg Asn Lys Ala Lys Leu
1040            1045            1050
Val Thr Ala Leu Met Glu Lys Leu Val Tyr Pro Asn Pro Gly Gly
1055            1060            1065
Tyr Arg Asp Leu Leu Val Arg Phe Ser Ser Leu Asn His Lys Arg
1070            1075            1080
Tyr Tyr Lys Leu Ala Leu Lys Ala Ser Glu Leu Leu Glu Gln Thr
1085            1090            1095
Lys Leu Ser Glu Leu Arg Ala Ser Val Ala Arg Ser Leu Ser Asp
1100            1105            1110
Leu Gly Met His Lys Gly Glu Met Ser Ile Lys Asp Asn Met Glu
1115            1120            1125
Asp Leu Val Ser Ala Pro Leu Pro Val Glu Asp Ala Leu Ile Ser
1130            1135            1140
Leu Phe Asp Tyr Ser Asp Arg Thr Val Gln Gln Lys Val Ile Glu
1145            1150            1155
Thr Tyr Ile Ser Arg Leu Tyr Gln Pro His Leu Val Lys Asp Ser
1160            1165            1170
Ile Gln Met Lys Phe Lys Glu Ser Gly Ala Ile Thr Phe Trp Glu
1175            1180            1185
Phe Tyr Glu Gly His Val Asp Thr Arg Asn Gly His Gly Ala Ile
1190            1195            1200
Ile Gly Gly Lys Arg Trp Gly Ala Met Val Val Leu Lys Ser Leu
1205            1210            1215
Glu Ser Ala Ser Thr Ala Ile Val Ala Ala Leu Lys Asp Ser Ala
1220            1225            1230
Gln Phe Asn Ser Ser Glu Gly Asn Met Met His Ile Ala Leu Leu
1235            1240            1245
Ser Ala Glu Asn Glu Ser Asn Ile Ser Gly Ile Ser Asp Asp Gln
1250            1255            1260
Ala Gln His Lys Met Glu Lys Leu Ser Lys Ile Leu Lys Asp Thr
1265            1270            1275
Ser Val Ala Ser Asp Leu Gln Ala Ala Gly Leu Lys Val Ile Ser
1280            1285            1290
Cys Ile Val Gln Arg Asp Glu Ala Arg Met Pro Met Arg His Thr
1295            1300            1305
Phe Leu Trp Leu Asp Asp Lys Ser Cys Tyr Glu Glu Glu Gln Ile
1310            1315            1320
Leu Arg His Val Glu Pro Pro Leu Ser Thr Leu Leu Glu Leu Asp
1325            1330            1335
```

```
Lys Leu Lys Val Lys Gly Tyr Asn Glu Met Lys Tyr Thr Pro Ser
1340                1345                1350

Arg Asp Arg Gln Trp His Ile Tyr Thr Leu Arg Asn Thr Glu Asn
1355                1360                1365

Pro Lys Met Leu His Arg Val Phe Phe Arg Thr Ile Val Arg Gln
1370                1375                1380

Pro Asn Ala Gly Asn Lys Phe Thr Ser Ala Gln Ile Ser Asp Ala
1385                1390                1395

Glu Val Gly Cys Pro Glu Glu Ser Leu Ser Phe Thr Ser Asn Ser
1400                1405                1410

Ile Leu Arg Ser Leu Met Thr Ala Ile Glu Glu Leu Glu Leu His
1415                1420                1425

Ala Ile Arg Thr Gly His Ser His Met Tyr Leu Cys Ile Leu Lys
1430                1435                1440

Glu Gln Lys Leu Leu Asp Leu Ile Pro Phe Ser Gly Ser Thr Ile
1445                1450                1455

Val Asp Val Gly Gln Asp Glu Ala Thr Ala Cys Ser Leu Leu Lys
1460                1465                1470

Ser Met Ala Leu Lys Ile His Glu Leu Val Gly Ala Arg Met His
1475                1480                1485

His Leu Ser Val Cys Gln Trp Glu Val Lys Leu Lys Leu Asp Cys
1490                1495                1500

Asp Gly Pro Ala Ser Gly Thr Trp Arg Val Val Thr Thr Asn Val
1505                1510                1515

Thr Gly His Thr Cys Thr Ile Asp Ile Tyr Arg Glu Val Glu Glu
1520                1525                1530

Ile Glu Ser Gln Lys Leu Val Tyr His Ser Ala Thr Ser Ser Ala
1535                1540                1545

Gly Pro Leu His Gly Val Ala Leu Asn Asn Pro Tyr Gln Pro Leu
1550                1555                1560

Ser Val Ile Asp Leu Lys Arg Cys Ser Ala Arg Asn Asn Arg Thr
1565                1570                1575

Thr Tyr Cys Tyr Asp Phe Pro Leu Ala Phe Glu Thr Ala Leu Gln
1580                1585                1590

Lys Ser Trp Gln Thr Asn Gly Ser Thr Val Ser Glu Gly Asn Glu
1595                1600                1605

Asn Ser Lys Ser Tyr Val Lys Ala Thr Glu Leu Val Phe Ala Glu
1610                1615                1620

Lys His Gly Ser Trp Gly Thr Pro Ile Ile Pro Met Glu Arg Pro
1625                1630                1635

Ala Gly Leu Asn Asp Ile Gly Met Val Ala Trp Ile Met Glu Met
1640                1645                1650

Ser Thr Pro Glu Phe Pro Asn Gly Arg Gln Ile Ile Val Val Ala
1655                1660                1665

Asn Asp Ile Thr Phe Arg Ala Gly Ser Phe Gly Pro Arg Glu Asp
1670                1675                1680

Ala Phe Phe Glu Thr Val Thr Asn Leu Ala Cys Glu Arg Lys Leu
1685                1690                1695

Pro Leu Ile Tyr Leu Ala Ala Asn Ser Gly Ala Arg Ile Gly Ile
1700                1705                1710

Ala Asp Glu Val Lys Ser Cys Phe Arg Val Gly Trp Ser Asp Glu
1715                1720                1725
```

```
Gly Ser Pro Glu Arg Gly Phe Gln Tyr Ile Tyr Leu Thr Glu Glu
    1730                1735                1740

Asp Tyr Ala Arg Ile Ser Ser Val Ile Ala His Lys Leu Glu
    1745                1750                1755

Leu Asp Ser Gly Glu Ile Arg Trp Ile Ile Asp Ser Val Val Gly
    1760                1765                1770

Lys Glu Asp Gly Leu Gly Val Glu Asn Ile His Gly Ser Ala Ala
    1775                1780                1785

Ile Ala Ser Ala Tyr Ser Arg Ala Tyr Glu Glu Thr Phe Thr Leu
    1790                1795                1800

Thr Phe Val Thr Gly Arg Thr Val Gly Ile Gly Ala Tyr Leu Ala
    1805                1810                1815

Arg Leu Gly Ile Arg Cys Ile Gln Arg Leu Asp Gln Pro Ile Ile
    1820                1825                1830

Leu Thr Gly Phe Ser Ala Leu Asn Lys Leu Leu Gly Arg Glu Val
    1835                1840                1845

Tyr Ser Ser His Met Gln Leu Gly Gly Pro Lys Ile Met Ala Thr
    1850                1855                1860

Asn Gly Val Val His Leu Thr Val Pro Asp Asp Leu Glu Gly Val
    1865                1870                1875

Ser Asn Ile Leu Arg Trp Leu Ser Tyr Val Pro Ala Asn Ile Gly
    1880                1885                1890

Gly Pro Leu Pro Ile Thr Lys Pro Leu Asp Pro Pro Asp Arg Pro
    1895                1900                1905

Val Ala Tyr Ile Pro Glu Asn Thr Cys Asp Pro Arg Ala Ala Ile
    1910                1915                1920

Cys Gly Val Asp Asp Ser Gln Gly Lys Trp Leu Gly Gly Met Phe
    1925                1930                1935

Asp Lys Asp Ser Phe Val Glu Thr Phe Glu Gly Trp Ala Lys Thr
    1940                1945                1950

Val Val Thr Gly Arg Ala Lys Leu Gly Gly Ile Pro Val Gly Val
    1955                1960                1965

Ile Ala Val Glu Thr Gln Thr Met Met Gln Ile Ile Pro Ala Asp
    1970                1975                1980

Pro Gly Gln Leu Asp Ser His Glu Arg Ser Val Pro Arg Ala Gly
    1985                1990                1995

Gln Val Trp Phe Pro Asp Ser Ala Thr Lys Thr Ala Gln Ala Leu
    2000                2005                2010

Leu Asp Phe Asn Arg Glu Gly Leu Pro Leu Phe Ile Leu Ala Asn
    2015                2020                2025

Trp Arg Gly Phe Ser Gly Gly Gln Arg Asp Leu Phe Glu Gly Ile
    2030                2035                2040

Leu Gln Ala Gly Ser Thr Ile Val Glu Asn Leu Arg Thr Tyr Asn
    2045                2050                2055

Gln Pro Ala Phe Val Tyr Ile Pro Met Ala Gly Glu Leu Arg Gly
    2060                2065                2070

Gly Ala Trp Val Val Asp Ser Lys Ile Asn Pro Asp Arg Ile
    2075                2080                2085

Glu Cys Tyr Ala Glu Arg Thr Ala Lys Gly Asn Val Leu Glu Pro
    2090                2095                2100

Gln Gly Leu Ile Glu Ile Lys Phe Arg Ser Glu Glu Leu Gln Asp
    2105                2110                2115

Cys Met Gly Arg Leu Asp Pro Glu Leu Ile Asn Leu Lys Ala Lys
```

| | | | | | | | | | | |
|---|---|---|---|---|---|---|---|---|---|---|
| | | 2120 | | | 2125 | | | 2130 | | |

Leu Gln Asp Val Asn His Gly Asn Gly Ser Leu Pro Asp Ile Glu
         2135                   2140                  2145

Gly Ile Arg Lys Ser Ile Glu Ala Arg Thr Lys Gln Leu Leu Pro
    2150                   2155                 2160

Leu Tyr Thr Gln Ile Ala Ile Arg Phe Ala Glu Leu His Asp Thr
    2165                   2170                 2175

Ser Leu Arg Met Ala Ala Lys Gly Val Ile Lys Val Val Asp
    2180                   2185                 2190

Trp Glu Glu Ser Arg Ser Phe Phe Tyr Lys Arg Leu Arg Arg Arg
    2195                   2200                 2205

Ile Ala Glu Asp Val Leu Ala Lys Glu Ile Arg Gln Ile Val Gly
    2210                   2215                 2220

Asp Lys Phe Thr His Gln Leu Ala Met Glu Leu Ile Lys Glu Trp
    2225                   2230                 2235

Tyr Leu Ala Ser Gln Ala Thr Thr Gly Ser Thr Gly Trp Asp Asp
    2240                   2245                 2250

Asp Asp Ala Phe Val Ala Trp Lys Asp Ser Pro Glu Asn Tyr Lys
    2255                   2260                 2265

Gly His Ile Gln Lys Leu Arg Ala Gln Lys Val Ser His Ser Leu
    2270                   2275                 2280

Ser Asp Leu Ala Asp Ser Ser Ser Asp Leu Gln Ala Phe Ser Gln
    2285                   2290                 2295

Gly Leu Ser Thr Leu Leu Asp Lys Met Asp Pro Ser Gln Arg Ala
    2300                   2305                 2310

Lys Phe Val Gln Glu Val Lys Lys Val Leu Asp
    2315                   2320

<210> SEQ ID NO 15
<211> LENGTH: 6936
<212> TYPE: DNA
<213> ORGANISM: Triticum aestivum

<400> SEQUENCE: 15

| | |
|---|---|
| atgggatcca cacatttgcc cattgtcggc cttaatgcct cgacaacacc atcgctatcc | 60 |
| actattcgcc cggtaaattc agccggtgct gcattccaac catctgcccc ttctagaacc | 120 |
| tccaagaaga aaagtcgtcg tgttcagtca ttaaggatg gaggcgatgg aggcgtgtca | 180 |
| gaccctaacc agtctattcg ccaaggtctt gccggcatca ttgacctccc aaaggagggc | 240 |
| acatcagctc cggaagtgga tatttcacat gggtccgaag aacccagggg ctcctaccaa | 300 |
| atgaatggga tactgaatga agcacataat gggaggcatg cttcgctgtc taaggttgtc | 360 |
| gaattttgta tggcattggg cggcaaaaca ccaattcaca gtgtattagt tgcgaacaat | 420 |
| ggaatggcag cagctaagtt catgcggagt gtccgaacat gggctaatga acatttggg | 480 |
| tcagagaagg caattcagtt gatagctatg ctactccag aagacatgag ataaatgca | 540 |
| gagcacatta gaattgctga tcaatttgtt gaagtacccg gtggaacaaa caataacaac | 600 |
| tatgcaaatg tccaactcat agtggagata gcagtgagaa ccggtgtttc tgctgtttgg | 660 |
| cctggttggg gccatgcatc tgagaatcct gaacttccag atgcactaaa tgcaaacgga | 720 |
| attgttttc ttgggccacc atcatcatca atgaacgcac taggtgacaa ggttggttca | 780 |
| gctctcattg ctcaagcagc aggggttccg actcttcctt ggagtggatc acaggtggaa | 840 |
| attccattag aagtttgttt ggactcgata cccgcggaga tgtataggaa agcttgtgtt | 900 |

```
agtactacgg aggaagcact tgcgagttgt cagatgattg ggtatcccgc catgattaaa      960
gcatcatggg gtggtggtgg taaagggatc cgaaaggtta ataatgacga tgatgtcaga     1020
gcactgttta agcaagtgca aggtgaagtt cctggctccc caatatttat catgagactt     1080
gcatctcaga gtcgacatct tgaagttcag ttgctttgtg atcaatatgg caatgtagct     1140
gcgcttcaca gtcgtgactg cagtgtgcaa cggcgacacc aaaagattat tgaggaagga     1200
ccagttactt ttgctcctcg cgagacagtg aaagagctag agcaagcagc aaggaggctt     1260
gctaaggctg tgggttatgt tggtgctgct actgttgaat atctctacag catggagact     1320
ggtgaatact attttctgga acttaatcca cggttgcagg ttgagcatcc agtcaccgag     1380
tggatagctg aagtaaactt gcctgcagct caagttgcag ttggaatggg tatacccctt     1440
tggcaggttc cagagatcag acgtttctat ggaatggaca atggaggagg ctatgacatt     1500
tggaggaaaa cagcagctct tgctactcca tttaacttcg atgaagtgga ttctcaatgg     1560
ccaaagggtc attgtgtagc agttaggata accagtgagg atccagatga cggattcaag     1620
cctaccggtg gaaaagtaaa ggagatcagt tttaaaagca agccaaatgt ttgggcctat     1680
ttctctgtta gtccggtgg aggcattcat gaatttgctg attctcagtt tggacatgtt     1740
tttgcatatg gagtgtctag agcagcagca ataaccaaca tgtctcttgc gctaaaagag     1800
attcaaattc gtggagaaat tcattcaaat gttgattaca cagttgatct cttgaatgcc     1860
tcagacttca agaaaacag gattcatact ggctggctgg ataacagaat agcaatgcga     1920
gtccaagctg agagacctcc gtggtatatt tcagtggttg gaggagctct atataaaaca     1980
ataacgagca cacagacac tgtttctgaa tatgttagct atctcgtcaa gggtcagatt     2040
ccaccgaagc atatatccct tgtccattca actgtttctt tgaatataga ggaaagcaaa     2100
tatacaattg aaactataag gagcggacag ggtagctaca gattgcgaat gaatggatca     2160
gttattgaag caaatgtcca acattatgt gatggtggac ttttaatgca gttggatgga     2220
aacagccatg taatttatgc tgaagaagag gccggtggta cacggcttct aattgatgga     2280
aagacatgct tgttacagaa tgatcacgat ccttcaaggt tattagctga gacaccctgc     2340
aaacttcttc gtttcttggt tgccgatggt gctcatgttg aagctgatgt accatatgcg     2400
gaagttgagg ttatgaagat gtgcatgccc ctcttgtcac ctgctgctgg tgtcattaat     2460
gttttgttgt ctgagggcca gcctatgcag gctggtgatc ttatagcaag acttgatctt     2520
gatgacccctt ctgctgtgaa gagagctgag ccatttaacg gatctttccc agaaatgagc     2580
cttcctattg ctgcttctgg ccaagttcac aaaagatgtg ccacaagctt gaatgctgct     2640
cggatggtcc ttgcaggata tgatcacccg atcaacaaag ttgtacaaga tctggtatcc     2700
tgtctagatg ctcctgagct tccttttccta caatgggaag agcttatgtc tgttttagca     2760
actagacttc caaggcttct taagagcgag ttggaggta aatacagtga atataagtta     2820
aatgttggcc atgggaagag caaggatttc ccttccaaga tgctaagaga gataatcgag     2880
gaaaatcttg cacatggttc tgagaaggaa attgctacaa atgagaggct tgttgagcct     2940
cttatgagcc tactgaagtc atatgagggt ggcagagaaa gccatgcaca ctttattgtg     3000
aagtcccttt tcgaggacta tctctcggtt gaggaactat tcagtgatgg cattcagtct     3060
gatgtgattg aacgcctgcg ccaacaacat agtaaagatc tccagaaggt tgtagacatt     3120
gtgttgtctc accagggtgt gagaaacaaa actaagctga tactaacact catggagaaa     3180
ctggtctatc caaaccctgc tgtctacaag gatcagttga ctcgcttttc ctccctcaat     3240
cacaaaagat attataagtt ggcccttaaa gctagcgagc ttcttgaaca aaccaagctt     3300
```

```
agtgagctcc gcacaagcat tgcaaggagc ctttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattataccca gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat gcgccatacc    3900
ttcctcttgt cggatgaaaa gctttgttat gaggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatataca cacttagaaa tacagagaac    4080
cccaaaatgt tgcacagggt gttttttcga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
gcgattagga caggtcactc tcatatgttt ttgtgcatat tgaaagagca aaagcttctt    4320
gatcttgttc ccgtttcagg gaacaaagtt gtggatattg ccaagatgaa agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggtcg aagatacaga atcacagaaa ctagtgtacc actctgctcc atcgtcatct    4620
ggtcctttgc atggcgttgc actgaatact ccatatcagc ctttgagtgt tattgatctg    4680
aaacgttgct ccgctagaaa taacagaact acatactgct atgattttcc gttggcattt    4740
gaaactgcag tgcagaagtc atggtctaac atttctagtg cacactaaccg atgttatgtt    4800 aaagcgacgg agctggtgtt tgctcacaag aacgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tacttttaga    4980
gctggatcgt ttggtccaag ggaagatgca ttttttgaaa ctgttaccaa cctagcttgt    5040
gagaggaagc ttcctctcat ctacttggca gcaaactctg gtgctcggat cggcatagca    5100
gatgaagtaa aatcttgctt ccgtgttgga tggtctgatg atggcagccc tgaacgtggg    5160
tttcaatata tttatctgac tgaagaagac catgctcgta ttagcgcttc tgttatagcg    5220
cacaagatgc agcttgataa tgtgaaattt aggtgggtta ttgattctgt tgtagggaag    5280
gaggatgggc taggtgtgga aacatacat  ggaagtgctg ctattgccag tgcctattct    5340
agggcctatg aggagacatt tacgcttaca tttgtgactg gaaggactgt tggaatagga    5400
gcatatcttg ctcgacttgg catacggtgc atacagcgta ctgaccagcc cattatccta    5460
actgggttct ctgccttgaa caagcttctt ggccgggaag tttacagctc ccacatgcag    5520
ttgggtggcc ccaaaattat ggcgacaaac ggtgttgtcc atctgacagt ttcagatgac    5580
cttgaaggtg tatctaatat attgaggtgg ctcagctatg ttcctgccaa cattggtgga    5640
```

```
cctcttccta ttacaaaatc tttggaccca cctgacagac ccgttgctta catccctgag    5700
aatacatgcg atcctcgtgc tgccatcagt ggcattgatg atagccaagg gaaatggttg    5760
gggggcatgt tcgacaaaga cagttttgtg gagacatttg aaggatgggc gaagtcagtt    5820
gttactggca gagcgaaact cggagggatt ccggtgggtg ttatagctgt ggagacacag    5880
actatgatgc agctcatccc tgctgatcca ggccagcttg attcccatga gcgatctgtt    5940
cctcgtgctg ggcaagtctg gtttccagat tcagctacta agacagcgca ggcaatgctg    6000
gacttcaacc gtgaaggatt acctctgttc atccttgcta actggagagg cttctctggt    6060
ggacaaagag atcttttga aggaatcctt caggctgggt caacaattgt tgagaacctt    6120
aggacataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct cgaacctcaa gggttgatcg agatcaagtt caggtcagag    6300
gaactccaag agtgcatggg taggcttgat ccagaattga taaatctgaa ggcaaagctc    6360
cagggagtaa agcatgaaaa tggaagtcta cctgagtcag aatcccttca gaagagcata    6420
gaagcccgga gaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcgttctt ctacaagaga ttacggagga ggatatccga ggatgttctt    6600
gcgaaggaaa ttagaggtgt aagtggcaag cagtttctc accaatcggc aatcgagctg    6660
atccagaaat ggtacttggc ctctaaggga gctgaaacag gaagcactga atgggatgat    6720
gacgatgctt ttgttgcctg gagggaaaac cctgaaaact accaggagta tatcaaagaa    6780
ctcagggctc aaagggtatc tcagttgctc tcagatgttg cagactccag tccagatcta    6840
gaagccttgc cacagggtct ttctatgcta ttagagaaga tggatccctc aaggagagca    6900
cagtttgttg aggaagtcaa gaaagtcctt aaatga                               6936
```

<210> SEQ ID NO 16  
<211> LENGTH: 2311  
<212> TYPE: PRT  
<213> ORGANISM: Triticum aestivum

<400> SEQUENCE: 16

```
Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Met Ala Ala
    130                 135                 140
```

```
Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
            165                 170                 175

Arg Ile Asn Ala Glu His Ile Arg Ile Ala Asp Gln Phe Val Glu Val
        180                 185                 190

Pro Gly Gly Thr Asn Asn Asn Tyr Ala Asn Val Gln Leu Ile Val
    195                 200                 205

Glu Ile Ala Val Arg Thr Gly Val Ser Ala Val Trp Pro Gly Trp Gly
210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
            245                 250                 255

Lys Val Gly Ser Ala Leu Ile Ala Gln Ala Ala Gly Val Pro Thr Leu
            260                 265                 270

Pro Trp Ser Gly Ser Gln Val Glu Ile Pro Leu Glu Val Cys Leu Asp
        275                 280                 285

Ser Ile Pro Ala Glu Met Tyr Arg Lys Ala Cys Val Ser Thr Thr Glu
290                 295                 300

Glu Ala Leu Ala Ser Cys Gln Met Ile Gly Tyr Pro Ala Met Ile Lys
305                 310                 315                 320

Ala Ser Trp Gly Gly Gly Lys Gly Ile Arg Lys Val Asn Asn Asp
            325                 330                 335

Asp Asp Val Arg Ala Leu Phe Lys Gln Val Gln Gly Glu Val Pro Gly
        340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Glu Leu Glu Gln Ala
            405                 410                 415

Ala Arg Arg Leu Ala Lys Ala Val Gly Tyr Val Gly Ala Ala Thr Val
        420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
            485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
        530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
```

```
                565                 570                 575
Phe Gly His Val Phe Ala Tyr Gly Val Ser Arg Ala Ala Ile Thr
                580                 585                 590
Asn Met Ser Leu Ala Leu Lys Glu Ile Gln Ile Arg Gly Glu Ile His
                595                 600                 605
Ser Asn Val Asp Tyr Thr Val Asp Leu Leu Asn Ala Ser Asp Phe Lys
        610                 615                 620
Glu Asn Arg Ile His Thr Gly Trp Leu Asp Asn Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Ile Thr Ser Asn Thr Asp Thr Val Ser Glu Tyr Val
                660                 665                 670
Ser Tyr Leu Val Lys Gly Gln Ile Pro Pro Lys His Ile Ser Leu Val
                675                 680                 685
His Ser Thr Val Ser Leu Asn Ile Glu Glu Ser Lys Tyr Thr Ile Glu
        690                 695                 700
Thr Ile Arg Ser Gly Gln Gly Ser Tyr Arg Leu Arg Met Asn Gly Ser
705                 710                 715                 720
Val Ile Glu Ala Asn Val Gln Thr Leu Cys Asp Gly Gly Leu Leu Met
                725                 730                 735
Gln Leu Asp Gly Asn Ser His Val Ile Tyr Ala Glu Glu Ala Gly
                740                 745                 750
Gly Thr Arg Leu Leu Ile Asp Gly Lys Thr Cys Leu Leu Gln Asn Asp
            755                 760                 765
His Asp Pro Ser Arg Leu Leu Ala Glu Thr Pro Cys Lys Leu Leu Arg
        770                 775                 780
Phe Leu Val Ala Asp Gly Ala His Val Glu Ala Asp Val Pro Tyr Ala
785                 790                 795                 800
Glu Val Glu Val Met Lys Met Cys Met Pro Leu Leu Ser Pro Ala Ala
                805                 810                 815
Gly Val Ile Asn Val Leu Leu Ser Glu Gly Gln Pro Met Gln Ala Gly
                820                 825                 830
Asp Leu Ile Ala Arg Leu Asp Leu Asp Asp Pro Ser Ala Val Lys Arg
        835                 840                 845
Ala Glu Pro Phe Asn Gly Ser Phe Pro Glu Met Ser Leu Pro Ile Ala
850                 855                 860
Ala Ser Gly Gln Val His Lys Arg Cys Ala Thr Ser Leu Asn Ala Ala
865                 870                 875                 880
Arg Met Val Leu Ala Gly Tyr Asp His Pro Ile Asn Lys Val Val Gln
                885                 890                 895
Asp Leu Val Ser Cys Leu Asp Ala Pro Glu Leu Pro Phe Leu Gln Trp
            900                 905                 910
Glu Glu Leu Met Ser Val Leu Ala Thr Arg Leu Pro Arg Leu Leu Lys
            915                 920                 925
Ser Glu Leu Glu Gly Lys Tyr Ser Glu Tyr Lys Leu Asn Val Gly His
        930                 935                 940
Gly Lys Ser Lys Asp Phe Pro Ser Lys Met Leu Arg Glu Ile Ile Glu
945                 950                 955                 960
Glu Asn Leu Ala His Gly Ser Glu Lys Glu Ile Ala Thr Asn Glu Arg
                965                 970                 975
Leu Val Glu Pro Leu Met Ser Leu Leu Lys Ser Tyr Glu Gly Gly Arg
        980                 985                 990
```

-continued

```
Glu Ser His Ala His Phe Ile Val Lys Ser Leu Phe Glu Asp Tyr Leu
        995                 1000                1005

Ser Val Glu Glu Leu Phe Ser Asp Gly Ile Gln Ser Asp Val Ile
    1010                1015                1020

Glu Arg Leu Arg Gln Gln His Ser Lys Asp Leu Gln Lys Val Val
    1025                1030                1035

Asp Ile Val Leu Ser His Gln Gly Val Arg Asn Lys Thr Lys Leu
    1040                1045                1050

Ile Leu Thr Leu Met Glu Lys Leu Val Tyr Pro Asn Pro Ala Val
    1055                1060                1065

Tyr Lys Asp Gln Leu Thr Arg Phe Ser Ser Leu Asn His Lys Arg
    1070                1075                1080

Tyr Tyr Lys Leu Ala Leu Lys Ala Ser Glu Leu Leu Glu Gln Thr
    1085                1090                1095

Lys Leu Ser Glu Leu Arg Thr Ser Ile Ala Arg Ser Leu Ser Glu
    1100                1105                1110

Leu Glu Met Phe Thr Glu Glu Arg Thr Ala Ile Ser Glu Ile Met
    1115                1120                1125

Gly Asp Leu Val Thr Ala Pro Leu Pro Val Glu Asp Ala Leu Val
    1130                1135                1140

Ser Leu Phe Asp Cys Ser Asp Gln Thr Leu Gln Gln Arg Val Ile
    1145                1150                1155

Glu Thr Tyr Ile Ser Arg Leu Tyr Gln Pro His Leu Val Lys Asp
    1160                1165                1170

Ser Ile Gln Leu Lys Tyr Gln Glu Ser Gly Val Ile Ala Leu Trp
    1175                1180                1185

Glu Phe Ala Glu Ala His Ser Glu Lys Arg Leu Gly Ala Met Val
    1190                1195                1200

Ile Val Lys Ser Leu Glu Ser Val Ser Ala Ala Ile Gly Ala Ala
    1205                1210                1215

Leu Lys Gly Thr Ser Arg Tyr Ala Ser Ser Glu Gly Asn Ile Met
    1220                1225                1230

His Ile Ala Leu Leu Gly Ala Asp Asn Gln Met His Gly Thr Glu
    1235                1240                1245

Asp Ser Gly Asp Asn Asp Gln Ala Gln Val Arg Ile Asp Lys Leu
    1250                1255                1260

Ser Ala Thr Leu Glu Gln Asn Thr Val Thr Ala Asp Leu Arg Ala
    1265                1270                1275

Ala Gly Val Lys Val Ile Ser Cys Ile Val Gln Arg Asp Gly Ala
    1280                1285                1290

Leu Met Pro Met Arg His Thr Phe Leu Leu Ser Asp Glu Lys Leu
    1295                1300                1305

Cys Tyr Glu Glu Glu Pro Val Leu Arg His Val Glu Pro Pro Leu
    1310                1315                1320

Ser Ala Leu Leu Glu Leu Gly Lys Leu Lys Val Lys Gly Tyr Asn
    1325                1330                1335

Glu Val Lys Tyr Thr Pro Ser Arg Asp Arg Gln Trp Asn Ile Tyr
    1340                1345                1350

Thr Leu Arg Asn Thr Glu Asn Pro Lys Met Leu His Arg Val Phe
    1355                1360                1365

Phe Arg Thr Leu Val Arg Gln Pro Gly Ala Ser Asn Lys Phe Thr
    1370                1375                1380
```

```
Ser Gly Asn Ile Ser Asp Val Glu Val Gly Gly Ala Glu Glu Ser
    1385                1390                1395

Leu Ser Phe Thr Ser Ser Ser Ile Leu Arg Ser Leu Met Thr Ala
    1400                1405                1410

Ile Glu Glu Leu Glu Leu His Ala Ile Arg Thr Gly His Ser His
    1415                1420                1425

Met Phe Leu Cys Ile Leu Lys Glu Gln Lys Leu Leu Asp Leu Val
    1430                1435                1440

Pro Val Ser Gly Asn Lys Val Val Asp Ile Gly Gln Asp Glu Ala
    1445                1450                1455

Thr Ala Cys Leu Leu Leu Lys Glu Met Ala Leu Gln Ile His Glu
    1460                1465                1470

Leu Val Gly Ala Arg Met His His Leu Ser Val Cys Gln Trp Glu
    1475                1480                1485

Val Lys Leu Lys Leu Asp Ser Asp Gly Pro Ala Ser Gly Thr Trp
    1490                1495                1500

Arg Val Val Thr Thr Asn Val Thr Ser His Thr Cys Thr Val Asp
    1505                1510                1515

Ile Tyr Arg Glu Val Glu Asp Thr Glu Ser Gln Lys Leu Val Tyr
    1520                1525                1530

His Ser Ala Pro Ser Ser Ser Gly Pro Leu His Gly Val Ala Leu
    1535                1540                1545

Asn Thr Pro Tyr Gln Pro Leu Ser Val Ile Asp Leu Lys Arg Cys
    1550                1555                1560

Ser Ala Arg Asn Asn Arg Thr Thr Tyr Cys Tyr Asp Phe Pro Leu
    1565                1570                1575

Ala Phe Glu Thr Ala Val Gln Lys Ser Trp Ser Asn Ile Ser Ser
    1580                1585                1590

Asp Thr Asn Arg Cys Tyr Val Lys Ala Thr Glu Leu Val Phe Ala
    1595                1600                1605

His Lys Asn Gly Ser Trp Gly Thr Pro Val Ile Pro Met Glu Arg
    1610                1615                1620

Pro Ala Gly Leu Asn Asp Ile Gly Met Val Ala Trp Ile Leu Asp
    1625                1630                1635

Met Ser Thr Pro Glu Tyr Pro Asn Gly Arg Gln Ile Val Val Ile
    1640                1645                1650

Ala Asn Asp Ile Thr Phe Arg Ala Gly Ser Phe Gly Pro Arg Glu
    1655                1660                1665

Asp Ala Phe Phe Glu Thr Val Thr Asn Leu Ala Cys Glu Arg Lys
    1670                1675                1680

Leu Pro Leu Ile Tyr Leu Ala Ala Asn Ser Gly Ala Arg Ile Gly
    1685                1690                1695

Ile Ala Asp Glu Val Lys Ser Cys Phe Arg Val Gly Trp Ser Asp
    1700                1705                1710

Asp Gly Ser Pro Glu Arg Gly Phe Gln Tyr Ile Tyr Leu Thr Glu
    1715                1720                1725

Glu Asp His Ala Arg Ile Ser Ala Ser Val Ile Ala His Lys Met
    1730                1735                1740

Gln Leu Asp Asn Gly Glu Ile Arg Trp Val Ile Asp Ser Val Val
    1745                1750                1755

Gly Lys Glu Asp Gly Leu Gly Val Glu Asn Ile His Gly Ser Ala
    1760                1765                1770

Ala Ile Ala Ser Ala Tyr Ser Arg Ala Tyr Glu Glu Thr Phe Thr
```

```
                    1775                1780                1785
Leu Thr  Phe Val Thr Gly Arg  Thr Val Gly Ile Gly  Ala Tyr Leu
    1790                1795                1800

Ala Arg  Leu Gly Ile Arg Cys  Ile Gln Arg Thr Asp  Gln Pro Ile
    1805                1810                1815

Ile Leu  Thr Gly Phe Ser Ala  Leu Asn Lys Leu Leu  Gly Arg Glu
    1820                1825                1830

Val Tyr  Ser Ser His Met Gln  Leu Gly Gly Pro Lys  Ile Met Ala
    1835                1840                1845

Thr Asn  Gly Val Val His Leu  Thr Val Ser Asp Asp  Leu Glu Gly
    1850                1855                1860

Val Ser  Asn Ile Leu Arg Trp  Leu Ser Tyr Val Pro  Ala Asn Ile
    1865                1870                1875

Gly Gly  Pro Leu Pro Ile Thr  Lys Ser Leu Asp Pro  Pro Asp Arg
    1880                1885                1890

Pro Val  Ala Tyr Ile Pro Glu  Asn Thr Cys Asp Pro  Arg Ala Ala
    1895                1900                1905

Ile Ser  Gly Ile Asp Asp Ser  Gln Gly Lys Trp Leu  Gly Gly Met
    1910                1915                1920

Phe Asp  Lys Asp Ser Phe Val  Glu Thr Phe Glu Gly  Trp Ala Lys
    1925                1930                1935

Ser Val  Val Thr Gly Arg Ala  Lys Leu Gly Gly Ile  Pro Val Gly
    1940                1945                1950

Val Ile  Ala Val Glu Thr Gln  Thr Met Met Gln Leu  Ile Pro Ala
    1955                1960                1965

Asp Pro  Gly Gln Leu Asp Ser  His Glu Arg Ser Val  Pro Arg Ala
    1970                1975                1980

Gly Gln  Val Trp Phe Pro Asp  Ser Ala Thr Lys Thr  Ala Gln Ala
    1985                1990                1995

Met Leu  Asp Phe Asn Arg Glu  Gly Leu Pro Leu Phe  Ile Leu Ala
    2000                2005                2010

Asn Trp  Arg Gly Phe Ser Gly  Gly Gln Arg Asp Leu  Phe Glu Gly
    2015                2020                2025

Ile Leu  Gln Ala Gly Ser Thr  Ile Val Glu Asn Leu  Arg Thr Tyr
    2030                2035                2040

Asn Gln  Pro Ala Phe Val Tyr  Ile Pro Lys Ala Ala  Glu Leu Arg
    2045                2050                2055

Gly Gly  Ala Trp Val Val Ile  Asp Ser Lys Ile Asn  Pro Asp Arg
    2060                2065                2070

Ile Glu  Phe Tyr Ala Glu Arg  Thr Ala Lys Gly Asn  Val Leu Glu
    2075                2080                2085

Pro Gln  Gly Leu Ile Glu Ile  Lys Phe Arg Ser Glu  Glu Leu Gln
    2090                2095                2100

Glu Cys  Met Gly Arg Leu Asp  Pro Glu Leu Ile Asn  Leu Lys Ala
    2105                2110                2115

Lys Leu  Gln Gly Val Lys His  Glu Asn Gly Ser Leu  Pro Glu Ser
    2120                2125                2130

Glu Ser  Leu Gln Lys Ser Ile  Glu Ala Arg Lys Lys  Gln Leu Leu
    2135                2140                2145

Pro Leu  Tyr Thr Gln Ile Ala  Val Arg Phe Ala Glu  Leu His Asp
    2150                2155                2160

Thr Ser  Leu Arg Met Ala Ala  Lys Gly Val Ile Lys  Lys Val Val
    2165                2170                2175
```

| | | | | | | | | | |
|---|---|---|---|---|---|---|---|---|---|
| Asp | Trp | Glu | Asp | Ser | Arg | Ser | Phe | Phe | Tyr | Lys | Arg | Leu | Arg | Arg |
| | 2180 | | | | 2185 | | | | 2190 | | | |

```
Asp Trp Glu Asp Ser Arg Ser Phe Phe Tyr Lys Arg Leu Arg Arg
    2180                2185                2190

Arg Ile Ser Glu Asp Val Leu Ala Lys Glu Ile Arg Gly Val Ser
    2195                2200                2205

Gly Lys Gln Phe Ser His Gln Ser Ala Ile Glu Leu Ile Gln Lys
    2210                2215                2220

Trp Tyr Leu Ala Ser Lys Gly Ala Glu Thr Gly Ser Thr Glu Trp
    2225                2230                2235

Asp Asp Asp Asp Ala Phe Val Ala Trp Arg Glu Asn Pro Glu Asn
    2240                2245                2250

Tyr Gln Glu Tyr Ile Lys Glu Leu Arg Ala Gln Arg Val Ser Gln
    2255                2260                2265

Leu Leu Ser Asp Val Ala Asp Ser Ser Pro Asp Leu Glu Ala Leu
    2270                2275                2280

Pro Gln Gly Leu Ser Met Leu Leu Glu Lys Met Asp Pro Ser Arg
    2285                2290                2295

Arg Ala Gln Phe Val Glu Glu Val Lys Lys Val Leu Lys
    2300                2305                2310
```

<210> SEQ ID NO 17
<211> LENGTH: 6966
<212> TYPE: DNA
<213> ORGANISM: Setaria italica

<400> SEQUENCE: 17

| | |
|---|---|
| atgtcgcaac ttggattagc tgcagctgcc tcaaaggcgc tgccactact tcctaatcgc | 60 |
| catagaactt cagctggaac tacattccca tcacctgtat catcgcggcc ctcaaaccga | 120 |
| aggaaaagcc gcactcgttc acttcgtgat ggaggagatg gggtatcaga tgccaaaaag | 180 |
| cacaaccagt ctgtccgtca aggtcttgct ggcatcatcg acctcccaaa tgaggcaaca | 240 |
| tcggaagtgg atatttctca tggatccgag atcccagggg gccaaccga ttcatatcaa | 300 |
| atgaatggga ttgtaagtga agcacataat ggcagacatg cctcagtgtc caaggttgtt | 360 |
| gaattttgtg cggcgctagg tggcaaaaca ccaattcaca gtatactagt ggccaacaat | 420 |
| ggaatggcag cagcaaagtt catgaggagt gtccggacat gggctaatga cttttgga | 480 |
| tcggagaagg cgattcagct catagctatg caactccag aagacatgag ataaatgca | 540 |
| gaacacatta gaattgctga tcaatttgtg gaggtgcctg gtggaacaaa caataacaac | 600 |
| tatgcaaatg ttcaactcat agtggaggta gcagaaagaa taggtgtttc tgctgttgg | 660 |
| cctggttggg gtcatgcttc tgagaatcct gaacttccag atgcattgac cgcaaaagga | 720 |
| gttgttttcc ttgggccacc tgcggcatca atgaatgcat gggagataa ggtcggttca | 780 |
| gctctcattg ctcaagcagc tggggtcccg acccttcgt ggagtggatc acatgttgaa | 840 |
| gttccattag agtgctgctt agatgcgata cctgaggaaa tgtatagaaa gcttgtgtt | 900 |
| actaccacag aagaagctgt tgcgagttgt caggtggttg ttatcctgc catgattaag | 960 |
| gcatcctggg gaggtggtgg taaaggaata agaaaggttc ataatgacga tgaggttaga | 1020 |
| gcactgttta gcaagtaca aggtgaagtc cctggctccc caatatttat catgaggctt | 1080 |
| gcatcccaga gtcgtcatct tgaagttcag ttgctttgtg atcaatatgg caatgtggca | 1140 |
| gcacttcaca gtcgtgattg cagtgtgcaa cggcgacacc aaaagattat tgaggaaggc | 1200 |
| ccagttactg ttgctcctcg tgagacagtt aaagcgcttg agcaggcagc aaggaggctt | 1260 |
| gctaaggctg tgggttatgt tggtgctgct actgttgaat acctttacag catggagact | 1320 |

```
gggaatact attttctgga gcttaatccc agattacagg tcgagcatcc agtcactgag    1380
tggattgctg aagtaaatct tcctgcagct caagttgcag ttggaatggg catacctctt    1440
tggcagattc cagaaatcag acgtttcgat ggaatggact atggaggagg atatgacatt    1500
tggaggaaaa cagcagctct tgccacacca tttaattttg atgaagtaga ttctcaatgg    1560
ccaaagggcc attgtgtagc agttagaatt actagcgagg atccagatga tggtttcaaa    1620
cctactggtg ggaaagtgaa ggagataagt tttaaaagca agcctaatgt ttgggcctac    1680
ttctcagtaa agtctggtgg aggcattcat gaatttgttg attctcagtt tgggcatgtt    1740
tttgcatatg ggctctctag atcagcagca ataacgaaca tggctcttgc attaaaagag    1800
attcaaattc gtggagaaat tcattcaaat gttgattaca cagttgatct cttaaatgct    1860
tcagacttca gagaaaataa gattcatact ggctggcttg ataccagaat agctatgcgt    1920
gttcaagctg agaggccccc atggtatatt tcagtggttg gaggagctct atataaaaca    1980
gtaactgcca atgcagccac tgtttctgat tatgtcagtt atctcaccaa gggccagatt    2040
ccaccaaagc atatatccct tgtcagttca acagttaatc tgaatatcga agggagcaaa    2100
tacacagttg aaactgtaag gactggacat ggtagctaca gattacgaat gaatgattca    2160
gcaattgaag cgaatgtaca atccttatgt gatggaggcc tcttaatgca gttggatgga    2220
aatagccatg taatttacgc ggaagaagaa gctggtggta cacgacttct gattgatgga    2280
aagacatgct tgttacagaa tgatcatgat ccatcaaagt tattagctga gacaccctgc    2340
aaacttcttc ggttcttggt tgctgatggt gcccatgttg atgctgatgt accatatgcg    2400
gaagttgagg ttatgaaaat gtgcatgcct ctcttgtcgc ctgcttctgg tgtcattcat    2460
gttatgatgt ctgagggcca ggcattgcag gctggtgatc ttatagcaag gctggatctt    2520 gatgacccttctgctgtgaa aagagctgaa ccatttcatg gaatatttcc acaaatggac    2580
cttcctgttg ctgcctctag ccaagtacac aaaagatatg ctgcaagttg gaatgctgct    2640
cgaatggtcc ttgcaggata cgagcataat atcaatgaag ttgtacaaga tttggtatgc    2700
tgcctggatg atcccgagct tcccttccta cagtgggatg aacttatgtc agttctagca    2760
actaggcttc caagaaatct taagagtgag ttagaggata aatacatgga atacaagttg    2820
aacttttacc atgggaaaaa caaggacttc ccgtccaagc tgctgagaga catcattgag    2880
gcaaatcttg catatggttc agagaaggaa aaagctacga atgagaggct tattgagcct    2940
cttatgagcc tacttaagtc atatgagggt gggagagaaa gccatgctca ttttgttgtc    3000
aagtcccttt tcaaggagta ccttgctgtg aagaactttt cagtgatgg gattcagtct    3060 gatgtgattg aaaccctgcg tcatcagcac agtaaagact tgcagaaggt tgtagacatt    3120
gtgttgtctc accagggtgt gaggaacaaa gctaagcttg taacagcact tatggaaaag    3180
ctggtttatc caaatcctgc tgcttacagg gatctgttgg ttcgcttttc ttcactcaat    3240
cataaaagat attataagtt ggcccttaaa gcaagcgaac ttcttgaaca aactaaacta    3300
agtgaactcc gtgcaagcat cgcaagaagc ctttctgatc tggggatgca taagggagaa    3360
atgactattg aagatagcat ggaagattta gtctctgccc cattacctgt cgaagatgca    3420
cttatttctt tgtttgatta cagtgatcca actgttcagc agaaagtgat cgagacatac    3480
atatctcgat tgtatcagcc tcttcttgtg aaagatagca tccaagtgaa atttaaggaa    3540
tctggtgcct ttgcttatgg gaattttct gaagggcatg ttgatactaa aaatggacaa    3600
gggaccgttc ttggtcgaac aagatggggt gccatggtag ctgtcaaatc agttgaatct    3660
```

-continued

```
gcacgaacag ccattgtagc tgcattaaag gattcggcac agcatgccag ctctgagggc 3720
aacatgatgc acattgcctt attgagtgct gaaaatgaaa ataatatcag tgatgatcaa 3780
gctcaacata ggatggaaaa acttaacaag atactcaagg atactagtgt cgcaaatgat 3840
cttcgagctg ctggtttgaa ggttataagt tgcattgttc aaagagatga agcacgcatg 3900
ccaatgcgcc acacattact ctggtcagat gaaaagagtt gttatgagga agagcagatt 3960
cttcggcatg tggagcctcc cctctccatg cttcttgaaa tggataagtt gaaagtgaaa 4020
ggatacaatg aaatgaagta tactccatca cgtgatcgtc aatggcatat ctacacacta 4080
agaaatactg aaaaccccaa aatgttgcat agggtatttt tccgaactat tgtcaggcaa 4140
cccaatgcag gcaacaagtt tatatcagcc caaattggcg acactgaagt aggaggtcct 4200
gaggaatctt tgtcatttac atctaatagc attttaagag ccttgatgac tgctattgaa 4260
```

```
gaattagagc ttcatgcaat taggactgat cattctcaca tgtatttgtg catattgaaa 4320
gaacaaaagc ttcttgatct cattccgttt tcagggagca caatcgtcga tgttgtccaa 4380
gacgaagcta ctgcttgttc acttttaaaa tcaatggctt tgaagataca cgaacttgtt 4440
ggtgcacaga tgcatcatct ttctgtatgc cagtgggagg tgaaactcaa gttgtactgc 4500
gatgggcctg ccagtggcac ctggagagtt gtaactacaa atgttactag tcacacttgc 4560
accgttgata tctaccggga agtggaagat actgaatcgc agaagttagt ataccattca 4620
gcttctccgt cagctagtcc tttgcatggt gtggccctgg ataatccgta tcaacctttg 4680
agtgtcattg atctaaaaca ctgctctgct aggaacaaca gaactacata ttgctatgat 4740
tttccactgg catttgaaac tgccctgcag aagtcatggc agtccaatgg ctccagtgtt 4800
tctgaaggca gtgaaaatag taggtcttat gtgaaagcaa cagagctggt gtttgctgaa 4860
aaacatgggt cctggggcac tcctataatt tccatggagc gtcccgctgg gctcaatgac 4920
attggcatgg tagcttggat cttagagatg tccactcctg aatttcccaa tggcaggcag 4980
attattgtca tagcaaatga tattactttc agagctggat catttggccc aagggaagat 5040
gcgtttttttg aagctgtcac gaacctggcc tgcgagagga agcttcctct tatatacttg 5100
gcagcaaact ccggtgctag gattggcata gccgatgaag tgaaatcttg cttccgtgtt 5160
gggtggtccg atgaaggcag ccctgaacgg ggttttcagt acatttatct gactgacgaa 5220
gactatgccc gtattagctt gtctgttata gcacacaagc tgcagctgga taatggtgaa 5280
attaggtgga ttattgactc tgttgtgggc aaggaggatg ggcttggtgt tgagaatata 5340
catggaagtg ctgctattgc cagtgcttat tctagggcat atgaggagac atttacactt 5400
acatttgtga ctgggcggac tgttggaata ggagcatatc ttgctcggct cggtatacgg 5460
tgcatacagc gtcttgacca gcctattatt ttaactgggt tttctgccct gaacaagctt 5520
cttgggcggg aagtgtacag ctcccacatg cagttgggtg gtcctaagat catggcgacc 5580
aatggtgttg tccacttgac tgtttcagat gaccttgaag gtgtttccaa tatattgagg 5640
tggctcagct atgttcctgc caacattggt ggacctcttc ctattacaaa acctttggac 5700
ccaccagaca gacctgttgc atacatccct gagaacacat gtgatccgcg cgcagccatt 5760
cgtggtgtag atgacagcca agggaaatgg ttgggtggta tgtttgacaa agacagcttt 5820
gtcgagacat ttgaaggatg ggcgaaaaca gtggttacgg gcagagcaaa gcttggagga 5880
attcctgttg gcgtcatagc tgtggagaca caaaccatga tgcagcttat ccctgctgat 5940
ccaggccagc ttgattccca tgagcgatct gttcctcggg ctggacaagt gtggttccca 6000
gattctgcaa ccaagacagc tcaggcattg ttggacttca accgtgaagg attgccgctg 6060
```

```
ttcatccttg ctaactggag aggattctct ggtggacaaa gagatctgtt tgaaggaatt      6120
cttcaggctg ggtcaacaat tgttgagaac cttaggacat acaatcagcc tgcttttgtc      6180
tacattccta tggctggaga gctgcgtgga ggagcttggg ttgtggttga tagcaaaata      6240
aatccagacc gaattgagtg ttatgctgag aggactgcta aaggcaatgt tctggaacct      6300
caagggttaa ttgaaatcaa attcagatca gaggagctcc aagactgtat gggtaggctt      6360
gacccagggt tgataaatct gaaagcaaaa ctccaaggtg caaagcttgg aaatggaagc      6420
ctaacagatg tagaatccct tcagaagagt atagatgctc gtacgaaaca gttgttgcct      6480
ttatacaccc agattgcaat acggtttgct gaattgcatg atacttccct cagaatggca      6540
gctaaaggtg tgattaagaa agttgtagat tgggaagaat cacgttcttt cttctacaga      6600
aggctacgga ggaggatctc tgaagatgtt cttgcaaaag aaataagagg aatagctggt      6660
gaccacttca ctcaccaatc agcagttgag ctgatcaagg aatggtactt ggcttctcaa      6720
gccacaacag gaagcactga atgggatgat gatgatgctc ttgttgcctg gaaggagaat      6780
cctgaaaact ataagggata tatccaagag ttaagggctc aaaaggtgtc tcagtcgctc      6840
tccgatcttg cagactccag ttcagatcta gaagcattct cacagggtct ttccacatta      6900
ttagataaga tggatccctc tcagagagcc aagttcattc aggaagtcaa gaaggtcctg      6960
ggttga                                                                 6966

<210> SEQ ID NO 18
<211> LENGTH: 2321
<212> TYPE: PRT
<213> ORGANISM: Setaria italica

<400> SEQUENCE: 18

Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
                20                  25                  30

Val Ser Ser Arg Pro Ser Asn Arg Arg Lys Ser Arg Thr Arg Ser Leu
            35                  40                  45

Arg Asp Gly Gly Asp Gly Val Ser Asp Ala Lys Lys His Asn Gln Ser
        50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Ser Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205
```

Glu Val Ala Glu Arg Ile Gly Val Ser Ala Val Trp Pro Gly Trp
    210                 215                 220

His Ala Ser Glu Asn Pro Glu Leu Pro Asp Ala Leu Thr Ala Lys Gly
225                 230                 235                 240

Val Val Phe Leu Gly Pro Pro Ala Ala Ser Met Asn Ala Leu Gly Asp
            245                 250                 255

Lys Val Gly Ser Ala Leu Ile Ala Gln Ala Ala Gly Val Pro Thr Leu
        260                 265                 270

Ser Trp Ser Gly Ser His Val Glu Val Pro Leu Glu Cys Cys Leu Asp
    275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
            325                 330                 335

Asp Glu Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
    355                 360                 365

Val Gln Leu Leu Cys Asp Gln Tyr Gly Asn Val Ala Ala Leu His Ser
370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
            405                 410                 415

Ala Arg Arg Leu Ala Lys Ala Val Gly Tyr Val Gly Ala Ala Thr Val
        420                 425                 430

Glu Tyr Leu Tyr Ser Met Glu Thr Gly Glu Tyr Tyr Phe Leu Glu Leu
    435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Asp Gly Met Asp Tyr Gly Gly
            485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
    515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Val Asp Ser Gln
            565                 570                 575

Phe Gly His Val Phe Ala Tyr Gly Leu Ser Arg Ser Ala Ala Ile Thr
        580                 585                 590

Asn Met Ala Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

| | | | | | | | | | | | |
|---|---|---|---|---|---|---|---|---|---|---|---|
|Glu|Asn|Lys|Ile|His|Thr|Gly|Trp|Leu|Asp|Thr|Arg|Ile|Ala|Met|Arg|
|625| | | | |630| | | |635| | | | |640| |

Val Gln Ala Glu Arg Pro Pro Trp Tyr Ile Ser Val Val Gly Gly Ala
            645             650             655

Leu Tyr Lys Thr Val Thr Ala Asn Ala Ala Thr Val Ser Asp Tyr Val
            660             665             670

Ser Tyr Leu Thr Lys Gly Gln Ile Pro Pro Lys His Ile Ser Leu Val
            675             680             685

Ser Ser Thr Val Asn Leu Asn Ile Glu Gly Ser Lys Tyr Thr Val Glu
690             695             700

Thr Val Arg Thr Gly His Gly Ser Tyr Arg Leu Arg Met Asn Asp Ser
705             710             715             720

Ala Ile Glu Ala Asn Val Gln Ser Leu Cys Asp Gly Gly Leu Leu Met
            725             730             735

Gln Leu Asp Gly Asn Ser His Val Ile Tyr Ala Glu Glu Ala Gly
            740             745             750

Gly Thr Arg Leu Leu Ile Asp Gly Lys Thr Cys Leu Leu Gln Asn Asp
            755             760             765

His Asp Pro Ser Lys Leu Leu Ala Glu Thr Pro Cys Lys Leu Leu Arg
770             775             780

Phe Leu Val Ala Asp Gly Ala His Val Asp Ala Asp Val Pro Tyr Ala
785             790             795             800

Glu Val Glu Val Met Lys Met Cys Met Pro Leu Leu Ser Pro Ala Ser
            805             810             815

Gly Val Ile His Val Met Met Ser Glu Gly Gln Ala Leu Gln Ala Gly
            820             825             830

Asp Leu Ile Ala Arg Leu Asp Leu Asp Asp Pro Ser Ala Val Lys Arg
            835             840             845

Ala Glu Pro Phe His Gly Ile Phe Pro Gln Met Asp Leu Pro Val Ala
850             855             860

Ala Ser Ser Gln Val His Lys Arg Tyr Ala Ala Ser Trp Asn Ala Ala
865             870             875             880

Arg Met Val Leu Ala Gly Tyr Glu His Asn Ile Asn Glu Val Val Gln
            885             890             895

Asp Leu Val Cys Cys Leu Asp Asp Pro Glu Leu Pro Phe Leu Gln Trp
            900             905             910

Asp Glu Leu Met Ser Val Leu Ala Thr Arg Leu Pro Arg Asn Leu Lys
            915             920             925

Ser Glu Leu Glu Asp Lys Tyr Met Glu Tyr Lys Leu Asn Phe Tyr His
930             935             940

Gly Lys Asn Lys Asp Phe Pro Ser Lys Leu Leu Arg Asp Ile Ile Glu
945             950             955             960

Ala Asn Leu Ala Tyr Gly Ser Glu Lys Glu Lys Ala Thr Asn Glu Arg
            965             970             975

Leu Ile Glu Pro Leu Met Ser Leu Lys Ser Tyr Glu Gly Gly Arg
            980             985             990

Glu Ser His Ala His Phe Val Val Lys Ser Leu Phe Lys Glu Tyr Leu
            995             1000            1005

Ala Val Glu Glu Leu Phe Ser Asp Gly Ile Gln Ser Asp Val Ile
            1010            1015            1020

Glu Thr Leu Arg His Gln His Ser Lys Asp Leu Gln Lys Val Val
            1025            1030            1035

Asp Ile Val Leu Ser His Gln Gly Val Arg Asn Lys Ala Lys Leu

-continued

```
                1040                1045                1050
Val Thr Ala Leu Met Glu Lys Leu Val Tyr Pro Asn Pro Ala Ala
    1055                1060                1065
Tyr Arg Asp Leu Leu Val Arg Phe Ser Ser Leu Asn His Lys Arg
    1070                1075                1080
Tyr Tyr Lys Leu Ala Leu Lys Ala Ser Glu Leu Leu Glu Gln Thr
    1085                1090                1095
Lys Leu Ser Glu Leu Arg Ala Ser Ile Ala Arg Ser Leu Ser Asp
    1100                1105                1110
Leu Gly Met His Lys Gly Glu Met Thr Ile Glu Asp Ser Met Glu
    1115                1120                1125
Asp Leu Val Ser Ala Pro Leu Pro Val Glu Asp Ala Leu Ile Ser
    1130                1135                1140
Leu Phe Asp Tyr Ser Asp Pro Thr Val Gln Gln Lys Val Ile Glu
    1145                1150                1155
Thr Tyr Ile Ser Arg Leu Tyr Gln Pro Leu Leu Val Lys Asp Ser
    1160                1165                1170
Ile Gln Val Lys Phe Lys Glu Ser Gly Ala Phe Ala Leu Trp Glu
    1175                1180                1185
Phe Ser Glu Gly His Val Asp Thr Lys Asn Gly Gln Gly Thr Val
    1190                1195                1200
Leu Gly Arg Thr Arg Trp Gly Ala Met Val Ala Val Lys Ser Val
    1205                1210                1215
Glu Ser Ala Arg Thr Ala Ile Val Ala Ala Leu Lys Asp Ser Ala
    1220                1225                1230
Gln His Ala Ser Ser Glu Gly Asn Met Met His Ile Ala Leu Leu
    1235                1240                1245
Ser Ala Glu Asn Glu Asn Asn Ile Ser Asp Asp Gln Ala Gln His
    1250                1255                1260
Arg Met Glu Lys Leu Asn Lys Ile Leu Lys Asp Thr Ser Val Ala
    1265                1270                1275
Asn Asp Leu Arg Ala Ala Gly Leu Lys Val Ile Ser Cys Ile Val
    1280                1285                1290
Gln Arg Asp Glu Ala Arg Met Pro Met Arg His Thr Leu Leu Trp
    1295                1300                1305
Ser Asp Glu Lys Ser Cys Tyr Glu Glu Glu Gln Ile Leu Arg His
    1310                1315                1320
Val Glu Pro Pro Leu Ser Met Leu Leu Glu Met Asp Lys Leu Lys
    1325                1330                1335
Val Lys Gly Tyr Asn Glu Met Lys Tyr Thr Pro Ser Arg Asp Arg
    1340                1345                1350
Gln Trp His Ile Tyr Thr Leu Arg Asn Thr Glu Asn Pro Lys Met
    1355                1360                1365
Leu His Arg Val Phe Phe Arg Thr Ile Val Arg Gln Pro Asn Ala
    1370                1375                1380
Gly Asn Lys Phe Ile Ser Ala Gln Ile Gly Asp Thr Glu Val Gly
    1385                1390                1395
Gly Pro Glu Glu Ser Leu Ser Phe Thr Ser Asn Ser Ile Leu Arg
    1400                1405                1410
Ala Leu Met Thr Ala Ile Glu Glu Leu Glu Leu His Ala Ile Arg
    1415                1420                1425
Thr Asp His Ser His Met Tyr Leu Cys Ile Leu Lys Glu Gln Lys
    1430                1435                1440
```

```
Leu Leu Asp Leu Ile Pro Phe Ser Gly Ser Thr Ile Val Asp Val
    1445            1450                1455

Val Gln Asp Glu Ala Thr Ala Cys Ser Leu Leu Lys Ser Met Ala
    1460            1465                1470

Leu Lys Ile His Glu Leu Val Gly Ala Gln Met His His Leu Ser
    1475            1480                1485

Val Cys Gln Trp Glu Val Lys Leu Lys Leu Tyr Cys Asp Gly Pro
    1490            1495                1500

Ala Ser Gly Thr Trp Arg Val Val Thr Thr Asn Val Thr Ser His
    1505            1510                1515

Thr Cys Thr Val Asp Ile Tyr Arg Glu Val Glu Asp Thr Glu Ser
    1520            1525                1530

Gln Lys Leu Val Tyr His Ser Ala Ser Pro Ser Ala Ser Pro Leu
    1535            1540                1545

His Gly Val Ala Leu Asp Asn Pro Tyr Gln Pro Leu Ser Val Ile
    1550            1555                1560

Asp Leu Lys His Cys Ser Ala Arg Asn Asn Arg Thr Thr Tyr Cys
    1565            1570                1575

Tyr Asp Phe Pro Leu Ala Phe Glu Thr Ala Leu Gln Lys Ser Trp
    1580            1585                1590

Gln Ser Asn Gly Ser Ser Val Ser Glu Gly Ser Glu Asn Ser Arg
    1595            1600                1605

Ser Tyr Val Lys Ala Thr Glu Leu Val Phe Ala Glu Lys His Gly
    1610            1615                1620

Ser Trp Gly Thr Pro Ile Ile Ser Met Glu Arg Pro Ala Gly Leu
    1625            1630                1635

Asn Asp Ile Gly Met Val Ala Trp Ile Leu Glu Met Ser Thr Pro
    1640            1645                1650

Glu Phe Pro Asn Gly Arg Gln Ile Ile Val Ile Ala Asn Asp Ile
    1655            1660                1665

Thr Phe Arg Ala Gly Ser Phe Gly Pro Arg Glu Asp Ala Phe Phe
    1670            1675                1680

Glu Ala Val Thr Asn Leu Ala Cys Glu Arg Lys Leu Pro Leu Ile
    1685            1690                1695

Tyr Leu Ala Ala Asn Ser Gly Ala Arg Ile Gly Ile Ala Asp Glu
    1700            1705                1710

Val Lys Ser Cys Phe Arg Val Gly Trp Ser Asp Glu Gly Ser Pro
    1715            1720                1725

Glu Arg Gly Phe Gln Tyr Ile Tyr Leu Thr Asp Glu Asp Tyr Ala
    1730            1735                1740

Arg Ile Ser Leu Ser Val Ile Ala His Lys Leu Gln Leu Asp Asn
    1745            1750                1755

Gly Glu Ile Arg Trp Ile Ile Asp Ser Val Val Gly Lys Glu Asp
    1760            1765                1770

Gly Leu Gly Val Glu Asn Ile His Gly Ser Ala Ala Ile Ala Ser
    1775            1780                1785

Ala Tyr Ser Arg Ala Tyr Glu Glu Thr Phe Thr Leu Thr Phe Val
    1790            1795                1800

Thr Gly Arg Thr Val Gly Ile Gly Ala Tyr Leu Ala Arg Leu Gly
    1805            1810                1815

Ile Arg Cys Ile Gln Arg Leu Asp Gln Pro Ile Ile Leu Thr Gly
    1820            1825                1830
```

```
Phe Ser Ala Leu Asn Lys Leu Leu Gly Arg Glu Val Tyr Ser Ser
1835                1840                1845

His Met Gln Leu Gly Gly Pro Lys Ile Met Ala Thr Asn Gly Val
1850                1855                1860

Val His Leu Thr Val Ser Asp Asp Leu Glu Gly Val Ser Asn Ile
1865                1870                1875

Leu Arg Trp Leu Ser Tyr Val Pro Ala Asn Ile Gly Gly Pro Leu
1880                1885                1890

Pro Ile Thr Lys Pro Leu Asp Pro Pro Asp Arg Pro Val Ala Tyr
1895                1900                1905

Ile Pro Glu Asn Thr Cys Asp Pro Arg Ala Ala Ile Arg Gly Val
1910                1915                1920

Asp Asp Ser Gln Gly Lys Trp Leu Gly Gly Met Phe Asp Lys Asp
1925                1930                1935

Ser Phe Val Glu Thr Phe Glu Gly Trp Ala Lys Thr Val Val Thr
1940                1945                1950

Gly Arg Ala Lys Leu Gly Gly Ile Pro Val Gly Val Ile Ala Val
1955                1960                1965

Glu Thr Gln Thr Met Met Gln Leu Ile Pro Ala Asp Pro Gly Gln
1970                1975                1980

Leu Asp Ser His Glu Arg Ser Val Pro Arg Ala Gly Gln Val Trp
1985                1990                1995

Phe Pro Asp Ser Ala Thr Lys Thr Ala Gln Ala Leu Leu Asp Phe
2000                2005                2010

Asn Arg Glu Gly Leu Pro Leu Phe Ile Leu Ala Asn Trp Arg Gly
2015                2020                2025

Phe Ser Gly Gly Gln Arg Asp Leu Phe Glu Gly Ile Leu Gln Ala
2030                2035                2040

Gly Ser Thr Ile Val Glu Asn Leu Arg Thr Tyr Asn Gln Pro Ala
2045                2050                2055

Phe Val Tyr Ile Pro Met Ala Gly Glu Leu Arg Gly Gly Ala Trp
2060                2065                2070

Val Val Val Asp Ser Lys Ile Asn Pro Asp Arg Ile Glu Cys Tyr
2075                2080                2085

Ala Glu Arg Thr Ala Lys Gly Asn Val Leu Glu Pro Gln Gly Leu
2090                2095                2100

Ile Glu Ile Lys Phe Arg Ser Glu Glu Leu Gln Asp Cys Met Gly
2105                2110                2115

Arg Leu Asp Pro Gly Leu Ile Asn Leu Lys Ala Lys Leu Gln Gly
2120                2125                2130

Ala Lys Leu Gly Asn Gly Ser Leu Thr Asp Val Glu Ser Leu Gln
2135                2140                2145

Lys Ser Ile Asp Ala Arg Thr Lys Gln Leu Leu Pro Leu Tyr Thr
2150                2155                2160

Gln Ile Ala Ile Arg Phe Ala Glu Leu His Asp Thr Ser Leu Arg
2165                2170                2175

Met Ala Ala Lys Gly Val Ile Lys Lys Val Val Asp Trp Glu Glu
2180                2185                2190

Ser Arg Ser Phe Phe Tyr Arg Arg Leu Arg Arg Arg Ile Ser Glu
2195                2200                2205

Asp Val Leu Ala Lys Glu Ile Arg Gly Ile Ala Gly Asp His Phe
2210                2215                2220

Thr His Gln Ser Ala Val Glu Leu Ile Lys Glu Trp Tyr Leu Ala
```

| | | | | | | | | |
|---|---|---|---|---|---|---|---|---|
| Ser | Gln | Ala | Thr | Thr | Gly | Ser | Thr | Glu | Trp | Asp | Asp | Asp | Ala |
| 2240 | | | | | 2245 | | | | | 2250 | | | |

Ser Gln Ala Thr Thr Gly Ser Thr Glu Trp Asp Asp Asp Ala
    2240              2245                2250

Phe Val Ala Trp Lys Glu Asn Pro Glu Asn Tyr Lys Gly Tyr Ile
    2255              2260                2265

Gln Glu Leu Arg Ala Gln Lys Val Ser Gln Ser Leu Ser Asp Leu
    2270              2275                2280

Ala Asp Ser Ser Ser Asp Leu Glu Ala Phe Ser Gln Gly Leu Ser
    2285              2290                2295

Thr Leu Leu Asp Lys Met Asp Pro Ser Gln Arg Ala Lys Phe Ile
    2300              2305                2310

Gln Glu Val Lys Lys Val Leu Gly
    2315              2320

<210> SEQ ID NO 19
<211> LENGTH: 6966
<212> TYPE: DNA
<213> ORGANISM: Setaria italica

<400> SEQUENCE: 19

| | |
|---|---|
| atgtcgcaac ttggattagc tgcagctgcc tcaaaggcgc tgccactact tcctaatcgc | 60 |
| catagaactt cagctggaac tacattccca tcacctgtat catcgcggcc ctcaaaccga | 120 |
| aggaaaagcc gcactcgttc acttcgtgat ggaggagatg gggtatcaga tgccaaaaag | 180 |
| cacaaccagt ctgtccgtca aggtcttgct ggcatcatcg acctcccaaa tgaggcaaca | 240 |
| tcggaagtgg atatttctca tggatccgag atcccagggg gccaaccga ttcatatcaa | 300 |
| atgaatggga ttgtaaatga agcacataat ggcagacatg cctcagtgtc caaggttgtt | 360 |
| gaattttgtg cggcgctagg tggcaaaaca ccaattcaca gtatactagt ggccaacaat | 420 |
| ggaatggcag cagcaaagtt catgaggagt gtccggacat gggctaatga cttttttgga | 480 |
| tcggagaagg cgattcagct catagctatg caactccag aagacatgag ataaatgca | 540 |
| gaacacatta gaattgctga tcaatttgta gaggtgcctg gtggaacaaa aataacaac | 600 |
| tatgcaaatg ttcaactcat agtggaggta gcagaaagaa taggtgtttc tgctgtttgg | 660 |
| cctggttggg gtcatgcttc tgagaatcct gaacttccag atgcattgac cgcaaaagga | 720 |
| attgttttcc ttgggccacc tgcggcatca atgaatgcat ggagataa ggtcggttca | 780 |
| gctctcattg ctcaagcagc tggggtcccg acccttcgt ggagtggatc acatgttgaa | 840 |
| gttccattag agtgctgctt agatgcgata cctgaggaaa tgtatagaaa agcttgtgtt | 900 |
| actaccacag aagaagctgt tgcgagttgt caggtggttg gttatcctgc catgattaag | 960 |
| gcatcctggg gaggtggtgg taaaggaata agaaaggttc ataatgacga tgaggttaga | 1020 |
| gcactgttta agcaagtaca aggtgaagtc cctggctccc caatatttat catgaggctt | 1080 |
| gcatcccaga tcgtcatct tgaagttcag ttgctttgtg atcaatatgg caatgtggca | 1140 |
| gcacttcaca gtcgtgattg cagtgtgcaa cggcgacacc aaaagattat tgaggaaggc | 1200 |
| ccagttactg ttgctcctcg tgagacagtt aaagcgcttg agcaggcagc aaggaggctt | 1260 |
| gctaaggctg tgggtatgt tggtgctgct actgttgaat accttacag catggagact | 1320 |
| ggggaatact atttctgga gcttaatccc agattacagg tcgagcatcc agtcactgag | 1380 |
| tggattgctg aagtaaatct tcctgcagct caagttgcag ttggaatggg catacctctt | 1440 |
| tggcagattc agaaatcag acgtttctat ggaatggact atgaggagg atatgacatt | 1500 |
| tggaggaaaa cagcagctct tgccacacca tttaattttg atgaagtaga ttctcaatgg | 1560 |

-continued

```
ccaaagggcc attgtgtagc agttagaatt actagcgagg atccagatga tggtttcaaa      1620
cctactggtg ggaaagtgaa ggagataagt tttaaaagca agcctaatgt ttgggcctac      1680
ttctcagtaa agtctggtgg aggcattcat gaatttgctg attctcagtt tgggcatgtt      1740
tttgcatatg ggctctctag atcagcagca ataacgaaca tggctcttgc attaaaagag      1800
attcaaattc gtggagaaat tcattcaaat gttgattaca cagttgatct cttaaatgct      1860
tcagacttca gagaaaataa gattcatact ggctggcttg ataccagaat agctatgcgt      1920
gttcaagctg agaggccccc atggtatatt tcagtggttg gaggagctct atataaaaca      1980
gtaactgcca atgcagccac tgtttctgat tatgtcagtt atctcaccaa gggccagatt      2040
ccaccaaagc atatatccct tgtcagttca acagttaatc tgaatatcga agggagcaaa      2100
tacacagttg aaactgtaag gactggacat ggtagctaca gattacgaat gaatgattca      2160
gcaattgaag cgaatgtaca atctttatgt gatggaggcc tcttaatgca gttggatgga      2220
aatagccatg taatttacgc ggaagaagaa gctggtggta cacgacttct gattgatgga      2280
aagacatgct tgttacagaa tgatcatgat ccatcaaagt tattagctga gacaccctgc      2340
aaacttcttc ggttcttggt tgctgatggt gctcatgttg atgctgatgt accatatgcg      2400
gaagttgagg ttatgaaaat gtgcatgcct ctcttgtcgc ctgcttctgg tgtcattcat      2460
gttatgatgt ctgagggcca ggcattgcag gctggtgatc ttatagcaag gctggatctt      2520 gatgacccett ctgctgtgaa aagagctgaa ccatttcatg gaatatttcc acaaatggac      2580
cttcctgttg ctgcctctag ccaagtacac aaaagatatg ctgcaagttt gaatgctgct      2640
cgaatggtcc ttgcaggata cgagcataat atcaatgaag ttgtacaaga tttggtatgc      2700
tgcctggatg atcccgagct tcccttccta cagtgggatg aacttatgtc agttctagca      2760
actaggcttc caagaaatct taagagtgag ttagaggata aatacatgga atacaagttg      2820
aacttttacc atgggaaaaa caaggacttc ccgtccaagc tgctgagaga catcattgag      2880
gcaaatcttg catatggttc agagaaggaa aaagctacga atgagaggct tattgagcct      2940
cttatgagcc tacttaagtc atatgagggt gggagagaaa gccatgctca ttttgttgtc      3000
aagtcccttt tcaaggagta ccttgctgtg aagaactttt cagtgatgg gattcagtct      3060 gatgtgattg aaaccctgcg tcatcagcac agtaaagact tgcagaaggt tgtagacatt      3120
gtgttgtctc accagggtgt gaggaacaaa gctaagcttg taacagcact tatggaaaag      3180
ctggtttatc caaatcctgc tgcttacagg gatctgttgg ttcgcttttc ttcactcaat      3240
cataaaagat attataagtt ggcccttaaa gcaagcgaac ttcttgaaca aactaaacta      3300
agtgaactcc gtgcaagcat cgcaagaagc ctttctgatc tggggatgca taagggagaa      3360
atgactattg aagatagcat ggaagattta gtctctgccc cattacctgt cgaagatgca      3420
cttatttctt tgtttgatta cagtgatcca actgttcagc agaaagtgat cgagacatac      3480
atatctcgat tgtatcagcc tcttcttgtg aagatagca tccaagtgaa atttaaggaa      3540
tctggtgcct ttgctttatg ggaattttct gaagggcatg ttgatactaa aaatggacaa      3600
gggaccgttc ttggtcgaac aagatggggt gccatggtag ctgtcaaatc agttgaatct      3660
gcacgaacag ccattgtagc tgcattaaag gattcggcac agcatgccag ctctgagggc      3720
aacatgatgc acattgcctt attgagtgct gaaaatgaaa ataatatcag tgatgatcaa      3780
gctcaacata ggatggaaaa acttaacaag atactcaagg atactagtgt cgcaaatgat      3840
cttcgagctg ctggtttgaa ggttataagt tgcattgttc aaagagatga agcacgcatg      3900
```

```
ccaatgcgcc acacattact ctggtcagat gaaaagagtt gttatgagga agagcagatt    3960
cttcggcatg tggagcctcc cctctccatg cttcttgaaa tggataagtt gaaagtgaaa    4020
ggatacaatg aaatgaagta tactccatca cgtgatcgtc aatggcatat ctacacacta    4080
agaaatactg aaaccccaa aatgttgcat agggtatttt tccgaactat tgtcaggcaa     4140
cccaatgcag gcaacaagtt tatatcagcc caaattggcg acactgaagt aggaggtcct    4200
gaggaatctt tgtcatttac atctaatagc attttaagag ccttgatgac tgctattgaa    4260
gaattagagc ttcatgcaat taggactggt cattctcaca tgtatttgtg catattgaaa    4320
gaacaaaagc ttcttgatct cattccgttt tcagggagca caatcgtcga tgttggccaa    4380
gacgaagcta ctgcttgttc acttttaaaa tcaatggctt tgaagataca cgaacttgtt    4440
ggtgcacaga tgcatcatct ttctgtatgc cagtgggagg tgaaactcaa gttgtactgc    4500
gatgggcctg ccagtggcac ctggagagtt gtaactacaa atgttactag tcacacttgc    4560
accattgata tctaccggga agtggaagat actgaatcgc agaagttagt ataccattca    4620
gcttctccgt cagctagtcc tttgcatggt gtggccctgg ataatccgta tcaacctttg    4680
agtgtcattg atctaaaacg ctgctctgct aggaacaaca gaactacata ttgctatgat    4740
tttccactgg catttgaaac tgccctgcag aagtcatggc agtccaatgg ctccagtgtt    4800
tctgaaggca gtgaaaatag taggtcttat gtgaaagcaa cagagctggt gtttgctgaa    4860
aaacatgggt cctgggcac tcctataatt tccatggagc gtcccgctgg gctcaatgac     4920
attggcatgg tagcttggat cttagagatg tccactcctg aatttcccaa tggcaggcag    4980
attattgtca tagcaaatga tattactttc agagctggat catttggccc aagggaagat    5040
gcgttttttg aagctgtcac gaacctggcc tgcgagagga gcttcctct tatatacttg      5100
gcagcaaact ccggtgctag gattggcata gccgatgaag tgaaatcttg cttccgtgtt    5160
gggtggtccg atgaaggcag ccctgaacgg ggttttcagt acatttatct gactgacgaa    5220
gactatgccc gtattagctt gtctgttata gcacacaagc tgcagctgga taatggtgaa    5280
attaggtgga ttattgactc tgttgtgggc aaggaggatg ggcttggtgt tgagaatcta    5340
catggaaagtg ctgctattgc cagtgcttat tctagggcat atgaggagac atttacactt    5400
acatttgtga ctgggcggac tgttggaata ggagcatatc tcgctcggct cggtatacgg    5460
tgcatacagc gtcttgacca gcctattatt ttaactgggt tttctgccct gaacaagctt    5520
cttgggcggg aagtgtacag ctcccacatg cagttgggtg gtcctaagat catggcgacc    5580
aatggtgttg tccacttgac tgtttcagat gaccttgaag gtgtttccaa tatattgagg    5640
tggctcagct atgttcctgc caacattggt ggacctcttc ctattacaaa acctttggac    5700
ccaccagaca gacctgttgc atacatccct gagaacacat gtgatccgcg cgcagccatt    5760
cgtggtgtag atgacagcca agggaaatgg ttgggtggta tgtttgacaa agacagcttt    5820
gtcgagacat ttgaaggatg ggcgaaaaca gtggttacgg gcagagcaaa gcttggagga    5880
attcctgttg gtgtcatagc tgtggagaca caaaccatga tgcagcttat ccctgctgat    5940
ccaggccagc ttgattccca tgagcgatct gttcctcggg ctggacaagt gtggttccca    6000
gattctgcaa ccaagacagc tcaggcattg ttggacttca accgtgaagg attgccgctg    6060
ttcatccttg ctaactggag aggattctct ggtggacaaa gagatctgtt tgaaggaatt    6120
cttcaggctg ggtcaacaat tgttgagaac cttaggacat acaatcagcc tgcttttgtc    6180
tacattccta tggctggaga gctgcgtgga ggagcttggg ttgtggttga tagcaaaata    6240
aatccagacc gaattgagtg ttatgctgag aggactgcta aaggcaatgt tcttgaacct    6300
```

```
caagggttaa ttgaaatcaa attcagatca gaggagctcc aagactgtat gggtaggctt    6360
gacccagagt tgataaatct gaaagcaaaa ctccaaggtg caaagcttgg aaatggaagc    6420
ctaacagatg tagaatccct tcagaagagt atagatgctc gtacgaaaca gttgttgcct    6480
ttatacaccc agattgcaat acggtttgct gaattgcatg atacttccct cagaatggca    6540
gctaaaggtg tgattaagaa agttgtagat tgggaagaat cacgttcttt cttctacaga    6600
aggctacgga ggaggatctc tgaagatgtt cttgcaaaag aaataagagg aatagctggt    6660
gaccacttca ctcaccaatc agcagttgag ctgatcaagg aatggtactt ggcttctcaa    6720
gccacaacag gaagcactga atgggatgat gatgatgctt tgttgcctg gaaggagaat    6780 cctgaaaact ataagggata tatccaagag ttaagggctc aaaaggtgtc tcagtcgctc    6840
tccgatcttg cagactccag ttcagatcta gaagcattct cacagggtct ttccacatta    6900
ttagataaga tggatccctc tcagagagcc aagttcattc aggaagtcaa gaaggtcctg    6960
ggttga                                                              6966
```

<210> SEQ ID NO 20
<211> LENGTH: 2321
<212> TYPE: PRT
<213> ORGANISM: Setaria italica

<400> SEQUENCE: 20

```
Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ala Ser Met Asn Ala Leu Gly Asp
```

-continued

```
                245                 250                 255
Lys Val Gly Ser Ala Leu Ile Ala Gln Ala Ala Gly Val Pro Thr Leu
                260                 265                 270

Ser Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
290                 295                 300

Glu Ala Val Ala Ser Cys Gln Val Val Gly Tyr Pro Ala Met Ile Lys
305                 310                 315                 320

Ala Ser Trp Gly Gly Gly Lys Gly Ile Arg Lys Val His Asn Asp
            325                 330                 335

Asp Glu Val Arg Ala Leu Phe Lys Gln Val Gln Gly Glu Val Pro Gly
                340                 345                 350

Ser Pro Ile Phe Ile Met Arg Leu Ala Ser Gln Ser Arg His Leu Glu
            355                 360                 365

Val Gln Leu Leu Cys Asp Gln Tyr Gly Asn Val Ala Ala Leu His Ser
370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Ala Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Ala Asn Ala Ala Thr Val Ser Asp Tyr Val
            660                 665                 670
```

```
Ser Tyr Leu Thr Lys Gly Gln Ile Pro Pro Lys His Ile Ser Leu Val
        675                 680                 685

Ser Ser Thr Val Asn Leu Asn Ile Glu Gly Ser Lys Tyr Thr Val Glu
        690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Gly Leu Leu Met
                725                 730                 735

Gln Leu Asp Gly Asn Ser His Val Ile Tyr Ala Glu Glu Ala Gly
            740                 745                 750

Gly Thr Arg Leu Leu Ile Asp Gly Lys Thr Cys Leu Leu Gln Asn Asp
                755                 760                 765

His Asp Pro Ser Lys Leu Leu Ala Glu Thr Pro Cys Lys Leu Leu Arg
770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Val Met Met Ser Glu Gly Gln Ala Leu Gln Ala Gly
            820                 825                 830

Asp Leu Ile Ala Arg Leu Asp Leu Asp Asp Pro Ser Ala Val Lys Arg
            835                 840                 845

Ala Glu Pro Phe His Gly Ile Phe Pro Gln Met Asp Leu Pro Val Ala
850                 855                 860

Ala Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asp Pro Glu Leu Pro Phe Leu Gln Trp
            900                 905                 910

Asp Glu Leu Met Ser Val Leu Ala Thr Arg Leu Pro Arg Asn Leu Lys
            915                 920                 925

Ser Glu Leu Glu Asp Lys Tyr Met Glu Tyr Lys Leu Asn Phe Tyr His
        930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
            980                 985                 990

Glu Ser His Ala His Phe Val Val Lys Ser Leu Phe Lys Glu Tyr Leu
        995                1000                1005

Ala Val Glu Glu Leu Phe Ser Asp Gly Ile Gln Ser Asp Val Ile
        1010                1015                1020

Glu Thr Leu Arg His Gln His Ser Lys Asp Leu Gln Lys Val Val
        1025                1030                1035

Asp Ile Val Leu Ser His Gln Gly Val Arg Asn Lys Ala Lys Leu
        1040                1045                1050

Val Thr Ala Leu Met Glu Lys Leu Val Tyr Pro Asn Pro Ala Ala
        1055                1060                1065

Tyr Arg Asp Leu Leu Val Arg Phe Ser Ser Leu Asn His Lys Arg
        1070                1075                1080
```

-continued

```
Tyr Tyr Lys Leu Ala Leu Lys Ala Ser Glu Leu Leu Glu Gln Thr
1085                1090                1095

Lys Leu Ser Glu Leu Arg Ala Ser Ile Ala Arg Ser Leu Ser Asp
1100                1105                1110

Leu Gly Met His Lys Gly Glu Met Thr Ile Glu Asp Ser Met Glu
1115                1120                1125

Asp Leu Val Ser Ala Pro Leu Pro Val Glu Asp Ala Leu Ile Ser
1130                1135                1140

Leu Phe Asp Tyr Ser Asp Pro Thr Val Gln Gln Lys Val Ile Glu
1145                1150                1155

Thr Tyr Ile Ser Arg Leu Tyr Gln Pro Leu Leu Val Lys Asp Ser
1160                1165                1170

Ile Gln Val Lys Phe Lys Glu Ser Gly Ala Phe Ala Leu Trp Glu
1175                1180                1185

Phe Ser Glu Gly His Val Asp Thr Lys Asn Gly Gln Gly Thr Val
1190                1195                1200

Leu Gly Arg Thr Arg Trp Gly Ala Met Val Ala Val Lys Ser Val
1205                1210                1215

Glu Ser Ala Arg Thr Ala Ile Val Ala Ala Leu Lys Asp Ser Ala
1220                1225                1230

Gln His Ala Ser Ser Glu Gly Asn Met Met His Ile Ala Leu Leu
1235                1240                1245

Ser Ala Glu Asn Glu Asn Asn Ile Ser Asp Asp Gln Ala Gln His
1250                1255                1260

Arg Met Glu Lys Leu Asn Lys Ile Leu Lys Asp Thr Ser Val Ala
1265                1270                1275

Asn Asp Leu Arg Ala Ala Gly Leu Lys Val Ile Ser Cys Ile Val
1280                1285                1290

Gln Arg Asp Glu Ala Arg Met Pro Met Arg His Thr Leu Leu Trp
1295                1300                1305

Ser Asp Glu Lys Ser Cys Tyr Glu Glu Glu Gln Ile Leu Arg His
1310                1315                1320

Val Glu Pro Pro Leu Ser Met Leu Leu Glu Met Asp Lys Leu Lys
1325                1330                1335

Val Lys Gly Tyr Asn Glu Met Lys Tyr Thr Pro Ser Arg Asp Arg
1340                1345                1350

Gln Trp His Ile Tyr Thr Leu Arg Asn Thr Glu Asn Pro Lys Met
1355                1360                1365

Leu His Arg Val Phe Phe Arg Thr Ile Val Arg Gln Pro Asn Ala
1370                1375                1380

Gly Asn Lys Phe Ile Ser Ala Gln Ile Gly Asp Thr Glu Val Gly
1385                1390                1395

Gly Pro Glu Glu Ser Leu Ser Phe Thr Ser Asn Ser Ile Leu Arg
1400                1405                1410

Ala Leu Met Thr Ala Ile Glu Glu Leu Glu Leu His Ala Ile Arg
1415                1420                1425

Thr Gly His Ser His Met Tyr Leu Cys Ile Leu Lys Glu Gln Lys
1430                1435                1440

Leu Leu Asp Leu Ile Pro Phe Ser Gly Ser Thr Ile Val Asp Val
1445                1450                1455

Gly Gln Asp Glu Ala Thr Ala Cys Ser Leu Leu Lys Ser Met Ala
1460                1465                1470

Leu Lys Ile His Glu Leu Val Gly Ala Gln Met His His Leu Ser
```

```
              1475                1480                1485

Val Cys Gln Trp Glu Val Lys Leu Lys Leu Tyr Cys Asp Gly Pro
    1490                1495                1500

Ala Ser Gly Thr Trp Arg Val Thr Thr Asn Val Thr Ser His
    1505                1510                1515

Thr Cys Thr Ile Asp Ile Tyr Arg Glu Val Glu Asp Thr Glu Ser
    1520                1525                1530

Gln Lys Leu Val Tyr His Ser Ala Ser Pro Ser Ala Ser Pro Leu
    1535                1540                1545

His Gly Val Ala Leu Asp Asn Pro Tyr Gln Pro Leu Ser Val Ile
    1550                1555                1560

Asp Leu Lys Arg Cys Ser Ala Arg Asn Asn Arg Thr Thr Tyr Cys
    1565                1570                1575

Tyr Asp Phe Pro Leu Ala Phe Glu Thr Ala Leu Gln Lys Ser Trp
    1580                1585                1590

Gln Ser Asn Gly Ser Ser Val Ser Glu Gly Ser Glu Asn Ser Arg
    1595                1600                1605

Ser Tyr Val Lys Ala Thr Glu Leu Val Phe Ala Glu Lys His Gly
    1610                1615                1620

Ser Trp Gly Thr Pro Ile Ile Ser Met Glu Arg Pro Ala Gly Leu
    1625                1630                1635

Asn Asp Ile Gly Met Val Ala Trp Ile Leu Glu Met Ser Thr Pro
    1640                1645                1650

Glu Phe Pro Asn Gly Arg Gln Ile Ile Val Ile Ala Asn Asp Ile
    1655                1660                1665

Thr Phe Arg Ala Gly Ser Phe Gly Pro Arg Glu Asp Ala Phe Phe
    1670                1675                1680

Glu Ala Val Thr Asn Leu Ala Cys Glu Arg Lys Leu Pro Leu Ile
    1685                1690                1695

Tyr Leu Ala Ala Asn Ser Gly Ala Arg Ile Gly Ile Ala Asp Glu
    1700                1705                1710

Val Lys Ser Cys Phe Arg Val Gly Trp Ser Asp Glu Gly Ser Pro
    1715                1720                1725

Glu Arg Gly Phe Gln Tyr Ile Tyr Leu Thr Asp Glu Asp Tyr Ala
    1730                1735                1740

Arg Ile Ser Leu Ser Val Ile Ala His Lys Leu Gln Leu Asp Asn
    1745                1750                1755

Gly Glu Ile Arg Trp Ile Ile Asp Ser Val Val Gly Lys Glu Asp
    1760                1765                1770

Gly Leu Gly Val Glu Asn Leu His Gly Ser Ala Ala Ile Ala Ser
    1775                1780                1785

Ala Tyr Ser Arg Ala Tyr Glu Glu Thr Phe Thr Leu Thr Phe Val
    1790                1795                1800

Thr Gly Arg Thr Val Gly Ile Gly Ala Tyr Leu Ala Arg Leu Gly
    1805                1810                1815

Ile Arg Cys Ile Gln Arg Leu Asp Gln Pro Ile Ile Leu Thr Gly
    1820                1825                1830

Phe Ser Ala Leu Asn Lys Leu Leu Gly Arg Glu Val Tyr Ser Ser
    1835                1840                1845

His Met Gln Leu Gly Gly Pro Lys Ile Met Ala Thr Asn Gly Val
    1850                1855                1860

Val His Leu Thr Val Ser Asp Asp Leu Glu Gly Val Ser Asn Ile
    1865                1870                1875
```

```
Leu Arg Trp Leu Ser Tyr Val Pro Ala Asn Ile Gly Gly Pro Leu
    1880            1885                1890

Pro Ile Thr Lys Pro Leu Asp Pro Pro Asp Arg Pro Val Ala Tyr
    1895            1900                1905

Ile Pro Glu Asn Thr Cys Asp Pro Arg Ala Ala Ile Arg Gly Val
    1910            1915                1920

Asp Asp Ser Gln Gly Lys Trp Leu Gly Gly Met Phe Asp Lys Asp
    1925            1930                1935

Ser Phe Val Glu Thr Phe Glu Gly Trp Ala Lys Thr Val Val Thr
    1940            1945                1950

Gly Arg Ala Lys Leu Gly Gly Ile Pro Val Gly Val Ile Ala Val
    1955            1960                1965

Glu Thr Gln Thr Met Met Gln Leu Ile Pro Ala Asp Pro Gly Gln
    1970            1975                1980

Leu Asp Ser His Glu Arg Ser Val Pro Arg Ala Gly Gln Val Trp
    1985            1990                1995

Phe Pro Asp Ser Ala Thr Lys Thr Ala Gln Ala Leu Leu Asp Phe
    2000            2005                2010

Asn Arg Glu Gly Leu Pro Leu Phe Ile Leu Ala Asn Trp Arg Gly
    2015            2020                2025

Phe Ser Gly Gly Gln Arg Asp Leu Phe Glu Gly Ile Leu Gln Ala
    2030            2035                2040

Gly Ser Thr Ile Val Glu Asn Leu Arg Thr Tyr Asn Gln Pro Ala
    2045            2050                2055

Phe Val Tyr Ile Pro Met Ala Gly Glu Leu Arg Gly Gly Ala Trp
    2060            2065                2070

Val Val Val Asp Ser Lys Ile Asn Pro Asp Arg Ile Glu Cys Tyr
    2075            2080                2085

Ala Glu Arg Thr Ala Lys Gly Asn Val Leu Glu Pro Gln Gly Leu
    2090            2095                2100

Ile Glu Ile Lys Phe Arg Ser Glu Glu Leu Gln Asp Cys Met Gly
    2105            2110                2115

Arg Leu Asp Pro Glu Leu Ile Asn Leu Lys Ala Lys Leu Gln Gly
    2120            2125                2130

Ala Lys Leu Gly Asn Gly Ser Leu Thr Asp Val Glu Ser Leu Gln
    2135            2140                2145

Lys Ser Ile Asp Ala Arg Thr Lys Gln Leu Leu Pro Leu Tyr Thr
    2150            2155                2160

Gln Ile Ala Ile Arg Phe Ala Glu Leu His Asp Thr Ser Leu Arg
    2165            2170                2175

Met Ala Ala Lys Gly Val Ile Lys Lys Val Val Asp Trp Glu Glu
    2180            2185                2190

Ser Arg Ser Phe Phe Tyr Arg Arg Leu Arg Arg Arg Ile Ser Glu
    2195            2200                2205

Asp Val Leu Ala Lys Glu Ile Arg Gly Ile Ala Gly Asp His Phe
    2210            2215                2220

Thr His Gln Ser Ala Val Glu Leu Ile Lys Glu Trp Tyr Leu Ala
    2225            2230                2235

Ser Gln Ala Thr Thr Gly Ser Thr Glu Trp Asp Asp Asp Asp Ala
    2240            2245                2250

Phe Val Ala Trp Lys Glu Asn Pro Glu Asn Tyr Lys Gly Tyr Ile
    2255            2260                2265
```

```
Gln Glu  Leu Arg Ala Gln Lys  Val Ser Gln Ser  Leu Ser Asp Leu
    2270             2275              2280

Ala Asp  Ser Ser Ser Asp Leu  Glu Ala Phe Ser  Gln Gly Leu Ser
    2285             2290              2295

Thr Leu  Leu Asp Lys Met Asp  Pro Ser Gln Arg  Ala Lys Phe Ile
    2300             2305              2310

Gln Glu  Val Lys Lys Val Leu  Gly
    2315             2320

<210> SEQ ID NO 21
<211> LENGTH: 6966
<212> TYPE: DNA
<213> ORGANISM: Setaria italica

<400> SEQUENCE: 21
```

| | | | | | |
|---|---|---|---|---|---|
| atgtcgcaac | ttggattagc | tgcagctgcc | tcaaaggcgc | tgccactact | tcctaatcgc | 60 |
| catagaactt | cagctggaac | tacattccca | tcacctgtat | catcgcggcc | ctcaaaccga | 120 |
| aggaaaagcc | gcactcgttc | acttcgtgat | ggaggagatg | gggtatcaga | tgccaaaaag | 180 |
| cacaaccagt | ctgtccgtca | aggtcttgct | ggcatcatcg | acctcccaaa | tgaggcaaca | 240 |
| tcggaagtgg | atatttctca | tggatccgag | atcccagggg | gccaaccga | ttcatatcaa | 300 |
| atgaatggga | ttgtaaatga | agcacataat | ggcagacatg | cctcagtgtc | caaggttgtt | 360 |
| gaattttgtg | cggcgctagg | tggcaaaaca | ccaattcaca | gtatactagt | ggccaacaat | 420 |
| ggaatggcag | cagcaaagtt | catgaggagt | gtccggacat | gggctaatga | tacttttgga | 480 |
| tcggagaagg | cgattcagct | catagctatg | caactccag | aagacatgag | gataaatgca | 540 |
| gaacacatta | gaattgctga | tcaatttgta | gaggtgcctg | gtggaacaaa | caataacaac | 600 |
| tatgcaaatg | ttcaactcat | agtggaggta | gcagaaagaa | taggtgtttc | tgctgttttgg | 660 |
| cctggttggg | gtcatgcttc | tgagaatcct | gaacttccag | atgcattgac | cgcaaaagga | 720 |
| attgttttcc | ttgggccacc | tcggcatca | atgaatgcat | tggagataa | ggtcggttca | 780 |
| gctctcattg | ctcaagcagc | tggggtcccg | acccttcgt | ggagtggatc | acatgttgaa | 840 |
| gttccattag | agtgctgctt | agatgcgata | cctgaggaaa | tgtatagaaa | agcttgtgtt | 900 |
| actaccacag | aagaagctgt | tgcgagttgt | caggtggttg | gttatcctgc | catgattaag | 960 |
| gcatcctggg | gaggtggtgg | taaaggaata | agaaaggttc | ataatgacga | tgaggttaga | 1020 |
| gcactgttta | agcaagtaca | aggtgaagtc | cctggctccc | caatatttat | catgaggctt | 1080 |
| gcatcccaga | tcgtcatct | tgaagttcag | ttgctttgtg | atcaatatgg | caatgtggca | 1140 |
| gcacttcaca | gtcgtgattg | cagtgtgcaa | cggcgacacc | aaaagattat | tgaggaaggc | 1200 |
| ccagttactg | ttgctcctcg | tgagacagtt | aaagcgcttg | agcaggcagc | aaggaggctt | 1260 |
| gctaaggctg | tgggttatgt | tggtgctgct | actgttgaat | acctttacag | catggagact | 1320 |
| ggggaatact | attttctgga | gcttaatccc | agattacagg | tcgagcatcc | agtcactgag | 1380 |
| tggattgctg | aagtaaatct | tcctgcagct | caagttgcag | ttggaatggg | catacctctt | 1440 |
| tggcagattc | cagaaatcag | acgtttctat | ggaatggact | atggaggagg | atatgacatt | 1500 |
| tggaggaaaa | cagcagctct | tgccacacca | tttaattttg | atgaagtaga | ttctcaatgg | 1560 |
| ccaaagggcc | attgtgtagc | agttagaatt | actagcgagg | atccagatga | tggtttcaaa | 1620 |
| cctactggtg | ggaaagtgaa | ggagataagt | tttaaaagca | agcctaatgt | ttgggcctac | 1680 |
| ttctcagtaa | agtctggtgg | aggcattcat | gaatttgctg | attctcagtt | tgggcatgtt | 1740 |
| tttgcatatg | ggctctctag | atcagcagca | ataacgaaca | tggctcttgc | attaaaagag | 1800 |

```
attcaaattc gtggagaaat tcattcaaat gttgattaca cagttgatct cttaaatgct    1860
tcagacttca gagaaaataa gattcatact ggctggcttg ataccagaat agctatgcgt    1920
gttcaagctg agaggccccc atggtatatt tcagtggttg gaggagctct atataaaaca    1980
gtaactgcca atgcagccac tgtttctgat tatgtcagtt atctcaccaa gggccagatt    2040
ccaccaaagc atatatccct tgtcagttca acagttaatc tgaatatcga agggagcaaa    2100
tacacagttg aaactgtaag gactggacat ggtagctaca gattacgaat gaatgattca    2160
gcaattgaag cgaatgtaca atctttatgt gatggaggcc tcttaatgca gttggatgga    2220
aatagccatg taatttacgc ggaagaagaa gctggtggta cacgacttct gattgatgga    2280
aagacatgct tgttacagaa tgatcatgat ccatcaaagt tattagctga cacccctgc    2340
aaacttcttc ggttcttggt tgctgatggt gctcatgttg atgctgatgt accatatgcg    2400
gaagttgagg ttatgaaaat gtgcatgcct ctcttgtcgc ctgcttctgg tgtcattcat    2460
gttatgatgt ctgagggcca ggcattgcag gctggtgatc ttatagcaag gctggatctt    2520
gatgacccct ctgctgtgaa aagagctgaa ccatttcatg gaatatttcc acaaatggac    2580
cttcctgttg ctgcctctag ccaagtacac aaaagatatg ctgcaagttt gaatgctgct    2640
cgaatggtcc ttgcaggata cgagcataat atcaatgaag ttgtacaaga tttggtatgc    2700
tgcctggata tcccgagct tcccttccta cagtgggatg aacttatgtc agttctagca    2760
actaggcttc aagaaatct taagagtgag ttagaggata aatacatgga atacaagttg    2820
aactttacc atgggaaaaa caaggacttc ccgtccaagc tgctgagaga catcattgag    2880
gcaaatcttg catatggttc agagaaggaa aaagctacga atgagaggct tattgagcct    2940
cttatgagcc tacttaagtc atatgagggt gggagagaaa gccatgctca ttttgttgtc    3000
aagtcccttt tcaaggagta ccttgctgtg gaagaacttt tcagtgatgg gattcagtct    3060
gatgtgattg aaaccctgcg tcatcagcac agtaaagact gcagaaggt tgtagacatt    3120
gtgttgtctc accagggtgt gaggaacaaa gctaagcttg taacagcact tatggaaaag    3180
ctggtttatc caaatcctgc tgcttacagg gatctgttgg ttcgcttttc ttcactcaat    3240
cataaaagat attataagtt ggcccttaaa gcaagcgaac ttcttgaaca aactaaacta    3300
agtgaactcc gtgcaagcat cgcaagaagc ctttctgatc tggggatgca taagggagaa    3360
atgactattg aagatagcat ggaagattta gtctctgccc cattacctgt cgaagatgca    3420
cttatttctt tgtttgatta cagtgatcca actgttcagc agaaagtgat cgagacatac    3480
atatctcgat tgtatcagcc tcttcttgtg aaagatagca tccaagtgaa atttaaggaa    3540
tctggtgcct ttgctttatg ggaattttct gaagggcatg ttgatactaa aaatggacaa    3600
gggaccgttc ttggtcgaac aagatggggt gccatggtag ctgtcaaatc agttgaatct    3660
gcacgaacag ccattgtagc tgcattaaag gattcggcac agcatgccag ctctgagggc    3720
aacatgatgc acattgcctt attgagtgct gaaaatgaaa ataatatcag tgatgatcaa    3780
gctcaacata ggatggaaaa acttaacaag atactcaagg atactagtgt cgcaaatgat    3840
cttcgagctg ctggttttgaa ggttataagt tgcattgttc aaagagatga agcacgcatg    3900
ccaatgcgcc acacattact ctggtcagat gaaaagagtt gttatgagga agagcagatt    3960
cttcggcatg tggagcctcc cctctccatg cttccttgaaa tggataagtt gaaagtgaaa    4020
ggatacaatg aaatgaagta tactccatca cgtgatcgtc aatggcatat ctacacacta    4080
agaaatactg aaaaccccaa aatgttgcat agggtatttt tccgaactat tgtcaggcaa    4140
```

```
cccaatgcag gcaacaagtt tatatcagcc caaattggcg acactgaagt aggaggtcct    4200
gaggaatctt tgtcatttac atctaatagc atttttaagag ccttgatgac tgctattgaa    4260
gaattagagc ttcatgcaat taggactggt cattctcaca tgtatttgtg catattgaaa    4320
gaacaaaagc ttcttgatct cattccgttt tcagggagca caatcgtcga tgttggccaa    4380
gacgaagcta ctgcttgttc acttttaaaa tcaatggctt tgaagataca cgaacttgtt    4440
ggtgcacaga tgcatcatct ttctgtatgc cagtgggagg tgaaactcaa gttgtactgc    4500
gatgggcctg ccagtggcac ctggagagtt gtaactacaa atgttactag tcacacttgc    4560
accgttgata tctaccggga agtggaagat actgaatcgc agaagttagt ataccattca    4620
gcttctccgt cagctagtcc tttgcatggt gtggccctgg ataatccgta tcaacctttg    4680
agtgtcattg atctaaaacg ctgctctgct aggaacaaca gaactacata ttgctatgat    4740
tttccactgg catttgaaac tgccctgcag aagtcatggc agtccaatgg ctccagtgtt    4800
tctgaaggca gtgaaaatag taggtcttat gtgaaagcaa cagagctggt gtttgctgaa    4860
aaacatgggt cctgggcac tcctataatt tccatggagc gtcccgctgg gctcaatgac    4920
attggcatgg tagcttggat cttagagatg tccactcctg aatttcccaa tggcaggcag    4980
attattgtca tagcaaatga tattactttc agagctggat catttggccc aagggaagat    5040 gcgtttttg aagctgtcac gaacctggcc tgcgagagga agcttcctct tatatacttg    5100
gcagcaaact ccggtgctag gattggcata gccgatgaag tgaaatcttg cttccgtgtt    5160
gggtggtccg atgaaggcag ccctgaacgg ggttttcagt acatttatct gactgacgaa    5220
gactatgccc gtattagctt gtctgttata gcacacaagc tgcagctgga taatggtgaa    5280
attaggtgga ttattgactc tgttgtgggc aaggaggatg ggcttggtgt tgagaatata    5340
catgaaagtg ctgctattgc cagtgcttat tctagggcat atgaggagac atttacactt    5400
acatttgtga ctgggcggac tgttggaata ggagcatatc ttgctcggct cggtatacgg    5460
tgcatacagc gtcttgacca gcctattatt ttaactgggt tttctgccct gaacaagctt    5520
cttgggcggg aagtgtacag ctcccacatg cagttgggtg gtcctaagat catggcgacc    5580
aatggtgttg tccacttgac tgtttcagat gaccttgaag tgtttccaa tatattgagg    5640 tggctcagct atgttcctgc caacattggt ggacctcttc ctattacaaa accttttggac    5700 ccaccagaca gacctgttgc atacatccct gagaacacat gtgatccgcg cgcagccatt    5760
cgtggtgtag atgacagcca agggaaatgg ttgggtggta tgtttgacaa agacagcttt    5820
gtcgagacat ttgaaggatg ggcgaaaaca gtggttacgg gcagagcaaa gcttggagga    5880
attcctgttg gtgtcatagc tgtggagaca caaaccatga tgcagcttat ccctgctgat    5940
ccaggccagc ttgattccca tgagcgatct gttcctcggg ctggacaagt gtggttccca    6000
gattctgcaa ccaagacagc tcaggcattg ttggacttca ccgtgaagg attgccgctg    6060 ttcatccttg ctaactggag aggattctct ggtggacaaa gagatctgtt tgaaggaatt    6120
cttcaggctg ggtcaacaat tgttgagaac cttaggacat acaatcagcc tgcttttgtc    6180
tacattccta tggctggaga gctgcgtgga ggagcttggg ttgtggttga tagcaaaata    6240
aatccagacc gaattgagtg ttatgctgag aggactgcta aaggcaatgt tctggaacct    6300
caagggttaa ttgaaatcaa attcagatca gaggagctcc aagactgtat gggtaggctt    6360
gacccagagt tgataaatct gaaagcaaaa ctccaaggtg caaagcttgg aaatggaagc    6420
ctaacagatg tagaatccct tcagaagagt atagatgctc gtacgaaaca gttgttgcct    6480
ttatacaccc agattgcaat acggtttgct gaattgcatg atacttccct cagaatggca    6540
```

```
gctaaaggtg tgattaagaa agttgtagat tgggaagaat tacgttcttt cttctacaga    6600
aggctacgga ggaggatctc tgaagatgtt cttgcaaaag aaataagagg aatagctggt    6660
gaccacttca ctcaccaatc agcagttgag ctgatcaagg aatggtactt ggcttctcaa    6720
gccacaacag gaagcactga atgggatgat gatgatgctt tgttgcctg gaaggagaat    6780 cctgaaaact ataagggata tatccaagag ttaagggctc aaaaggtgtc tcagtcgctc    6840
tccgatcttg cagactccag ttcagatcta gaagcattct cacagggtct ttccacatta    6900
ttagataaga tggatccctc tcagagagcc aagttcattc aggaagtcaa gaaggtcctg    6960
ggttga                                                              6966
```

<210> SEQ ID NO 22
<211> LENGTH: 2321
<212> TYPE: PRT
<213> ORGANISM: Setaria italica

<400> SEQUENCE: 22

```
Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ala Ser Met Asn Ala Leu Gly Asp
                245                 250                 255

Lys Val Gly Ser Ala Leu Ile Ala Gln Ala Ala Gly Val Pro Thr Leu
            260                 265                 270

Ser Trp Ser Gly Ser His Val Glu Val Pro Leu Glu Cys Cys Leu Asp
        275                 280                 285
```

```
Ala Ile Pro Glu Glu Met Tyr Arg Lys Ala Cys Val Thr Thr Thr Glu
290                 295                 300
Glu Ala Val Ala Ser Cys Gln Val Val Gly Tyr Pro Ala Met Ile Lys
305                 310                 315                 320
Ala Ser Trp Gly Gly Gly Lys Gly Ile Arg Lys Val His Asn Asp
            325                 330                 335
Asp Glu Val Arg Ala Leu Phe Lys Gln Val Gln Gly Glu Val Pro Gly
                340                 345                 350
Ser Pro Ile Phe Ile Met Arg Leu Ala Ser Gln Ser Arg His Leu Glu
        355                 360                 365
Val Gln Leu Leu Cys Asp Gln Tyr Gly Asn Val Ala Ala Leu His Ser
370                 375                 380
Arg Asp Cys Ser Val Gln Arg His Gln Lys Ile Glu Glu Gly
385                 390                 395                 400
Pro Val Thr Val Ala Pro Arg Glu Thr Val Lys Ala Leu Glu Gln Ala
                405                 410                 415
Ala Arg Arg Leu Ala Lys Ala Val Gly Tyr Val Gly Ala Ala Thr Val
            420                 425                 430
Glu Tyr Leu Tyr Ser Met Glu Thr Gly Glu Tyr Tyr Phe Leu Glu Leu
        435                 440                 445
Asn Pro Arg Leu Gln Val Glu His Pro Val Thr Glu Trp Ile Ala Glu
450                 455                 460
Val Asn Leu Pro Ala Ala Gln Val Ala Val Gly Met Gly Ile Pro Leu
465                 470                 475                 480
Trp Gln Ile Pro Glu Ile Arg Arg Phe Tyr Gly Met Asp Tyr Gly Gly
                485                 490                 495
Gly Tyr Asp Ile Trp Arg Lys Thr Ala Ala Leu Ala Thr Pro Phe Asn
        500                 505                 510
Phe Asp Glu Val Asp Ser Gln Trp Pro Lys Gly His Cys Val Ala Val
    515                 520                 525
Arg Ile Thr Ser Glu Asp Pro Asp Gly Phe Lys Pro Thr Gly Gly
530                 535                 540
Lys Val Lys Glu Ile Ser Phe Lys Ser Lys Pro Asn Val Trp Ala Tyr
545                 550                 555                 560
Phe Ser Val Lys Ser Gly Gly Ile His Glu Phe Ala Asp Ser Gln
                565                 570                 575
Phe Gly His Val Phe Ala Tyr Gly Leu Ser Arg Ser Ala Ala Ile Thr
        580                 585                 590
Asn Met Ala Leu Ala Leu Lys Glu Ile Gln Ile Arg Gly Glu Ile His
    595                 600                 605
Ser Asn Val Asp Tyr Thr Val Asp Leu Leu Asn Ala Ser Asp Phe Arg
610                 615                 620
Glu Asn Lys Ile His Thr Gly Trp Leu Asp Thr Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Val Thr Ala Asn Ala Ala Thr Val Ser Asp Tyr Val
        660                 665                 670
Ser Tyr Leu Thr Lys Gly Gln Ile Pro Pro Lys His Ile Ser Leu Val
    675                 680                 685
Ser Ser Thr Val Asn Leu Asn Ile Glu Gly Ser Lys Tyr Thr Val Glu
690                 695                 700
Thr Val Arg Thr Gly His Gly Ser Tyr Arg Leu Arg Met Asn Asp Ser
```

```
                705                 710                 715                 720
            Ala Ile Glu Ala Asn Val Gln Ser Leu Cys Asp Gly Gly Leu Leu Met
                        725                 730                 735

Gln Leu Asp Gly Asn Ser His Val Ile Tyr Ala Glu Glu Ala Gly
                        740                 745                 750

Gly Thr Arg Leu Leu Ile Asp Gly Lys Thr Cys Leu Leu Gln Asn Asp
                        755                 760                 765

His Asp Pro Ser Lys Leu Leu Ala Glu Thr Pro Cys Lys Leu Leu Arg
                        770                 775                 780

Phe Leu Val Ala Asp Gly Ala His Val Asp Ala Asp Val Pro Tyr Ala
            785                 790                 795                 800

Glu Val Glu Val Met Lys Met Cys Met Pro Leu Leu Ser Pro Ala Ser
                        805                 810                 815

Gly Val Ile His Val Met Met Ser Glu Gly Gln Ala Leu Gln Ala Gly
                        820                 825                 830

Asp Leu Ile Ala Arg Leu Asp Leu Asp Pro Ser Ala Val Lys Arg
                        835                 840                 845

Ala Glu Pro Phe His Gly Ile Phe Pro Gln Met Asp Leu Pro Val Ala
            850                 855                 860

Ala Ser Ser Gln Val His Lys Arg Tyr Ala Ala Ser Leu Asn Ala Ala
            865                 870                 875                 880

Arg Met Val Leu Ala Gly Tyr Glu His Asn Ile Asn Glu Val Val Gln
                        885                 890                 895

Asp Leu Val Cys Cys Leu Asp Asp Pro Glu Leu Pro Phe Leu Gln Trp
                        900                 905                 910

Asp Glu Leu Met Ser Val Leu Ala Thr Arg Leu Pro Arg Asn Leu Lys
                        915                 920                 925

Ser Glu Leu Glu Asp Lys Tyr Met Glu Tyr Lys Leu Asn Phe Tyr His
                        930                 935                 940

Gly Lys Asn Lys Asp Phe Pro Ser Lys Leu Leu Arg Asp Ile Ile Glu
            945                 950                 955                 960

Ala Asn Leu Ala Tyr Gly Ser Glu Lys Glu Lys Ala Thr Asn Glu Arg
                        965                 970                 975

Leu Ile Glu Pro Leu Met Ser Leu Leu Lys Ser Tyr Glu Gly Gly Arg
                        980                 985                 990

Glu Ser His Ala His Phe Val Val Lys Ser Leu Phe Lys Glu Tyr Leu
                        995                1000                1005

Ala Val Glu Glu Leu Phe Ser Asp Gly Ile Gln Ser Asp Val Ile
                       1010                1015                1020

Glu Thr Leu Arg His Gln His Ser Lys Asp Leu Gln Lys Val Val
                       1025                1030                1035

Asp Ile Val Leu Ser His Gln Gly Val Arg Asn Lys Ala Lys Leu
                       1040                1045                1050

Val Thr Ala Leu Met Glu Lys Leu Val Tyr Pro Asn Pro Ala Ala
                       1055                1060                1065

Tyr Arg Asp Leu Leu Val Arg Phe Ser Ser Leu Asn His Lys Arg
                       1070                1075                1080

Tyr Tyr Lys Leu Ala Leu Lys Ala Ser Glu Leu Leu Glu Gln Thr
                       1085                1090                1095

Lys Leu Ser Glu Leu Arg Ala Ser Ile Ala Arg Ser Leu Ser Asp
                       1100                1105                1110

Leu Gly Met His Lys Gly Glu Met Thr Ile Glu Asp Ser Met Glu
                       1115                1120                1125
```

```
Asp Leu Val Ser Ala Pro Leu Pro Val Glu Asp Ala Leu Ile Ser
    1130                1135                1140

Leu Phe Asp Tyr Ser Asp Pro Thr Val Gln Gln Lys Val Ile Glu
    1145                1150                1155

Thr Tyr Ile Ser Arg Leu Tyr Gln Pro Leu Leu Val Lys Asp Ser
    1160                1165                1170

Ile Gln Val Lys Phe Lys Glu Ser Gly Ala Phe Ala Leu Trp Glu
    1175                1180                1185

Phe Ser Glu Gly His Val Asp Thr Lys Asn Gly Gln Gly Thr Val
    1190                1195                1200

Leu Gly Arg Thr Arg Trp Gly Ala Met Val Ala Val Lys Ser Val
    1205                1210                1215

Glu Ser Ala Arg Thr Ala Ile Val Ala Ala Leu Lys Asp Ser Ala
    1220                1225                1230

Gln His Ala Ser Ser Glu Gly Asn Met Met His Ile Ala Leu Leu
    1235                1240                1245

Ser Ala Glu Asn Glu Asn Asn Ile Ser Asp Asp Gln Ala Gln His
    1250                1255                1260

Arg Met Glu Lys Leu Asn Lys Ile Leu Lys Asp Thr Ser Val Ala
    1265                1270                1275

Asn Asp Leu Arg Ala Ala Gly Leu Lys Val Ile Ser Cys Ile Val
    1280                1285                1290

Gln Arg Asp Glu Ala Arg Met Pro Met Arg His Thr Leu Leu Trp
    1295                1300                1305

Ser Asp Glu Lys Ser Cys Tyr Glu Glu Glu Gln Ile Leu Arg His
    1310                1315                1320

Val Glu Pro Pro Leu Ser Met Leu Leu Glu Met Asp Lys Leu Lys
    1325                1330                1335

Val Lys Gly Tyr Asn Glu Met Lys Tyr Thr Pro Ser Arg Asp Arg
    1340                1345                1350

Gln Trp His Ile Tyr Thr Leu Arg Asn Thr Glu Asn Pro Lys Met
    1355                1360                1365

Leu His Arg Val Phe Phe Arg Thr Ile Val Arg Gln Pro Asn Ala
    1370                1375                1380

Gly Asn Lys Phe Ile Ser Ala Gln Ile Gly Asp Thr Glu Val Gly
    1385                1390                1395

Gly Pro Glu Glu Ser Leu Ser Phe Thr Ser Asn Ser Ile Leu Arg
    1400                1405                1410

Ala Leu Met Thr Ala Ile Glu Glu Leu Glu Leu His Ala Ile Arg
    1415                1420                1425

Thr Gly His Ser His Met Tyr Leu Cys Ile Leu Lys Glu Gln Lys
    1430                1435                1440

Leu Leu Asp Leu Ile Pro Phe Ser Gly Ser Thr Ile Val Asp Val
    1445                1450                1455

Gly Gln Asp Glu Ala Thr Ala Cys Ser Leu Leu Lys Ser Met Ala
    1460                1465                1470

Leu Lys Ile His Glu Leu Val Gly Ala Gln Met His His Leu Ser
    1475                1480                1485

Val Cys Gln Trp Glu Val Lys Leu Lys Leu Tyr Cys Asp Gly Pro
    1490                1495                1500

Ala Ser Gly Thr Trp Arg Val Val Thr Thr Asn Val Thr Ser His
    1505                1510                1515
```

```
Thr Cys Thr Val Asp Ile Tyr Arg Glu Val Glu Asp Thr Glu Ser
    1520                1525                1530

Gln Lys Leu Val Tyr His Ser Ala Ser Pro Ser Ala Ser Pro Leu
    1535                1540                1545

His Gly Val Ala Leu Asp Asn Pro Tyr Gln Pro Leu Ser Val Ile
    1550                1555                1560

Asp Leu Lys Arg Cys Ser Ala Arg Asn Asn Arg Thr Thr Tyr Cys
    1565                1570                1575

Tyr Asp Phe Pro Leu Ala Phe Glu Thr Ala Leu Gln Lys Ser Trp
    1580                1585                1590

Gln Ser Asn Gly Ser Ser Val Ser Glu Gly Ser Glu Asn Ser Arg
    1595                1600                1605

Ser Tyr Val Lys Ala Thr Glu Leu Val Phe Ala Glu Lys His Gly
    1610                1615                1620

Ser Trp Gly Thr Pro Ile Ile Ser Met Glu Arg Pro Ala Gly Leu
    1625                1630                1635

Asn Asp Ile Gly Met Val Ala Trp Ile Leu Glu Met Ser Thr Pro
    1640                1645                1650

Glu Phe Pro Asn Gly Arg Gln Ile Ile Val Ile Ala Asn Asp Ile
    1655                1660                1665

Thr Phe Arg Ala Gly Ser Phe Gly Pro Arg Glu Asp Ala Phe Phe
    1670                1675                1680

Glu Ala Val Thr Asn Leu Ala Cys Glu Arg Lys Leu Pro Leu Ile
    1685                1690                1695

Tyr Leu Ala Ala Asn Ser Gly Ala Arg Ile Gly Ile Ala Asp Glu
    1700                1705                1710

Val Lys Ser Cys Phe Arg Val Gly Trp Ser Asp Glu Gly Ser Pro
    1715                1720                1725

Glu Arg Gly Phe Gln Tyr Ile Tyr Leu Thr Asp Glu Asp Tyr Ala
    1730                1735                1740

Arg Ile Ser Leu Ser Val Ile Ala His Lys Leu Gln Leu Asp Asn
    1745                1750                1755

Gly Glu Ile Arg Trp Ile Ile Asp Ser Val Val Gly Lys Glu Asp
    1760                1765                1770

Gly Leu Gly Val Glu Asn Ile His Gly Ser Ala Ala Ile Ala Ser
    1775                1780                1785

Ala Tyr Ser Arg Ala Tyr Glu Glu Thr Phe Thr Leu Thr Phe Val
    1790                1795                1800

Thr Gly Arg Thr Val Gly Ile Gly Ala Tyr Leu Ala Arg Leu Gly
    1805                1810                1815

Ile Arg Cys Ile Gln Arg Leu Asp Gln Pro Ile Ile Leu Thr Gly
    1820                1825                1830

Phe Ser Ala Leu Asn Lys Leu Leu Gly Arg Glu Val Tyr Ser Ser
    1835                1840                1845

His Met Gln Leu Gly Gly Pro Lys Ile Met Ala Thr Asn Gly Val
    1850                1855                1860

Val His Leu Thr Val Ser Asp Asp Leu Glu Gly Val Ser Asn Ile
    1865                1870                1875

Leu Arg Trp Leu Ser Tyr Val Pro Ala Asn Ile Gly Gly Pro Leu
    1880                1885                1890

Pro Ile Thr Lys Pro Leu Asp Pro Pro Asp Arg Pro Val Ala Tyr
    1895                1900                1905

Ile Pro Glu Asn Thr Cys Asp Pro Arg Ala Ala Ile Arg Gly Val
```

-continued

```
            1910                1915                1920
Asp Asp Ser Gln Gly Lys Trp Leu Gly Gly Met Phe Asp Lys Asp
            1925                1930                1935
Ser Phe Val Glu Thr Phe Glu Gly Trp Ala Lys Thr Val Val Thr
            1940                1945                1950
Gly Arg Ala Lys Leu Gly Gly Ile Pro Val Gly Val Ile Ala Val
            1955                1960                1965
Glu Thr Gln Thr Met Met Gln Leu Ile Pro Ala Asp Pro Gly Gln
            1970                1975                1980
Leu Asp Ser His Glu Arg Ser Val Pro Arg Ala Gly Gln Val Trp
            1985                1990                1995
Phe Pro Asp Ser Ala Thr Lys Thr Ala Gln Ala Leu Leu Asp Phe
            2000                2005                2010
Asn Arg Glu Gly Leu Pro Leu Phe Ile Leu Ala Asn Trp Arg Gly
            2015                2020                2025
Phe Ser Gly Gly Gln Arg Asp Leu Phe Glu Gly Ile Leu Gln Ala
            2030                2035                2040
Gly Ser Thr Ile Val Glu Asn Leu Arg Thr Tyr Asn Gln Pro Ala
            2045                2050                2055
Phe Val Tyr Ile Pro Met Ala Gly Glu Leu Arg Gly Gly Ala Trp
            2060                2065                2070
Val Val Val Asp Ser Lys Ile Asn Pro Asp Arg Ile Glu Cys Tyr
            2075                2080                2085
Ala Glu Arg Thr Ala Lys Gly Asn Val Leu Glu Pro Gln Gly Leu
            2090                2095                2100
Ile Glu Ile Lys Phe Arg Ser Glu Glu Leu Gln Asp Cys Met Gly
            2105                2110                2115
Arg Leu Asp Pro Glu Leu Ile Asn Leu Lys Ala Lys Leu Gln Gly
            2120                2125                2130
Ala Lys Leu Gly Asn Gly Ser Leu Thr Asp Val Glu Ser Leu Gln
            2135                2140                2145
Lys Ser Ile Asp Ala Arg Thr Lys Gln Leu Leu Pro Leu Tyr Thr
            2150                2155                2160
Gln Ile Ala Ile Arg Phe Ala Glu Leu His Asp Thr Ser Leu Arg
            2165                2170                2175
Met Ala Ala Lys Gly Val Ile Lys Lys Val Val Asp Trp Glu Glu
            2180                2185                2190
Leu Arg Ser Phe Phe Tyr Arg Arg Leu Arg Arg Arg Ile Ser Glu
            2195                2200                2205
Asp Val Leu Ala Lys Glu Ile Arg Gly Ile Ala Gly Asp His Phe
            2210                2215                2220
Thr His Gln Ser Ala Val Glu Leu Ile Lys Glu Trp Tyr Leu Ala
            2225                2230                2235
Ser Gln Ala Thr Thr Gly Ser Thr Glu Trp Asp Asp Asp Ala
            2240                2245                2250
Phe Val Ala Trp Lys Glu Asn Pro Glu Asn Tyr Lys Gly Tyr Ile
            2255                2260                2265
Gln Glu Leu Arg Ala Gln Lys Val Ser Gln Ser Leu Ser Asp Leu
            2270                2275                2280
Ala Asp Ser Ser Ser Asp Leu Glu Ala Phe Ser Gln Gly Leu Ser
            2285                2290                2295
Thr Leu Leu Asp Lys Met Asp Pro Ser Gln Arg Ala Lys Phe Ile
            2300                2305                2310
```

```
Gln Glu  Val Lys Lys Val Leu  Gly
    2315            2320
```

<210> SEQ ID NO 23
<211> LENGTH: 6963
<212> TYPE: DNA
<213> ORGANISM: Alopecurus myosuroides

<400> SEQUENCE: 23

| | | | | | |
|---|---|---|---|---|---|
| atgggatcca | cacatctgcc | cattgtcggg | tttaatgcat | ccacaacacc | atcgctatcc | 60 |
| actcttcgcc | agataaactc | agctgctgct | gcattccaat | cttcgtcccc | ttcaaggtca | 120 |
| tccaagaaga | aaagccgacg | tgttaagtca | ataagggatg | atggcgatgg | aagcgtgcca | 180 |
| gaccctgcag | gccatggcca | gtctattcgc | caaggtctcg | ctggcatcat | cgacctccca | 240 |
| aaggagggcg | catcagctcc | agatgtggac | atttcacatg | ggtctgaaga | ccacaaggcc | 300 |
| tcctaccaaa | tgaatgggat | actgaatgaa | tcacataacg | ggaggcacgc | ctctctgtct | 360 |
| aaagtttatg | aattttgcac | ggaattgggt | ggaaaaacac | caattcacag | tgtattagtc | 420 |
| gccaacaatg | gaatggcagc | agctaagttc | atgcggagtg | tccggacatg | ggctaatgat | 480 |
| acatttgggt | cagagaaggc | gattcagttg | atagctatgg | caactccgga | agacatgaga | 540 |
| ataaatgcag | agcacattag | aattgctgat | cagtttgttg | aagtacctgg | tggaacaaac | 600 |
| aataacaact | atgcaaatgt | ccaactcata | gtggagatag | cagagagaac | tggtgtctcc | 660 |
| gccgtttggc | ctggttgggg | ccatgcatct | gagaatcctg | aacttccaga | tgcactaact | 720 |
| gcaaaaggaa | ttgttttct | gggccacca | gcatcatcaa | tgaacgcact | aggcgacaag | 780 |
| gttggttcag | ctctcattgc | tcaagcagca | ggggttccca | ctcttgcttg | gagtggatca | 840 |
| catgtggaaa | ttccattaga | actttgtttg | gactcgatac | ctgaggagat | gtataggaaa | 900 |
| gcctgtgtta | caaccgctga | tgaagcagtt | gcaagttgtc | agatgattgg | ttaccctgcc | 960 |
| atgatcaagg | catcctgggg | tggtggtggt | aaagggatta | gaaaggttaa | taatgatgac | 1020 |
| gaggtgaaag | cactgttaa | gcaagtacag | ggtgaagttc | ctggctcccc | gatatttatc | 1080 |
| atgagacttg | catctcagag | tcgtcatctt | gaagtccagc | tgctttgtga | tgaatatggc | 1140 |
| aatgtagcag | cacttcacag | tcgtgattgc | agtgtgcaac | gacgacacca | aaagattatc | 1200 |
| gaggaaggac | cagttactgt | tgctcctcgt | gaaacagtga | agagctaga | gcaagcagca | 1260 |
| aggaggcttg | ctaaggccgt | gggttacgtc | ggtgctgcta | ctgttgaata | tctctacagc | 1320 |
| atggagactg | tgaatacta | ttttctggag | cttaatccac | ggttgcaggt | tgagcaccca | 1380 |
| gtcaccgagt | cgatagctga | agtaaatttg | cctgcagccc | aagttgcagt | tgggatgggt | 1440 |
| atcccctttt | ggcagattcc | agagatcaga | cgtttctacg | gaatggacaa | tggaggaggc | 1500 |
| tatgatattt | ggaggaaaac | agcagctctc | gctactccat | tcaactttga | tgaagtagat | 1560 |
| tctcaatggc | cgaagggtca | ttgtgtggca | gttaggataa | ccagtgagaa | tccagatgat | 1620 |
| ggattcaagc | tactggtgg | aaaagtaaag | gagataagtt | ttaaaagtaa | gccaaatgtc | 1680 |
| tggggatatt | tctcagttaa | gtctggtgga | ggcattcatg | aatttgcgga | ttctcagttt | 1740 |
| ggacacgttt | ttgcctatgg | agagactaga | tcagcagcaa | taaccagcat | gtctcttgca | 1800 |
| ctaaaagaga | ttcaaattcg | tggagaaatt | catacaaacg | ttgattacac | ggttgatctc | 1860 |
| ttgaatgccc | cagacttcag | agaaaacacg | atccataccg | ttggctgga | taccagaata | 1920 |
| gctatgcgtg | ttcaagctga | gaggcctccc | tggtatattt | cagtggttgg | aggagctcta | 1980 |
| tataaaacaa | taaccaccaa | tgcggagacc | gtttctgaat | atgttagcta | tctccatcaag | 2040 |

```
ggtcagattc caccaaagca catatcccctt gtccattcaa ctatttcttt gaatatagag    2100
gaaagcaaat atacaattga gattgtgagg agtggacagg gtagctacag attgagactg    2160
aatggatcac ttattgaagc caatgtacaa acattatgtg atggaggcct tttaatgcag    2220
ctggatggaa atagccatgt tatttatgct gaagaagaag cgggtggtac acggcttctt    2280
attgatggaa aaacatgctt gctacagaat gaccatgatc cgtcaaggtt attagctgag    2340
acaccctgca aacttcttcg tttcttgatt gccgatggtg ctcatgttga tgctgatgta    2400
ccatacgcgg aagttgaggt tatgaagatg tgcatgcccc tcttgtcgcc tgctgctggt    2460
gtcattaatg ttttgttgtc tgagggccag gcgatgcagg ctggtgatct tatagcgaga    2520
cttgatctcg atgacccttc tgctgtgaag agagccgagc catttgaagg atcttttcca    2580
gaaatgagcc ttcctattgc tgcttctggc caagttcaca aaagatgtgc tgcaagtttg    2640
aacgctgctc gaatggtcct tgcaggatat gaccatgcgg ccaacaaagt tgtgcaagat    2700
ttggtatggt gccttgatac acctgctctt cctttcctac aatgggaaga gcttatgtct    2760
gttttagcaa ctagacttcc aagacgtctt aagagcgagt tggagggcaa atacaatgaa    2820
tacaagttaa atgttgacca tgtgaagatc aaggatttcc ctaccgagat gcttagagag    2880
acaatcgagg aaaatcttgc atgtgtttcc gagaaggaaa tggtgacaat tgagaggctt    2940
gttgaccctc tgatgagcct gctgaagtca tacgagggtg ggagagaaag ccatgcccac    3000
tttattgtca agtccctttt tgaggagtat ctctcggttg aggaactatt cagtgatggc    3060
attcagtctg acgtgattga acgcctgcgc tacaatatat gtaaagacct ccagaaggtt    3120
gtagacattg ttttgtctca ccagggtgtg agaaacaaaa caaagctgat actcgcgctc    3180
atggagaaac tggtctatcc aaaccctgct gcctacagag atcagttgat tcgcttttct    3240
tccctcaacc ataaaagata ttataagttg gctcttaaag ctagtgaact tcttgaacaa    3300
accaagctca gcgaactccg cacaagcatt gcaggaacc tttcagcgct ggatatgttc    3360
accgaggaaa aggcagattt ctccttgcaa gacagaaaat tggccattaa tgagagcatg    3420
ggagatttag tcactgcccc actgccagtt gaagatgcac ttgtttcttt gtttgattgt    3480
actgatcaaa ctcttcagca gagagtgatt cagacataca tatctcgatt ataccagcct    3540
caacttgtga aggatagcat ccagctgaaa tatcaggatt ctggtgttat tgctttatgg    3600
gaattcactg aaggaaatca tgaagagaga ttgggtgcta tggttatcct gaagtcacta    3660
gaatctgtgt caacagccat tggagctgct ctaaaggatg catcacatta tgcaagctct    3720
gcgggcaaca cggtgcatat tgctttgttg gatgctgata cccaactgaa tacaactgaa    3780
gatagtggtg ataatgacca agctcaagac aagatggata aactttcttt tgtactgaaa    3840
caagatgttg tcatgctgga tctacgtgct gctgatgtca aggttgttag ttgcattgtt    3900
caaagagatg gagcaatcat gcctatgcgc cgtaccttcc tcttgtcaga ggaaaaactt    3960
tgttacgagg aagagccgat tcttcggcat gtggagcctc cactttctgc acttcttgag    4020
ttggataaat tgaaagtgaa aggatacaat gagatgaagt atacaccgtc acgtgatcgt    4080
cagtggcata tatacacact tagaaatact gaaaatccaa aaatgctgca cagggtattt    4140
ttccgaacac ttgtcagaca acccagtgca ggcaacaggt ttacatcaga ccatatcact    4200
gatgttgaag taggacacgc agaggaacct ctttcattta cttcaagcag catattaaaa    4260
tcgttgaaga ttgctaaaga agaattggag cttcacgcga tcaggactgg ccattctcat    4320
atgtacttgt gcatattgaa agagcaaaag cttcttgacc ttgttcctgt ttcagggaac    4380
```

-continued

```
actgttgtgg atgttggtca agatgaagct actgcatgct ctcttttgaa agaaatggct      4440
ttaaagatac atgaacttgt tggtgcaaga atgcatcatc tttctgtatg ccagtgggaa      4500
gtgaaactta agttggtgag cgatgggcct gccagtggta gctggagagt tgtaacaacc      4560
aatgttactg gtcacacctg cactgtggat atctaccggg aggtcgaaga tacagaatca      4620
cagaaactag tataccactc caccgcattg tcatctggtc ctttgcatgg tgttgcactg      4680
aatacttcgt atcagccttt gagtgttatt gatttaaaac gttgctctgc caggaacaac      4740
aaaactacat actgctatga ttttccattg acatttgaag ctgcagtgca gaagtcgtgg      4800
tctaacattt ccagtgaaaa caaccaatgt tatgttaaag cgacagagct tgtgtttgct      4860
gaaaagaatg ggtcgtgggg cactcctata attcctatgc agcgtgctgc tgggctgaat      4920
gacattggta tggtagcctg gatcttggac atgtccactc ctgaatttcc cagcggcaga      4980
cagatcattg ttatcgcaaa tgatattaca tttagagctg gatcatttgg cccaagggaa      5040
gatgcatttt tcgaagctgt aaccaacctg gcttgtgaga agaagcttcc acttatctac      5100
ttggctgcaa actctggtgc tcggattggc attgctgatg aagtaaaatc ttgcttccgt      5160
gttggatgga ctgatgatag cagccctgaa cgtggattta ggtacattta tatgactgac      5220
gaagaccatg atcgtattgg ctcttcagtt atagcacaca agatgcagct agatagtggc      5280
gagatcaggt gggttattga ttctgttgtg ggaaaagagg atggactagg tgtggagaac      5340
atacatggaa gtgctgctat tgccagtgcc tattctaggg cgtacgagga gacatttaca      5400
cttacattcg ttactggacg aactgttgga atcggagcct atcttgctcg acttggcata      5460
cggtgcatac agcgtattga ccagcccatt attttgaccg ggttttctgc cctgaacaag      5520
cttcttgggc gggaggtgta cagctcccac atgcagttgg gtggtcccaa aatcatggcg      5580
acgaatggtg ttgtccatct gactgttcca gatgaccttg aaggtgtttc taatatattg      5640
aggtggctca gctatgttcc tgcaaacatt ggtggacctc ttcctattac aaaatctttg      5700
gacccaatag acagacccgt tgcatacatc cctgagaata catgtgatcc tcgtgcagcc      5760
atcagtggca ttgatgacag ccaagggaaa tggttgggtg gcatgtttga caaagacagt      5820
tttgtggaga catttgaagg atgggcgaag acagtagtta ctggcagagc aaaacttgga      5880
gggattcctg ttggtgttat agctgtggag acacagacca tgatgcagct cgtccccgct      5940
gatccaggcc agcctgattc ccacgagcgg tctgttcctc gtgctgggca agtttggttt      6000
ccagattctg ctaccaagac agcgcaggcg atgttggact caaccgtga aggattacct      6060 ctgttcatac ttgctaactg gagaggcttc tctggagggc aaagagatct ttttgaagga      6120
attctgcagg ctgggtcaac aattgttgag aaccttagga catacaatca gcctgccttt      6180
gtatatatcc ccaaggctgc agagctacgt ggaggagcct gggtcgtgat tgatagcaag      6240
ataaacccag atcgcatcga gtgctatgct gagaggactg caaagggtaa tgttctcgaa      6300
cctcaagggt tgattgagat caagttcagg tcagaggaac tcaaagaatg catgggtagg      6360
cttgatccag aattgataga tctgaaagca agactccagg gagcaaatgg aagcctatct      6420
gatggagaat cccttcagaa gagcatagaa gctcggaaga acagttgct gcctctgtac      6480 acccaaatcg cggtacgttt tgcggaattg cacgacactt cccttagaat ggctgctaaa      6540
ggtgtgatca ggaaagttgt agactgggaa gactctcggt ctttcttcta caagagatta      6600
cggaggaggc tatccgagga cgttctggca aaggagatta gaggtgtaat tggtgagaag      6660
tttcctcaca aatcagcgat cgagctgatc aagaaatggt acttggcttc tgaggcagct      6720
gcagcaggaa gcaccgactg ggatgacgac gatgcttttg tcgcctggag ggagaaccct      6780
```

```
gaaaactata aggagtatat caaagagctt agggctcaaa gggtatctcg gttgctctca    6840
gatgttgcag gctccagttc ggatttacaa gccttgccgc agggtctttc catgctacta    6900
gataagatgg atccctctaa gagagcacag tttatcgagg aggtcatgaa ggtcctgaaa    6960
tga                                                                 6963
```

<210> SEQ ID NO 24
<211> LENGTH: 2320
<212> TYPE: PRT
<213> ORGANISM: Alopecurus myosuroides

<400> SEQUENCE: 24

```
Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Ser Arg Arg Val
        35                  40                  45

Lys Ser Ile Arg Asp Asp Gly Asp Gly Ser Val Pro Asp Pro Ala Gly
 50                  55                  60

His Gly Gln Ser Ile Arg Gln Gly Leu Ala Gly Ile Ile Asp Leu Pro
 65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335
```

```
Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
            355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
            435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
            515                 520                 525

Val Ala Val Arg Ile Thr Ser Glu Asn Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
            595                 600                 605

Glu Ile His Thr Asn Val Asp Tyr Thr Val Asp Leu Leu Asn Ala Pro
    610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
            675                 680                 685

Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
            725                 730                 735

Leu Leu Met Gln Leu Asp Gly Asn Ser His Val Ile Tyr Ala Glu Glu
            740                 745                 750
```

-continued

Glu Ala Gly Gly Thr Arg Leu Leu Ile Asp Gly Lys Thr Cys Leu Leu
            755                 760                 765

Gln Asn Asp His Asp Pro Ser Arg Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
                820                 825                 830

Gln Ala Gly Asp Leu Ile Ala Arg Leu Asp Leu Asp Asp Pro Ser Ala
                835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
                900                 905                 910

Leu Gln Trp Glu Glu Leu Met Ser Val Leu Ala Thr Arg Leu Pro Arg
            915                 920                 925

Arg Leu Lys Ser Glu Leu Glu Gly Lys Tyr Asn Glu Tyr Lys Leu Asn
                930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
                980                 985                 990

Gly Gly Arg Glu Ser His Ala His Phe Ile Val Lys Ser Leu Phe Glu
                995                 1000                1005

Glu Tyr Leu Ser Val Glu Glu Leu Phe Ser Asp Gly Ile Gln Ser
    1010                1015                1020

Asp Val Ile Glu Arg Leu Arg Leu Gln Tyr Ser Lys Asp Leu Gln
    1025                1030                1035

Lys Val Val Asp Ile Val Leu Ser His Gln Gly Val Arg Asn Lys
    1040                1045                1050

Thr Lys Leu Ile Leu Ala Leu Met Glu Lys Leu Val Tyr Pro Asn
    1055                1060                1065

Pro Ala Ala Tyr Arg Asp Gln Leu Ile Arg Phe Ser Ser Leu Asn
    1070                1075                1080

His Lys Arg Tyr Tyr Lys Leu Ala Leu Lys Ala Ser Glu Leu Leu
    1085                1090                1095

Glu Gln Thr Lys Leu Ser Glu Leu Arg Thr Ser Ile Ala Arg Asn
    1100                1105                1110

Leu Ser Ala Leu Asp Met Phe Thr Glu Glu Lys Ala Asp Phe Ser
    1115                1120                1125

Leu Gln Asp Arg Lys Leu Ala Ile Asn Glu Ser Met Gly Asp Leu
    1130                1135                1140

Val Thr Ala Pro Leu Pro Val Glu Asp Ala Leu Val Ser Leu Phe
    1145                1150                1155

Asp Cys Thr Asp Gln Thr Leu Gln Gln Arg Val Ile Gln Thr Tyr

```
            1160                1165                1170

Ile Ser Arg Leu Tyr Gln Pro Gln Leu Val Lys Asp Ser Ile Gln
    1175                1180                1185

Leu Lys Tyr Gln Asp Ser Gly Val Ile Ala Leu Trp Glu Phe Thr
    1190                1195                1200

Glu Gly Asn His Glu Lys Arg Leu Gly Ala Met Val Ile Leu Lys
    1205                1210                1215

Ser Leu Glu Ser Val Ser Thr Ala Ile Gly Ala Ala Leu Lys Asp
    1220                1225                1230

Ala Ser His Tyr Ala Ser Ser Ala Gly Asn Thr Val His Ile Ala
    1235                1240                1245

Leu Leu Asp Ala Asp Thr Gln Leu Asn Thr Thr Glu Asp Ser Gly
    1250                1255                1260

Asp Asn Asp Gln Ala Gln Asp Lys Met Asp Lys Leu Ser Phe Val
    1265                1270                1275

Leu Lys Gln Asp Val Val Met Ala Asp Leu Arg Ala Ala Asp Val
    1280                1285                1290

Lys Val Val Ser Cys Ile Val Gln Arg Asp Gly Ala Ile Met Pro
    1295                1300                1305

Met Arg Arg Thr Phe Leu Leu Ser Glu Glu Lys Leu Cys Tyr Glu
    1310                1315                1320

Glu Glu Pro Ile Leu Arg His Val Glu Pro Pro Leu Ser Ala Leu
    1325                1330                1335

Leu Glu Leu Asp Lys Leu Lys Val Lys Gly Tyr Asn Glu Met Lys
    1340                1345                1350

Tyr Thr Pro Ser Arg Asp Arg Gln Trp His Ile Tyr Thr Leu Arg
    1355                1360                1365

Asn Thr Glu Asn Pro Lys Met Leu His Arg Val Phe Phe Arg Thr
    1370                1375                1380

Leu Val Arg Gln Pro Ser Ala Gly Asn Arg Phe Thr Ser Asp His
    1385                1390                1395

Ile Thr Asp Val Glu Val Gly His Ala Glu Glu Pro Leu Ser Phe
    1400                1405                1410

Thr Ser Ser Ser Ile Leu Lys Ser Leu Lys Ile Ala Lys Glu Glu
    1415                1420                1425

Leu Glu Leu His Ala Ile Arg Thr Gly His Ser His Met Tyr Leu
    1430                1435                1440

Cys Ile Leu Lys Glu Gln Lys Leu Leu Asp Leu Val Pro Val Ser
    1445                1450                1455

Gly Asn Thr Val Val Asp Val Gly Gln Asp Glu Ala Thr Ala Cys
    1460                1465                1470

Ser Leu Leu Lys Glu Met Ala Leu Lys Ile His Glu Leu Val Gly
    1475                1480                1485

Ala Arg Met His His Leu Ser Val Cys Gln Trp Glu Val Lys Leu
    1490                1495                1500

Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560
```

-continued

Tyr Gln Pro Leu Ser Val Ile Asp Leu Lys Arg Cys Ser Ala Arg
1565                1570                1575

Asn Asn Lys Thr Thr Tyr Cys Tyr Asp Phe Pro Leu Thr Phe Glu
1580                1585                1590

Ala Ala Val Gln Lys Ser Trp Ser Asn Ile Ser Ser Glu Asn Asn
1595                1600                1605

Gln Cys Tyr Val Lys Ala Thr Glu Leu Val Phe Ala Glu Lys Asn
1610                1615                1620

Gly Ser Trp Gly Thr Pro Ile Ile Pro Met Gln Arg Ala Ala Gly
1625                1630                1635

Leu Asn Asp Ile Gly Met Val Ala Trp Ile Leu Asp Met Ser Thr
1640                1645                1650

Pro Glu Phe Pro Ser Gly Arg Gln Ile Ile Val Ile Ala Asn Asp
1655                1660                1665

Ile Thr Phe Arg Ala Gly Ser Phe Gly Pro Arg Glu Asp Ala Phe
1670                1675                1680

Phe Glu Ala Val Thr Asn Leu Ala Cys Glu Lys Lys Leu Pro Leu
1685                1690                1695

Ile Tyr Leu Ala Ala Asn Ser Gly Ala Arg Ile Gly Ile Ala Asp
1700                1705                1710

Glu Val Lys Ser Cys Phe Arg Val Gly Trp Thr Asp Asp Ser Ser
1715                1720                1725

Pro Glu Arg Gly Phe Arg Tyr Ile Tyr Met Thr Asp Glu Asp His
1730                1735                1740

Asp Arg Ile Gly Ser Ser Val Ile Ala His Lys Met Gln Leu Asp
1745                1750                1755

Ser Gly Glu Ile Arg Trp Val Ile Asp Ser Val Val Gly Lys Glu
1760                1765                1770

Asp Gly Leu Gly Val Glu Asn Ile His Gly Ser Ala Ala Ile Ala
1775                1780                1785

Ser Ala Tyr Ser Arg Ala Tyr Glu Glu Thr Phe Thr Leu Thr Phe
1790                1795                1800

Val Thr Gly Arg Thr Val Gly Ile Gly Ala Tyr Leu Ala Arg Leu
1805                1810                1815

Gly Ile Arg Cys Ile Gln Arg Ile Asp Gln Pro Ile Ile Leu Thr
1820                1825                1830

Gly Phe Ser Ala Leu Asn Lys Leu Leu Gly Arg Glu Val Tyr Ser
1835                1840                1845

Ser His Met Gln Leu Gly Gly Pro Lys Ile Met Ala Thr Asn Gly
1850                1855                1860

Val Val His Leu Thr Val Pro Asp Asp Leu Glu Gly Val Ser Asn
1865                1870                1875

Ile Leu Arg Trp Leu Ser Tyr Val Pro Ala Asn Ile Gly Gly Pro
1880                1885                1890

Leu Pro Ile Thr Lys Ser Leu Asp Pro Ile Asp Arg Pro Val Ala
1895                1900                1905

Tyr Ile Pro Glu Asn Thr Cys Asp Pro Arg Ala Ala Ile Ser Gly
1910                1915                1920

Ile Asp Asp Ser Gln Gly Lys Trp Leu Gly Gly Met Phe Asp Lys
1925                1930                1935

Asp Ser Phe Val Glu Thr Phe Glu Gly Trp Ala Lys Thr Val Val
1940                1945                1950

Thr Gly Arg Ala Lys Leu Gly Gly Ile Pro Val Gly Val Ile Ala
1955             1960             1965

Val Glu Thr Gln Thr Met Met Gln Leu Val Pro Ala Asp Pro Gly
1970             1975             1980

Gln Pro Asp Ser His Glu Arg Ser Val Pro Arg Ala Gly Gln Val
1985             1990             1995

Trp Phe Pro Asp Ser Ala Thr Lys Thr Ala Gln Ala Met Leu Asp
2000             2005             2010

Phe Asn Arg Glu Gly Leu Pro Leu Phe Ile Leu Ala Asn Trp Arg
2015             2020             2025

Gly Phe Ser Gly Gly Gln Arg Asp Leu Phe Glu Gly Ile Leu Gln
2030             2035             2040

Ala Gly Ser Thr Ile Val Glu Asn Leu Arg Thr Tyr Asn Gln Pro
2045             2050             2055

Ala Phe Val Tyr Ile Pro Lys Ala Ala Glu Leu Arg Gly Gly Ala
2060             2065             2070

Trp Val Val Ile Asp Ser Lys Ile Asn Pro Asp Arg Ile Glu Cys
2075             2080             2085

Tyr Ala Glu Arg Thr Ala Lys Gly Asn Val Leu Glu Pro Gln Gly
2090             2095             2100

Leu Ile Glu Ile Lys Phe Arg Ser Glu Glu Leu Lys Glu Cys Met
2105             2110             2115

Gly Arg Leu Asp Pro Glu Leu Ile Asp Leu Lys Ala Arg Leu Gln
2120             2125             2130

Gly Ala Asn Gly Ser Leu Ser Asp Gly Glu Ser Leu Gln Lys Ser
2135             2140             2145

Ile Glu Ala Arg Lys Lys Gln Leu Leu Pro Leu Tyr Thr Gln Ile
2150             2155             2160

Ala Val Arg Phe Ala Glu Leu His Asp Thr Ser Leu Arg Met Ala
2165             2170             2175

Ala Lys Gly Val Ile Arg Lys Val Val Asp Trp Glu Asp Ser Arg
2180             2185             2190

Ser Phe Phe Tyr Lys Arg Leu Arg Arg Arg Leu Ser Glu Asp Val
2195             2200             2205

Leu Ala Lys Glu Ile Arg Gly Val Ile Gly Glu Lys Phe Pro His
2210             2215             2220

Lys Ser Ala Ile Glu Leu Ile Lys Lys Trp Tyr Leu Ala Ser Glu
2225             2230             2235

Ala Ala Ala Ala Gly Ser Thr Asp Trp Asp Asp Asp Ala Phe
2240             2245             2250

Val Ala Trp Arg Glu Asn Pro Glu Asn Tyr Lys Glu Tyr Ile Lys
2255             2260             2265

Glu Leu Arg Ala Gln Arg Val Ser Arg Leu Leu Ser Asp Val Ala
2270             2275             2280

Gly Ser Ser Ser Asp Leu Gln Ala Leu Pro Gln Gly Leu Ser Met
2285             2290             2295

Leu Leu Asp Lys Met Asp Pro Ser Lys Arg Ala Gln Phe Ile Glu
2300             2305             2310

Glu Val Met Lys Val Leu Lys
2315             2320

<210> SEQ ID NO 25
<211> LENGTH: 6936
<212> TYPE: DNA

<213> ORGANISM: Aegilops tauschii

<400> SEQUENCE: 25

```
atgggatcca cacatttgcc cattgtcggc cttaatgcct cgacaacacc atcgctatcc    60
actattcgcc cggtaaattc agccggtgct gcattccaac catctgcccc ttctagaacc   120
tccaagaaga aaagtcgtcg tgttcagtca ttaagggatg gaggcgatgg aggcgtgtca   180
gaccctaacc agtctattcg ccaaggtctt gccggcatca ttgacctccc aaaggagggc   240
acatcagctc cggaagtgga tatttcacat gggtccgaag aacccagggg ctcctaccaa   300
atgaatggga tactgaatga agcacataat gggaggcatg cttcgctgtc taaggttgtc   360
gaattttgta tggcattggg cggcaaaaca ccaattcata gtgtattagt tgcgaacaat   420
ggaatggcag cagctaagtt catgcggagt gtccgaacat gggctaatga aacatttggg   480
tcagagaagg caattcagtt gatagctatg gctactccag aagacatgag gataaatgca   540
gagcacatta gaattgctga tcaatttgtt gaagtacccg gtggaacaaa caataacaac   600
tatgcaaatg tccaactcat agtggagata gcagtgagaa ccggtgtttc tgctgtttgg   660
cctggttggg gccatgcatc tgagaatcct gaacttccag atgcactaaa tgcaacgga   720
attgtttttc ttgggccacc atcatcatca atgaacgcac taggtgacaa ggttggttca   780
gctctcattg ctcaagcagc aggggttccg actcttcctt ggagtggatc acaggtggaa   840
attccattag aagtttgttt ggactcgata cctgcggata tgtataggaa gcttgtgtt   900
agtactacgg aggaagcact tgcgagttgt cagatgattg ggtatccagc catgattaaa   960
gcatcatggg gtggtggtgg taaagggatc cgaaaggtta ataacgacga tgatgtcaga  1020
gcactgttta gcaagtgca aggtgaagtt cctggctccc caatatttat catgagactt  1080
gcatctcaga gtcgacatct tgaagttcag ttgctttgtg atcaatatgg caatgtagct  1140
gcgcttcaca gtcgtgactg cagtgtgcaa cggcgacacc aaaagattat tgaggaagga  1200
ccagttactg ttgctcctcg cgagacagtg aaagagctag agcaagcagc aaggaggctt  1260
gctaaggctg tgggttatgt tggtgctgct actgttgaat atctctacag catggagact  1320
ggtgaatact attttctgga acttaatcca cggttgcagg ttgagcatcc agtcaccgag  1380
tggatagctg aagtaaactt gcctgcagct caagttgcag ttggaatggg tatcccctt  1440
tggcaggttc cagagatcag acgtttctat ggaatggaca atggaggagg ctatgacatt  1500
tggaggaaaa cagcagctct tgctaccccca tttaactttg atgaagtgga ttctcaatgg  1560
ccaaagggtc attgtgtagc agttaggata accagtgagg atccagatga cggattcaag  1620
cctaccggtg gaaaagtaaa ggagatcagt tttaaagca agccaaatgt ttgggcctat  1680
ttctctgtta agtccggtgg aggcattcat gaatttgctg attctcagtt tggacatgtt  1740
tttgcatatg gagtgtctag agcagcagca ataaccaaca tgtctcttgc gctaaaagag  1800
attcaaattc gtggagaaat tcattcaaat gttgattaca cagttgatct cttgaatgcc  1860
tcagacttca aagaaaacag gattcatact ggctggctgg ataacagaat agcaatgcga  1920
gtccaagctg agagacctcc gtggtatatt tcagtggttg gaggagctct atataaaaca  1980
ataacgagca acacagacac tgttttctgaa tatgttagct atctcgtcaa gggtcagatt  2040
ccaccgaagc atatatccct tgtccattca actgtttctt tgaatataga ggaaagcaaa  2100
tatacaattg aaactataag gagcggacag ggtagctaca gattgcgaat gaatggatca  2160
gttattgaag caaatgtcca aacattatgt gatggtggac ttttaatgca gttggatgga  2220
aacagccatg taatttatgc tgaagaagag gccggtggta cacggcttct aattgatgga  2280
```

```
aagacatgct tgttacagaa tgatcacgat ccttcaaggt tattagctga gacaccctgc    2340
aaacttcttc gtttcttggt tgccgatggt gctcatgttg aagctgatgt accatatgcg    2400
gaagttgagg ttatgaagat gtgcatgccc ctcttgtcac ctgctgctgg tgtcattaat    2460
gttttgttgt ctgagggcca gcctatgcag gctggtgatc ttatagcaag acttgatctt    2520
gatgacccct tctgctgtgaa gagagctgag ccgtttaacg gatctttccc agaaatgagc    2580
cttcctattg ctgcttctgg ccaagttcac aaaagatgtg ccacaagctt gaatgctgct    2640
cggatggtcc ttgcaggata tgatcacccg atcaacaaag ttgtacaaga tctggtatcc    2700
tgtctagatg ctcctgagct tccttttccta caatgggaag agcttatgtc tgttttagca    2760
actagacttc caaggcttct taagagcgag ttggagggta aatacagtga atataagtta    2820
aatgttggcc atggaaagag caaggatttc ccttccaaga tgctaagaga gataatcgag    2880
gaaaatcttg cacatggttc tgagaaggaa attgctacaa atgagaggct tgttgagcct    2940
cttatgagcc tactgaagtc atatgagggt ggcagagaaa gccatgcaca ctttattgtg    3000
aagtcccttt tcgaggacta tctctcggtt gaggaactat tcagtgatgg cattcagtct    3060
gatgtgattg aacgcctgcg ccaacaacat agtaaagatc tccagaaggt tgtagacatt    3120
gtgttgtctc accagggtgt gagaaacaaa actaagctga tactaacact catggagaaa    3180
ctggtctatc caaaccctgc tgcctacaag gatcagttga ctcgcttttc ctccctcaat    3240
cacaaaagat attataagtt ggcccttaaa gctagcgagc ttcttgaaca aaccaagctt    3300
agtgagctcc gcacaagcat tgcaaggagc ctttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattataccc gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat gcgccatacc    3900
ttcctcttgt cggatgaaaa gctttgttat gaggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatataca cacttagaaa tacagagaac    4080
cccaaaatgt tgcacagggt gttttttccga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
gcgattagga caggtcactc tcatatgttt ttgtgcatat tgaaagagca aaagcttctt    4320
gatcttgttc ccgtttcagg gaacaaagtt gtggatattg ccaagatgaa agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggttg aagatacaga atcacagaaa ctagtgtacc actctgctcc atcgtcatct    4620
```

```
ggtcctttgc atggcgttgc actgaatact ccatatcagc ctttgagtgt tattgatctg    4680
aaacgttgct ccgctagaaa taacagaact acatactgct atgattttcc gttggcattt    4740
gaaactgcag tgcagaagtc atggtctaac atttctagtg acactaaccg atgttatgtt    4800
aaagcgacgg agctggtgtt tgctcacaag aacgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tactttttaga   4980
gctggatcgt ttggtccaag ggaagatgca ttttttgaaa ctgttaccaa cctagcttgt    5040
gagaggaagc ttcctctcat ctacttggca gcaaactctg gtgctcggat cggcatagca    5100
gatgaagtaa aatcttgctt ccgtgttgga tggtctgatg atggcagccc tgaacgtggg    5160
tttcaatata tttatctgac tgaagaagac catgctcgta ttagcgcttc tgttatagcg    5220
cacaagatgc agcttgataa tggtgaaatt aggtgggtta ttgattctgt tgtagggaag    5280
gaggatgggc taggtgtgga gaacatacat ggaagtgctg ctattgccag tgcctattct    5340
agggcctatg aggagacatt tacgcttaca tttgtgactg aaggactgt tggaatagga     5400
gcatatcttg ctcgacttgg catacggtgc attcagcgta ctgaccagcc cattatccta    5460
actgggttct ctgccttgaa caagcttctt ggccgggaag tgtacagctc ccacatgcag    5520
ttgggtggcc ccaaaattat ggccacaaac ggtgttgtcc atctgacagt ttcagatgac    5580
cttgaaggtg tatctaatat attgaggtgg ctcagctatg ttcctgccaa cattggtgga    5640
cctcttccta ttacaaaatc tttggaccca cctgacagac ccgttgctta catccctgag    5700
aatacatgtg atcctcgtgc agccatcagt ggcattgatg atagccaagg gaaatggttg    5760
gggggtatgt tcgacaaaga cagttttgtg agacatttg aaggatgggc gaagtcagta    5820
gttactggca gagcgaaact cggagggatt ccggtgggtg ttatagctgt ggagacacag    5880
actatgatgc agctcatccc tgctgatcca ggtcagcttg attcccatga gcggtctgtt    5940
cctcgtgctg ggcaagtctg gtttccagat tcagctacta agacagcgca ggcaatgctg    6000
gacttcaacc gtgaaggatt acctctgttc atccttgcta actggagagg cttctctggt    6060
gggcaaagag atcttttttga aggaatcctt caggctgggt caacaattgt tgagaacctt    6120
aggacataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct tgaacctcaa gggttgattg agatcaagtt caggtcagag    6300
gaactccaag agtgcatggg caggcttgac ccagaattga taaatttgaa ggcaaaactc    6360
ctgggagcaa agcatgaaaa tggaagtcta tctgagtcag aatcccttca gaagagcata    6420
gaagcccgga gaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtctttctt ctacaagaga ttacggagga ggatatccga ggatgttctt    6600
gcaaaggaaa ttagaggtgt aagtggcaag cagttttctc accaatcggc aatcgagctg    6660
atccagaaat ggtacttggc ctctaaggga gctgaaacgg gaaacactga atgggatgat    6720
gacgatgctt ttgttgcctg gagggaaaac cctgaaaact accaggagta tatcaaagaa    6780
ctcagggctc aaagggtatc tcagttgctc tcagatgttg cagactccag tccagatcta    6840
gaagccttgc cacagggtct ttctatgcta ctagagaaga tggatccctc aaggagagca    6900
cagtttgttg aggaagtcaa gaaggccctt aaatga                              6936
```

<210> SEQ ID NO 26
<211> LENGTH: 2311
<212> TYPE: PRT
<213> ORGANISM: Aegilops tauschii

<400> SEQUENCE: 26

```
Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Met Ala Ala
130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Ile Ala Val Arg Thr Gly Val Ser Ala Val Trp Pro Gly Trp Gly
210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Ser Gly Ser Gln Val Glu Ile Pro Leu Glu Val Cys Leu Asp
        275                 280                 285

Ser Ile Pro Ala Asp Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380
```

```
Arg Asp Cys Ser Val Gln Arg His Gln Lys Ile Ile Glu Glu Gly
385                 390                 395                 400

Pro Val Thr Val Ala Pro Arg Glu Thr Val Lys Glu Leu Glu Gln Ala
        405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
        450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
            485                 490                 495

Gly Tyr Asp Ile Trp Arg Lys Thr Ala Ala Leu Ala Thr Pro Phe Asn
                500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
            565                 570                 575

Phe Gly His Val Phe Ala Tyr Gly Val Ser Arg Ala Ala Ala Ile Thr
        580                 585                 590

Asn Met Ser Leu Ala Leu Lys Glu Ile Gln Ile Arg Gly Glu Ile His
            595                 600                 605

Ser Asn Val Asp Tyr Thr Val Asp Leu Leu Asn Ala Ser Asp Phe Lys
        610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
            645                 650                 655

Leu Tyr Lys Thr Ile Thr Ser Asn Thr Asp Thr Val Ser Glu Tyr Val
        660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
            725                 730                 735

Gln Leu Asp Gly Asn Ser His Val Ile Tyr Ala Glu Glu Ala Gly
        740                 745                 750

Gly Thr Arg Leu Leu Ile Asp Gly Lys Thr Cys Leu Leu Gln Asn Asp
        755                 760                 765

His Asp Pro Ser Arg Leu Leu Ala Glu Thr Pro Cys Lys Leu Leu Arg
        770                 775                 780

Phe Leu Val Ala Asp Gly Ala His Val Glu Ala Asp Val Pro Tyr Ala
785                 790                 795                 800

Glu Val Glu Val Met Lys Met Cys Met Pro Leu Leu Ser Pro Ala Ala
```

```
                805                 810                 815
Gly Val Ile Asn Val Leu Leu Ser Glu Gly Gln Pro Met Gln Ala Gly
            820                 825                 830

Asp Leu Ile Ala Arg Leu Asp Leu Asp Pro Ser Ala Val Lys Arg
        835                 840                 845

Ala Glu Pro Phe Asn Gly Ser Phe Pro Glu Met Ser Leu Pro Ile Ala
        850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
                885                 890                 895

Asp Leu Val Ser Cys Leu Asp Ala Pro Glu Leu Pro Phe Leu Gln Trp
            900                 905                 910

Glu Glu Leu Met Ser Val Leu Ala Thr Arg Leu Pro Arg Leu Leu Lys
        915                 920                 925

Ser Glu Leu Glu Gly Lys Tyr Ser Glu Tyr Lys Leu Asn Val Gly His
    930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Lys Ser Tyr Gly Gly Arg
            980                 985                 990

Glu Ser His Ala His Phe Ile Val Lys Ser Leu Phe Glu Asp Tyr Leu
        995                 1000                1005

Ser Val Glu Glu Leu Phe Ser Asp Gly Ile Gln Ser Asp Val Ile
    1010                1015                1020

Glu Arg Leu Arg Gln Gln His Ser Lys Asp Leu Gln Lys Val Val
    1025                1030                1035

Asp Ile Val Leu Ser His Gln Gly Val Arg Asn Lys Thr Lys Leu
    1040                1045                1050

Ile Leu Thr Leu Met Glu Lys Leu Val Tyr Pro Asn Pro Ala Ala
    1055                1060                1065

Tyr Lys Asp Gln Leu Thr Arg Phe Ser Ser Leu Asn His Lys Arg
    1070                1075                1080

Tyr Tyr Lys Leu Ala Leu Lys Ala Ser Glu Leu Leu Glu Gln Thr
    1085                1090                1095

Lys Leu Ser Glu Leu Arg Thr Ser Ile Ala Arg Ser Leu Ser Glu
    1100                1105                1110

Leu Glu Met Phe Thr Glu Glu Arg Thr Ala Ile Ser Glu Ile Met
    1115                1120                1125

Gly Asp Leu Val Thr Ala Pro Leu Pro Val Glu Asp Ala Leu Val
    1130                1135                1140

Ser Leu Phe Asp Cys Ser Asp Gln Thr Leu Gln Gln Arg Val Ile
    1145                1150                1155

Glu Thr Tyr Ile Ser Arg Leu Tyr Gln Pro His Leu Val Lys Asp
    1160                1165                1170

Ser Ile Gln Leu Lys Tyr Gln Glu Ser Gly Val Ile Ala Leu Trp
    1175                1180                1185

Glu Phe Ala Glu Ala His Ser Glu Lys Arg Leu Gly Ala Met Val
    1190                1195                1200

Ile Val Lys Ser Leu Glu Ser Val Ser Ala Ala Ile Gly Ala Ala
    1205                1210                1215
```

```
Leu Lys Gly Thr Ser Arg Tyr Ala Ser Ser Glu Gly Asn Ile Met
1220             1225                 1230

His Ile Ala Leu Leu Gly Ala Asp Asn Gln Met His Gly Thr Glu
1235             1240                 1245

Asp Ser Gly Asp Asn Asp Gln Ala Gln Val Arg Ile Asp Lys Leu
1250             1255                 1260

Ser Ala Thr Leu Glu Gln Asn Thr Val Thr Ala Asp Leu Arg Ala
1265             1270                 1275

Ala Gly Val Lys Val Ile Ser Cys Ile Val Gln Arg Asp Gly Ala
1280             1285                 1290

Leu Met Pro Met Arg His Thr Phe Leu Leu Ser Asp Glu Lys Leu
1295             1300                 1305

Cys Tyr Glu Glu Glu Pro Val Leu Arg His Val Glu Pro Pro Leu
1310             1315                 1320

Ser Ala Leu Leu Glu Leu Gly Lys Leu Lys Val Lys Gly Tyr Asn
1325             1330                 1335

Glu Val Lys Tyr Thr Pro Ser Arg Asp Arg Gln Trp Asn Ile Tyr
1340             1345                 1350

Thr Leu Arg Asn Thr Glu Asn Pro Lys Met Leu His Arg Val Phe
1355             1360                 1365

Phe Arg Thr Leu Val Arg Gln Pro Gly Ala Ser Asn Lys Phe Thr
1370             1375                 1380

Ser Gly Asn Ile Ser Asp Val Glu Val Gly Gly Ala Glu Glu Ser
1385             1390                 1395

Leu Ser Phe Thr Ser Ser Ser Ile Leu Arg Ser Leu Met Thr Ala
1400             1405                 1410

Ile Glu Glu Leu Glu Leu His Ala Ile Arg Thr Gly His Ser His
1415             1420                 1425

Met Phe Leu Cys Ile Leu Lys Glu Gln Lys Leu Leu Asp Leu Val
1430             1435                 1440

Pro Val Ser Gly Asn Lys Val Val Asp Ile Gly Gln Asp Glu Ala
1445             1450                 1455

Thr Ala Cys Leu Leu Leu Lys Glu Met Ala Leu Gln Ile His Glu
1460             1465                 1470

Leu Val Gly Ala Arg Met His His Leu Ser Val Cys Gln Trp Glu
1475             1480                 1485

Val Lys Leu Lys Leu Asp Ser Asp Gly Pro Ala Ser Gly Thr Trp
1490             1495                 1500

Arg Val Val Thr Thr Asn Val Thr Ser His Thr Cys Thr Val Asp
1505             1510                 1515

Ile Tyr Arg Glu Val Glu Asp Thr Glu Ser Gln Lys Leu Val Tyr
1520             1525                 1530

His Ser Ala Pro Ser Ser Gly Pro Leu His Gly Val Ala Leu
1535             1540                 1545

Asn Thr Pro Tyr Gln Pro Leu Ser Val Ile Asp Leu Lys Arg Cys
1550             1555                 1560

Ser Ala Arg Asn Asn Arg Thr Thr Tyr Cys Tyr Asp Phe Pro Leu
1565             1570                 1575

Ala Phe Glu Thr Ala Val Gln Lys Ser Trp Ser Asn Ile Ser Ser
1580             1585                 1590

Asp Thr Asn Arg Cys Tyr Val Lys Ala Thr Glu Leu Val Phe Ala
1595             1600                 1605
```

```
His Lys Asn Gly Ser Trp Gly Thr Pro Val Ile Pro Met Glu Arg
1610                1615                1620

Pro Ala Gly Leu Asn Asp Ile Gly Met Val Ala Trp Ile Leu Asp
1625                1630                1635

Met Ser Thr Pro Glu Tyr Pro Asn Gly Arg Gln Ile Val Val Ile
1640                1645                1650

Ala Asn Asp Ile Thr Phe Arg Ala Gly Ser Phe Gly Pro Arg Glu
1655                1660                1665

Asp Ala Phe Phe Glu Thr Val Thr Asn Leu Ala Cys Glu Arg Lys
1670                1675                1680

Leu Pro Leu Ile Tyr Leu Ala Ala Asn Ser Gly Ala Arg Ile Gly
1685                1690                1695

Ile Ala Asp Glu Val Lys Ser Cys Phe Arg Val Gly Trp Ser Asp
1700                1705                1710

Asp Gly Ser Pro Glu Arg Gly Phe Gln Tyr Ile Tyr Leu Thr Glu
1715                1720                1725

Glu Asp His Ala Arg Ile Ser Ala Ser Val Ile Ala His Lys Met
1730                1735                1740

Gln Leu Asp Asn Gly Glu Ile Arg Trp Val Ile Asp Ser Val Val
1745                1750                1755

Gly Lys Glu Asp Gly Leu Gly Val Glu Asn Ile His Gly Ser Ala
1760                1765                1770

Ala Ile Ala Ser Ala Tyr Ser Arg Ala Tyr Glu Glu Thr Phe Thr
1775                1780                1785

Leu Thr Phe Val Thr Gly Arg Thr Val Gly Ile Gly Ala Tyr Leu
1790                1795                1800

Ala Arg Leu Gly Ile Arg Cys Ile Gln Arg Thr Asp Gln Pro Ile
1805                1810                1815

Ile Leu Thr Gly Phe Ser Ala Leu Asn Lys Leu Leu Gly Arg Glu
1820                1825                1830

Val Tyr Ser Ser His Met Gln Leu Gly Gly Pro Lys Ile Met Ala
1835                1840                1845

Thr Asn Gly Val Val His Leu Thr Val Ser Asp Asp Leu Glu Gly
1850                1855                1860

Val Ser Asn Ile Leu Arg Trp Leu Ser Tyr Val Pro Ala Asn Ile
1865                1870                1875

Gly Gly Pro Leu Pro Ile Thr Lys Ser Leu Asp Pro Pro Asp Arg
1880                1885                1890

Pro Val Ala Tyr Ile Pro Glu Asn Thr Cys Asp Pro Arg Ala Ala
1895                1900                1905

Ile Ser Gly Ile Asp Asp Ser Gln Gly Lys Trp Leu Gly Gly Met
1910                1915                1920

Phe Asp Lys Asp Ser Phe Val Glu Thr Phe Glu Gly Trp Ala Lys
1925                1930                1935

Ser Val Val Thr Gly Arg Ala Lys Leu Gly Gly Ile Pro Val Gly
1940                1945                1950

Val Ile Ala Val Glu Thr Gln Thr Met Met Gln Leu Ile Pro Ala
1955                1960                1965

Asp Pro Gly Gln Leu Asp Ser His Glu Arg Ser Val Pro Arg Ala
1970                1975                1980

Gly Gln Val Trp Phe Pro Asp Ser Ala Thr Lys Thr Ala Gln Ala
1985                1990                1995

Met Leu Asp Phe Asn Arg Glu Gly Leu Pro Leu Phe Ile Leu Ala
```

-continued

```
            2000                2005                2010
Asn Trp Arg Gly Phe Ser Gly Gly Gln Arg Asp Leu Phe Glu Gly
            2015                2020                2025
Ile Leu Gln Ala Gly Ser Thr Ile Val Glu Asn Leu Arg Thr Tyr
            2030                2035                2040
Asn Gln Pro Ala Phe Val Tyr Ile Pro Lys Ala Ala Glu Leu Arg
            2045                2050                2055
Gly Gly Ala Trp Val Val Ile Asp Ser Lys Ile Asn Pro Asp Arg
            2060                2065                2070
Ile Glu Phe Tyr Ala Glu Arg Thr Ala Lys Gly Asn Val Leu Glu
            2075                2080                2085
Pro Gln Gly Leu Ile Glu Ile Lys Phe Arg Ser Glu Glu Leu Gln
            2090                2095                2100
Glu Cys Met Gly Arg Leu Asp Pro Glu Leu Ile Asn Leu Lys Ala
            2105                2110                2115
Lys Leu Leu Gly Ala Lys His Glu Asn Gly Ser Leu Ser Glu Ser
            2120                2125                2130
Glu Ser Leu Gln Lys Ser Ile Glu Ala Arg Lys Lys Gln Leu Leu
            2135                2140                2145
Pro Leu Tyr Thr Gln Ile Ala Val Arg Phe Ala Glu Leu His Asp
            2150                2155                2160
Thr Ser Leu Arg Met Ala Ala Lys Gly Val Ile Lys Lys Val Val
            2165                2170                2175
Asp Trp Glu Asp Ser Arg Ser Phe Phe Tyr Lys Arg Leu Arg Arg
            2180                2185                2190
Arg Ile Ser Glu Asp Val Leu Ala Lys Glu Ile Arg Gly Val Ser
            2195                2200                2205
Gly Lys Gln Phe Ser His Gln Ser Ala Ile Glu Leu Ile Gln Lys
            2210                2215                2220
Trp Tyr Leu Ala Ser Lys Gly Ala Glu Thr Gly Asn Thr Glu Trp
            2225                2230                2235
Asp Asp Asp Asp Ala Phe Val Ala Trp Arg Glu Asn Pro Glu Asn
            2240                2245                2250
Tyr Gln Glu Tyr Ile Lys Glu Leu Arg Ala Gln Arg Val Ser Gln
            2255                2260                2265
Leu Leu Ser Asp Val Ala Asp Ser Ser Pro Asp Leu Glu Ala Leu
            2270                2275                2280
Pro Gln Gly Leu Ser Met Leu Leu Glu Lys Met Asp Pro Ser Arg
            2285                2290                2295
Arg Ala Gln Phe Val Glu Glu Val Lys Lys Ala Leu Lys
            2300                2305                2310
```